US012312401B2

(12) United States Patent
Hoofd et al.

(10) Patent No.: US 12,312,401 B2
(45) Date of Patent: *May 27, 2025

(54) ANTI-TIGIT ANTIBODIES

(71) Applicant: iTeos Belgium SA, Gosselies (BE)

(72) Inventors: Catherine Hoofd, Chastre-Villeroux-Blanmont (BE); Gregory Driessens, Ottignies (BE); Julia Cuende, Bertem (BE)

(73) Assignee: iTeos Belguim SA, Gosselies (BE)

( * ) Notice: Subject to any disclaimer, the term of this patent is extended or adjusted under 35 U.S.C. 154(b) by 585 days.

This patent is subject to a terminal disclaimer.

(21) Appl. No.: 17/420,987

(22) PCT Filed: Jan. 7, 2020

(86) PCT No.: PCT/EP2020/050203
§ 371 (c)(1),
(2) Date: Jul. 6, 2021

(87) PCT Pub. No.: WO2020/144178
PCT Pub. Date: Jul. 16, 2020

(65) Prior Publication Data
US 2022/0306733 A1 Sep. 29, 2022

Related U.S. Application Data

(60) Provisional application No. 62/789,466, filed on Jan. 7, 2019.

(51) Int. Cl.
| C07K 16/28 | (2006.01) |
| A61K 31/704 | (2006.01) |
| A61K 39/395 | (2006.01) |
| A61P 35/00 | (2006.01) |
| C12N 5/0783 | (2010.01) |
| A61K 39/00 | (2006.01) |

(52) U.S. Cl.
CPC ............ *C07K 16/28* (2013.01); *A61K 31/704* (2013.01); *A61K 39/3955* (2013.01); *A61P 35/00* (2018.01); *C07K 16/2818* (2013.01); *C12N 5/0636* (2013.01); *A61K 2039/505* (2013.01); *A61K 2039/507* (2013.01); *C07K 2317/21* (2013.01); *C07K 2317/35* (2013.01); *C07K 2317/565* (2013.01); *C07K 2317/732* (2013.01); *C07K 2317/734* (2013.01); *C07K 2317/76* (2013.01); *C07K 2317/92* (2013.01); *C12N 2501/998* (2013.01)

(58) Field of Classification Search
CPC ........................... C07K 16/28; C07K 16/2818; C07K 2317/21; C07K 2317/35; C07K 2317/565; C07K 2317/732; C07K 2317/734; C07K 2317/76; C07K 2317/92; A61K 31/704; A61K 39/3955; A61K 2039/505; A61K 2039/507; A61P 35/00; C12N 5/0636; C12N 2501/998
See application file for complete search history.

(56) References Cited

U.S. PATENT DOCUMENTS

| 5,892,019 A | 4/1999 | Schlom et al. |
| 10,329,349 B2* | 6/2019 | Cooper ................. A61K 45/06 |
| 10,766,957 B2 | 9/2020 | Williams et al. |
| 11,439,705 B2* | 9/2022 | Cooper ............. C07K 16/2827 |
| 2016/0176963 A1 | 6/2016 | Maurer et al. |
| 2016/0376365 A1 | 12/2016 | Gurney et al. |
| 2018/0371083 A1 | 12/2018 | Williams et al. |
| 2021/0017276 A1 | 1/2021 | Williams et al. |

FOREIGN PATENT DOCUMENTS

| WO | 2009036379 A2 | 3/2009 |
| WO | 2010105256 A1 | 9/2010 |
| WO | 2012009568 A2 | 1/2012 |
| WO | 2014179363 A1 | 11/2014 |
| WO | 2016/028656 A1 | 2/2016 |
| WO | 2016/106302 A1 | 6/2016 |
| WO | 2016/191643 A2 | 12/2016 |
| WO | 2017030823 A2 | 2/2017 |
| WO | 2017053748 A2 | 3/2017 |
| WO | 2017152088 A1 | 9/2017 |
| WO | 2018043968 A1 | 3/2018 |

(Continued)

OTHER PUBLICATIONS

Yan, Y. et al. "Combining Immune Checkpoint inhibitors with Conventional Cancer Therapy", 2018, Frontiers in Immunology, 9(1739), 1-13. (Year: 2018).*
Solomon, BL and Garrido-Laguna, I, "TIGIT: a novel immunotherapy target moving from bench to bedside", 2018, Cancer Immunology Immunotherapy, 67, 1659-1667. (Year: 2018).*
Cari, L et al. "Potential effect of tumor-specific Treg-targeted antibodies in the treatment of human cancers: A bioinformatics analysis", 2018, Oncoimmunology, 7(2), 1-17. (Year: 2018).*
Johnston, RJ et al. "The Immunoreceptor TIGIT Regulates Antitumor and Antiviral CD8+ T Cell Effector Function", 2014, Cancer Cell, 26, 923-937. (Year: 2014).*

(Continued)

*Primary Examiner* — Nelson B Moseley, II
*Assistant Examiner* — Alyssa Rae Stonebraker
(74) *Attorney, Agent, or Firm* — William Peter Long

(57) ABSTRACT

Anti-TIGIT antibodies and antigen binding fragments that inhibit TIGIT-mediated signaling, plus related details, are provided on consultation of the full patent text. Combinations of these anti-TIGIT antibodies and antigen binding fragments with additional therapeutic agents, plus related details, are also provided on consultation of the full patent text. Methods for promoting T cell activity and methods of treating cancer with these anti-TIGIT antibodies and antigen binding fragments, plus related details, are provided as well on consultation of the full patent text. These methods can be applied to a human subject and details relating to this are provided on consultation of the full patent text.

20 Claims, 68 Drawing Sheets

Specification includes a Sequence Listing.

(56) References Cited

FOREIGN PATENT DOCUMENTS

| WO | 2019/023504 A1 | 1/2019 |
| WO | 2019074208 A1 | 4/2019 |

OTHER PUBLICATIONS

Chew, Glen M., et al., "TIGIT Marks Exhausted T Cells, Correlates with Disease Progression, and Serves as a Target for Immune Restoration in HIV and SIV Infection", PLOS PATHOGENS, (Jan. 7, 2016), vol. 12, No. 1, p. e1005349, p. 8-p. 10.
Urlaub et al., Proc. Natl. Acad. Sci. USA, (1980), vol. 77, p. 4216.
Chothia et al., J. Mol. Biol., (1987), vol. 196, pp. 901-917.
Chothia et al., J. Mol. Biol., (1992), vol. 227, pp. 799-817.
De Groot et al., Blood, (2008), vol. 112, p. 3303.
De Groot et al., Clinical Immunol., (2009), vol. 131, p. 189.
De Witte, et al., "Early Reconsititution of NK and gd T Cells and its Implication for the design of Post-Transplant Immunotherapy", Biology of Blood and Marrow Transplantation, vol. 24, No. 6, Mar. 2, 2018, pp. 1152-1162.
Estep et al., Mabs, (2013), vol. 5, No. 2, pp. 270-278.
Genbank, "Homo sapiens T cell immunoreceptor with Ig and ITIM domain (TIGIT) mRNA" NCBI Reference sequence NM 173799.3, Aua 28, 2016, four pages.
Graham et al., J. Gen. Virol., (1977), vol. 36, pp. 59-74.
Guerois et al., J. Mol. Biol., (2002), vol. 320, No. 2, pp. 369-387.
Harlow; Lane, Antibodies, A Laboratory Manual, Cold Spring Harbor Laboratory Press, (1988), pp. 567-569.
Holliger; Hudson, Nature Biotechnol., (2005), vol. 23, pp. 1126-1136.
Jariwala, Net al (2017) TIGIT and Helios are highly expressed on CD4+ T cells in Sezary syndrome patients. Journal of Investigative Dermatology 137: 257-260.
Johnston Robert J et al: "The Immunoreceptor TIGIT Regulates Antitumor and Antiviral CD8+T Cell Effector Function", Cancer Cell, Cell Press, US, vol. 26, No. 6, Nov. 26, 2014 (Nov. 26, 2014), pp. 923-937.
Joller et al. (2014) Treg cells expressing the coinhibitory molecule TIGIT selectively inhibit proinflammatory Th1 and Th17 cell responses. Immunity: Apr. 17;40(4):569-81.
Kabat et al., J. Biol. Chem., (1977), vol. 252, pp. 6609 6616.
Kao; Puck, "Genetics of somatic mammalian cells, VII. Induction and isolation of nutritional mutants in Chinese hamster cells", Proc. Natl. Acad. Sci., (1968), vol. 60, pp. 1275-1281.
Kurtulus et al. (2015) TIGIT predominantly regulates the immune response via regulatory T cells. J.Clin.Invest: 276:112.
Maccallum et al., J. Mol. Biol., (1996), vol. 262, pp. 732-745.
Malik S et al., Front Immunol., (2016), vol. 7, p. 14.
Mather et al., Annals N.Y. Acad. Sci., (1982), vol. 383, pp. 44-68.
Mather, Biol. Reprod., (1980), vol. 23, pp. 243-252.
Morea et al., Methods, (2000), vol. 20, pp. 267-279.
Silva et al., J Biol Chem., (20150227), vol. 290, No. 9, pp. 5462-5469.
Southwood et al., J. Immunol, (1998), vol. 160, p. 3363 (Not Cited in Div).
Tatusova et al., "Blast 2 sequences a new tool for comparing protein and nucleotide sequences", FEMS Microbiol ett., vol. 174, pp. 247-250.
Tramontano et al., J. Mol. Biol, (1990), vol. 215, pp. 175-182.
Wang et al., Journal of Pharmaceutical Sciences, (2007), vol. 96, pp. 1-26.
Ku et al., Protein Eng Des Sel, (2013), vol. 26, No. 10, pp. 663-670.
Yu et al. (2009) The surface protein TIGIT suppresses T cell activation by promoting the generation of mature Immunoregulatory dendritic cells. Nat Immunol:Jan. 10(1):48-57.
Zhao et al., J Transl Med., (2018), vol. 16, p. 122.

* cited by examiner

FIG. 1 — VH CDR sequences

| Antibody | VH CDR1 | SEQ ID NO: | VH CDR2 | SEQ ID NO: | VH CDR3 | SEQ ID NO: |
|---|---|---|---|---|---|---|
| 26518 | FTFSSYGMS | 1 | NIKQDGSEKYYVDSVKG | 2 | ARVSYYYDSSKLRWAEYFQH | 3 |
| 29478 | FTFESYGMV | 4 | SILYDGSNRYYADSVKG | 5 | ARVSYYYDSVELRWAEYFQH | 6 |
| 26452 | YTFTSYYMH | 7 | VINPSGGSTSYAQKFQG | 8 | ARDHSDYWSGILDV | 9 |
| 29487 | YTFEKYYMH | 10 | VIGPSGASTSYAQKFQG | 11 | ARDHSDYWSGILHS | 12 |
| 29489 | YTFTSYYMH | 13 | VIGPSGASTSYAQKFQG | 14 | ARDHSDYWSGIMEV | 15 |
| 31282 | YTFTSYYMH | 16 | VIGPSGASTSYAQKFQG | 17 | ARDHSDYWSGIMEV | 18 |
| 26486 | YSISSGYYWA | 19 | SIYHSGSTYYNPSLKS | 20 | AIEGANYYDFGYVAFDI | 21 |
| 29494 | GSISSGSYYLA | 22 | SIFRSGSTYYNPSLES | 23 | AIEGANFKDFGYVAFDI | 24 |
| 29499 | GSISSSRYYWA | 25 | SIGTSGSTYYNPSLKS | 26 | AIEGANFRDFGYVAFDI | 27 |
| 26521 | GTFSSYAIS | 28 | GIIPIFGTANYAQKFQG | 29 | ARLHLGSSAYYGMDV | 30 |
| 29513 | GTFQNYAIS | 31 | VIVPIFGTANYAQKFQG | 32 | ARLHLGQKAYYGMDV | 33 |
| 26493 | FTFGDYAMH | 34 | GITWNSGSIGYADSVKG | 35 | AKPVPKSRGLDV | 36 |
| 29520 | FTFRDYAMH | 37 | GITWNSGLIGYADSVKG | 38 | AKPVPRLRGLDV | 39 |
| 29523 | FTFGSYYMH | 40 | VIWPDGSNKLYADSVKG | 41 | AKPVPKSRALDV | 42 |
| 29527 | FTFSSSYMH | 43 | VIGADGSNKYYADSVEG | 44 | AKPVPRRRGLDV | 45 |
| 31288 | GSISSGSYYLA | 271 | SIFRSGSTYYNPSLES | 272 | AIEGANFKDFGYVAFDI | 273 |
| 32919 | GSISSGSYYLA | 274 | SIFRSGSTYYNPSLES | 275 | AIEGANFKDFGYVAFDI | 276 |
| 32931 | GSISSGSYYLA | 277 | SIFRSGSTYYNPSLES | 278 | AIEGANFKDFGYVAFDI | 279 |
| 26432 | GTFSSYAIS | 280 | GIIPIFGTANYAQKFQG | 281 | AREAQSYRVPFDI | 282 |
| 32959 | GTFSSYLIS | 353 | GIYPIFATANYAQKFQG | 354 | AREAQSYRVPFDI | 355 |

FIG. 2 – VL CDR sequences

| Antibody | VL CDR1 | SEQ ID NO: | VL CDR2 | SEQ ID NO: | VL CDR3 | SEQ ID NO: |
|---|---|---|---|---|---|---|
| 26518 | RASQSVSSYLA | 46 | DASKRAT | 47 | QQVHNFPLT | 48 |
| 29478 | RASQSVSSYLA | 49 | DASKRAT | 50 | QQVHNFPLT | 51 |
| 26452 | RASQSVRSSYLA | 52 | GASSRAT | 53 | QQYFSPPWT | 54 |
| 29487 | RASQSVRSSYLA | 55 | GASSRAT | 56 | QQYFSPPWT | 57 |
| 29489 | RASQSVRSSYLA | 58 | GASSRAT | 59 | QQYFSPPWT | 60 |
| 31282 | RASQSVRSSYLA | 61 | GASSRAT | 62 | QQYFSPPWT | 63 |
| 26486 | RASQSVSSNLA | 64 | GASTRAT | 65 | QQSPPWPRT | 66 |
| 29494 | RASQSVSSNLA | 67 | GASTRAT | 68 | QQSPPWPRT | 69 |
| 29499 | RASQSVSSNLA | 70 | AASSLQS | 71 | QQRYVFPPT | 72 |
| 26521 | RASQSISSYLN | 73 | AASSLQS | 74 | QQRYVFPPT | 75 |
| 29513 | RASQSISSYLN | 76 | GASSLQS | 77 | QQAFYLPWT | 78 |
| 26493 | RASQGISSWLA | 79 | GASSLQS | 80 | QQAFYLPWT | 81 |
| 29520 | RASQGISSWLA | 82 | GASSLQS | 83 | QQAFYLPWT | 84 |
| 29523 | RASQGISSWLA | 85 | GASSLQS | 86 | QQAFYLPWT | 87 |
| 29527 | RASQGISSWLA | 88 | GASTRAT | 89 | QQSPPWPRT | 90 |
| 31288 | RASQSVSSNLA | 283 | GASTRAT | 284 | QQSPPWPRT | 285 |
| 32919 | RASQSVSSYLA | 286 | DASNRAT | 287 | QQENPRPRT | 288 |
| 32931 | RASKSVSSNLA | 289 | FASTRAT | 290 | QQTSPWPRT | 291 |
| 26432 | RASQSVSSNLA | 292 | GASTRAT | 293 | QQYAIWPPFT | 294 |
| 32959 | RASQSVSSNLA | 356 | GASTRAT | 357 | QQYAIWPPFT | 358 |

FIG. 3 — VH FR sequences

| Antibody | VH FR1 | SEQ ID NO: | VH FR2 | SEQ ID NO: | VH FR3 | SEQ ID NO: | VH FR4 | SEQ ID NO: |
|---|---|---|---|---|---|---|---|---|
| 26518 | EVQLVESGGGLVQPGGSLRLSCAASG | 91 | WVRQAPGKGLEWVA | 92 | RFTISRDNAKNSLYLQMNSLRAEDTAVYYC | 93 | WGQGTLVTVSS | 94 |
| 29478 | EVQLVESGGGVVQPGRSLRLSCAASG | 95 | WVRQAPGKGLEWVA | 96 | RFTVSRDNSKNTLYLQMNSLRAEDTAVYYC | 97 | WGQGTLVTVSS | 98 |
| 26452 | QVQLVQSGAEVKKPGASVKVSCKASG | 99 | WVRQAPGQGLEWMG | 100 | RVTMTRDTSTSTVYMELSSLRSEDTAVYYC | 101 | WGQGTMVTVSS | 102 |
| 29487 | QVQLVQSGAEVKKPGASVKVSCKASG | 103 | WVRQAPGQGLEWMG | 104 | RVTMTRDTSTSTVYMELSSLRSEDTAVYYC | 105 | WGQGTMVTVSS | 106 |
| 29489 | QVQLVQSGAEVKKPGASVKVSCKASG | 107 | WVRQAPGQGLEWMG | 108 | RVTLTRDTSTSTVYMELSSLRSEDTAVYYC | 109 | WGQGTMVTVSS | 110 |
| 31282 | QVQLVQSGAEVKKPGASVKVSCKASG | 111 | WIRQPPGKGLEWIG | 112 | RVTLTRDTSTSTVYMELSSLRSEDTAVYYC | 113 | WGQGTMVTVSS | 114 |
| 26486 | QVQLQESGPGLVKPSETLSLTCAVSG | 115 | WIRQPPGKGLEWIG | 116 | RVTISVDTSKNQFSLKLSSVTAADTAVYYC | 117 | WGQGTMVTVSS | 118 |
| 29494 | QVQLQESGPGLVKPSETLSLTCTVSG | 119 | WIRQPPGKGLEWIG | 120 | RVTISVDTSKNQFSLKLSSVTAADTAVYYC | 121 | WGQGTMVTVSS | 122 |
| 29499 | QLQLQESGPGLVKPSETLSLTCTVSG | 123 | WVRQAPGQGLEWIG | 124 | RVTISVDTSKNQFSLKLSSVTATDTAVYYC | 125 | WGQGTMVTVSS | 126 |
| 26521 | QVQLVQSGAEVKKPGSSVKVSCKASG | 127 | WVRQAPGQGLEWMG | 128 | RVTITADESTSTAYMELSSLRSEDTAVYYC | 129 | WGQGTTVTVSS | 130 |
| 29513 | QVQLVQSGAEVKKPGSSVKVSCKASG | 131 | WVRQAPGQGLEWMG | 132 | RVTVTADESTSTAYMELSSLRSEDTAVYYC | 133 | WGQGTTVTVSS | 134 |
| 26493 | EVQLVESGGGLVQPGRSLRLSCAASG | 135 | WVRQAPGKGLEWVS | 136 | RFTISRDNAKNSLYLQMNSLRAEDTALYYC | 137 | WGQGTMVTVSS | 138 |
| 29520 | EVQLVESGGGLVQPGRSLRLSCAASG | 139 | WVRQAPGKGLEWVS | 140 | RFTISRDNAKNSLYLQMNSLRAEDTALYYC | 141 | WGQGTMVTVSS | 142 |
| 29523 | EVQLVESGGGVVQPGRSLRLSCAASG | 143 | WVRQAPGKGLEWVA | 144 | RFTISRDNSKNTLYLQMNSLRAEDTALYYC | 145 | WGQGTMVTVSS | 146 |
| 29527 | QVQLVESGGGVVQPGRSLRLSCAASG | 147 | WVRQAPGKGLEWVA | 148 | RFTISRDNSKNTLYLQMNSLRAEDTALYYC | 149 | WGQGTMVTVSS | 150 |
| 31288 | QLQLQESGPGLVKPSETLSLTCTVSG | 295 | WIRQPPGKGLEWIG | 296 | RVTISVDTSKNQFSLKLSSVTAADTAVYYC | 297 | WGQGTTVTVSS | 298 |
| 32919 | QLQLQESGPGLVKPSETLSLTCTVSG | 299 | WIRQPPGKGLEWIG | 300 | RVTISVDTSKNQFSLKLSSVTAADTAVYYC | 301 | WGQGTTVTVSS | 302 |

FIG. 3 (Cont.)

| | | | | | | | |
|---|---|---|---|---|---|---|---|
| 32931 | QLQLQESGPGLVKPSETLSLTCTVSG | 303 | WIRQPPGKGLEWIG | 304 | RVTISVDTSKNQFSLKLSSVTAADTAVYYC | 305 | WGQGTTVTVSS | 306 |
| 26432 | QVQLVQSGAEVKKPGSSVKVSCKASG | 307 | WVRQAPGQGLEWMG | 308 | RVTITADESTSTAYMELSSLRSEDTAVYYC | 309 | WGQGTMVTVSS | 310 |
| 32959 | QVQLVQSGAEVKKPGSSVKVSCKASG | 359 | WVRQAPGQGLEWMG | 360 | RVTITADESTSTAYMELSSLRSEDTAVYYC | 361 | WGQGTMVTVSS | 362 |

FIG. 4 — VL FR sequences

| Antibody | VL FR1 | SEQ ID NO: | VL FR2 | SEQ ID NO: | VL FR3 | SEQ ID NO: | VL FR4 | SEQ ID NO: |
|---|---|---|---|---|---|---|---|---|
| 26518 | EIVLTQSPATLSLSPGE RATLSC | 151 | WYQQKPGQAPRLLIY | 152 | GIPARFSGSGSGTDFTLTISS LEPEDFAVYYC | 153 | FGGGTK VEIK | 154 |
| 29478 | EIVLTQSPATLSLSPGE RATLSC | 155 | WYQQKPGQAPRLLIY | 156 | GIPARFSGSGSGTDFTLTISS LEPEDFAVYYC | 157 | FGGGTK VEIK | 158 |
| 26452 | EIVLTQSPGTLSLSPGE RATLSC | 159 | WYQQKPGQAPRLLIY | 160 | GIPDRFSGSGSGTDFTLTISR LEPEDFAVYYC | 161 | FGGGTK VEIK | 162 |
| 29487 | EIVLTQSPGTLSLSPGE RATLSC | 163 | WYQQKPGQAPRLLIY | 164 | GIPDRFSGSGSGTDFTLTISR LEPEDFAVYYC | 165 | FGGGTK VEIK | 166 |
| 29489 | EIVLTQSPGTLSLSPGE RATLSC | 167 | WYQQKPGQAPRLLIY | 168 | GIPDRFSGSGSGTDFTLTISR LEPEDFAVYYC | 169 | FGGGTK VEIK | 170 |
| 31282 | EIVLTQSPGTLSLSPGE RATLSC | 171 | WYQQKPGQAPRLLIY | 172 | GIPDRFSGSGSGTDFTLTISR LEPEDFAVYYC | 173 | FGGGTK VEIK | 174 |
| 26486 | EIVMTQSPATLSVSPG ERATLSC | 175 | WYQQKPGQAPRLLIY | 176 | GIPARFSGSGSGTEFTLTISS LQSEDFAVYYC | 177 | FGGGTK VEIK | 178 |
| 29494 | EIVMTQSPATLSVSPG ERATLSC | 179 | WYQQKPGQAPRLLIY | 180 | GIPARFSGSGSGTEFTLTISS LQSEDFAVYYC | 181 | FGGGTK VEIK | 182 |
| 29499 | EIVMTQSPATLSVSPG ERATLSC | 183 | WYQQKPGQAPRLLIY | 184 | GIPARFSGSGSGTEFTLTISS LQSEDFAVYYC | 185 | FGGGTK VEIK | 186 |
| 26521 | DIQMTQSPSSLSASVG DRVTITC | 187 | WYQQKPGKAPKLLIY | 188 | GVPSRFSGSGSGTDFTLTISS LQPEDFATYYC | 189 | FGGGTK VEIK | 190 |
| 29513 | DIQMTQSPSSLSASVG DRVTITC | 191 | WYQQKPGKAPKLLIY | 192 | GVPSRFSGSGSGTDFTLTISS LQPEDFATYYC | 193 | FGGGTK VEIK | 194 |
| 26493 | DIQLTQSPSSVSASVG DRVTITC | 195 | WYQQKPGKAPKLLIY | 196 | GVPSRFSGSGSGTDFTLTISS LQPEDFATYYC | 197 | FGGGTK VEIK | 198 |
| 29520 | DIQLTQSPSSVSASVG DRVTITC | 199 | WYQQKPGKAPKLLIY | 200 | GVPSRFSGSGSGTDFTLTISS LQPEDFATYYC | 201 | FGGGTK VEIK | 202 |
| 29523 | DIQLTQSPSSVSASVG DRVTITC | 203 | WYQQKPGKAPKLLIY | 204 | GVPSRFSGSGSGTDFTLTISS LQPEDFATYYC | 205 | FGGGTK VEIK | 206 |
| 29527 | DIQLTQSPSSVSASVG DRVTITC | 207 | WYQQKPGKAPKLLIY | 208 | GVPSRFSGSGSGTDFTLTISS LQPEDFATYYC | 209 | FGGGTK VEIK | 210 |
| 31288 | EIVMTQSPATLSLSPGE RATLSC | 311 | WYQQKPGQAPRLLIY | 312 | GIPARFSGSGSGTEFDAVYYC LQSEDFAVYYC | 313 | FGGGTK VEIK | 314 |
| 32919 | EIVLTQSPATLSLSPGE RATLSC | 315 | WYQQKPGQAPRLLIY | 316 | GIPARFSGSGSGTDFTLTISS LEPEDFAVYYC | 317 | FGGGTK VEIK | 318 |

FIG. 4 (Cont.)

| | | | | | | | |
|---|---|---|---|---|---|---|---|
| 32931 | EIVMTQSPATLSVSPG ERATLSC | 319 | WYQQKPGQAPRLLIY | 320 | GIPARFSGSGSGTEFTLTISS LQSEDFAVYYC | 321 | FGGGTK VEIK | 322 |
| 26432 | EIVMTQSPATLSVSPG ERATLSC | 323 | WYQQKPGQAPRLLIY | 324 | GIPARFSGSGSGTEFTLTISS LQSEDFAVYYC | 325 | FGGGTK VEIK | 326 |
| 32959 | EIVMTQSPATLSVSPG ERATLSC | 363 | WYQQKPGQAPRLLIY | 364 | GIPARFSGSGSGTEFTLTISS LQSEDFAVYYC | 365 | FGGGTK VEIK | 366 |

FIG. 5 — variable domain protein sequences

| Antibody | VH protein | SEQ ID NO: | VL protein | SEQ ID NO: |
|---|---|---|---|---|
| 26518 | EVQLVESGGGLVQPGGSLRLSCAASGFTFSSYGMSWVRQAPGKGLEWVANIKQDGSEKYYVDSVKGRFTISRDNAKNSLYLQMNSLRAEDTAVYYCARVSYYYDSSKLRWAEYFQHWGQGTLVTVSS | 211 | EIVLTQSPATLSLSPGERATLSCRASQSVSSYLAWYQQKPGQAPRLLIYDASKRATGIPARFSGSGSGTDFTLTISSLEPEDFAVYYCQQVHNFPLTFGGGTKVEIK | 212 |
| 29478 | EVQLVESGGGVVQPGRSLRLSCAASGFTFESYGMVWVRQAPGKGLEWVASILYDGSNRYYADSVKGRFTVSRDNSKNTLYLQMNSLRAEDTAVYYCARVSYYYDSVELRWAEYFQHWGQGTLVTVSS | 213 | EIVLTQSPATLSLSPGERATLSCRASQSVSSYLAWYQQKPGQAPRLLIYDASKRATGIPARFSGSGSGTDFTLTISSLEPEDFAVYYCQQVHNFPLTFGGGTKVEIK | 214 |
| 26452 | QVQLVQSGAEVKKPGASVKVSCKASGYTFTSYYMHWVRQAPGQGLEWMGVINPSGGSTSYAQKFQGRVTMTRDTSTSTVYMELSSLRSEDTAVYYCARDHSDYWSGILDVWGQGTMVTVSS | 215 | EIVLTQSPGTLSLSPGERATLSCRASQSVRSSYLAWYQQKPGQAPRLLIYGASSRATGIPDRFSGSGSGTDFTLTISRLEPEDFAVYYCQQYFSPPWTFGGGTKVEIK | 216 |
| 29487 | QVQLVQSGAEVKKPGASVKVSCKASGYTFEKYYMHWVRQAPGQGLEWMGVIGPSGASTSYAQKFQGRVTMTRDTSTSTVYMELSSLRSEDTAVYYCARDHSDYWSGILHSWGQGTMVTVSS | 217 | EIVLTQSPGTLSLSPGERATLSCRASQSVRSSYLAWYQQKPGQAPRLLIYGASSRATGIPDRFSGSGSGTDFTLTISRLEPEDFAVYYCQQYFSPPWTFGGGTKVEIK | 218 |
| 29489 | QVQLVQSGAEVKKPGASVKVSCKASGYTFTSYYMHWVRQAPGQGLEWMGVIGPSGASTSYAQKFQGRVTLTRDTSTSTVYMELSSLRSEDTAVYYCARDHSDYWSGIMEVWGQGTMVTVSS | 219 | EIVLTQSPGTLSLSPGERATLSCRASQSVRSSYLAWYQQKPGQAPRLLIYGASSRATGIPDRFSGSGSGTDFTLTISRLEPEDFAVYYCQQYFSPPWTFGGGTKVEIK | 220 |
| 31282 | QVQLVQSGAEVKKPGASVKVSCKASGYTFTSYYMHWVRQAPGQGLEWMGVIGPSGASTSYAQKFQGRVTLTRDTSTSTVYMELSSLRSEDTAVYYCARDHSDYWSGIMEVWGQGTTVTVSS | 221 | EIVLTQSPGTLSLSPGERATLSCRASQSVRSSYLAWYQQKPGQAPRLLIYGASSRATGIPDRFSGSGSGTDFTLTISRLEPEDFAVYYCQQYFSPPWTFGGGTKVEIK | 222 |
| 26486 | QVQLQESGPGLVKPSETLSLTCAVSGYSISSGYYWAWIRQPPGKGLEWIGSIYHSGSTYYNPSLKSRVTISVDTSKNQFSLKLSSVTAADTAVYYCAIEGANYYDFGYVAFDIWGQGTMVTVSS | 223 | EIVMTQSPATLSVSPGERATLSCRASQSVSSNLAWYQQKPGQAPRLLIYGASTRATGIPARFSGSGSGTEFTLTISSLQSEDFAVYYCQQSPPWPRTFGGGTKVEIK | 224 |
| 29494 | QVQLQESGPGLVKPSETLSLTCTVSGGSISSGSSYYLAWIRQPPGKGLEWIGSIFRSGSTYYNPSLESRVTISVDTSKNQFSLKLSSVTAADTAVYYCAIEGANFKDFGYVAFDIWGQGTMVTVSS | 225 | EIVMTQSPATLSVSPGERATLSCRASQSVSSNLAWYQQKPGQAPRLLIYGASTRATGIPARFSGSGSGTEFTLTISSLQSEDFAVYYCQQSPPWPRTFGGGTKVEIK | 226 |

FIG. 5 (Cont.)

| ID | Seq# (H) | Heavy Chain | Seq# (L) | Light Chain |
|---|---|---|---|---|
| 29499 | 227 | QLQLQESGPGLVKPSETLSLTCTVSGGSISSSRYYWAWIRQPPGKGLEWIGSIGTSGSTYYNPSLKSRVTISVDTSKNQFSLKLSSVTATDTAVYYCAIEGANFRDFGYVAFDIWGQGTMVTVSS | 228 | EIVMTQSPATLSVSPGERATLSCRASQSVSSNLAWYQQKPGQAPRLLIYGASTRATGIPARFSGSGSGTEFTLTISSLQSEDFAVYYCQQSPPWPRTFGGGTKVEIK |
| 26521 | 229 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARLHLGSSAAYYGMDVWGQGTTVTVSS | 230 | DIQMTQSPSSLSASVGDRVTITCRASQSISSYLNWYQQKPGKAPKLLIYAASSLQSGVPSRFSGSGSGTDFTLTISSLQPEDFATYYCQQRYVFPPTFGGGTKVEIK |
| 29513 | 231 | QVQLVQSGAEVKKPGSSVKVSCKASGGTFQNYAISWVRQAPGQGLEWMGVIVPIFGTANYAQKFQGRVTVTADESTSTAYMELSSLRSEDTAVYYCARLHLGQKAYYGMDVWGQGTTVTVSS | 232 | DIQMTQSPSSLSASVGDRVTITCRASQSISSYLNWYQQKPGKAPKLLIYAASSLQSGVPSRFSGSGSGTDFTLTISSLQPEDFATYYCQQRYVFPPTFGGGTKVEIK |
| 26493 | 233 | EVQLVESGGGLVQPGRSLRLSCAASGFTFGDYAMHWVRQAPGKGLEWVSGITWNSGIGYADSVKGRFTISRDNAKNSLYLQMNSLRAEDTALYYCAKPVPKSRGLDVWGQGTMVTVSS | 234 | DIQLTQSPSVSASVGDRVTITCRASQGISSWLAWYQQKPGKAPKLLIYGASSLQSGVPSRFSGSGSGTDFTLTISSLQPEDFATYYCQQAFYLPWTFGGGTKVEIK |
| 29520 | 235 | QVQLVESGGGLVQPGRSLRLSCAASGFTFRDYAMHWVRQAPGKGLEWVSGITWNSGLIGYADSVKGRFTISRDNAKNSLYLQMNSLRAEDTALYYCAKPVPRLRGLDVWGQGTMVTVSS | 236 | DIQLTQSPSVSASVGDRVTITCRASQGISSWLAWYQQKPGKAPKLLIYGASSLQSGVPSRFSGSGSGTDFTLTISSLQPEDFATYYCQQAFYLPWTFGGGTKVEIK |
| 29523 | 237 | EVQLVESGGGLVQPGRSLRLSCAASGFTFGSYYMHWVRQAPGKGLEWVAVIWPDGSNKLYADSVKGRFTISRDNSKNTLYLQMNSLRAEDTALYYCAKPVPKSRALDVWGQGTMVTVSS | 238 | DIQLTQSPSVSASVGDRVTITCRASQGISSWLAWYQQKPGKAPKLLIYGASSLQSGVPSRFSGSGSGTDFTLTISSLQPEDFATYYCQQAFYLPWTFGGGTKVEIK |
| 29527 | 239 | QVQLVESGGGVVQPGRSLRLSCAASGFTFSSSYMHWVRQAPGKGLEWVAVIGADGSNKYYADSVEGRFTISRDNSKNTLYLQMNSLRAEDTALYYCAKPVPRRRGLDVWGQGTMVTVSS | 240 | DIQLTQSPSVSASVGDRVTITCRASQGISSWLAWYQQKPGKAPKLLIYGASSLQSGVPSRFSGSGSGTDFTLTISSLQPEDFATYYCQQAFYLPWTFGGGTKVEIK |
| 31288 | 327 | QLQLQESGPGLVKPSETLSLTCTVSGGSISSGSYYLAWIRQPPGKGLEWIGSIFRSGSTYYNPSLESRVTISVDTSKNQFSLKLSSVTAADTAVYYCAIEGANFKDFGYVAFDIWGQGTTVTVSS | 328 | EIVMTQSPATLSVSPGERATLSCRASQSVSSNLAWYQQKPGQAPRLLIYGASTRATGIPARFSGSGSGTEFTLTISSLQSPPWPRTFGGGTKVEIK |
| 32919 | 329 | QLQLQESGPGLVKPSETLSLTCTVSGGSISSGSYYLAWIRQPPGKGLEWIGSIFRSGSTYYNPSLESRVTISVDTSKNQFSLKLSSVTAADTAVYYCAIEGANFKDFGYVAFDIWGQGTTVTVSS | 330 | EIVLTQSPATLSLSPGERATLSCRASQSVSSYLAWYQQKPGQAPRLLIYDASNRATGIPARFSGSGSGTDFTLTISSLEPEDFAVYYCQQENPRPRTFGGGTKVEIK |
| 32931 | 331 | QLQLQESGPGLVKPSETLSLTCTVSGGSISSGSYYLAWIRQPPGKGLEWIGSIFRSGSTYYNPSLESRVTISVDTSKNQFSLKLSSVTAADTAVYYCAIEGANFKDFGYVAFDIWGQGTTVTVSS | 332 | EIVMTQSPATLSVSPGERATLSCRASKSVSSNLAWYQQKPGQAPRLLIYFASTRATGIPARFSGSGSGTEFTLTISSLQSEDFAVYYCQQTSPWPRTFGGGTKVEIK |

FIG. 5 (Cont.)

| | | | | |
|---|---|---|---|---|
| 26432 | QVQLVQSGAEVKKPGSSVKVSCKASGGTFSSYAISWVRQAPGQ GLEWMGGIIPIFGTANYAQKFQGRVTITADESTSTAYMELSSLRS EDTAVYYCAREAQSYRVPFDIWGQGTMVTVSS | 333 | EIVMTQSPATLSVSPGERATLSCRASQSVSSNLAWYQQKPGQA PRLLIYGASTRATGIPARFSGSGSGTEFLTISSLQSEDFAVYYCQ QYAIWPPFTFGGGTKVEIK | 334 |
| 32959 | QVQLVQSGAEVKKPGSSVKVSCKASGGTFSSYLISWVRQAPGQG LEWMGGIYPIFATANYAQKFQGRVTITADESTSTAYMELSSLRSE DTAVYYCAREAQSYRVPFDIWGQGTMVTVSS | 367 | EIVMTQSPATLSVSPGERATLSCRASQSVSSNLAWYQQKPGQA PRLLIYGASTRATGIPARFSGSGSGTEFLTISSLQSEDFAVYYCQ QYAIWPPFTFGGGTKVEIK | 368 |

FIG. 6 – variable domain DNA sequences

| Antibody | VH DNA | SEQ ID NO: | VL DNA | SEQ ID NO: |
|---|---|---|---|---|
| 26518 | GAGGTGCAGCTGGTGGAGTCTGGGGGAGGCTTGGTCCAGC CTGGGGGGTCCCTGAGACTCTCCTGTGCAGCCTCTGGATTC ACCTTTAGTAGCTATGAGATGAGCTGGGTCCGCCAGGCTCCA GGGAAGGGGCTGGAGTGGGTGGCCAACATAAAGCAAGATGG AAGTGAGAAATACTATGTGGACTCTGTGAAGGGCCGATTCAC CATCTCCAGAGACAACGCCAAGAACTCACTGTATCTGCAAAT GAACAGCCTGAGAGCCGAGGACACGGCGGTGTATACTGCG CTAGAGTATCTTACTACTACGACAGCAGCAAACTACGATGGG CAGAATACTTCCAACACTGGGGACCAGGGTACATTGGTCACCG TCTCCTCA | 241 | GAAATTGTGTTGACACAGTCTCCAGCCACCCTGTCTTTGTC TCCAGGGGAAAGAGCCACCCTCTCCTGCAGGGCCAGTCAG AGTGTTAGCAGCTACTTAGCCTGGTACCAACAGAAACCTGG CCAGGCTCCCAGGCTCCTCATCTATGATGCATCCAAAAGGG CCACTGGCATCCCAGCCAGGTTCAGTGGCAGTGGGTCTGG GACAGACTTCACTCTCACCATCAGCAGCCTAGAGCCTGAAG ATTTTGCAGTTTATTACTGTCAGCAGGTCCACAATTTCCCTC TCACTTTTGGCGGAGGGACCAAGGTTGAGATCAAA | 242 |
| 29478 | GAAGTCCAGCTGGTGGAATCTGGGGGAGGCGTGGTCCAGCC TGGGGAGGTCCCTGAGACTCTCCTGTGCAGCGTCTGGATTCAC CTTCGAGAGCTATGGCATGGTTTGGGTCCGCCAGGCCCCAG GCAAGGGGCTGGAGTGGCTGGCAGTTATTGTATGATGGA AGTAATAGACTACTATGCAGACTCCGTGAAGGGCCGATTCACC GTCTCCAGAGACAATTCCAAGAACACGCTGTATCTGCAAATG AACAGCCTGAGAGCCGAGGACACGGCGGTGTATACTGCGC TAGAGTATCTTACTACTACGACAGCAGCTACGATGGGC AGAATACTTCCAACACTGGGGACCAGGGTACATTGGTCACCGT CTCCTCA | 243 | GAAATTGTGTTGACACAGTCTCCAGCCACCCTGTCTTTGTC TCCAGGGGAAAGAGCCACCCTCTCCTGCAGGGCCAGTCAG AGTGTTAGCAGCTACTTAGCCTGGTACCAACAGAAACCTGG CCAGGCTCCCAGGCTCCTCATCTATGATGCATCCAAAAGGG CCACTGGCATCCCAGCCAGGTTCAGTGGCAGTGGGTCTGG GACAGACTTCACTCTCACCATCAGCAGCCTAGAGCCTGAAG ATTTTGCAGTTTATTACTGTCAGCAGGTCCACAATTTCCCTC TCACTTTTGGCGGAGGGACCAAGGTTGAGATCAAA | 244 |
| 26452 | CAGGTGCAGCTGGTGCAGTCTGGGGCTGAGGTGAAGAAGCC TGGGGCCTCAGTGAAGGTTTCCTGCAAGGCATCTGGATACAC CTTCACCAGCTACTATATGCACTGGGTGCGACAGGCCCTGG ACAAGGGCTTGAGTGGATGGGAGTCATCAACCCTAGTGTG GTAGCACAAGCTACGCACAGAAGTTCCAGGGCAGAGTCACC ATGACCAGGGACACGTCCACGAGCACAGTCTACATGGAGCT GAGCAGCCTGAGATCTGAGGACACGGCGGTGTACTACTGCG CCAGAACCACTCCGACTACTGGAGCGGGAATACTAGACGTAT GGGGTCAGGGTACAATGGTCACCGTCTCCTCA | 245 | GAAATTGTGTTGACGCAGTCTCCAGGCACCCTGTCTTTGTC TCCAGGGGAAAGAGCCACCCTCTCTGCAGGGCCAGTCAG AGTGTTAGGAGCTACTTAGCCTGGTACCAGCAGAAACC TGGCCAGGCTCCCAGGCTCCTCATCTATGGTGCATCCAGC AGGGCCACTGGCATCCCAGACAGGTTCAGTGGCAGTGGGT CTGGGACAGACTTCACTCTCACCATCAGCAGACTGGAGCCT GAAGATTTTGCAGTGTATTACTGTCAGCAGTACTTCAGTCCT CCTTGGACGTTTTGGCGGAGGGACCAAGGTTGAGATCAAA | 246 |
| 29487 | CAGGTGCAGCTGGTGCAGTCTGGGGCTGAGGTGAAGAAGCC TGGGGCCTCAGTGAAGGTTTCCTGCAAGGCATCTGGATACAC CTTCGAGAGTACTATATGCACTGGGATGGGATGGATCGGTCTAGTGGT GCTAGCAAGCTGGACACAGGGAAGTTCCAGGGCAGAGTCAC CATGACCAGGGACACGTCCACGAGCACAGTCTACATGGAGC TGAGCAGCCTGAGATCTGAGGACACGGCGGTGTACTACTGC GCCAGAGACCACTCCGACTACTGGAGCGGGAATACTAGACTACTACCG TGGGGTCAGGGGTACAATGGTCACCGTCTCCTCA | 247 | GAAATTGTGTTGACGCAGTCTCCAGGCACCCTGTCTTTGTC TCCAGGGGAAAGAGCCACCCTCTCCTGCAGGGCCAGTCAG AGTGTTAGGAGCTACTTAGCCTGGTACCAGCAGAAACC TGGCCAGGCTCCCAGGCTCCTCATCTATGGTGCATCCAGC AGGGCCACTGGCATCCCAGACAGGTTCAGTGGCAGTGGGT CTGGGACAGACTTCACTCTCACCATCAGCAGCAGACTGGAGCCT GAAGATTTTGCAGTGTATTACTGTCAGCAGTACTTCAGTCCT CCTTGGACGTTTTGGCGGAGGGACCAAGGTTGAGATCAAA | 248 |

FIG. 6 (Cont.)

| Antibody | VH DNA | SEQ ID NO: | VL DNA | SEQ ID NO: |
|---|---|---|---|---|
| 29489 | CAGGTGCAGCTGGTGGTGCAGTCTGGGGGCTGAGGTGAAGAAGCC TGGGGCCTCAGTGAAGGTTTCCTGCAAGGCATCTGGATACAC CTTCACTAGCTACTATATGCACTGGGTGCGACAGGCCCCTGG ACAAGGGCTTGAGTGGATGGGAGTGATCGGTCCTAGTGGTG CTAGCACAAGCTACGCACAGAAGTTCCAGGGCAGAGTCACCT TGACCAGGGACACGTCCACGAGCACAGTCTACATGGAGCTG AGCAGCCTGAGATCTGAGGACACGGCGGTGTACTACTGCGC CAGAGACCACTCCGACTACTGGAGCGGAATAATGGAGGTAT GGGGTCAGGGTACAATGGTCACCGTCTCCTCA | 249 | GAAATTGTGTTGACGCAGTCTCCAGGCACCCTGTCTTTGTC TCCAGGGGAAAGAGCCAGCCACCCTCTCCTGCAGGGCCAGTCAG AGTGTTAGGAGCAGCTACTTAGCCTGGTACCAGCAGAAACC TGGCCAGGCTCCCAGGCTCCTCATCTATGGTGCATCCAGC AGGGCCACTGGCATCCCAGACAGGTTCAGTGGCAGTGGGT CTGGGACAGACTTCACTCTCACCATCAGCAGACTGGAGCCT GAAGATTTTGCAGTGTATTACTGTCAGCAGTACTTCAGTCGT CCTTGGACTTTTGGCGGAGGGACCAAGGTTGAGATCAAA | 250 |
| 31282 | CAGGTGCAGCTGGTGCAGTCTGGGGGCTGAGGTGAAGAAGCC TGGGGCCTCAGTGAAGGTTTCCTGCAAGGCATCTGGATACAC CTTCACTAGCTACTATATGCACTGGGTGCGACAGGCCCCTGG ACAAGGGCTTGAGTGGATGGGAGTGATCGGTCCTAGTGGTG CTAGCACAAGCTACGCACAGAAGTTCCAGGGCAGAGTCACCT TGACCAGGGACACGTCCACGAGCACAGTCTACATGGAGCTG AGCAGCCTGAGATCTGAGGACACGGCGGTGTACTACTGCGC CAGAGACCACTCCGACTACTGGAGCGGAATAATGGAGGTAT GGGGTCAGGGTACAATGGTCACCGTCTCCTCA | 251 | GAAATTGTGTTGACGCAGTCTCCAGGCACCCTGTCTTTGTC TCCAGGGGAAAGAGCCAGCCACCCTCTCCTGCAGGGCCAGTCAG AGTGTTAGGAGCAGCTACTTAGCCTGGTACCAGCAGAAACC TGGCCAGGCTCCCAGGCTCCTCATCTATGGTGCATCCAGC AGGGCCACTGGCATCCCAGACAGGTTCAGTGGCAGTGGGT CTGGGACAGACTTCACTCTCACCATCAGCAGACTGGAGCCT GAAGATTTTGCAGTGTATTACTGTCAGCAGTACTTCAGTCGT CCTTGGACTTTTGGCGGAGGGACCAAGGTTGAGATCAAA | 252 |
| 26486 | CAGGTGCAGCTGCAGGAGTCGGGCCCAGGACTGGTGAAGC CTTCGGAGACCCTGTCCCTCACCTGCGCTGTCTCTGGTTACT CCATCAGCAGTAGCAGTTACTACTTGGCGTGGATCCGGCAGC CCCAGGGAAGGGCCTGGAGTGGATTGGGAGTATCTATCATAG TGGGAGCACCTACTACAACCCGTCCCTCAAGAACCAGTCAC CATATCAGTAGACACGTCCAAGAACCAGTTCTCCCTGAAGCT GAGTTCTGTGACCGCTGCGGACACGGCGGTGTACTACTGCG CCATAGAAGGAGCTAACTACTACGACTTCGATATGTAGCAT TCGACATATGGGGGTCAGGGTACAACCGTCACCGTCTCCTCA | 253 | GAAATAGTGATGACGCAGTCTCCAGCCACCCTGTCTGTGTC TCCAGGGGAAAGAGCCAGCCACCCTCTCCTGCAGGGCCAGTCAG AGTGTTAGCAGCAACTTAGCCTGGTACCAGCAGAAACCTGG CCAGGCTCCCAGGCTCCTCATCTATGGTGCATCCACCAGG GCCACTGGTATCCCAGCCAGGTTCAGTGGCAGTGGGTCTG GGACACAGAGTTCACTCTCACCATCAGCAGCCTGCAGTCTGAA GATTTTGCAGTTTATTACTGTCAGCAGTACAGTGGCC TAGGACTTTTGGCGGAGGGACCAAGGTTGAGATCAAA | 254 |
| 29494 | CAGGTGCAGCTGCAGGAGTCGGGCCCAGGACTGGTGAAGC CTTCGGAGACCCTGTCCCTCACTGCTGTCTCTGGTGGCT CCATCAGCAGTGGTAGTTACTACTGGGCCTGGATCCGGCCAG CCCCCAGGGAAGGGCCACTGGAGTGGATTGGGAGTATCTTTCG AGTGGGAGCACCACCTACAACCCGTCCCTCAAGAGTCACC TCACCATATCGGTAGACACGTCCAAGAACCAGTTCTCCCTGA AGCTGAGTTCTGTGACCGCTGCGGACACGGCGGTGTATAC TGCGCCATAGAAGGAGCTAACTTTAAGGACTTCGGTACTAC GCATTCGACATATGGGGTCAGGGTACAACCGTCACCGTCTCC TCA | 255 | GAAATAGTGATGACGCAGTCTCCAGCCACCCTGTCTGTGTC TCCAGGGGAAAGAGCCAGCCACCCTCTCCTGCAGGGCCAGTCAG AGTGTTAGCAGCAACTTAGCCTGGTACCAGCAGAAACCTGG CCAGGCTCCCAGGCTCCTCATCTATGGTGCATCCACCAGG GCCACTGGTATCCCAGCCAGGTTCAGTGGCAGTGGGTCTG GGACACAGAGTTCACTCTCACCATCAGCAGCCTGCAGTCTGAA GATTTTGCAGTTTATTACTGTCAGCAGTACAGTGGCC CTCCCCCCTGGCC TAGGACTTTTGGCGGAGGGACCAAGGTTGAGATCAAA | 256 |

FIG. 6 (Cont.)

| Antibody | VH DNA | SEQ ID NO: | VL DNA | SEQ ID NO: |
|---|---|---|---|---|
| 29499 | CAGGTGCAGCTGCAGGAGTCGGGCCCAGGACTGGTGAAGCC TTCGGAGACCCTGTCCCTCACCTGCACTGTCTCTGGTGGCTC CATCAGCAGTAGTAGTTACTGGGGCTGGATCCGCCAGC CCCCAGGGAAGGGGCTGGAGTGGATTGGGAGTATCGGGAC GAGTGGGAGCACCTACTACAACCCGTCCCTCAAGAGTCGAG TCACCATATCGGTAGACACGTCCAAGAACCAGTTCTCCCTGA AGCTGAGTTCTGTGACCGCCGCAGACACGGCGGTGTACTACT GCGCCATAGAAGGAGCTAACTTTCGGGACTTCGGATATGTAG CATTCGACATATGGGGTCAGGGTACAATGGTCACCGTCTCCT CA | 257 | GAAATAGTGATGACGCAGTCTCCAGCCACCCTGTCTGTGTC TCCAGGGGAAAGAGCCACCCTCTCTGCAGGCCAGTCAG AGTGTTAGCAGCAACTTAGCCTGGTACCAGCAGAAACCTGG CCAGGCTCCCAGGCTCCTCATCTATGGTGCATCCACCAGG GCCACTGGTATCCCAGCCAGGTTCAGTGCAGTGGGTCTG GGACAGAGTTCACTCTCACCATCAGCAGCCTGCAGTCTGAA GATTTTGCAGTTTATTATTGTGCAGCAGTCTCCCCCCCTGGCC TAGGACTTTTGGCCAGGGGACCAAGGTTGAGATCAAA | 258 |
| 26521 | CAGGTGCAGCTGGTGCAGTCTGGGGCTGAGGTGAAGAAGCC TGGGTCCTCGGTGAAGGTCTCCTGCAAGGCTTCTGGAGGCA CCTTCAGCAGCTATGCTATCAGCTGGGTGCGACAGGCCCCT GGACAAGGGCTTGAGTGGATGGGAGGGATCATCCCTATCTTT GGTACAGCAAACTACGCACAGAAGTTCCAGGGCAGAGTCAC GATTACGCGGACGAATCCACGAGCACAGCCTACATGGAGCT GAGCAGCCTGAGATCTGAGGACACGGCCGTGTACTACTGC GCTAGGTTGCACCTGGGACGAACAACTGTCACCGTCTCCTCA | 259 | GACATCCAGATGACCCAGTCTCCATCCTCCTGTCTGCATC TGTAGGAGACAGAGTCACCATCACTTGCCGGGCAAGTCAG AGCATTAGCAGCTATTTAAATTGGTATCAGCAGAAACCAGG AAAGCCCCCTAAGCTCCTGATCTATGCTGCATCCAGTTTGC AAAGTGGGGTCCCATCAAGGTTCAGTGGCAGTGGATCTGG GACAGATTTCACTCTCACCATCAGCAGTCTGCAACCTGAAG ATTTTGCAACTTACTACTGTCAGCAAAGATACGTCTTCCCTC CTACTTTTGGCCAGGGGACCAAGGTTGAGATCAAA | 260 |
| 29513 | CAGGTGCAGCTGGTGCAGTCTGGGGCTGAGGTGAAGAAGCC TGGGTCCTCGGTGAAGGTCTCCTGCAAGGCTTCTGGAGGCA CCTTCAGAACTATGCTATCAGCTGGGTGCGACAGGCCCCCTG GACAAGCTTGAGTGGATGGGAGTTATCGTGCCTACATCTTTG GTACAGCAAACTACGCACAGAAGTTCCAGGGCAGAGTCAC GTTACGCGGACGAATCACCAGCAGACCTACATGGAGCT GAGCAGCCTGAGATCTGAGGACACGGCCGTGTACTACTGCG CTAGGTTGCACCTGGGACGAACAACTGTCACCGTCCTCA | 261 | GACATCCAGATGACCCAGTCTCCATCCTCCTGTCTGCATC TGTAGGAGACAGAGTCACCATCACTTGCCGGGCAAGTCAG AGCATTAGCAGCTATTTAAATTGGTATCAGCAGAAACCAGG AAAGCCCCCTAAGCTCCTGATCTATGCTGCATCCAGTTTGC AAAGTGGGGTCCCATCAAGGTTCAGTGGCAGTGGATCTGG GACAGATTTCACTCTCACCATCAGCAGTCTGCAACCTGAAG ATTTTGCAACTTACTACTGTCAGCAAAGATACGTCTTCCCTC CTACTTTTGGCCAGGGGACCAAGGTTGAGATCAAA | 262 |
| 26493 | GAAGTGCAGCTGGTGGAGTCTGGGGGAGGCTTGGTACAGCC TGGCAGGTCCCTGAGACTCTCCTGTGCAGCCTCTGGATTCAC CTTTGTGATTATGCCATGGGTCCGGCAAGCTCCAGG GAAGGGGCTGGAGTGGGTCTCAGTTATTACTTGGAATAGTG GTACATAGGCTATGCGGACTCTGTGAAGGGCCGATTCACCA TCTCCAGAGACAACAGCCAAGAACTCCCTGTATCTGCAAATGA ACAGTCTGAGAGCTGAGGACACGGCCGTGTACTACTGCGCC AAGCCAGTGCCAAAATCTAGAGGCCTAGACGTATGGGGTCA GGGTACAATGGTCACCGTCTCCTCA | 263 | GACATCCAGTTGACCCAGTCTCCATCTTCCGTGTCTGCATC TGTAGGAGACAGAGTCACCATCACTTGTGGGGCGAGTCAG GGTATTAGCAGCTGGTTAGCCTGGTATCAGCAGAAACCAGG GAAAGCCCCTAAGCTCCTGATCTATGGTGCATCCAGTTTGC AAAGTGGGGTCCCATCAAGGTTCAGCGGCAGTGGATCTGG GACAGATTTCACTCTCACCATCAGCAGCCTGCAGCCTGAAG ATTTTGCAACTTATTACTGTCAGCAGGCATTCTACTCCCTT GGACTTTTTGGCCGGGGACCAAGGTTGAGATCAAA | 264 |

FIG. 6 (Cont.)

| Antibody | VH DNA | SEQ ID NO: | VL DNA | SEQ ID NO: |
|---|---|---|---|---|
| 29520 | CAGGTGCAGCTGGTGGAGTCTGGGGGAGGCTTGGTACAGCCTGGCAGGTCCCTGAGACTCTCCTGTGCAGCCTCTGGATTCACCTTCCGGGATTATGCCATGCACTGGGTCCGGCAAGCTCCAGGGAAGGGCCTGGAGTGGGTCTCAGTTATTACTTGGAATAGTGGTTTGATAGGCTATGCGGACTCTGTGAAGGGCCGATTCACCATCTCCAGAGACAACGCCAAGAACTCCCTGTATCTGCAAATGAACAGTCTGAGAGCTGAGGACACGGCGGTTGTATTACTGTGCGCAAGCCAGTGCCCACGTTTGAGAGCCTAGACGTATGGGGTCAGGGTACAATGGTCACCGTCTCCTCA | 265 | GACATCCAGTTGACCCAGTCTCCATCTTCCGTGTCTGCATCTGTAGGAGACAGAGTCACCATCACTTGTCGGGCGAGTCAGGGTATTAGCAGCTGGTTAGCCTGGTATCAGCAGAAACCAGGGAAAGCCCCTAAGCTCCTGATCTATGCTGCATCCAGTTTGCAAAGTGGGGTCCCATCAAGGTTCAGCGGCAGTGGATCTGGGACAGATTTCACTCTCACCATCAGCAGCCTGCAGCCTGAAGATTTTGCAACTTATTACTGTCAGCAGGCATTCTACCTCCCTTGGACTTTTGGCGGAGGGACCAAGGTTGAGATCAAA | 266 |
| 29523 | GAAGTCCAGCTGGTGGAATCTGGGGGAGGCGTGGTCCAGCCTGGGAGGTCCCTGAGACTCTCCTGTGCAGCGTCTGGATTCACCTTCGGGAGCTATTATGCACTGGGTCCGCCAGGCTCCAGGCAAGGGGCTGGAGTGGGTGGCAGACTCCGTGAAGGCCGATTCACCAGTAATAAACTGTATGCAGACTCCGTGAAGGGCCGATTCACCATCTCCAGAGACAATTCCAAGAACACGCTGTATCTGCAAATGAACAGCCTGAGAGCTGAGGACACGGCCGTTTATTACTGTGCGCAACAGCCAGTGCCAAAATCTAGCACGCTTGACGTATGGGGTCAGGGTACAATGGTCACCGTCTCCTCA | 267 | GACATCCAGTTGACCCAGTCTCCATCTTCCGTGTCTGCATCTGTAGGAGACAGAGTCACCATCACTTGTCGGGCGAGTCAGGGTATTAGCAGCTGGTTAGCCTGGTATCAGCAGAAACCAGGGAAAGCCCCTAAGCTCCTGATCTATGCGGCATCCAGTTTGCAAAGTGGGGTCCCATCAAGGTTCAGCGGCAGTGGATCTGGGACAGATTTCACTCTCACCATCAGCAGCCTGCAGCCTGAAGATTTTGCAACTTATTACTGTCAGCAGGCATTCTACCTCCCTTGGACTTTTGGCGGAGGGACCAAGGTTGAGATCAAA | 268 |
| 29527 | CAGGTGCAGCTGCAGGAGTCGGGCCCAGGACTGGTGAAGCCCTCGGAGACCCTGTCCCTCACCTGCACTGTCTCTGGTGGCTCCATCAGCAGTAGCAGTTACTACTGGGGCTGGATCCGCCAGCCCCCAGGGAAGGGGCTGGAGTGGATTGGGAGTATCTATTATAGTGGGAGCACCTACTACAACCCGTCCCTCAAGAGTCGAGTCACCATATCAGTAGACACGTCCAAGAACCAGTTCTCCCTGAAGCTGAGCTCTGTGACCGCCGCGGACACGGCCGTGTATTACTGTGCGAGAGTCGGTAGACACGGCCAGGACTGGGGCCAGGGGACCACGGTCACCGTCTCCTCA | 269 | GACATCCAGTTGACCCAGTCTCCATCTTCCGTGTCTGCATCTGTAGGAGACAGAGTCACCATCACTTGTCGGGCGAGTCAGGGTATTAGCAGCTGGTTAGCCTGGTATCAGCAGAAACCAGGGAAAGCCCCTAAGCTCCTGATCTATGGTGCATCCAGTTTGCAAAGTGGGGTCCCATCAAGGTTCAGCGGCAGTGGATCTGGGACAGATTTCACTCTCACCATCAACAGCCTGCAGCCTGAAGATTTTGCAACTTATTACTGTCAGCAGGCATTCTACCTCCCTTGGACTTTTGGCGGAGGGACCAAGGTTGAGATCAAA | 270 |
| 31288 | CAGCTGCAGCTGCAGGAGTCGGGCCCAGGACTGGTGAAGCCTTCGGAGACCCTGTCCCTCACCTGCACTGTCTCTGGTGGCTCCATCAGCAGTGGTGGTTACTACTGGAGCTGGATCCGCCAGCACCCAGGGAAGGGACTGGAGTGGATTGGGTATATCTATTACAGTGGGAGCACCAACTACAACCCGTCCCTCAAGAGTCGAGTCACCATATCAGTAGACACGTCTAAGAACCAGTTCTCCCTGAAGCTGAGCTCTGTGACCGCCGCGGACACGGCCGTGTATTACTGTGCGAGATAGGGATATGTAGCATTGGACATATGGGGCAGGGGACCACGGTCACCGTCTCCTCA | 335 | GAAATAGTGATGACGCAGTCTCCAGCCACCCTGTCTGTGTCTCCAGGGGAAAGAGCCACCCTCTCCTGCAGGGCCAGTCAGAGTGTTAGCAGCAACTTAGCCTGGTACCAGCAGAAACCTGGCCAGGCTCCCAGGCTCCTCATCTATGGTGCATCCACCAGGGCCACTGGTATCCCAGCCAGGTTCAGTGGCAGTGGGTCTGGGACAGAGTTCACTCTCACCATCAGCAGCCTGCAGTCTGAAGATTTTGCAGTTTATTACTGTCAGCAGTATAATAATTGGCCTCCCCCCGCCTAGGACTTTTGGCGGAGGGACCAAGGTTGAGATCAAA | 336 |

FIG. 6 (Cont.)

| Antibody | VH DNA | SEQ ID NO: | VL DNA | SEQ ID NO: |
|---|---|---|---|---|
| 32919 | CAGCTGCAGCTGCAGGAGTCGGGCCCAGGACTGGTGAAGCCT TCGGAGACCCTGTCCCTCACCTGCACTGTCTCTGGTGGCTCCA TCAGCAGTGGGAGTTACTACTTGGCGTGGATCCGCCAGCCC CAGGGAAGGGCTGGAGTGGATTGGGAGTATCTTTCGGAGTG GAGCACCTACTACAACCCGTCCCTCGAGAGTCGAGTCACCAT ATCGGTAGACACGTCCAAGAACCAGTTCTCCCTGAAGCTGAGT TCTGTGACCGCCGCAGACACGGCGGTGTACTACTGCGCCATA GAAGAGCTAACTTTAAGGACTTCGGATATGTAGCATTCGACAT ATGGGGTCAGGGTACAACTGTCACCGTCTCCTCA | 336 | GAAATTGTGTTGACACAGTCTCCAGCCACCCTGTCTTTGTCTC CAGGGGAAAGAGCCACCCTCTCCTGCAGGCCAGTCAGAGT GTTAGCAGTACTTAGCCTGGTACCAACAGAAACCTGGCCAG GCTCCCAGGCTCCTCATCTATGATGCATCCAACAGGGCCACT GGCATCTCCAGCAGGTTCAGTGGCAGTGGGTCTGGGACAGA CTTCACTCTCACCATCAGCAGCCTAGAGCCTGAAGATTTTGC AGTTTATTACTGTCAGCAGGAGAACCCCAGCCTAGGACTTT TGGCGGAGGGACCAAGGTTGAGATCAAA | 337 |
| 32931 | CAGCTGCAGCTGCAGGAGTCGGGCCCAGGACTGGTGAAGCCT TCGGAGACCCTGTCCCTCACTGTCTCTGGTGGCTCCA TCAGCAGTGGGAGTTACTACTTGGCGTGGATCCGCCAGCCC CAGGGAAGGGCTGGAGTGGATTGGGAGTATCTTTCGGAGTG GAGCACCTACTACAACCCGTCCCTCGAGAGTCGAGTCACCAT ATCGGTAGACACGTCCAAGAACCAGTTCTCCCTGAAGCTGAGT TCTGTGACCGCCGCAGACACGGCGGTGTACTACTGCGCCATA GAAGAGCTAACTTTAAGGACTTCGGATATGTAGCATTCGACAT ATGGGGTCAGGGTACAACTGTCACCGTCTCCTCA | 338 | GAAATAGTGATGACGCAGTCTCCAGCCACCCTGTCTGTCT CCAGGGGAAAGAGCCACCCTCTCCTGCAGGGCCAGTAAAAG TGTTCAGCAACTTAGCCTGGTACCAGCAGAAACCTGGCCA GGCTCCCAGGCTCCTCATCTATTCGCAGGCCAGTGGGACACC CGGTATCCCAGCCAGGTTCAGTGGCAGTGGGTCTGGGACAG AGTTCACTCTCACCATCAGCAGCCTGCAGTCTGAAGATTTTG CAGTTTATTACTGTCAGCAGAGTTCGCCCTGCTAGGACTT TTGGCGGAGGGACCAAGGTTGAGATCAAA | 339 |
| 26432 | CAGCTGCAGCTGCAGGAGTCTGGGCTGAGGTGAAGAAGCCT GGGTCCTCGGTGAAGGTCTCCTGCAAGGCTTCTGGAGGCACC TTCAGCAGTATGCTATCAGCTGGGTGCGACAGGCCCCTGGA CAAGGGCTTGAGTGGATGGGAAGTTCCAGGCAGAGTCACGATTAC CAGCAAACTACGCACAGACGAGAGCACAATCACAGCGATCAGCAGCAG CGCGGACGAATCCATCCTACAGGTTCAGAGTCACTACTGCGCCAGA CCTGAGATCTCAATCCTACTAGGGTTCCATTCGACATATGGGGTCAGGGT ACAATGGTCACCGTCTCCTCA | 340 | GAAATAGTGATGACGCAGTCTCCAGCCACCCTGTCTGTCT CCAGGGGAAAGAGCCACCCTCTCCTGCAGGCCAGTCAGAG TGTTAGCAGCAACTTAGCCTGGTACCAGCAGAAACCTGGCCA GGCTCCCAGGCTCCTCATCTATGGTGCATCCACCAGGGCCA CTGGTATCCCAGCCAGGTTCAGTGGCAGTGGGTCTGGGACA GAGTTCACTCTCACCATCAGCAGCCTGCAGTCTGAAGATTTT GCAGTTTATTACTGTCAGCAGTACGACCATCTGGCCTCCTTTCA CTTTTGGCGGAGGGACCAAGGTTGAGATCAAA | 341 |
| 32959 | CAGCTGCAGCTGCAGGAGTCTGGGCTGAGGTGAAGAAGCCT GGGTCCTCGGTGAAGGTCTCCTGCAAGGCTTCTGGAGGCACC TTCAGCAGTATGCTATCAGCTGGGTGCGACAGGCCCCTGGA CAAGGGCTTGAGTGGATGGGAAGTTCCAGGCAGAGTCACGATTAC CAGCAAACTACGCACAGACGAGAGCACAGGCGATCAGCAGCAG CGCGGACGAATCCATCCTACAGGTACACTACTGCGCCAGA GGCTCAATCCTACAGGTTCCATTCGACATATGGGGTCAGGGT ACAATGGTCACCGTCTCCTCA | 369 | GAAATAGTGATGACGCAGTCTCCAGCCACCCTGTCTGTCT CCAGGGGAAAGAGCCACCCTCTCCTGCAGGCCAGTCAGAG TGTTAGCAGCAACTTAGCCTGGTACCAGCAGAAACCTGGCCA GGCTCCCAGGCTCCTCATCTATGGTGCATCCACCAGGGCCA CTGGTATCCCAGCCAGGTTCAGTGGCAGTGGGTCTGGGACA GAGTTCACTCTCACCATCAGCAGCCTGCAGTCTGAAGATTTT GCAGTTTATTACTGTCAGCAGTACGACCATCTGGCCTCCTTTCA CTTTTGGCGGAGGGACCAAGGTTGAGATCAAA | 370 |

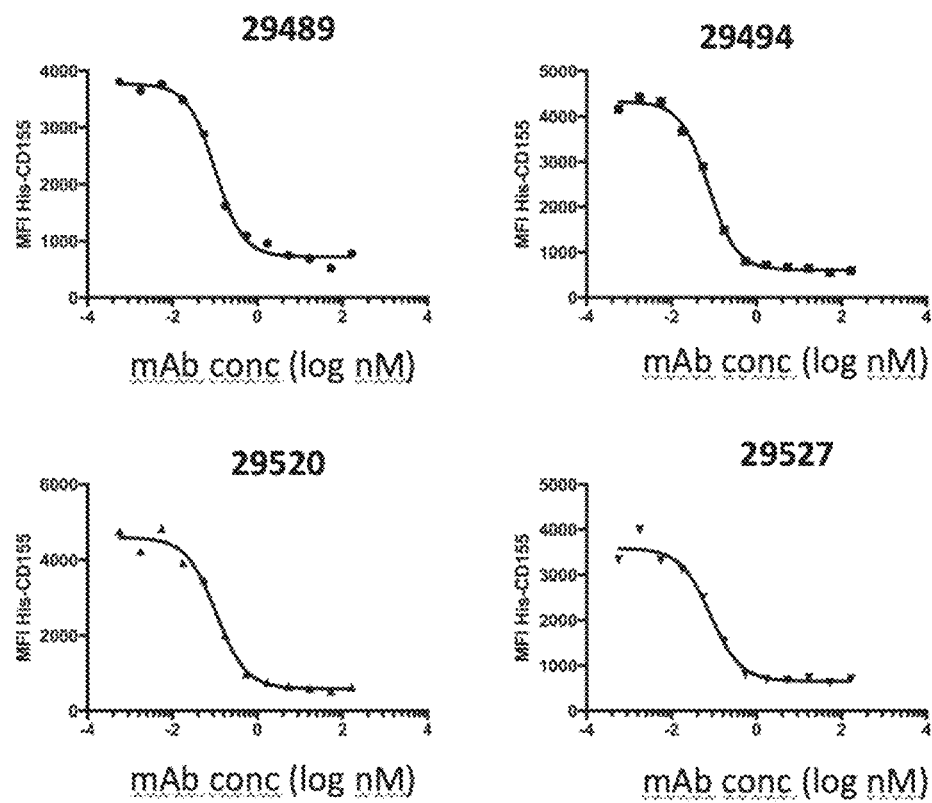
FIG. 7 — Competition with human CD155 ligand

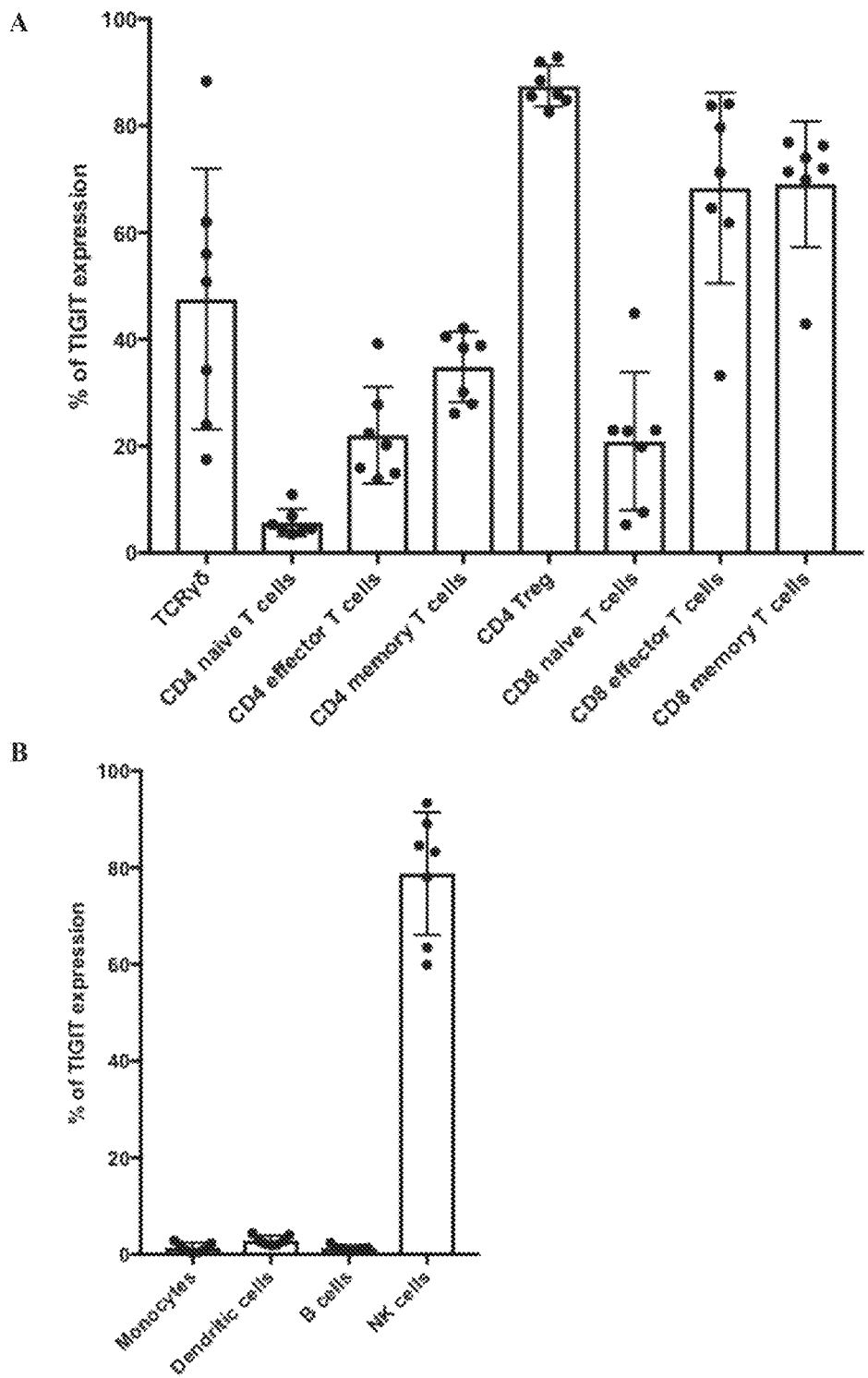
FIG. 8 – TIGIT expression on different immune populations from healthy donors PBMC FIG. 9 — Binding to Jurkat-hTIGIT
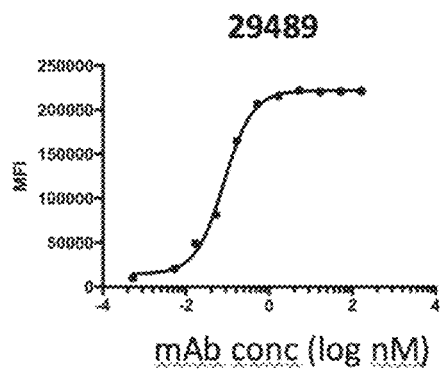
29489
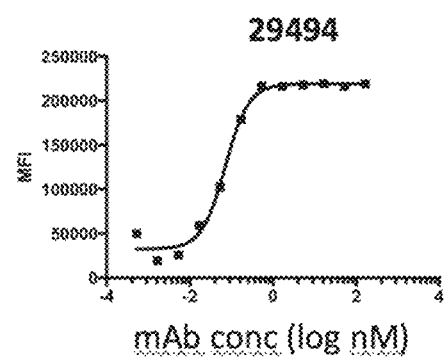
29494
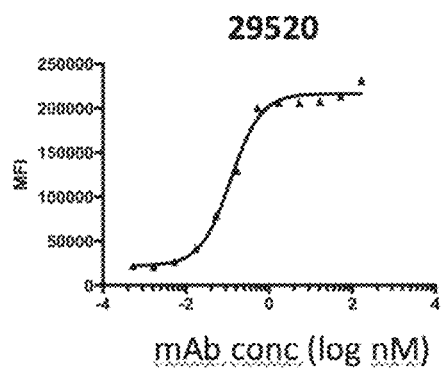
29520
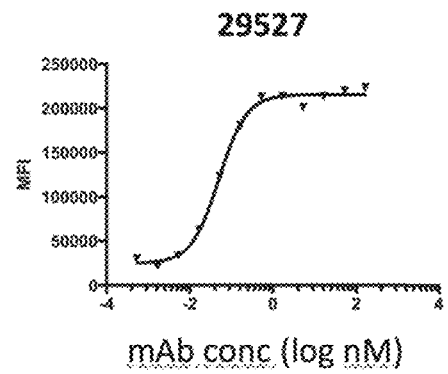
29527

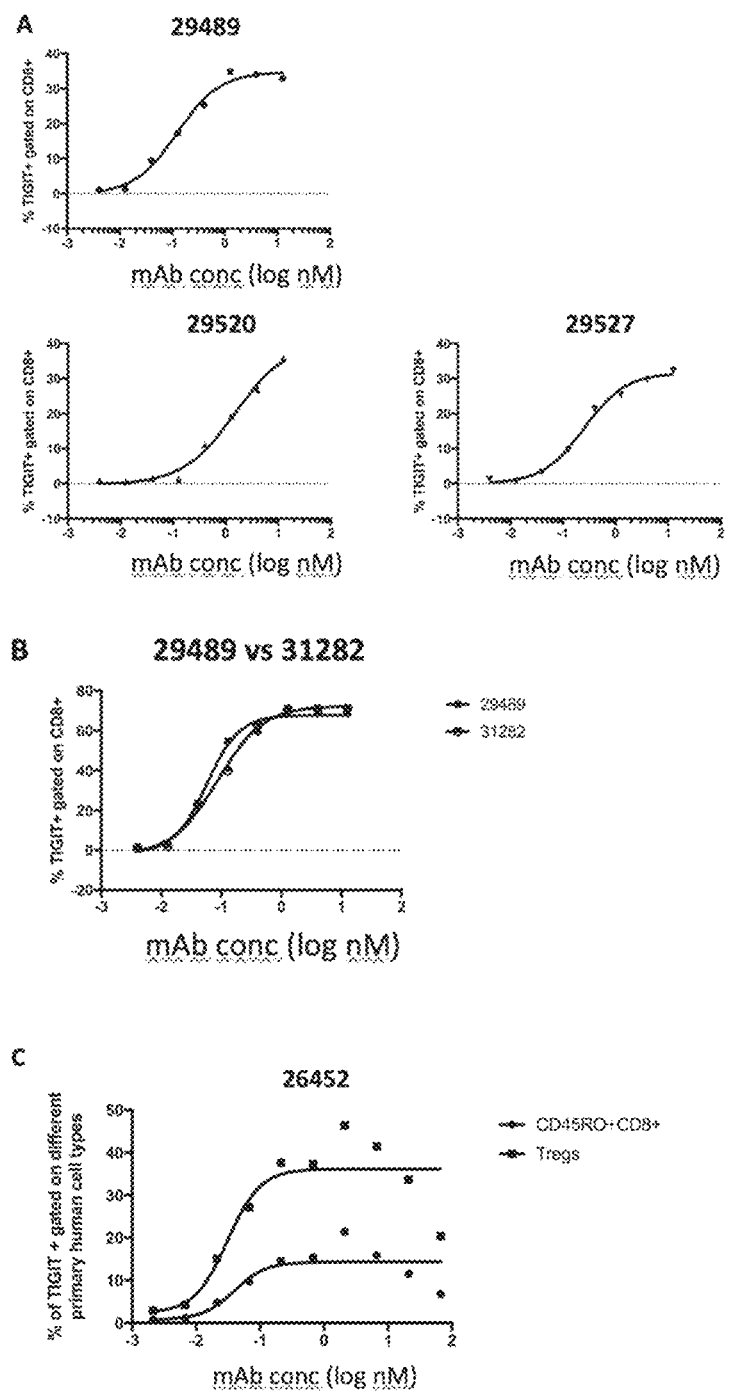

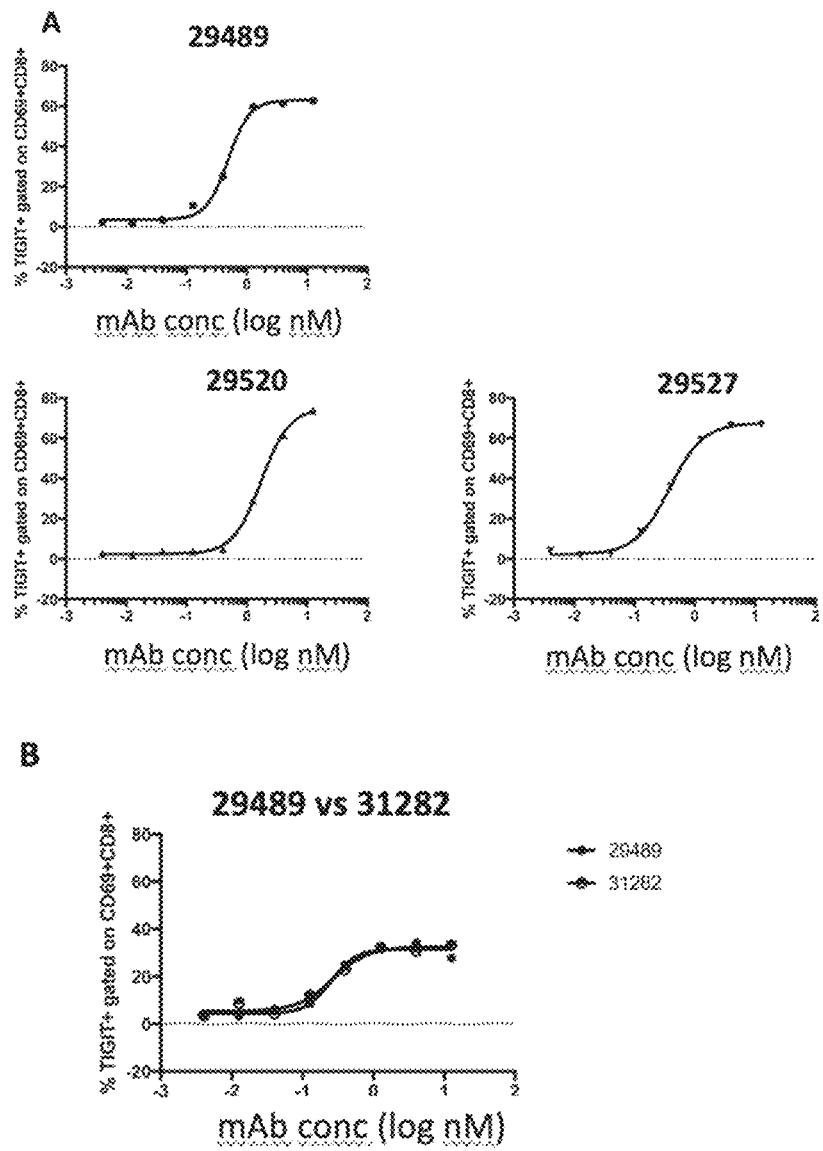

FIG. 12 — Effect of anti-TIGIT antibodies in a CHO-TCR-CD155 and Jurkat-hTIGIT Bioassay
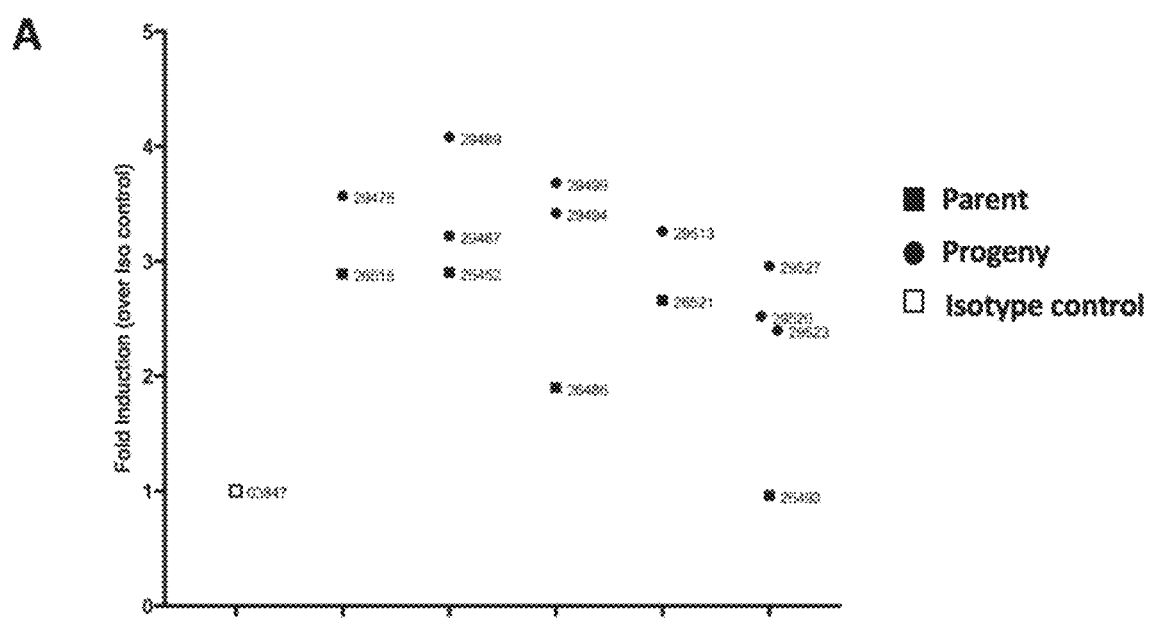

FIG. 13 — Effect of anti-TIGIT antibodies in Human CD8+ T cell based functional assay
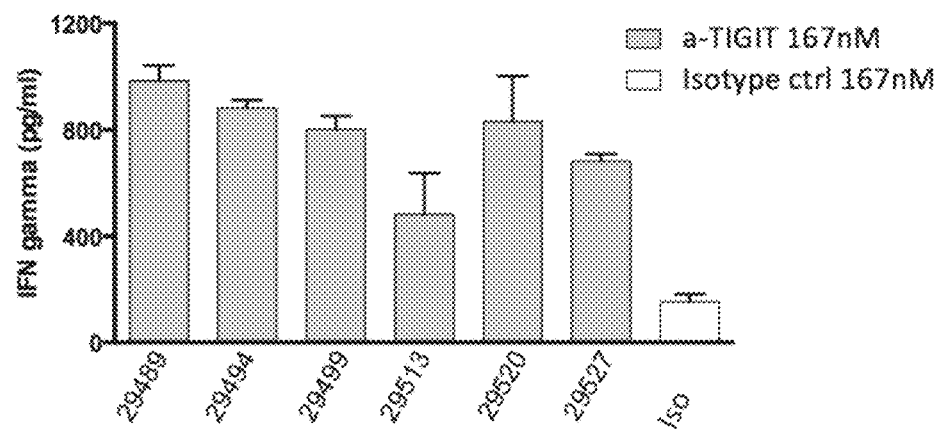
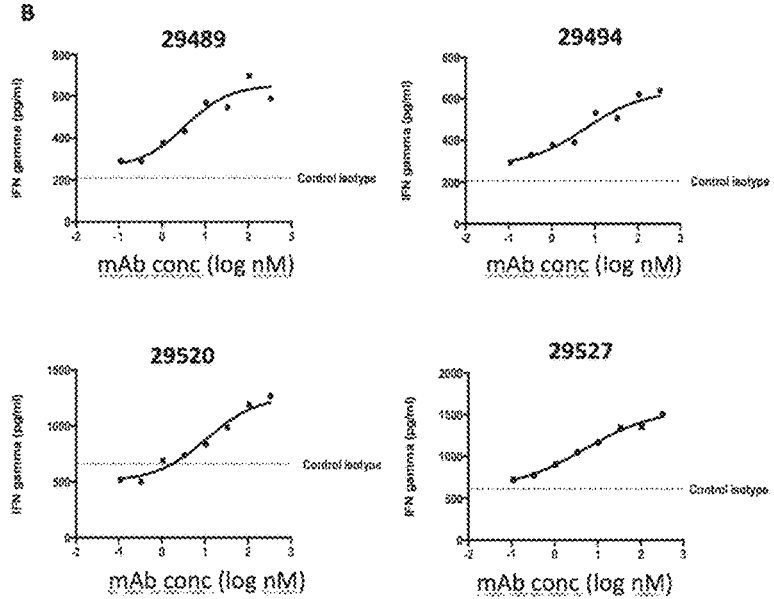
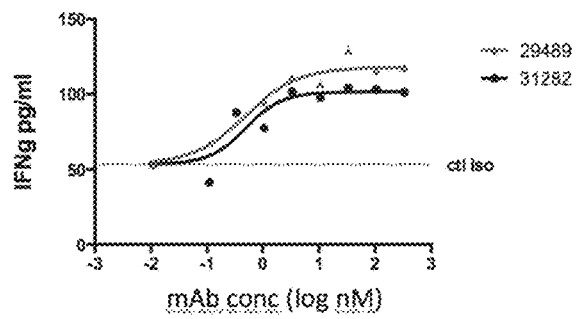

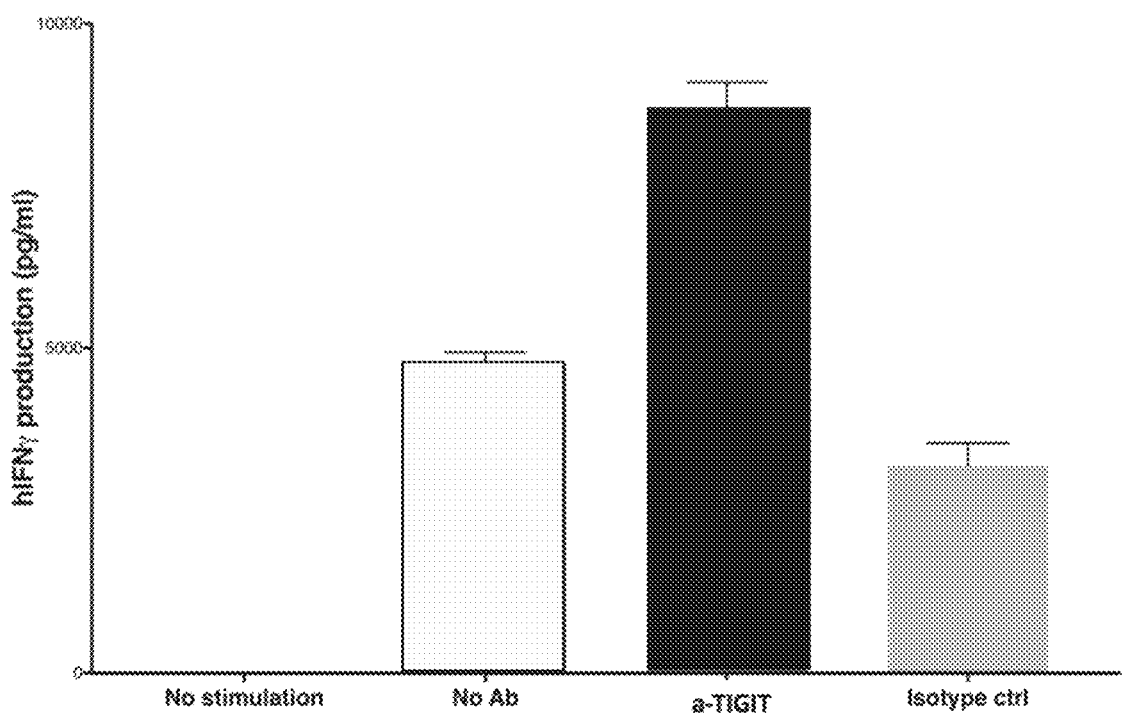
FIG. 14 — Effect of anti-TIGIT antibodies in Human TIL based functional assay FIG. 15 — Characterization of mouse surrogate anti-TIGIT antibody that demonstrates functional activity in mouse
A
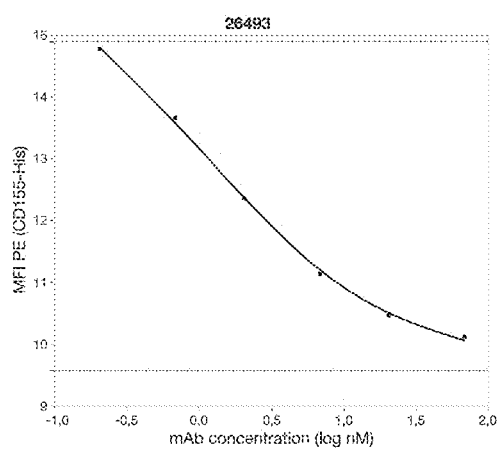
B
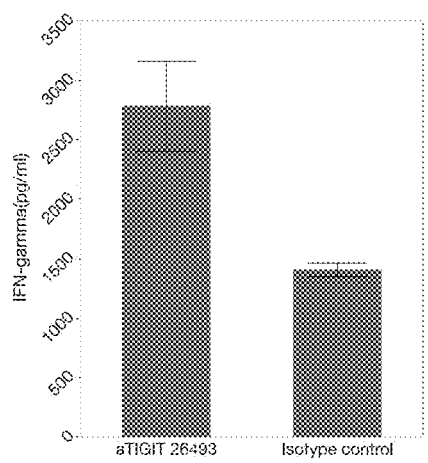
C
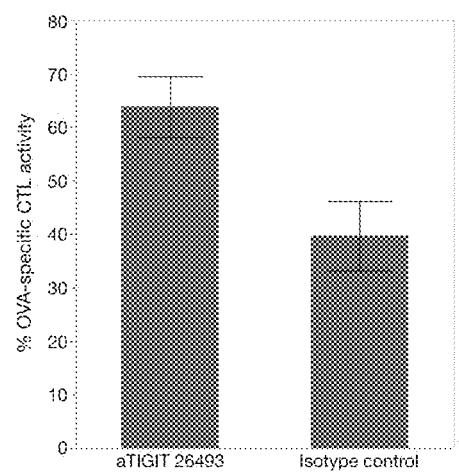

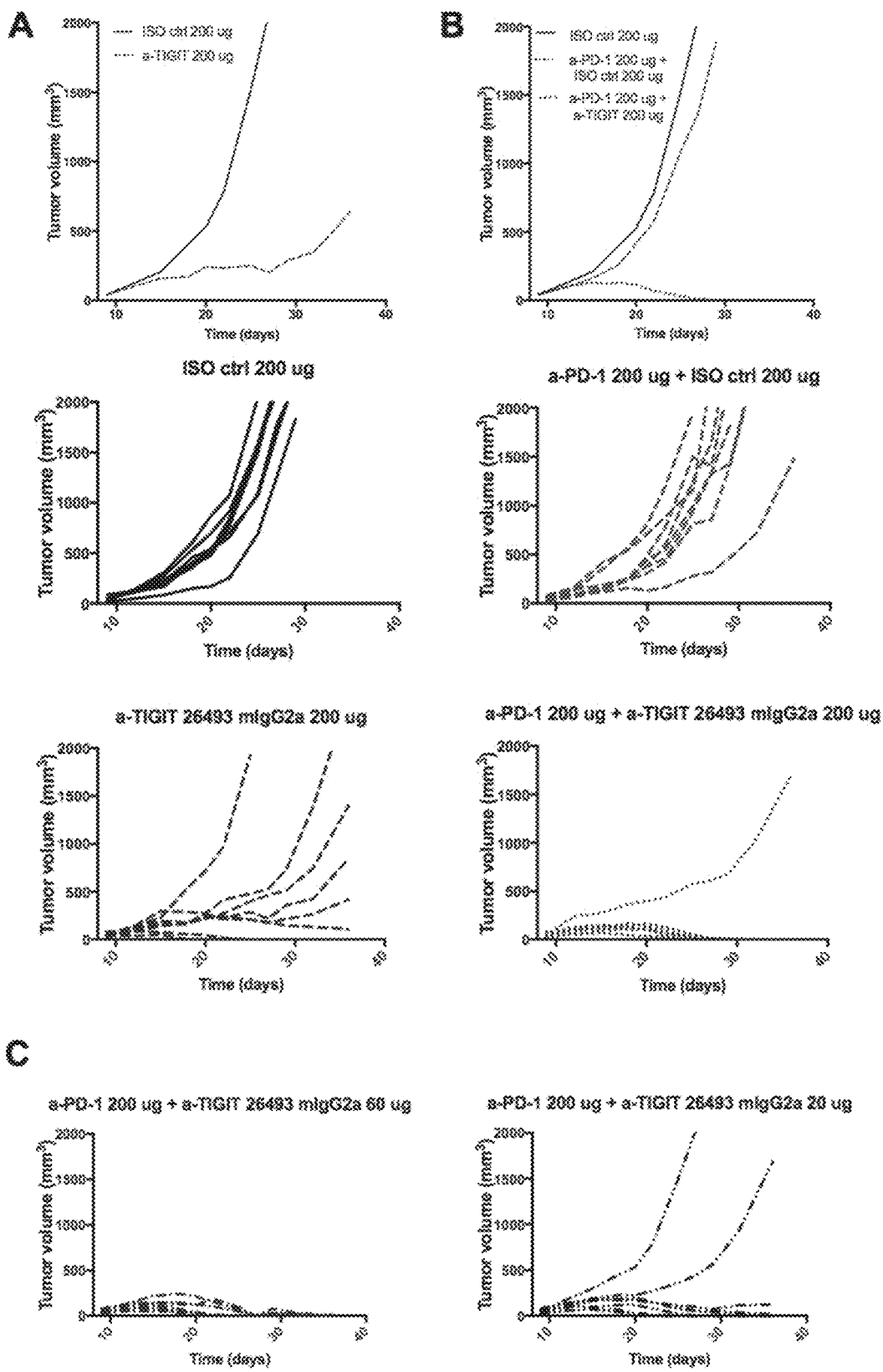
FIG. 16 — Anti-tumour efficacy of anti-TIGIT antagonistic antibody

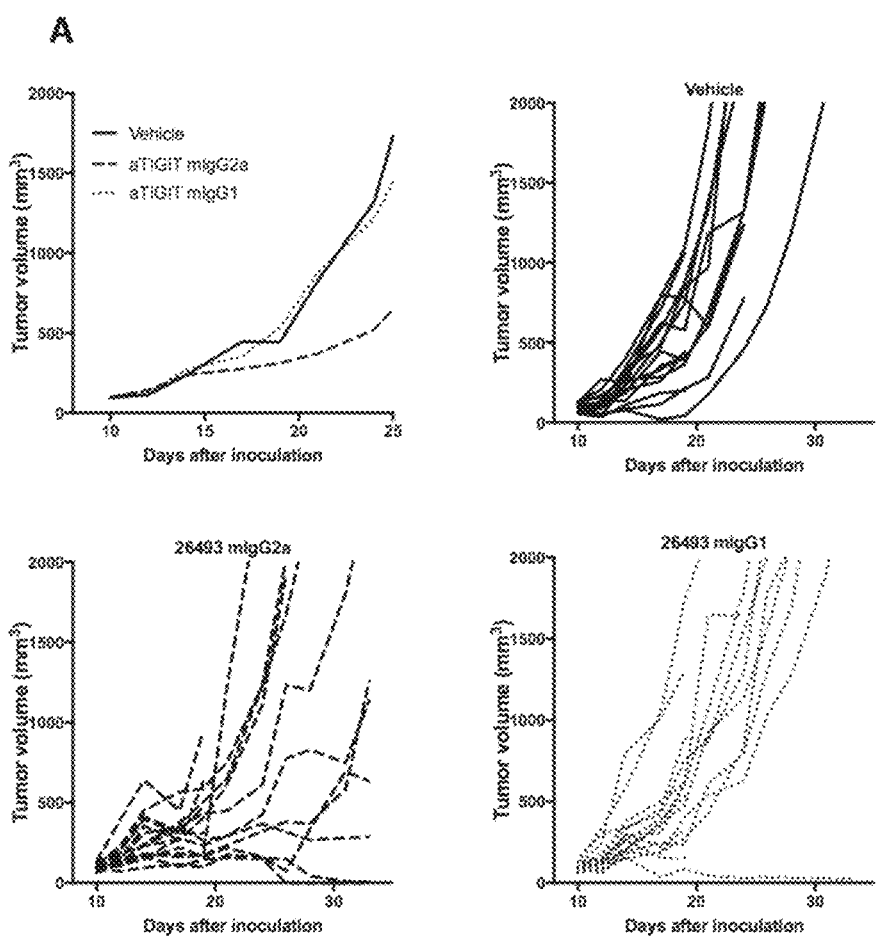
FIG. 17 — Isotype-dependent anti-tumour efficacy of anti-TIGIT antagonistic antibody FIG. 17 — Isotype-dependent anti-tumour efficacy of anti-TIGIT antagonistic antibody (Cont.)
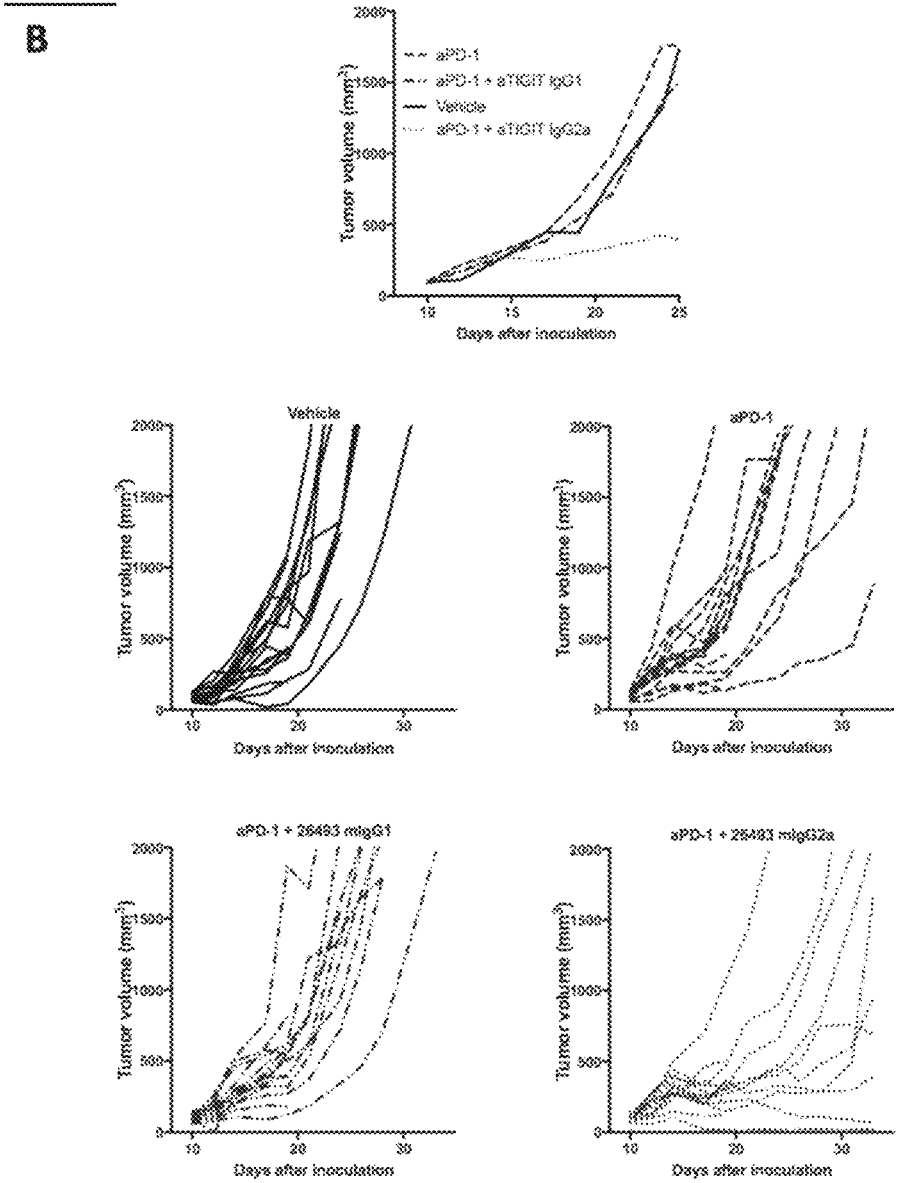

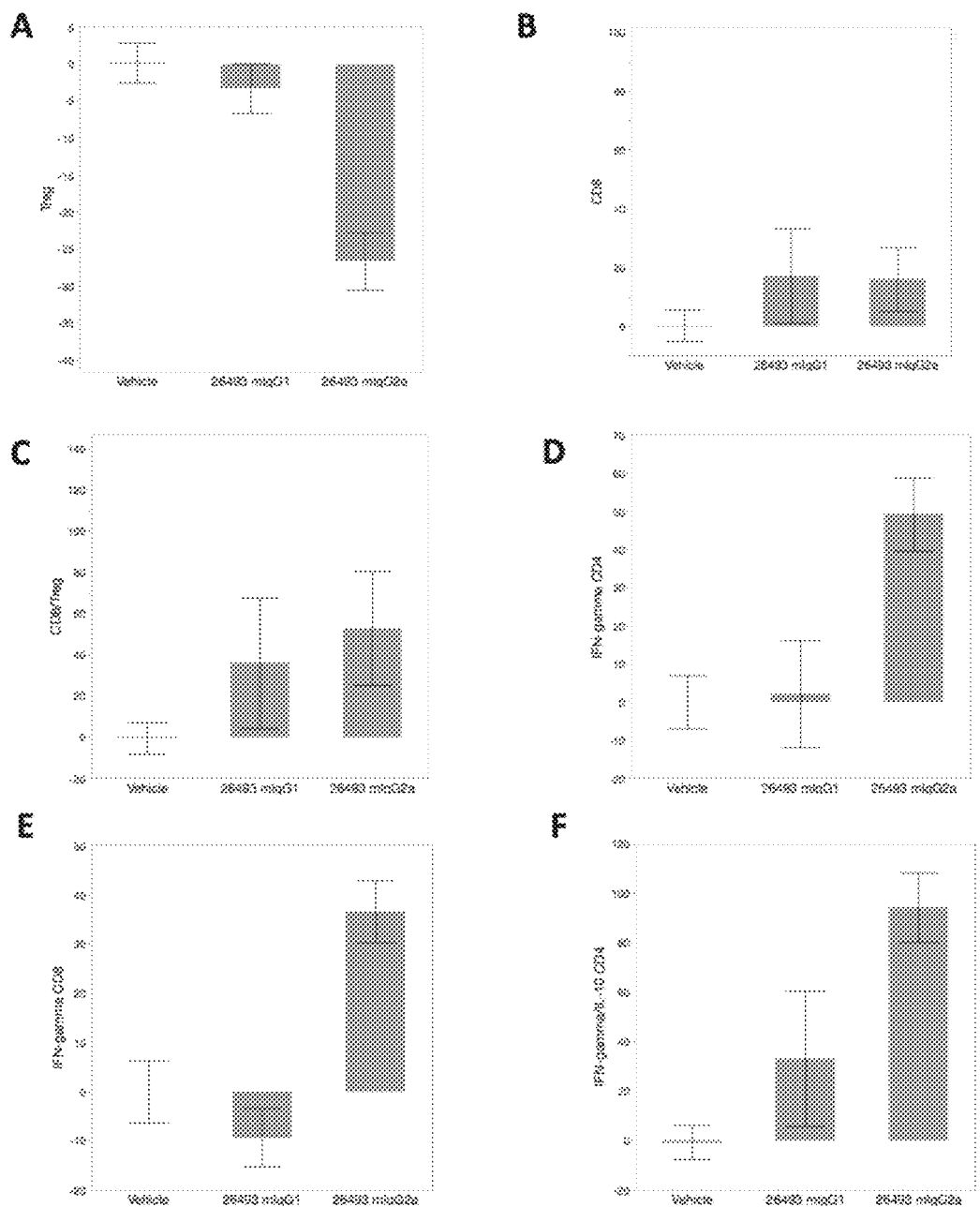
FIG. 18 — Mechanism of anti-tumor efficacy of anti-TIGIT antagonistic antibody FIG. 18 – Mechanism of anti-tumor efficacy of anti-TIGIT antagonistic antibody (Cont.)
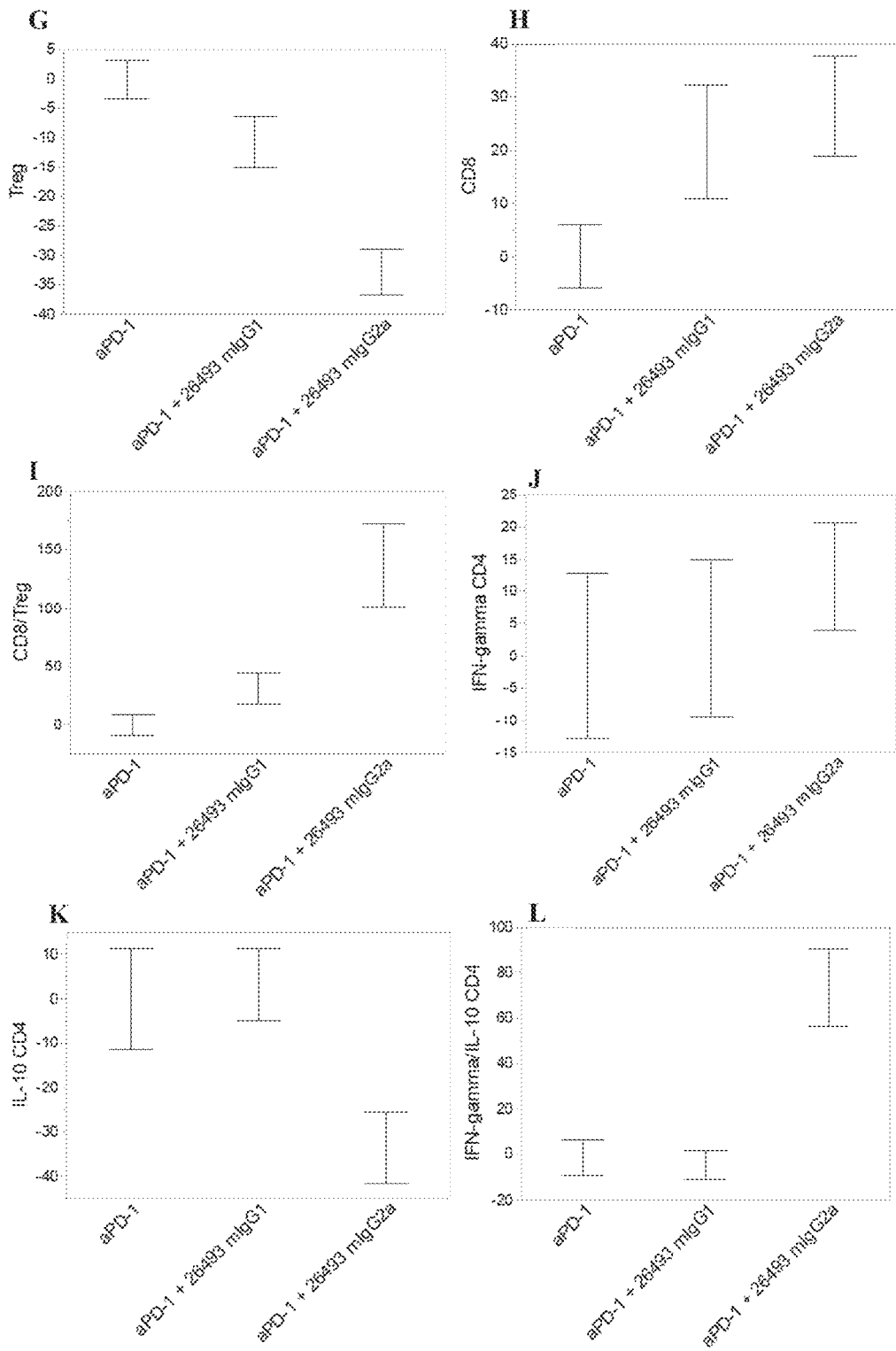

FIG. 19 — Mechanism of anti-tumor efficacy of anti-TIGIT antagonistic antibody (transcriptional analysis)
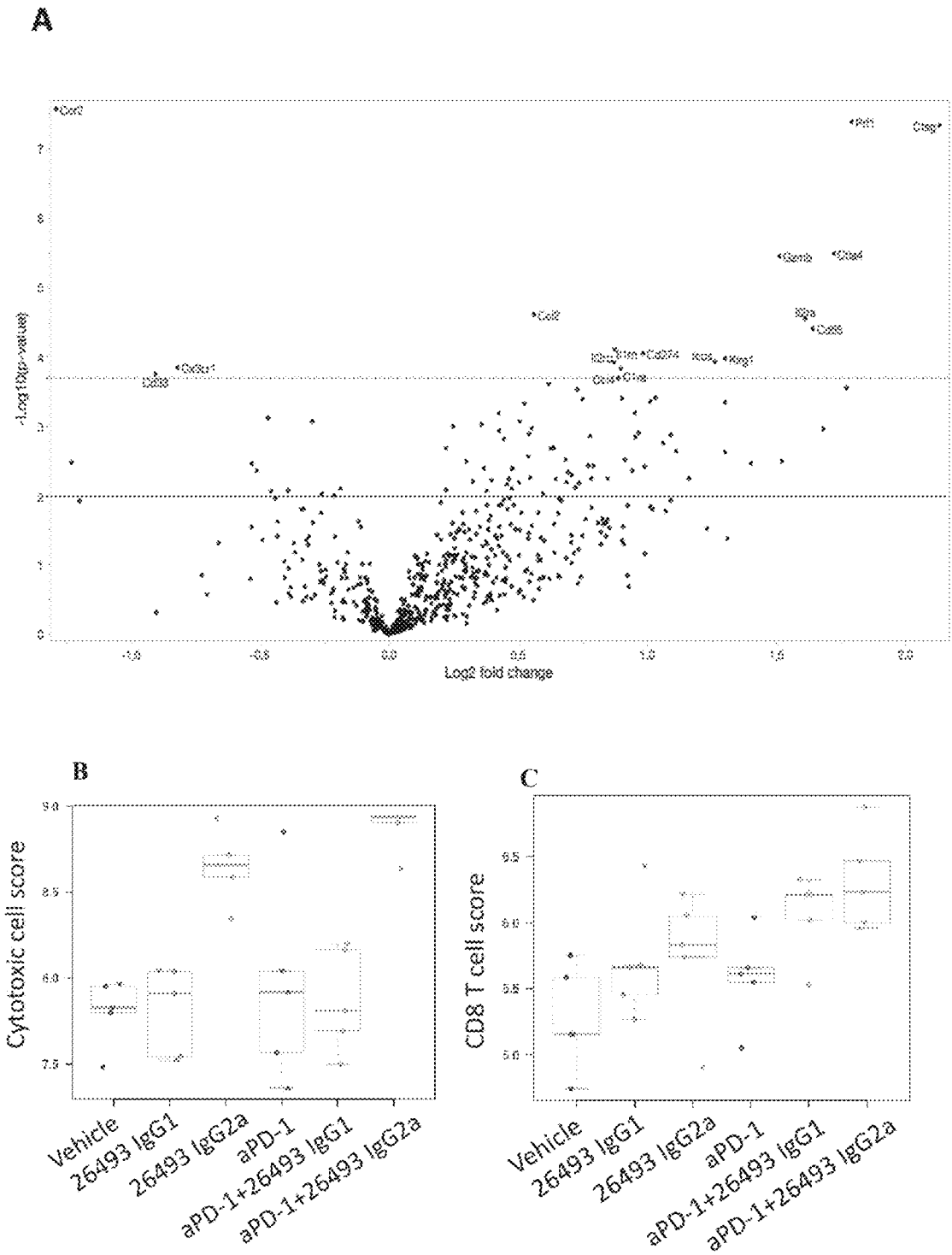

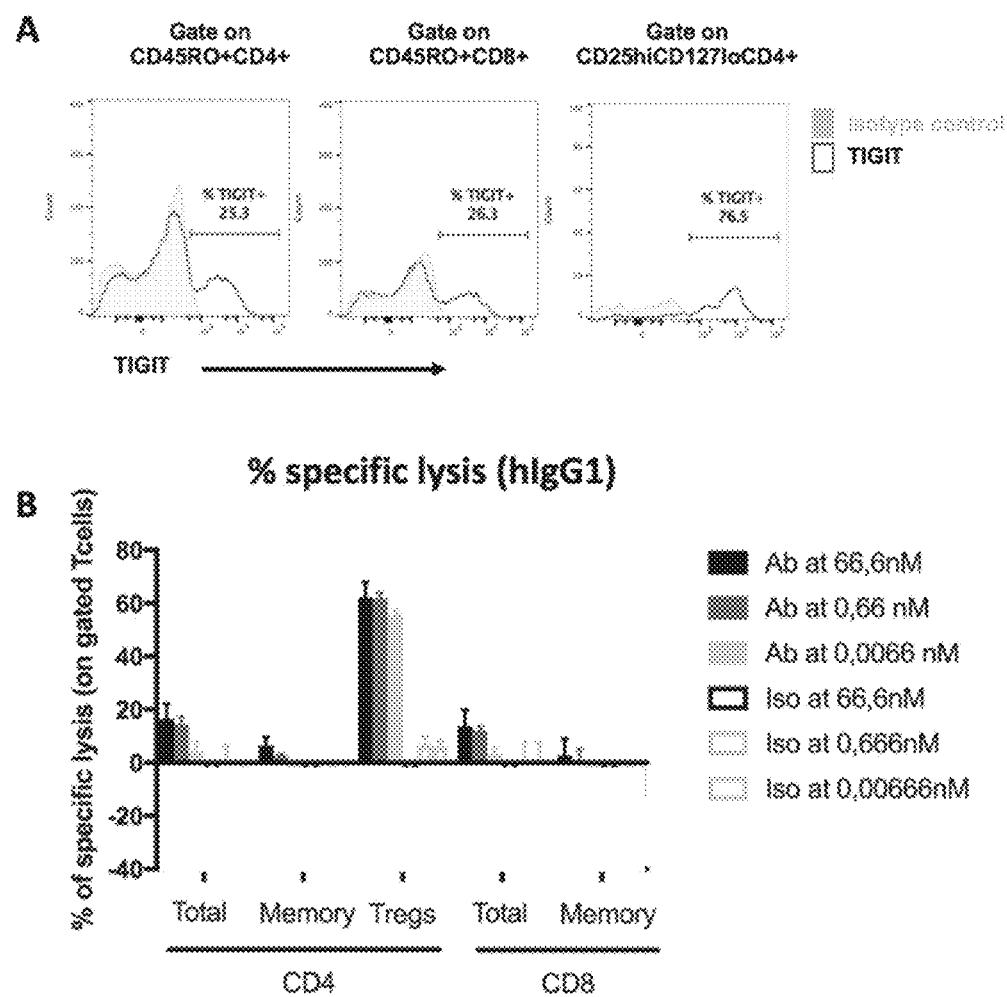
FIG. 20 - ADCC activity on healthy human PBMC

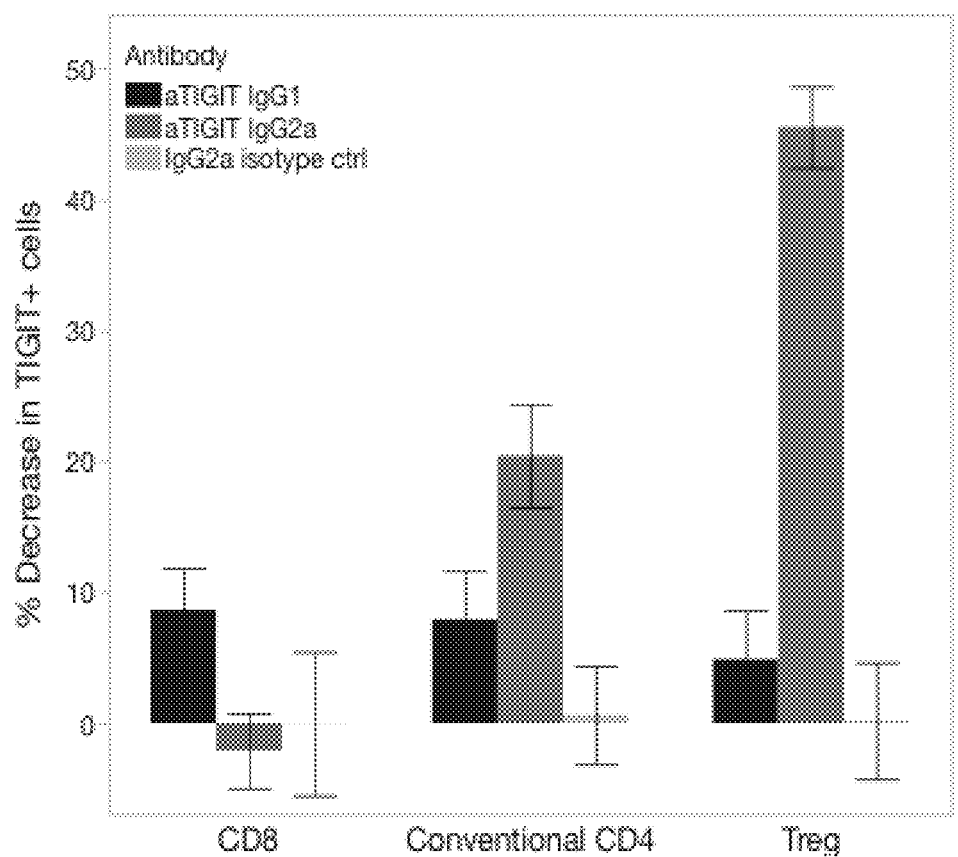
FIG. 21 — Preferential depletion of Treg cells in mouse tumor suspension FIG. 22
A
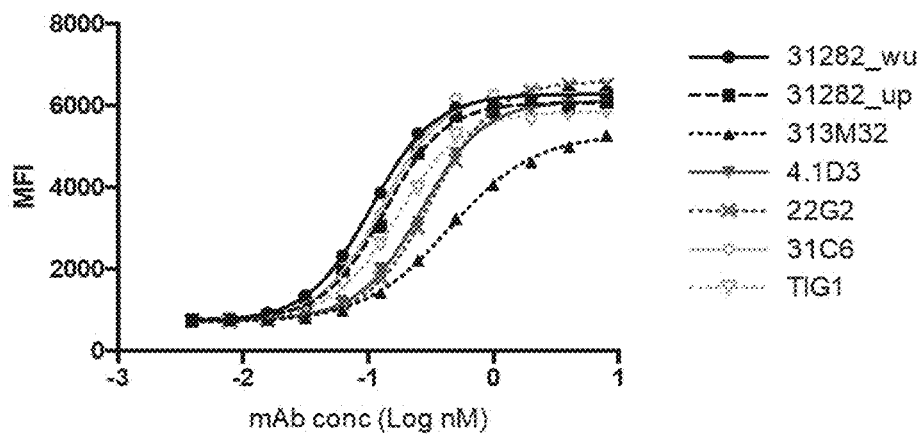
B
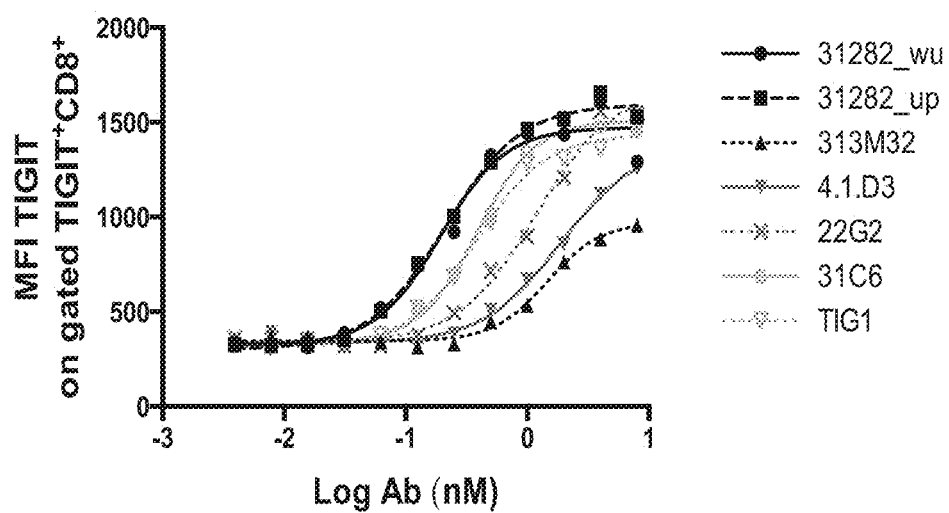
C
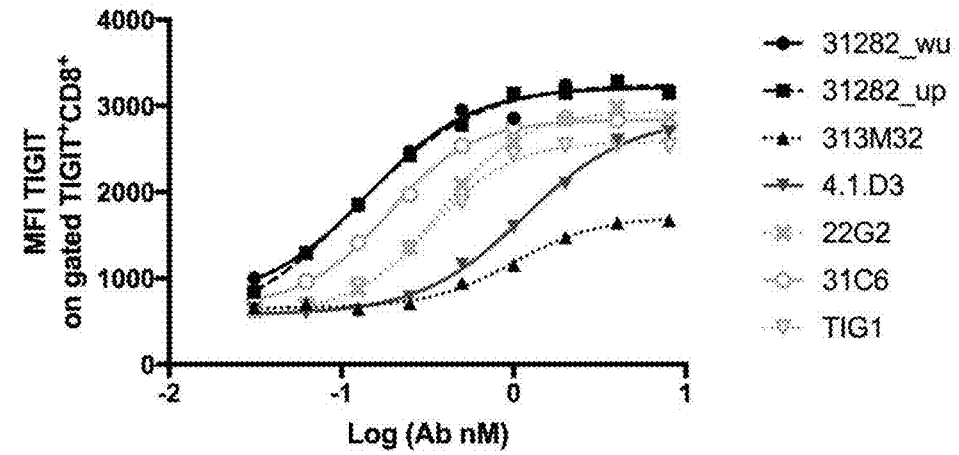

FIG. 24
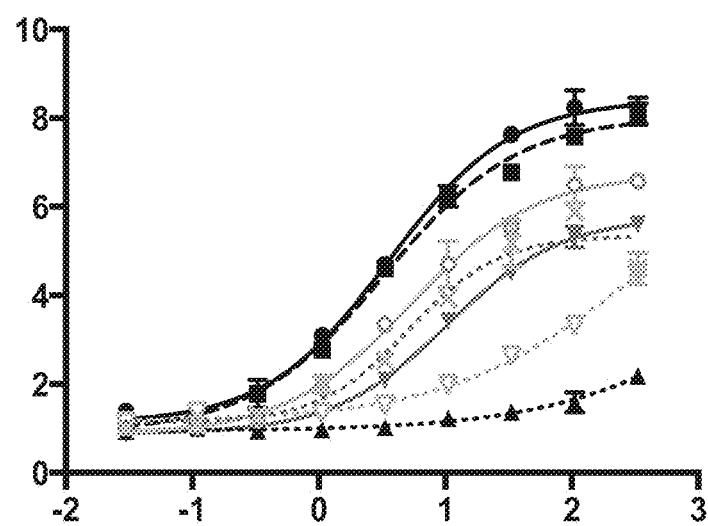
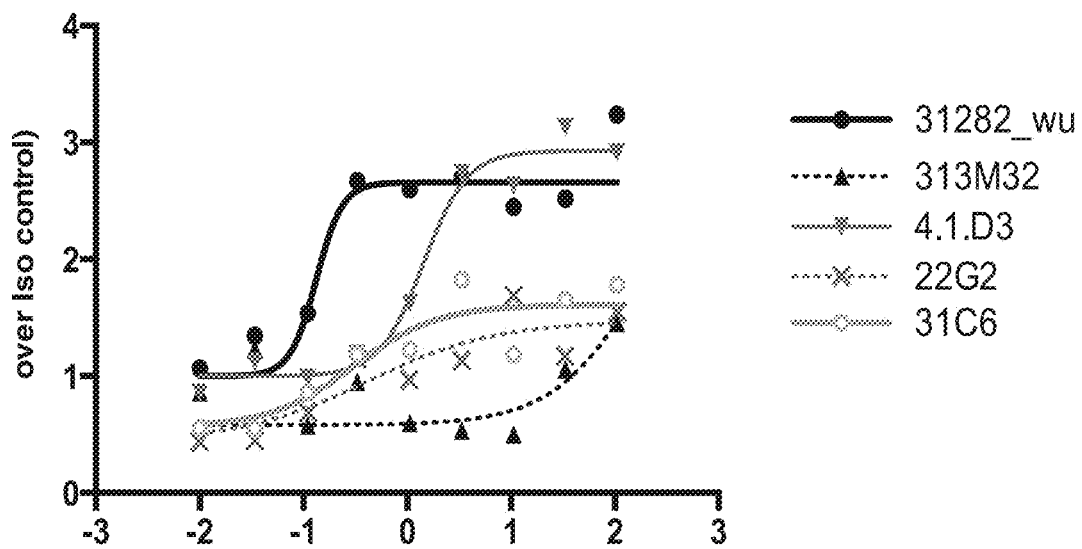

FIG. 24 (Cont.)
C
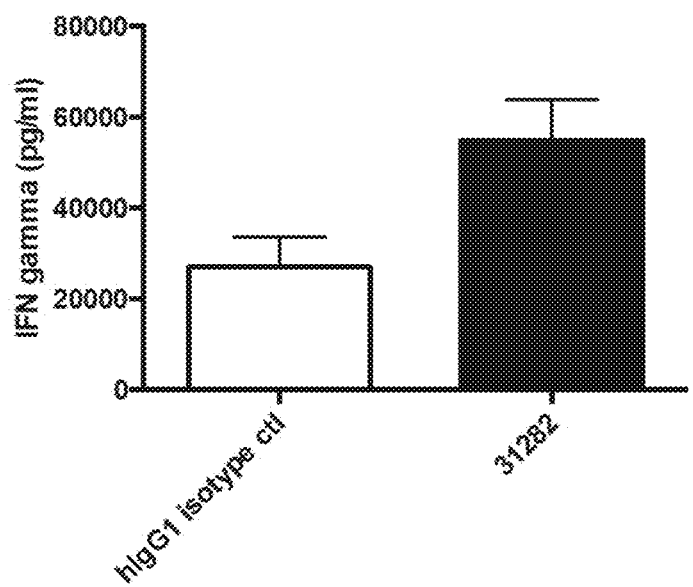
D
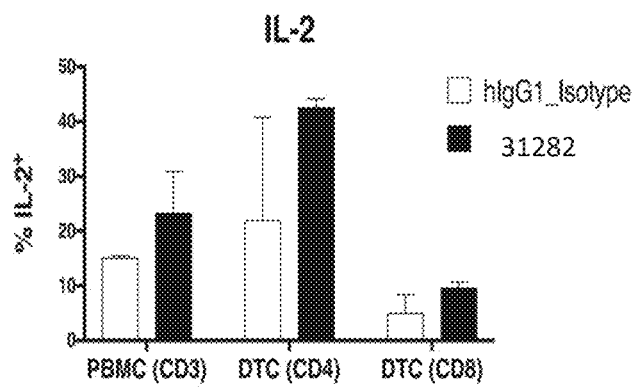
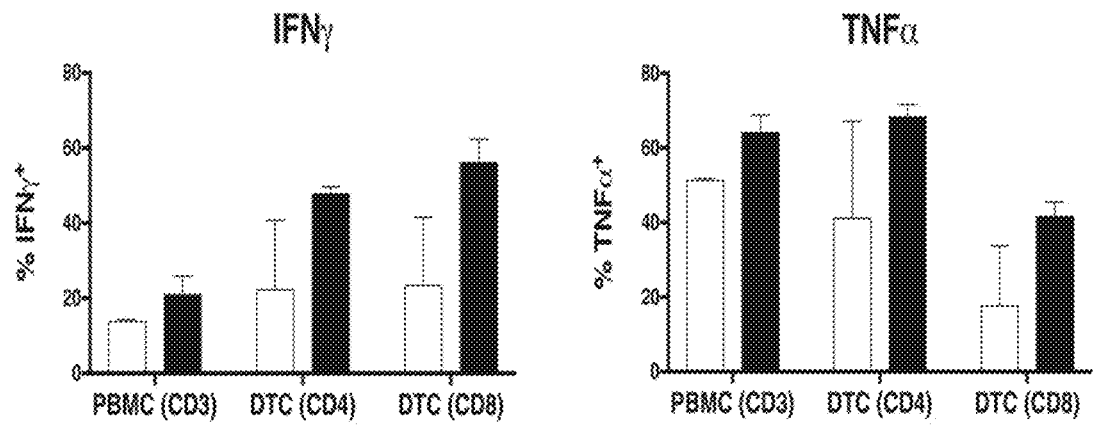

FIG. 26
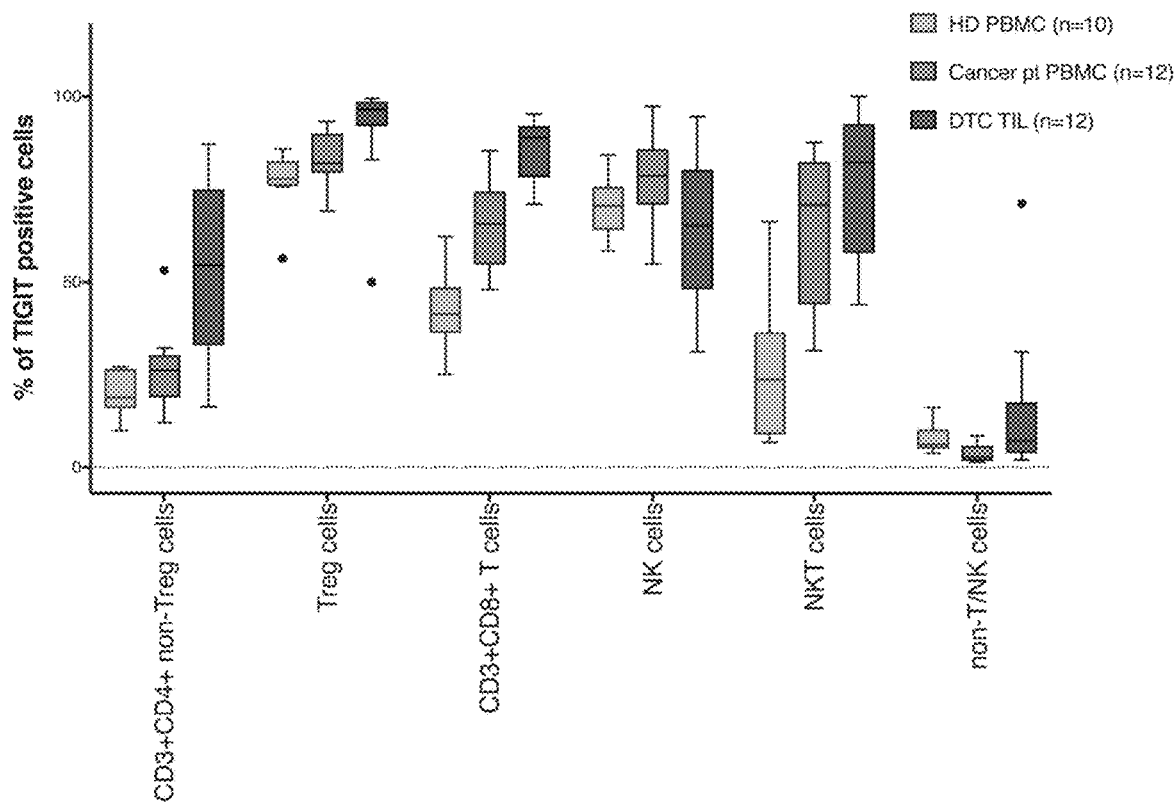
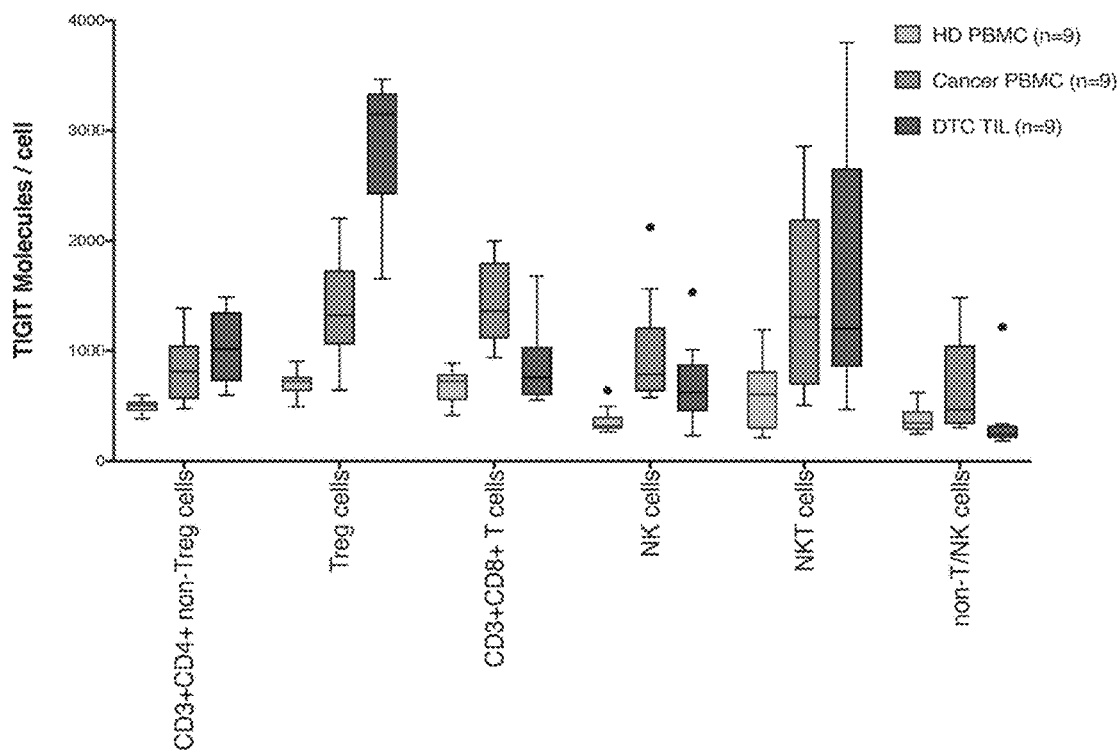

A

B

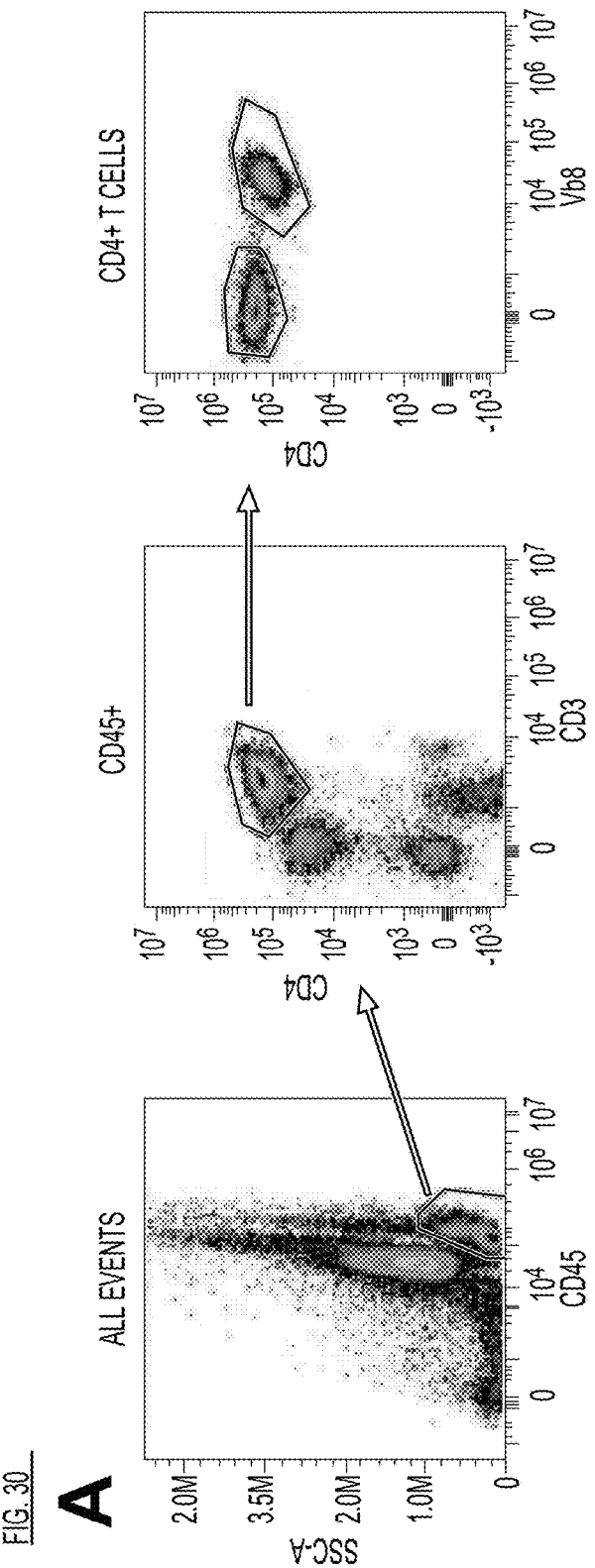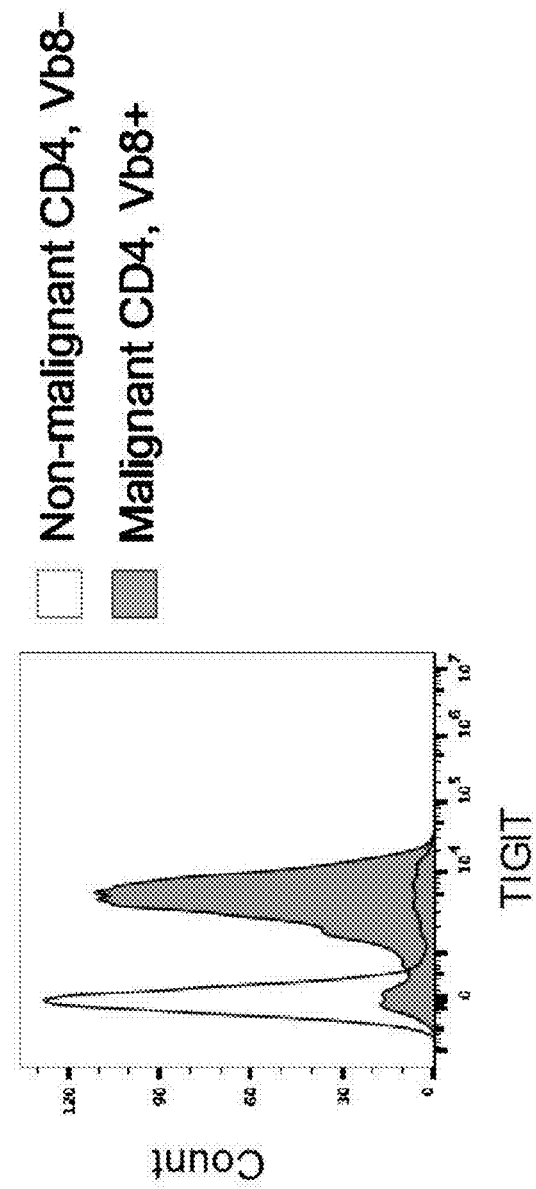
FIG. 30

FIG. 32
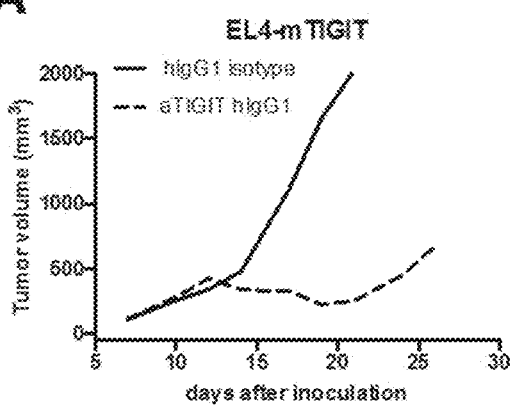
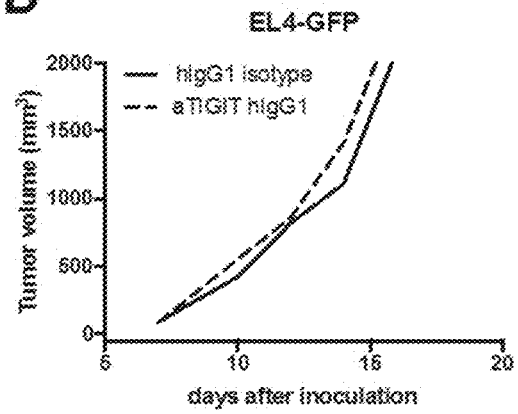
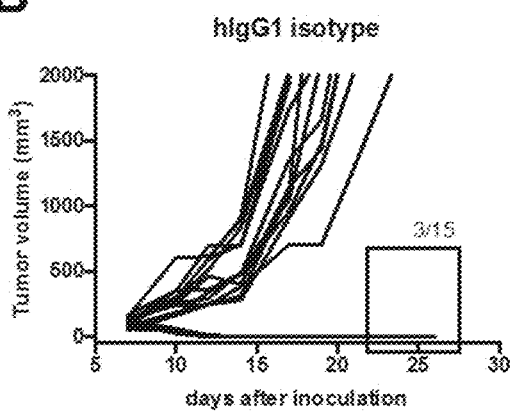
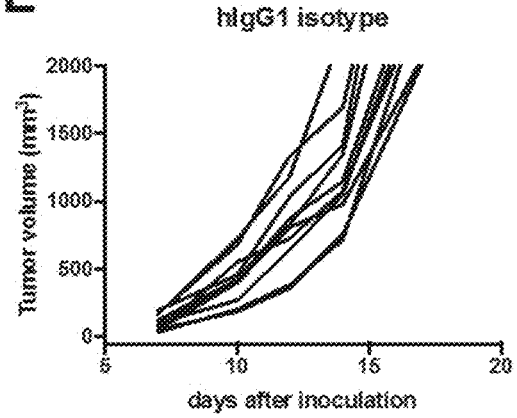
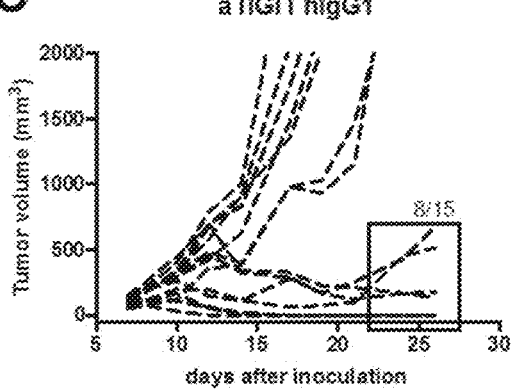
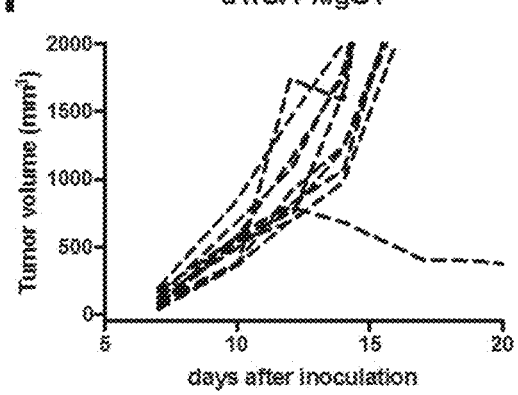

A

B

C

D

FIG. 34
A
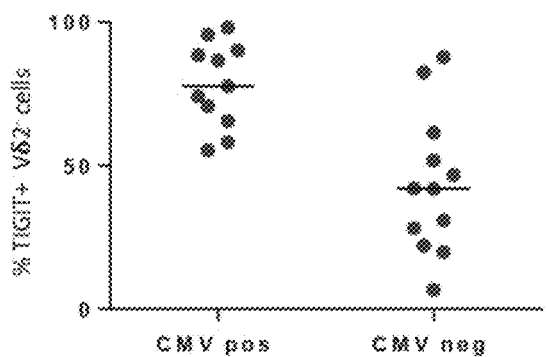
B
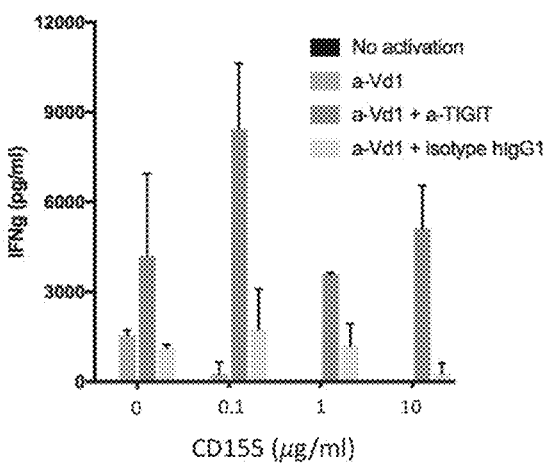
C
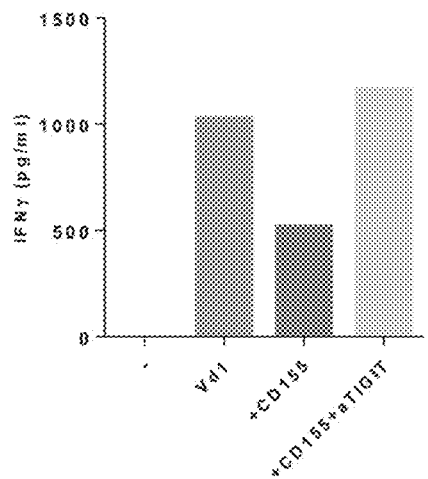

FIG. 36
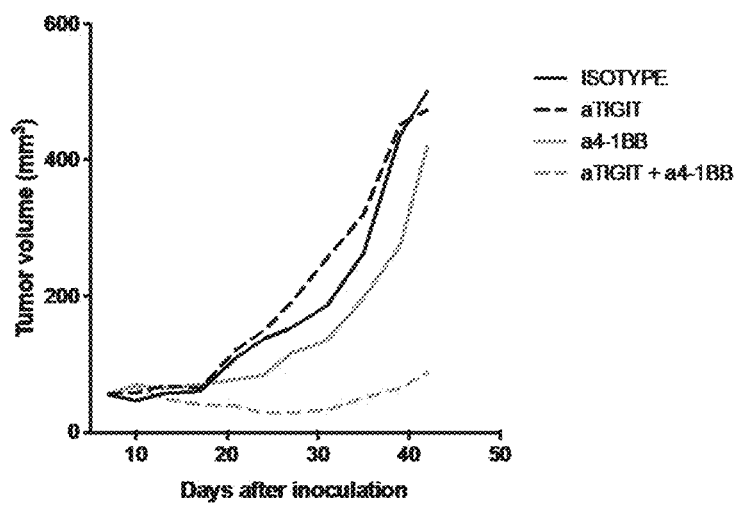
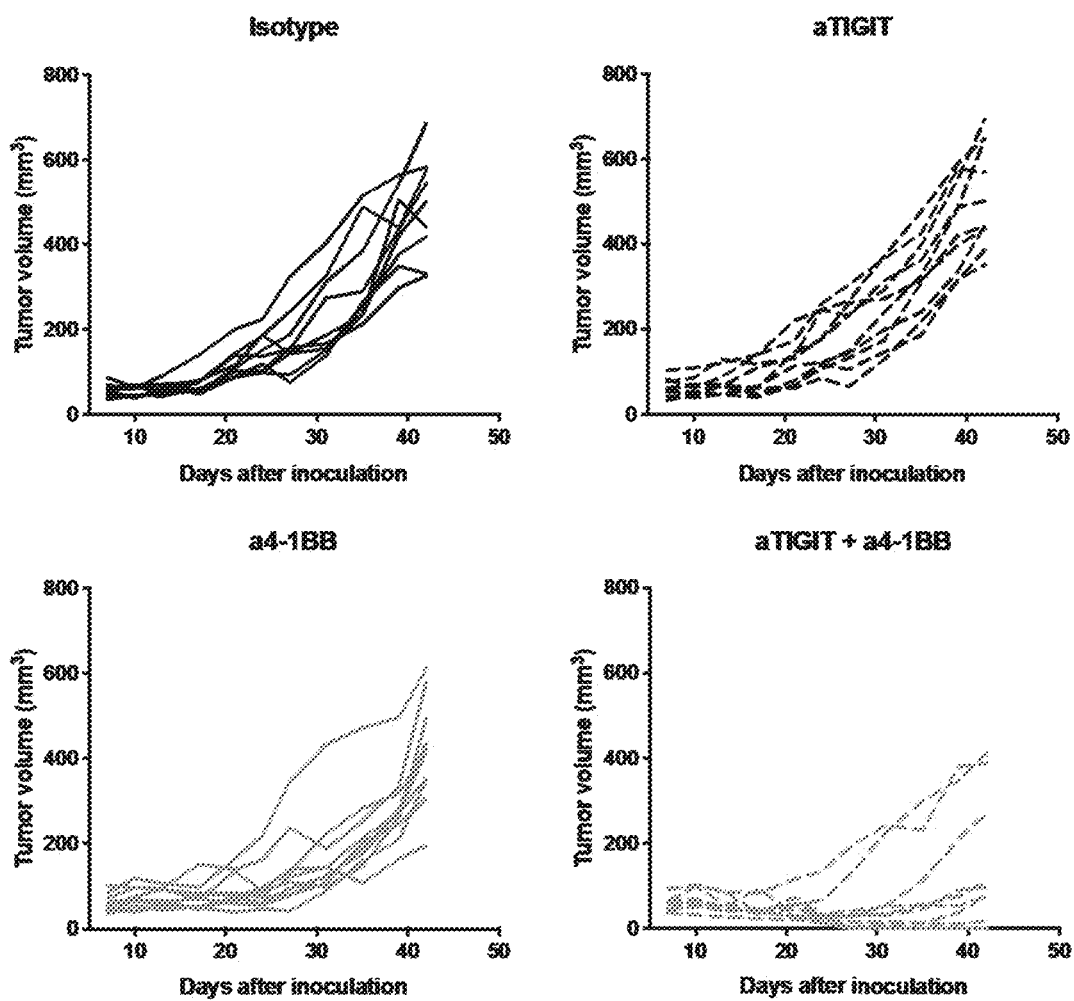

FIG. 40
A
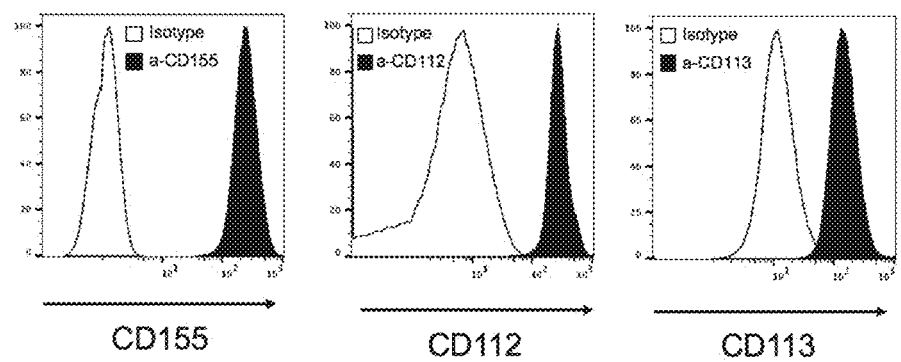
B
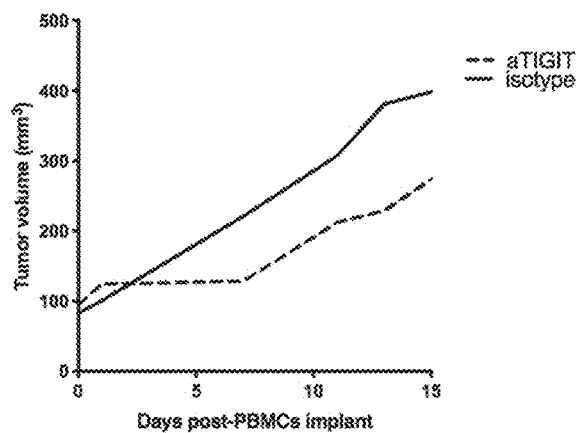
C
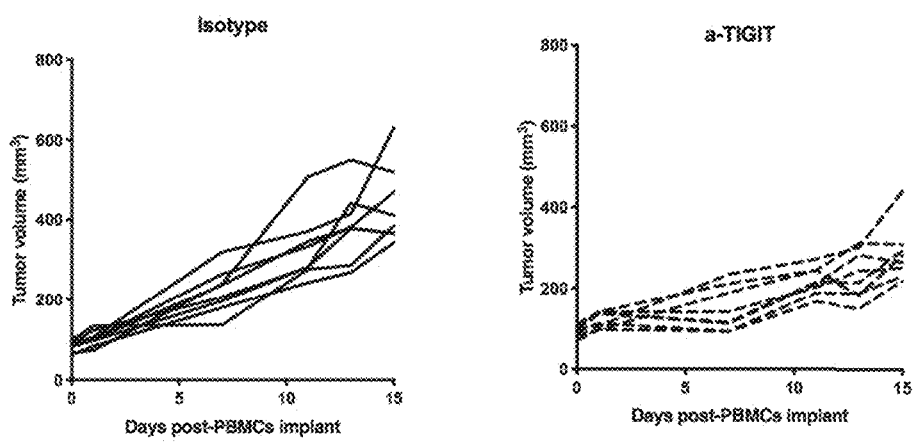

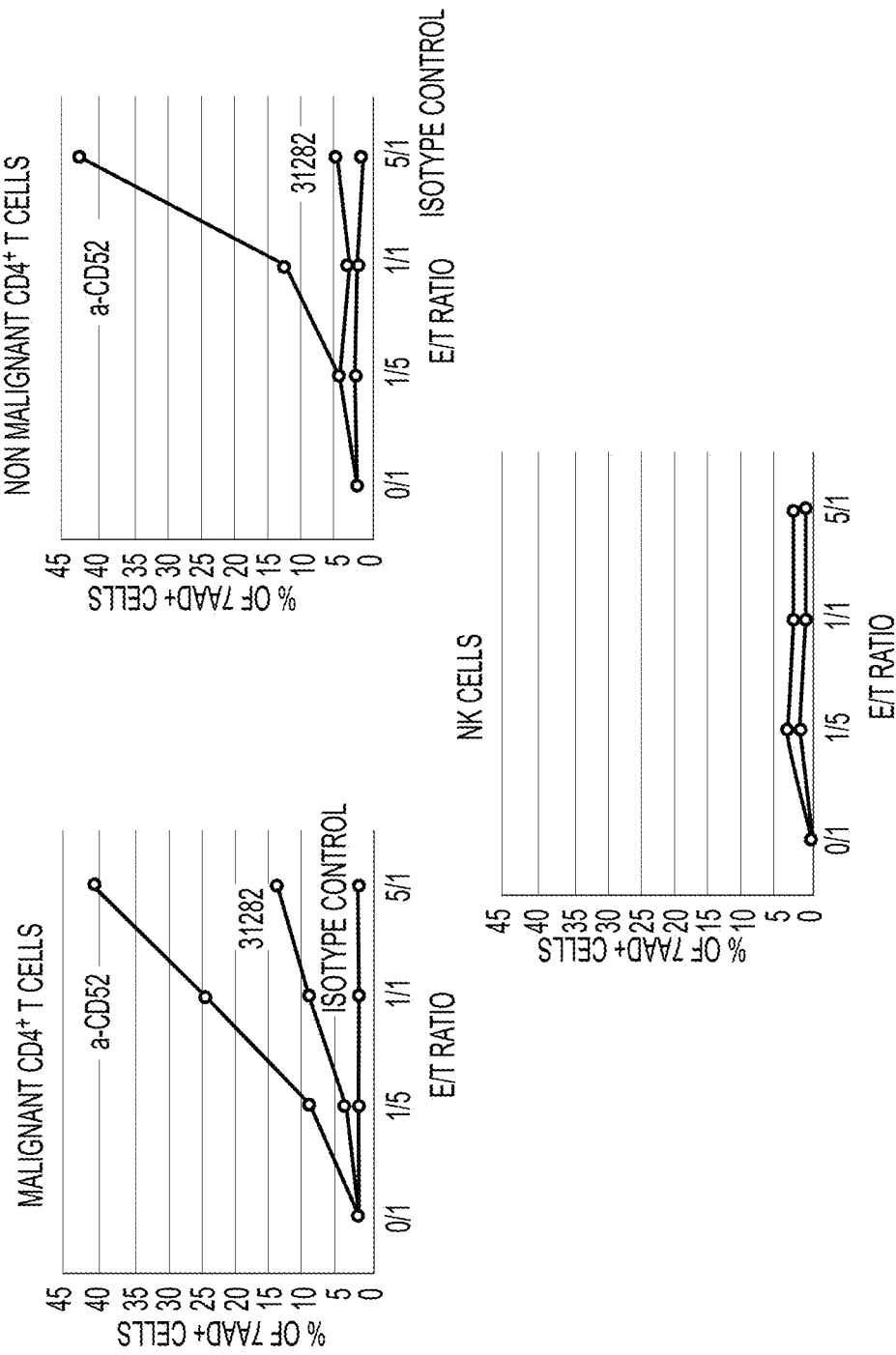
FIG. 42 (Cont.) B

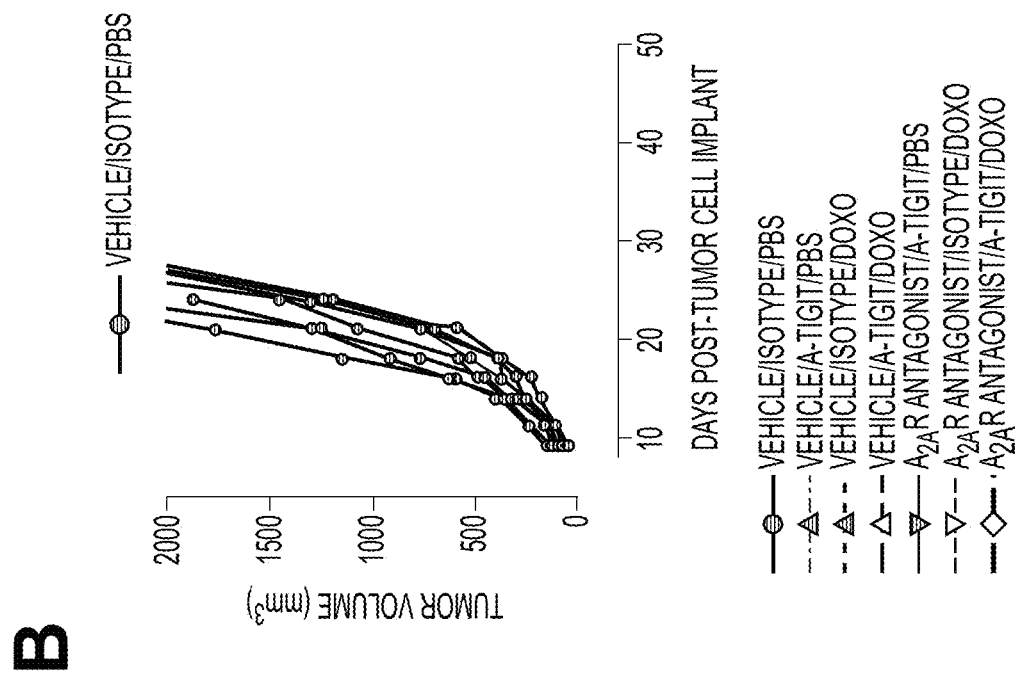
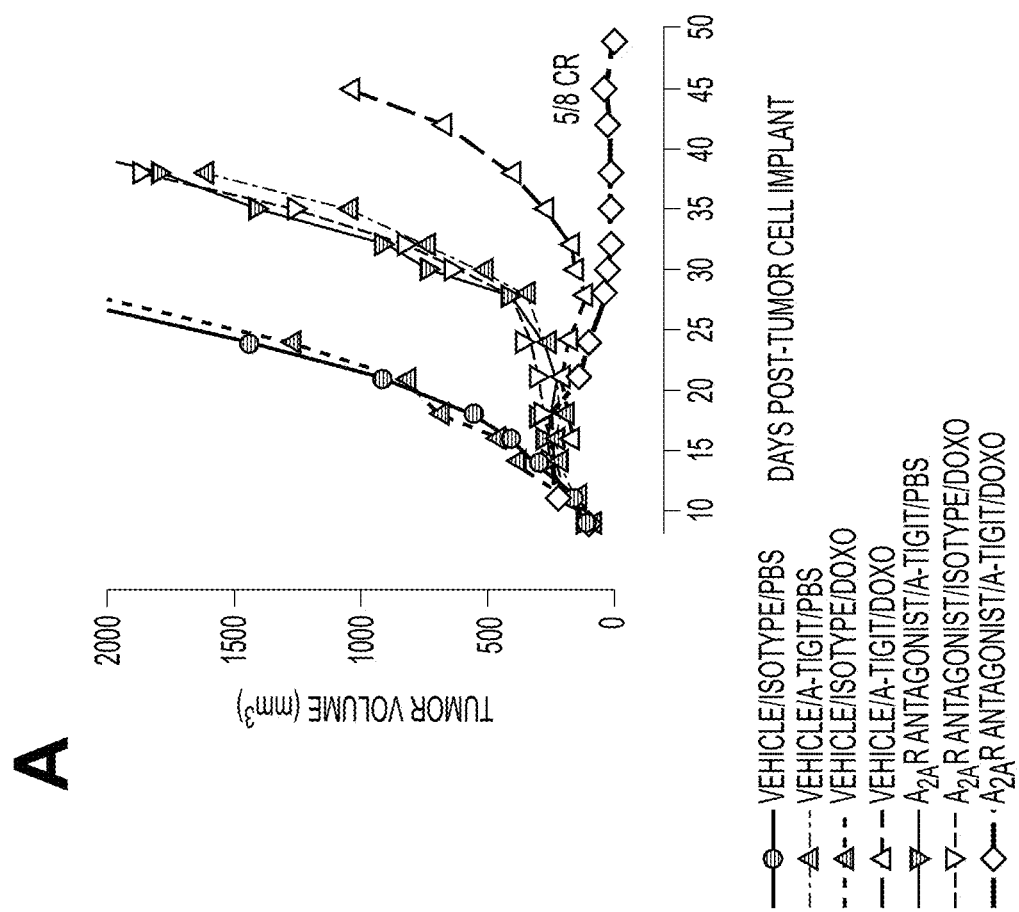
FIG. 43

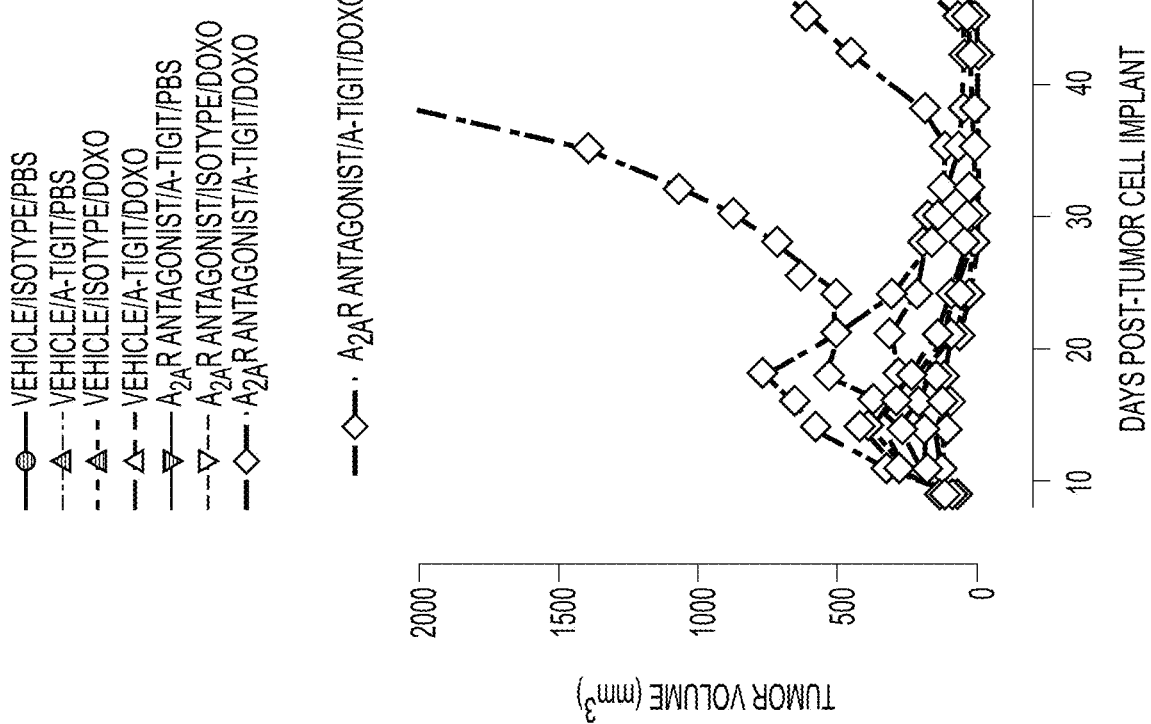
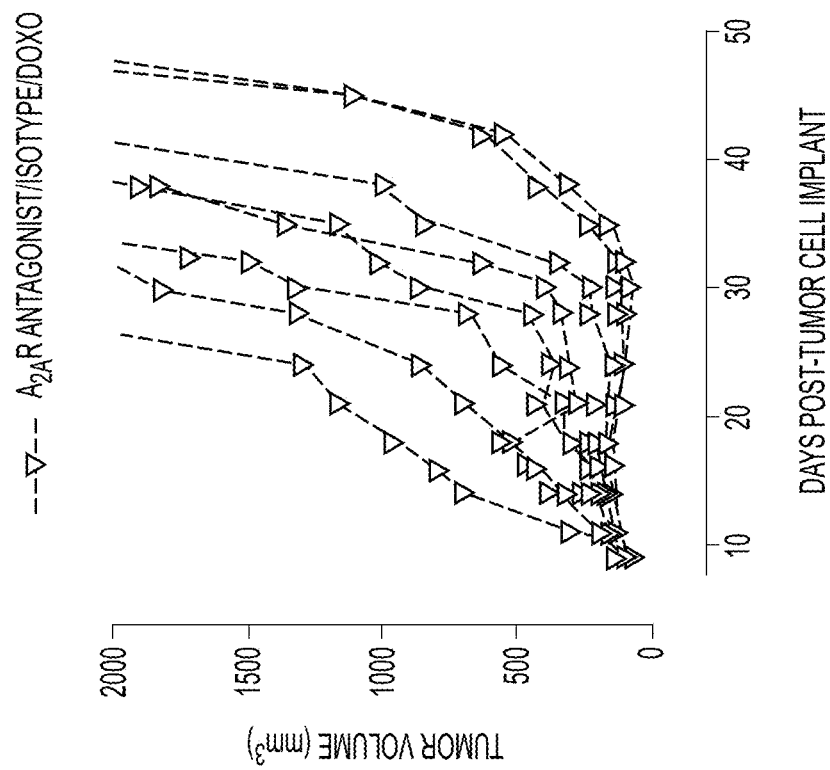
FIG. 43 (Cont.)
B

Concentration Clone 31282 (ug/ml)

ANTI-TIGIT ANTIBODIES

CROSS-REFERENCE TO RELATED APPLICATIONS

This application is the National Stage of International Application No. PCT/EP2020/050203, filed Jan. 7, 2020, which claims the benefit of and priority to U.S. Patent Application Ser. No. 62/789,466, filed on Jan. 7, 2019, the contents of which are incorporated by reference in their entirety.

SEQUENCE LISTING

The instant application contains a Sequence Listing which has been submitted via EFS-Web and is hereby incorporated by reference in its entirety. Said ASCII copy, created on Jul. 6, 2021, is named IST-007WOUS_Sequence_Listing.txt, and is 142,483 bytes in size.

BACKGROUND

Cancer immunotherapy relies on the modulation of the immune system to increase recognition and response against tumour cells. Such modulation can be achieved by multiple mechanisms including the activation of co-stimulatory molecules present on immune cells or through the inhibition of co-inhibitory receptors. The activation of an immune response is a complex mechanism involving numerous cell populations like antigen-presenting cells important for the initiation of the antigen-specific response and effector cells responsible for tumour cell destruction. The mechanisms modulating the activity of effector cells like cytotoxic T cells are numerous and represent target of choice in the context of cancer immunotherapy.

TIGIT (T cell Immunoreceptor with Ig and ITIM domains), also called WUCAM, VSIG9 or Vstm3, is a co-inhibitory receptor preferentially expressed on NK, CD8+ and CD4+ T cells as well as on regulatory T cells (Treg cells, or simply "Tregs"). TIGIT is transmembrane protein containing a known ITIM domain in its intracellular portion, a transmembrane domain and an immunoglobulin variable domain on the extracellular part of the receptor. Several ligands were described to bind to TIGIT receptor with CD155/PVR showing the best affinity followed by CD113/PVRL3 and CD112/PVRL2 (Yu et al. (2009) Nat. Immunol. 10:48.). DNAM/CD226, a known co-stimulatory receptor also expressed on NK and T cells competes with TIGIT for CD155 and CD112 binding but with a lower affinity, which suggests a tight control of the activation of these effector cells to avoid uncontrolled cytotoxicity against normal cells expressing CD155 ligand.

TIGIT expression is increased on tumour infiltrating lymphocytes (TILs) and in disease settings such as HIV infection. TIGIT expression marks exhausted T cells that have lower effector function as compared to TIGIT negative counterparts (Kurtulus et al. (2015) J. Clin. Invest. 276:112; Chew et al. (2016) Plos Pathogens. 12). Conversely, Treg cells that express TIGIT show enhanced immunosuppressive activity as compared to TIGIT negative Treg population (Joller et al. (2014) Immunity. 40:569).

Like other co-inhibitory receptors (PD1 or CTLA4) expressed on T cells that have been proven to be relevant target for immunotherapy and for which antagonistic antibodies have been approved for the treatment of human cancer, the development of antagonistic anti-TIGIT antibody may help to turn-on the immune system and better fight cancer cells. It has been suggested that antagonistic anti-TIGIT antibodies in monotherapy or in combination with a-PD1 antibody could achieve strong anti-tumour efficacy in preclinical models (Johnston et al. (2014) Cancer Cell 26:1; WO2016/028656; US2016/0176963; US2016/0376365, all of which are incorporated herein by reference).

Thus, antagonistic antibodies specific for TIGIT that could inhibit TIGIT receptor activity represent an opportunity to decrease the immunosuppressive effect associated with tumour microenvironments and thereby increase antitumor immune response against tumour cells.

SUMMARY OF INVENTION

The present invention provides anti-TIGIT antibodies that can decrease the immunosuppressive effect of TIGIT-mediated signalling. In particular, antibodies or antigen binding fragments of the invention can inhibit TIGIT-mediated immunosuppression through prevention of ligand binding on T cells (conventional αβ T cells and non-conventional γδ T cells) and NK cells and/or depletion of TIGIT positive Treg cells, and/or by inducing internalisation of the TIGIT receptor.

In one aspect, the present invention provides an isolated antibody or antigen binding fragment thereof which binds to human TIGIT and which comprises a heavy chain variable domain comprising a heavy chain CDR1 (HCDR1), a heavy chain CDR2 (HCDR2), and a heavy chain CDR3 (HCDR3) selected from the HCDR1, HCDR2 and HCDR3 sequences shown in FIG. 1 and which further comprises a light chain variable domain comprising a light chain CDR1 (LCDR1), a light chain CDR2 (LCDR2), and a light chain CDR3 (LCDR3) selected from the LCDR1, LCDR2, and LCDR3 sequences shown in FIG. 2.

In certain embodiments the antibody or antigen binding fragment comprises a combination of HCDR1, HCDR2, HCDR3, LCDR1, LCDR2 and LCDR3, wherein the combination is selected from the group of combinations formed by the HCDRs from each antibody in FIG. 1 taken with the LCDRs from the corresponding antibody in FIG. 2.

In certain embodiments, an antibody or antigen binding fragment according the invention may comprise a heavy chain variable domain having an amino acid sequence selected from the group consisting of: SEQ ID Nos: 211, 213, 215, 217, 219, 221, 223, 225, 227, 229, 231, 233, 235, 237, 239, 327, 329, and 331 and amino acid sequences exhibiting at least 90%, 95%, 97%, 98% or 99% sequence identity thereto; and optionally comprise a light chain variable domain having an amino acid sequence selected from the group consisting of: the amino acid sequences of SEQ ID Nos: 212, 214, 216, 218, 220, 222, 224, 226, 228, 230, 232, 234, 236, 238, 240, 328, 330, and 332 and amino acid sequences exhibiting at least 90%, 95%, 97%, 98% or 99% sequence identity thereto.

In certain embodiments the antibody or antigen binding fragment comprises a combination of a heavy chain variable domain and a light chain variable domain, wherein the combination is selected from the group of combinations formed by the VH from each antibody in FIG. 5, or an amino acid sequence exhibiting at least 90%, 95%, 97%, 98% or 99% sequence identity thereto, taken with the VL from the same antibody in FIG. 5, or an amino acid sequence exhibiting at least 90%, 95%, 97%, 98% or 99% sequence identity thereto.

The most-preferred antibodies and antigen binding fragments provided herein are those based on the CDRs or complete variable domains of antibody 31282 provided herein.

As demonstrated herein, these preferred anti-TIGIT antibodies and antigen binding fragments based on antibody 31282 have particularly surprising and advantageous properties. These properties include: a higher affinity for TIGIT expressed on CD8 T cells (from healthy donors or from cancer patients) compared to each previously described anti-TIGIT antibody tested; a better $IC_{50}$ for competition with CD155/PVR compared to each previously described anti-TIGIT antibody tested; a better $EC_{50}$ in T cell activation assays compared to each previously described anti-TIGIT antibody tested; and potently increasing activity in T cells from cancer patient peripheral blood, and importantly in tumour infiltrating lymphocytes. Furthermore, it is surprisingly shown herein that antibodies and antigen binding fragments according to the invention, especially those based on antibody 31282, preferentially deplete Treg cells. That is, TIGIT-expressing Treg cells exposed to the provided anti-TIGIT antibodies undergo lysis to a greater proportion compared to conventional CD4 and CD8 T cells. This is surprising because conventional CD4 and CD8 T cells also express TIGIT, but do not undergo cell lysis to the same extent when contacted with the antibodies. It is further surprisingly shown that antibodies and antigen binding fragments according to the invention, especially those based on antibody 31282 not only promote conventional T cell pro-inflammatory activity, but also increase activity of non-conventional γδ T cells.

Thus, in certain preferred embodiments, provided herein is an antibody or antigen binding fragment comprising HCDR1, HCDR2, HCDR3, LCDR1, LCDR2, and LCDR3 wherein:
HCDR1 comprises or consists of SEQ ID NO: 16 (YTFT-SYYMH),
HCDR2 comprises or consists of SEQ ID NO: 17 (VIGPSGASTSYAQKFQG),
HCDR3 comprises or consists of SEQ ID NO: 18 (AR-DHSDYWSGIMEV),
LCDR1 comprises or consists of SEQ ID NO: 61 (RASQSVRSSYLA),
LCDR2 comprises or consists of SEQ ID NO: 62 (GASSRAT), and
LCDR3 comprises or consists of SEQ ID NO: 63 (QQYFSPPWT).

In certain such embodiments, the heavy chain variable domain comprises or consists of an amino acid sequence according to SEQ ID NO: 221 or an amino acid sequence exhibiting at least 90%, 95%, 97%, 98% or 99% sequence identity thereto, and the light chain variable domain comprises or consists of an amino acid sequence according to SEQ ID NO: 222 or an amino acid sequence exhibiting at least 90%, 95%, 97%, 98% or 99% sequence identity thereto.

In certain preferred embodiments the anti-TIGIT antibody is antibody 31282 described herein.

In a further aspect the invention provides an isolated antibody or antigen binding fragment thereof, which cross-competes for binding to human TIGIT with an antibody according to the first aspect of the invention, for example an antibody exemplified herein.

In a further aspect, the invention provides an isolated antibody or antigen binding fragment thereof, which binds to the same epitope as an antibody according to the first aspect of the invention, for example an antibody exemplified herein.

In a further aspect, the invention provides an antibody or antigen binding fragment thereof which binds to an epitope of human TIGIT comprising TIGIT residues Q56, and I109, optionally comprising residues Q56, N58 and I109. In preferred embodiments is provided an antibody or antigen binding fragment thereof which binds to an epitope of human TIGIT comprising TIGIT residues Q56, N58, E60, I68, L73, H76, and I109.

In certain embodiments, the antibody or antigen binding fragment thereof binds to an epitope of human TIGIT consisting of TIGIT residues Q56, N58, E60, I68, L73, H76, and I109.

In a further aspect, the invention provides an isolated antibody or antigen binding fragment thereof which binds to human TIGIT and which does not compete with CD155 for TIGIT binding.

In certain embodiments, the antibody or antigen binding fragment which binds to human TIGIT and which does not compete with CD155 for TIGIT binding comprises HCDR1, HCDR2, HCDR3, LCDR1, LCDR2, and LCDR3 wherein HCDR1 comprises or consists of SEQ ID NO: 280, HCDR2 comprises or consists of SEQ ID NO: 281, HCDR3 comprises or consists of SEQ ID NO: 282, and LCDR1 comprises or consists of SEQ ID NO: 292, LCDR2 comprises or consists of SEQ ID NO: 293, and LCDR3 comprises or consists of SEQ ID NO: 294.

In certain such embodiments, the heavy chain variable domain comprises or consists of the amino acid sequence shown as SEQ ID NO: 333 or an amino acid sequence exhibiting at least 90%, 95%, 97%, 98% or 99% sequence identity thereto, and the light chain variable domain comprises or consists of the amino acid sequence shown as SEQ ID NO: 334 or an amino acid sequence exhibiting at least 90%, 95%, 97%, 98% or 99% sequence identity thereto.

In certain preferred embodiments, the antibody which binds to human TIGIT and which does not compete with CD155 for TIGIT binding comprises a heavy chain variable domain and a light chain variable domain wherein HCDR1 comprises SEQ ID NO: 353, HCDR2 comprises SEQ ID NO: 354, HCDR3 comprises SEQ ID NO: 355, and LCDR1 comprises SEQ ID NO: 356, LCDR2 comprises SEQ ID NO: 357, and LCDR3 comprises SEQ ID NO: 358.

In certain such embodiments, the heavy chain variable domain may comprise the amino acid sequence shown as SEQ ID NO: 367 or an amino acid sequence exhibiting at least 90%, 95%, 97%, 98% or 99% sequence identity thereto, and the light chain variable domain may comprise the amino acid sequence shown as SEQ ID NO: 368 or an amino acid sequence exhibiting at least 90%, 95%, 97%, 98% or 99% sequence identity thereto.

In a further aspect, the invention provides an isolated anti-TIGIT antibody or antigen binding fragment thereof which preferentially depletes TIGIT-expressing Treg cells, optionally wherein the antibody or antigen binding fragment is an antibody or antigen binding fragment according to the first aspect of the invention, for example an antibody exemplified herein.

In a further aspect the invention provides an affinity variant of an antibody according to other aspects of the invention, for example an antibody exemplified herein.

In a further aspect the invention provides an isolated polynucleotide or combination of isolated polynucleotides encoding an antibody or antigen binding fragment according to any other aspect of the invention, for example an antibody exemplified herein.

In a further aspect the invention provides an isolated polynucleotide encoding a VH and/or a VL domain of an anti-TIGIT antibody, wherein the polynucleotide comprises one or more sequences selected from the group consisting of SEQ ID Nos: 241-270, 335-342 and 369-370.

In a further aspect the invention provides an expression vector comprising a polynucleotide or combination of polynucleotides according to the invention operably linked to regulatory sequences which permit expression of the antigen binding polypeptide in a host cell or cell-free expression system.

In a further aspect the invention provides a host cell or cell-free expression system containing an expression vector according to the invention.

In a further aspect the invention provides a method of producing a recombinant antibody or antigen binding fragment thereof which comprises culturing a host cell or cell free expression system according to the invention under conditions which permit expression of the antibody or antigen binding fragment and recovering the expressed antibody or antigen binding fragment.

In a further aspect the invention provides a pharmaceutical composition comprising an antibody or antigen binding fragment according to the invention, for example an antibody exemplified herein, and at least one pharmaceutically acceptable carrier or excipient.

In a further aspect the invention provides an antibody or antigen-binding fragment according to the invention or pharmaceutical composition according to the invention for use in therapy.

In a further aspect, the invention provides an antibody or antigen-binding fragment according to the invention (for example an antibody exemplified herein) or pharmaceutical composition according to the invention for use in a method of treating cancer.

In a further aspect the invention provides a method of treating cancer in a subject comprising administering an effective amount of an antibody or antigen-binding fragment according to the invention (for example an antibody exemplified herein) or pharmaceutical composition according to the invention to the subject, thereby treating the cancer.

In certain preferred embodiments, the method is a method of treating cancer selected from lung cancer, pancreatic cancer and T-cell lymphoma. In certain preferred embodiments, the cancer is hepatocellular carcinoma. In certain preferred embodiments, the cancer is pancreatic adenocarcinoma. In certain preferred embodiments, the cancer is lung carcinoma. In certain preferred embodiments, the cancer is Sezary Syndrome.

In a further aspect, the invention provides an antibody or antigen-binding fragment according to the invention (for example an antibody exemplified herein) or pharmaceutical composition according to the invention for use in a method of treating viral infection, optionally CMV infection.

In a further aspect is provided a method of treating viral infection in a subject comprising administering an effective amount of an antibody or antigen-binding fragment according to the invention or pharmaceutical composition according to the invention to the subject, thereby treating the viral infection. In preferred embodiments the viral infection is CMV infection.

In a further aspect is provided a method of promoting T cell activity comprising contacting a population of T cells with an antibody or antigen binding fragment according to the invention. In certain embodiments the method promotes αβ T cell activity. In certain embodiments the method promotes γδ T cell activity. In certain embodiments the method is performed in vitro. In certain embodiments the method is performed in vivo, for example in a human subject.

In certain embodiments is provided a method according to the invention, or an antibody or antigen-binding fragment or pharmaceutical composition for use in a method according to the invention, wherein the method further comprises administration of one or more additional therapeutic agents. In certain preferred embodiments, the one or more additional agents are selected from: a chemotherapeutic agent, an anti-PD1 antibody, an anti-PD-L1 antibody, an anti-41BB antibody, an anti-OX40 antibody, an anti-GITR antibody, and an anti-ICOS antibody.

In a further aspect is provided a combination comprising an anti-TIGIT antibody or antigen binding fragment thereof and one or more of a chemotherapeutic agent, an anti-PD1 antibody, an anti-PD-L1 antibody, an anti-41BB antibody, an anti-OX40 antibody, an anti-GITR antibody, and an anti-ICOS antibody. In a further aspect is provided a combination according to the invention for use in therapy. In a further aspect is provided a combination according to the invention for use in a method of treating cancer or for use in a method of treating viral infection. In a further aspect is provided a combination according to the invention for use in a method according to the invention. In a preferred embodiment the anti-TIGIT antibody or antigen binding fragment thereof is an antibody of the invention or an antigen binding fragment thereof.

In a further aspect is provided a composition or combination for reducing tumor volume. In some embodiments, the combination further comprises administration of one or more additional therapeutic agents. In certain preferred embodiments, the one or more additional agents are selected from: a chemotherapeutic agent, an anti-PD1 antibody, an anti-PD-L1 antibody, an anti-41BB antibody, an anti-OX40 antibody, an anti-GITR antibody, and an anti-ICOS antibody.

In a further aspect is provided a combination comprising an anti-TIGIT antibody or antigen binding fragment thereof according to the invention, and a chemotherapeutic agent. In preferred embodiments the chemotherapeutic agent is doxorubicin. In preferred embodiments, the combination further comprises an adenosine A2A receptor (A2AR) antagonist. In a further aspect the combination is provided for use in therapy. In a further aspect the combination is provided for use in treating cancer. In preferred embodiments the combination is for use in treating colon carcinoma.

In a further aspect is provided an anti-TIGIT antibody or antigen binding fragment thereof according to the invention for use in a method of treating cancer, wherein the method comprises administering the antibody in combination with a chemotherapeutic agent. In preferred embodiments, the method further comprises administering an A2AR antagonist, wherein the antibody or antigen binding fragment, the chemotherapeutic agent, and the A2AR antagonist are administered in combination. In preferred embodiments the cancer is colon carcinoma. In preferred embodiments the chemotherapeutic agent is doxorubicin. In all relevant aspects, it is preferred that any subject to be treated is a human subject. In all relevant aspects it is preferred that cells (e.g. T cells) contacted with antibodies according to the invention are human cells (e.g. human T cells).

Unless technically incompatible or indicated to the contrary, any preferred embodiment described can optionally be used in combination with one or more of all other preferred embodiments.

BRIEF DESCRIPTION OF FIGURES

FIG. 1 Table providing heavy chain variable domain (VH) complementarity determining region (CDR) sequences of antibodies of the invention FIG. 2 Table providing light chain variable domain (VL) CDR sequences of antibodies of the invention FIG. 3 Table providing heavy chain variable domain (VH) framework (FR) sequences of antibodies of the invention FIG. 4 Table providing light chain variable domain (VL) framework (FR) sequences of antibodies of the invention FIG. 5 Table providing heavy chain variable domain (VH) and light chain variable domain (VL) amino acid sequences of antibodies of the invention FIG. 6 Table providing sequences of polynucleotides encoding VH and VL domains of antibodies according to the invention FIG. 7 Graph showing the results of a competition assay between hCD155 and anti-TIGIT antibody for binding to Jurkat-hTIGIT FIG. 8 (A) Graph showing the proportion of TIGIT positive cells within specific T cell populations of PBMC from 7 healthy human donors. (B) Graph showing the proportion of TIGIT positive cells within different immune populations of PBMC from 7 healthy human donors.

FIG. 9 Graph showing the results of a binding assay of anti-TIGIT antibody on Jurkat-hTIGIT FIG. 10 (A and B) Graphs showing the results of a binding assay of anti-TIGIT antibody on primary CD8 T cells from human healthy PBMCs. (C) Graph showing the results of a binding assay of anti-TIGIT antibody on primary memory $CD8^+$ T cells and Treg from human healthy PBMCs FIG. 11 Graphs showing the results of a binding assay of anti-TIGIT antibody on primary $CD8^+$ T cells from cynomolgus healthy PBMCs FIG. 12 Graphs showing the effect of anti-TIGIT antibodies in a CHO-TCR-CD155 and Jurkat-hTIGIT Bioassay FIG. 13 Graphs showing the effect of anti-TIGIT antibodies to increase IFNg secretion in a functional assay on human primary CD8 T cells from healthy donors activated with CHO-TCR-CD155 cells FIG. 14 Histogram plots showing the effect of anti-TIGIT antibody to increase IFNg secretion in a functional assay on human primary $CD8^+$ TILs from an ovarian ascites activated with CHO-TCR-CD155 cells FIG. 15 (A) Graph showing the results of a competition assay between mouse CD155 and anti-TIGIT antibody for binding to Jurkat-mTIGIT. (B) Graph showing the effect of anti-TIGIT antibody to increase IFNg secretion in a functional assay on mouse OT-1 T cells. (C) Graph showing the effect of anti-TIGIT antibody to increase cytotoxicity in a functional assay on mouse OT-1 T cells.

FIG. 16 (A) Graph showing the anti-tumor efficacy of anti-TIGIT antibody in monotherapy in a CT26 tumor model. (B and C) Graphs showing the anti-tumor efficacy of anti-TIGIT antibody in combination with anti-PD1 in a CT26 tumor model.

FIG. 17 (A) Graph showing the isotype dependant anti-tumor efficacy of anti-TIGIT antibody in monotherapy in a CT26 tumor model. (B) Graph showing the isotype dependant anti-tumor efficacy of anti-TIGIT antibody in combination with anti-PD1 in a CT26 tumor model.

FIG. 18 (A and G) Graphs showing the modulation of proportion of Treg cell within total $CD4^+$ T cell population in CT26 tumor treated with anti-TIGIT antibody in monotherapy or combination with anti-PD1. (B and H) Graphs showing the modulation of proportion of $CD8^+$ T cell within total $CD45^+$ population in CT26 tumor treated with anti-TIGIT antibody in monotherapy or combination with anti-PD1. (C and I) Graphs showing the modulation of $CD8^+$/Treg T cell ratio in CT26 tumor treated with anti-TIGIT antibody in monotherapy or combination with anti-PD1. (D and J) Graph showing the modulation of IFNg secreting $CD4^+$ T cells in CT26 tumor treated with anti-TIGIT antibody in monotherapy or combination with anti-PD1. (E) Graph showing the modulation of IFNg secreting $CD8^+$ T cells in CT26 tumor treated with anti-TIGIT antibody. (L and F) Graphs showing the ratio of IFNg/IL-10 secreting $CD4^+$ T cells in CT26 tumor treated with anti-TIGIT antibody in monotherapy or combination with anti-PD1. (K) Graph showing the modulation of IL-10 secreting $CD4^+$ T cells in CT26 tumor treated by anti-TIGIT antibody in combination with anti-PD1 antibody.

FIG. 19 (A) Volcano plot showing the effect of anti-TIGIT antibody treatment to modulate gene expression in CT26 tumor and measured by NanoString analysis. (B) Box plot showing the modulation of cytotoxic score in CT26 tumor treated with anti-TIGIT antibody in monotherapy or combination with anti-PD1. (C) Box plot showing the modulation of $CD8^+$ T cell score in CT26 tumor treated with anti-TIGIT antibody in monotherapy or combination with anti-PD1

FIG. 20 (A) Histogram plots showing the proportion of $TIGIT^+$ $CD4^+$, $CD8^+$ T cell and Treg populations in PBMC from human healthy volunteers. (B) Graph showing the in vitro cytotoxicity effect of anti-TIGIT antibody on conventional $CD4^+$, $CD8^+$ T cell and Treg populations in PBMC from human healthy volunteers.

FIG. 21 Graph showing the ex-vivo cytotoxicity effect of anti-TIGIT antibody on conventional $CD4^+$, $CD8^+$ T cell and Treg populations in CT26 tumour.

FIG. 22 (A) Graph showing the results of a binding assay of anti-TIGIT antibody clones on Jurkat-hTIGIT cells. (B) Graph showing the results of a binding assay of anti-TIGIT antibody clones on primary $CD8^+$ T cells from healthy human PBMCs. (C) Graph showing the results of a binding assay of anti-TIGIT antibody clones on primary $CD8^+$ T cells from cancer patients PBMCs.

Frequency of TIGIT expression on immune populations from cancer patient PBMC and TILs. (B) Absolute quantification of TIGIT expression on immune populations from cancer patient PBMC and TILs.

Figure 27:
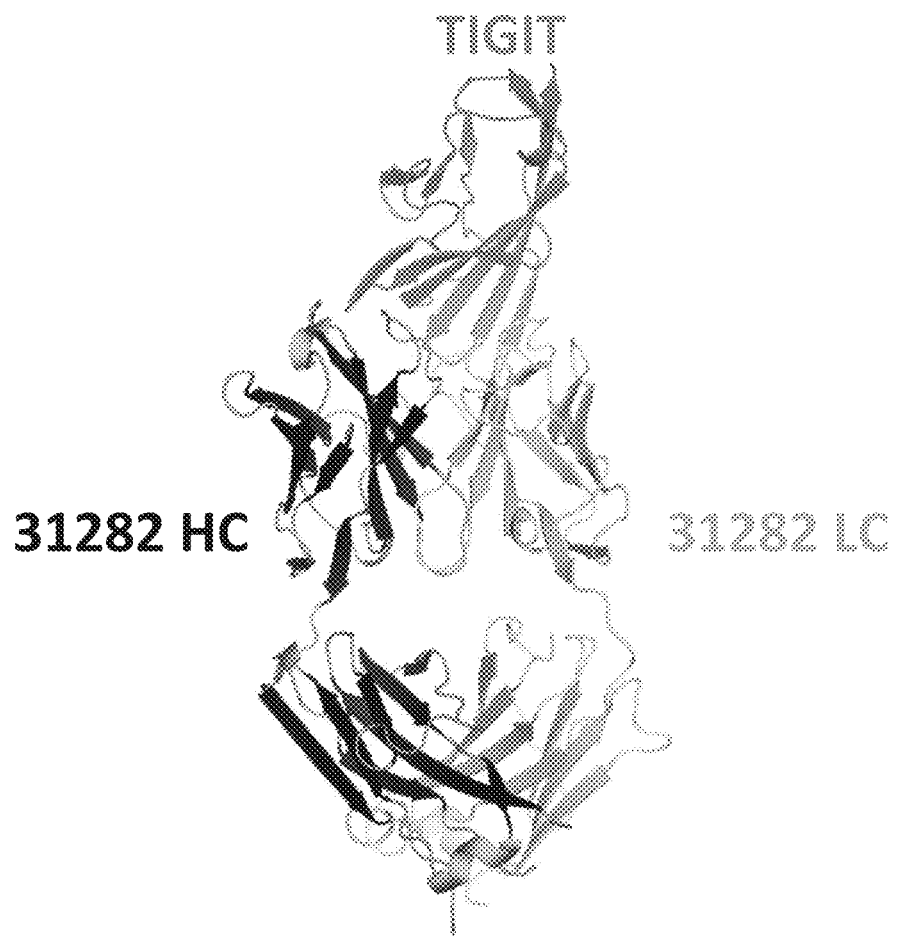
Figure 27:
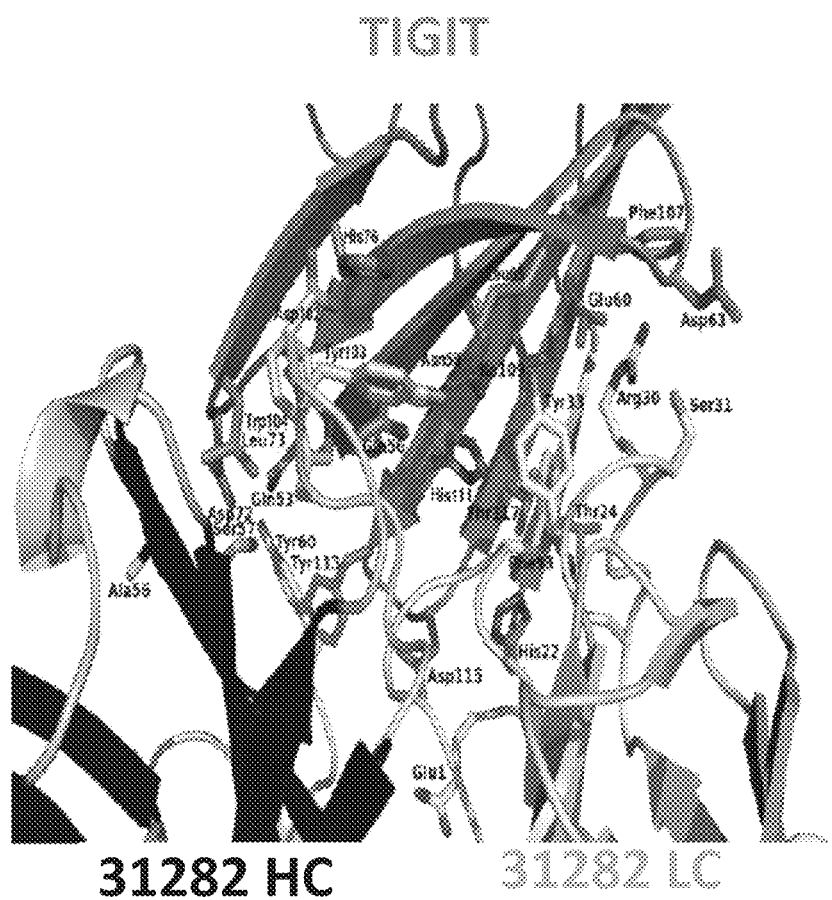
Figure 27:
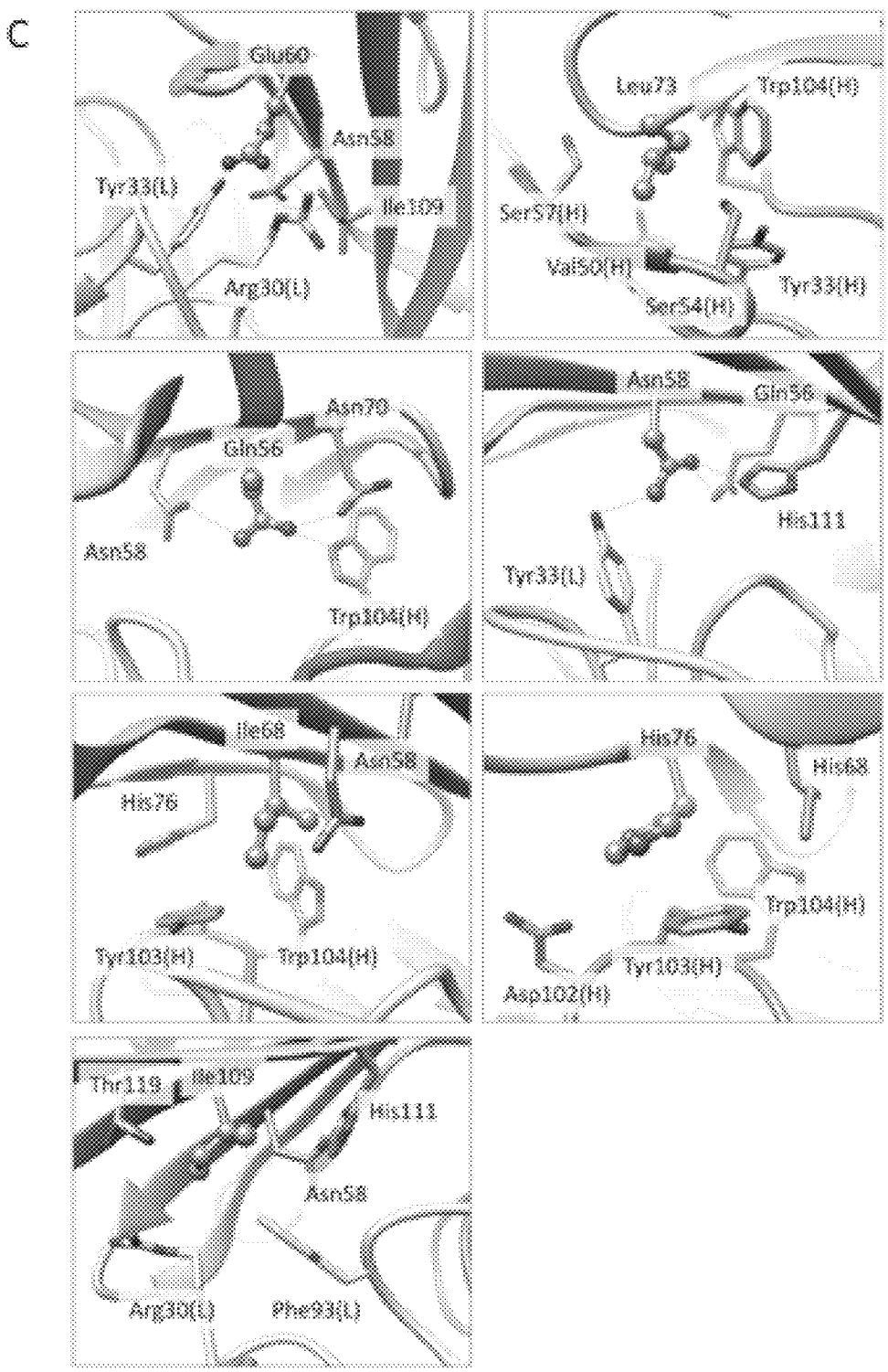

FIG. 27 (A) Structure of the Fab:TIGIT complex shown as ribbon diagram; (B) Full binding interface between clone 31282 and TIGIT; (C) Binding interface between clone 31282 and TIGIT showing contacted residues.

Figure 28:
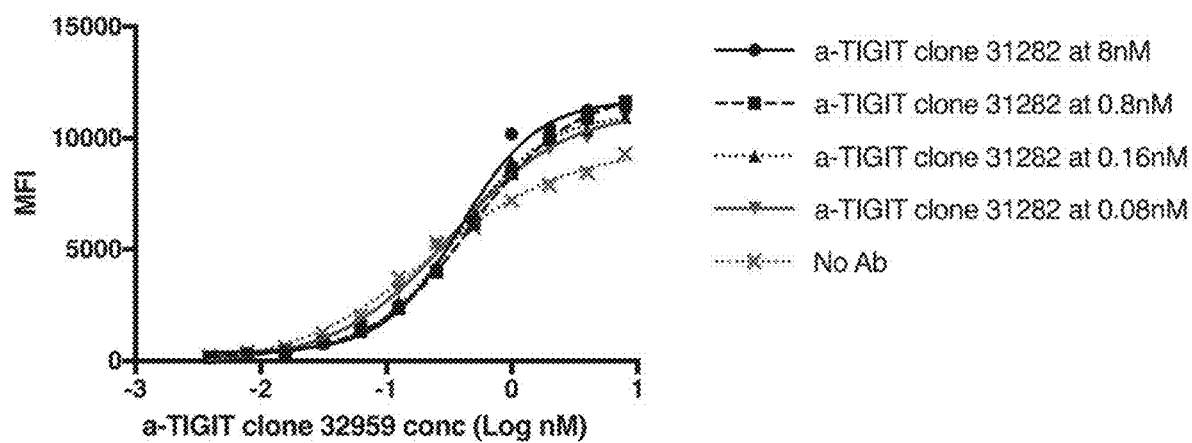

FIG. 28 Competition assay between anti-TIGIT clones 31282 and 32959.

Figure 29:
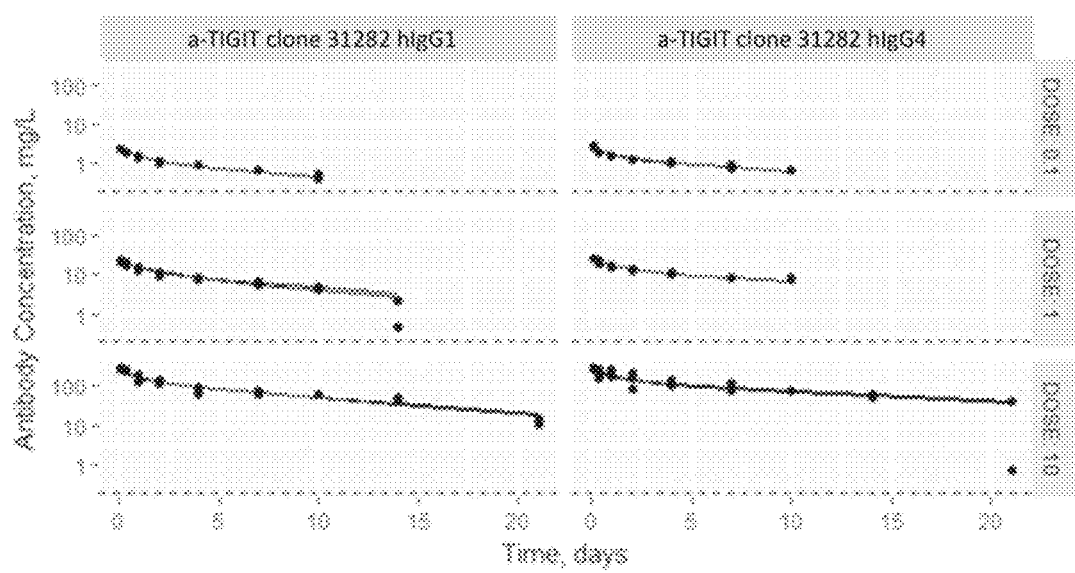

FIG. 29 Measure of plasma concentration of anti-TIGIT clone 31282 after i.v. injection of a single dose at 0.1 mg/kg (top row), 1 mg/kg (middle row) or 10 mg/kg (bottom row) in Cynomolgus monkey. Left column: 31282 IgG1; right column 31282 IgG4.

FIG. 30 Graph showing the characterization of TIGIT expression on malignant and normal $CD4^+$ T cell populations from patient with Sezary Syndrome. (A) Gating strategy to separate malignant and normal $CD4^+$ T cells. (B) MFI for TIGIT staining on the 2 distinct populations.

Figure 31:
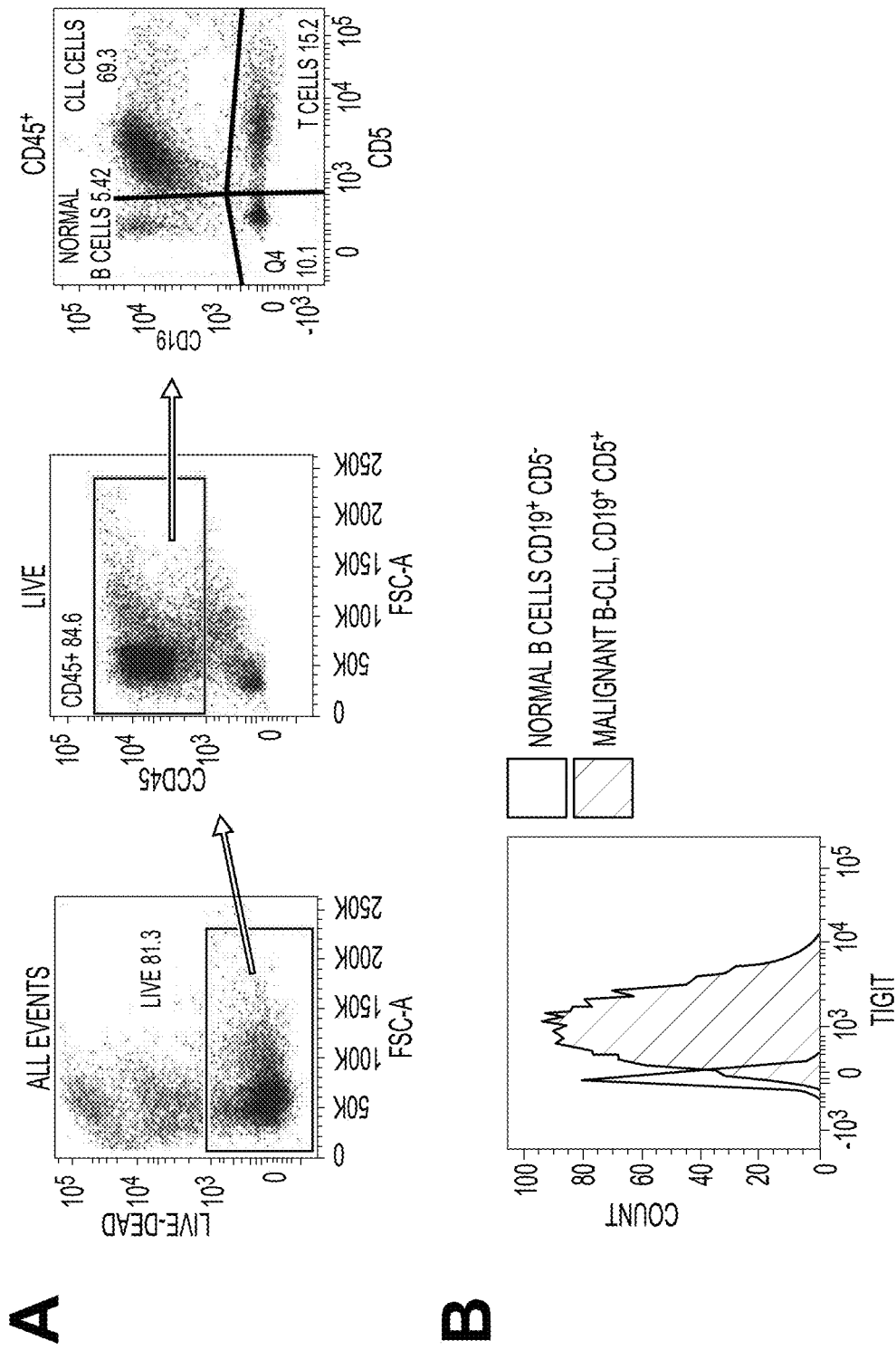

FIG. 31 Graph showing the characterization of TIGIT expression on malignant and normal B cell populations from patient with CLL. (A) Gating strategy to separate malignant and normal B cells. (B) MFI for TIGIT staining on the 2 distinct populations.

FIG. 32 (A-C) Graph showing the tumor growth curves in mice inoculated with EL4-mTIGIT tumors. (A) Median tumor growth curves. (B) Individual tumor growth curves in mice treated with hIgG1 isotype control antibody. (C) Individual tumor growth curves in mice treated with mouse surrogate antagonist a-TIGIT antibody (hIgG1). (D-F) Graph showing the tumor growth curves in mice inoculated with EL4-GFP tumors. (D) Median tumor growth curves. (E) Individual tumor growth curves in mice treated with hIgG1 isotype control antibody. (F) Individual tumor growth curves in mice treated with surrogate antagonist a-TIGIT (hIgG1).

Figure 33:
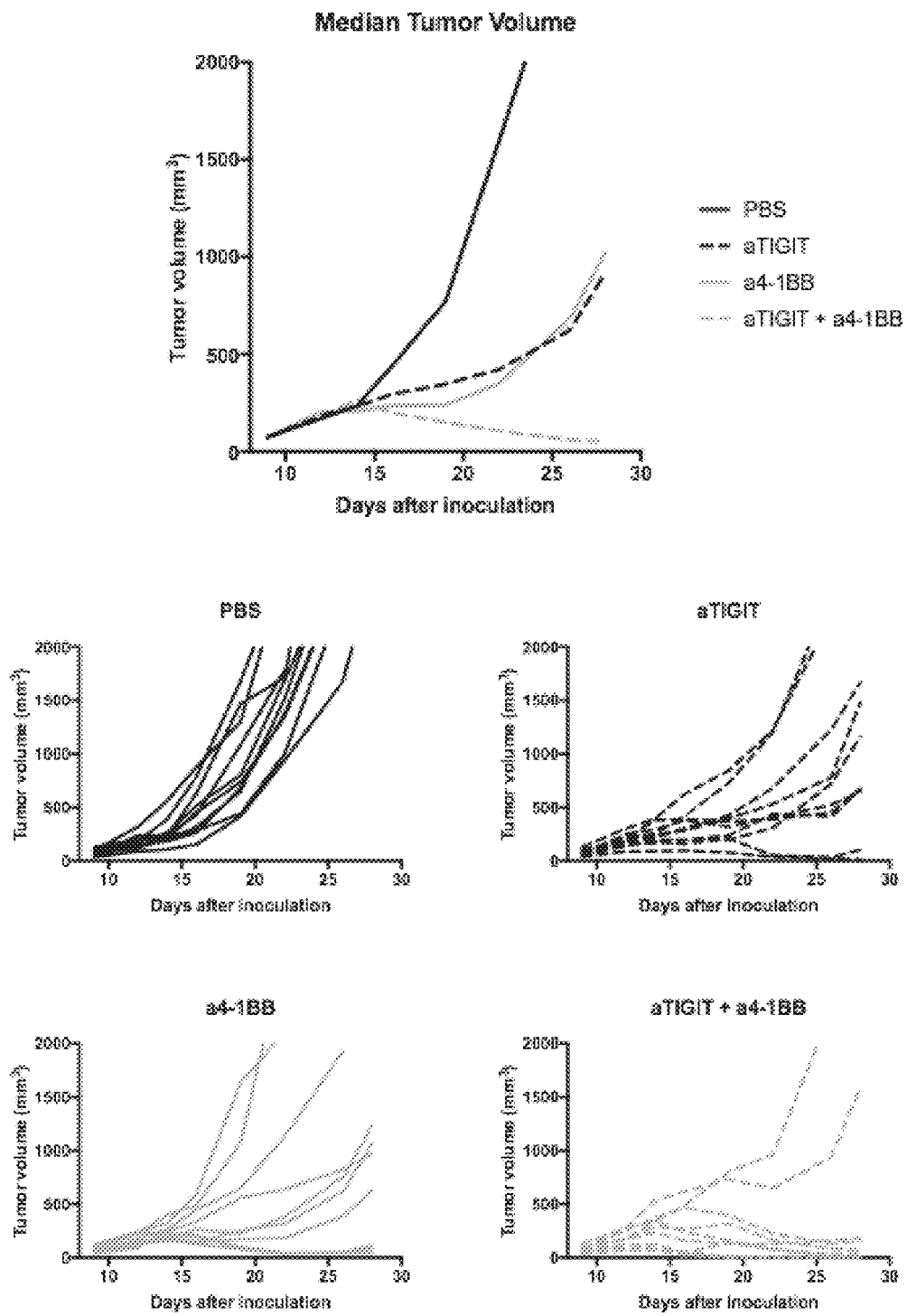
Figure 33:
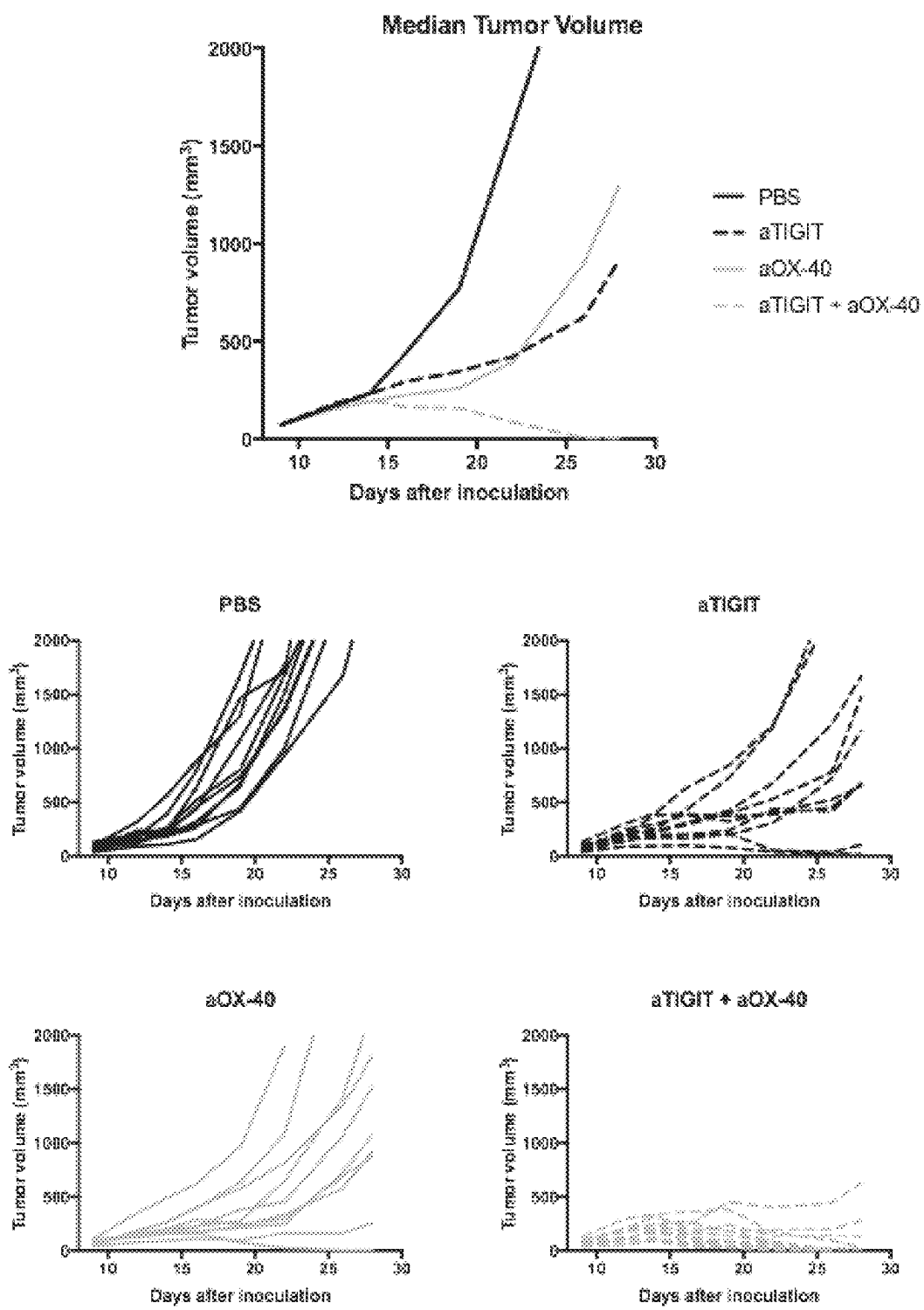
Figure 33:
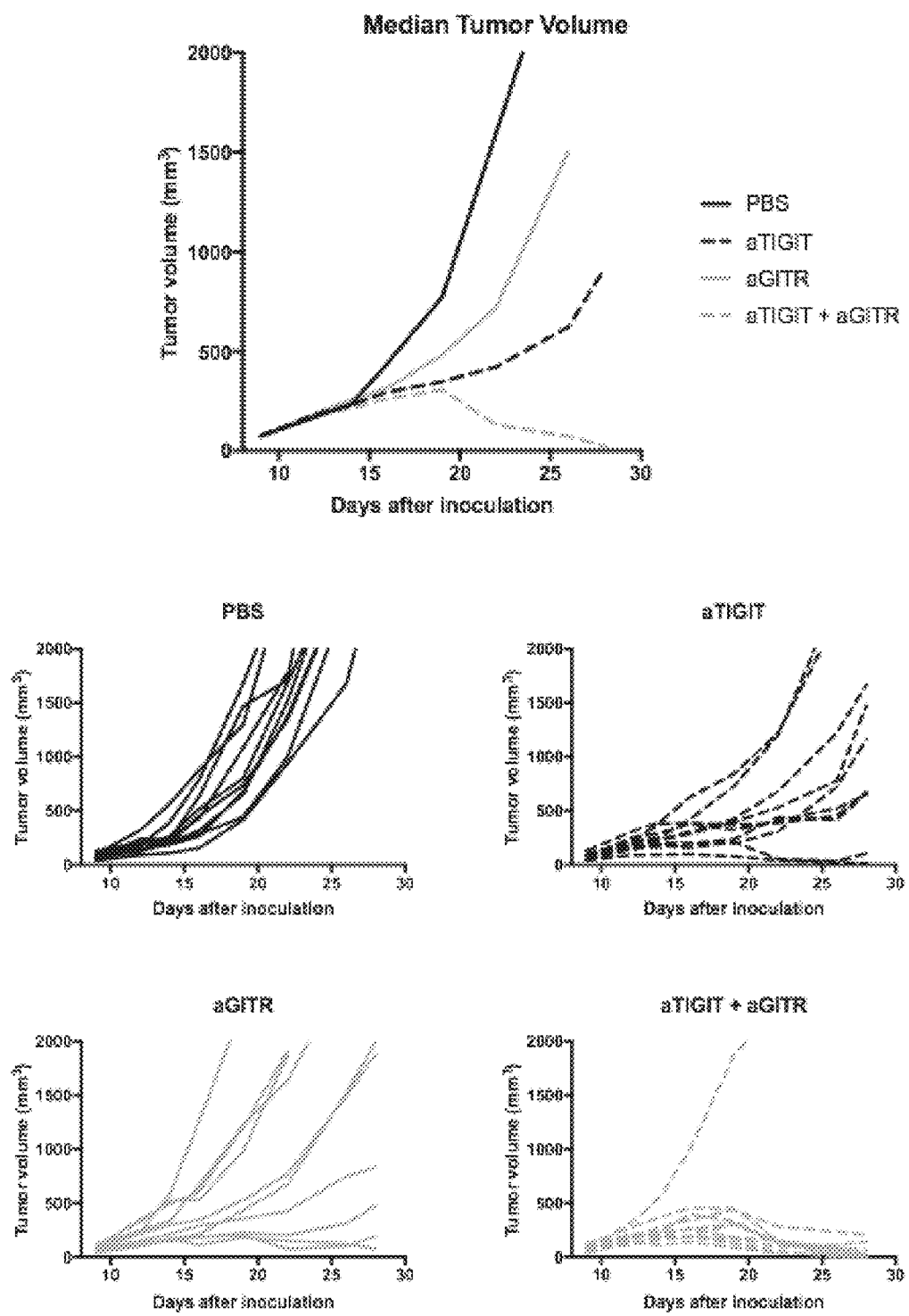
Figure 33:
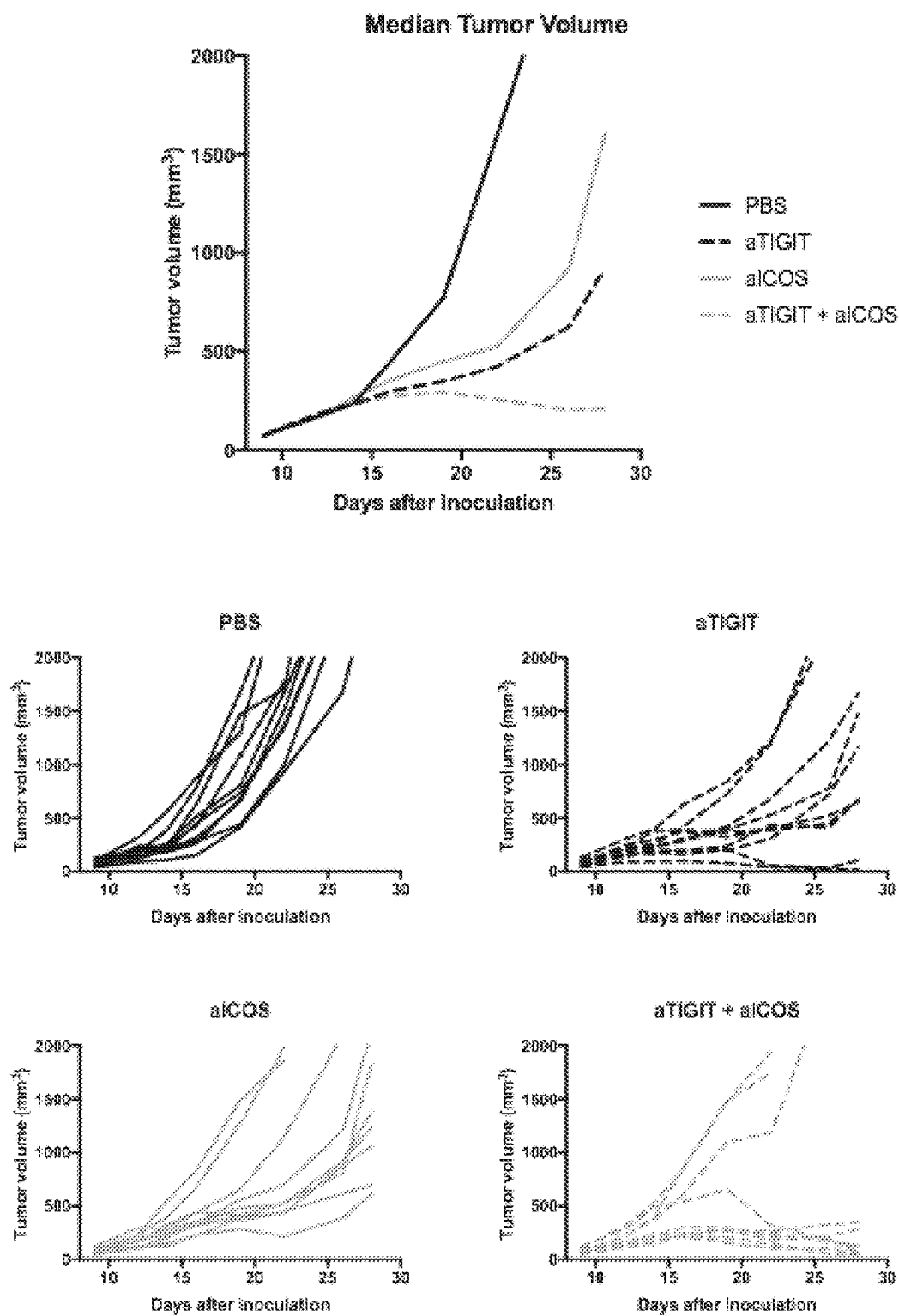

FIG. 33 (A-D) Graphs showing the tumor growth curves in mice inoculated with CT26 tumors. (A) Median and individual tumor growth curves for mice treated with anti-TIGIT and anti-4-1 BB antibodies. (B) Median and individual tumor growth curves for mice treated with anti-TIGIT and anti-OX-40 antibodies. (C) Median and individual tumor growth curves for mice treated with anti-TIGIT and anti-GITR antibodies. (D) Median and individual tumor growth curves for mice treated with anti-TIGIT and anti-ICOS antibodies.

FIG. 34 Graphs showing the effect of anti-TIGIT antibodies on γδ T cells. (A) Median proportion of TIGIT positive cells and TIGIT MFI signal within $Vδ2^-$ γδ T cell populations of PBMC from CMV positive and negative human donors. (B) Graph showing the activity of anti-TIGIT Ab to increase IFNg secretion in a functional assay on isolated human primary $Vδ1^+$ γδ T cells. (C) Graph showing the activity of anti-TIGIT Ab to increase IFNg secretion in a functional assay on total PBMC.

Figure 35:
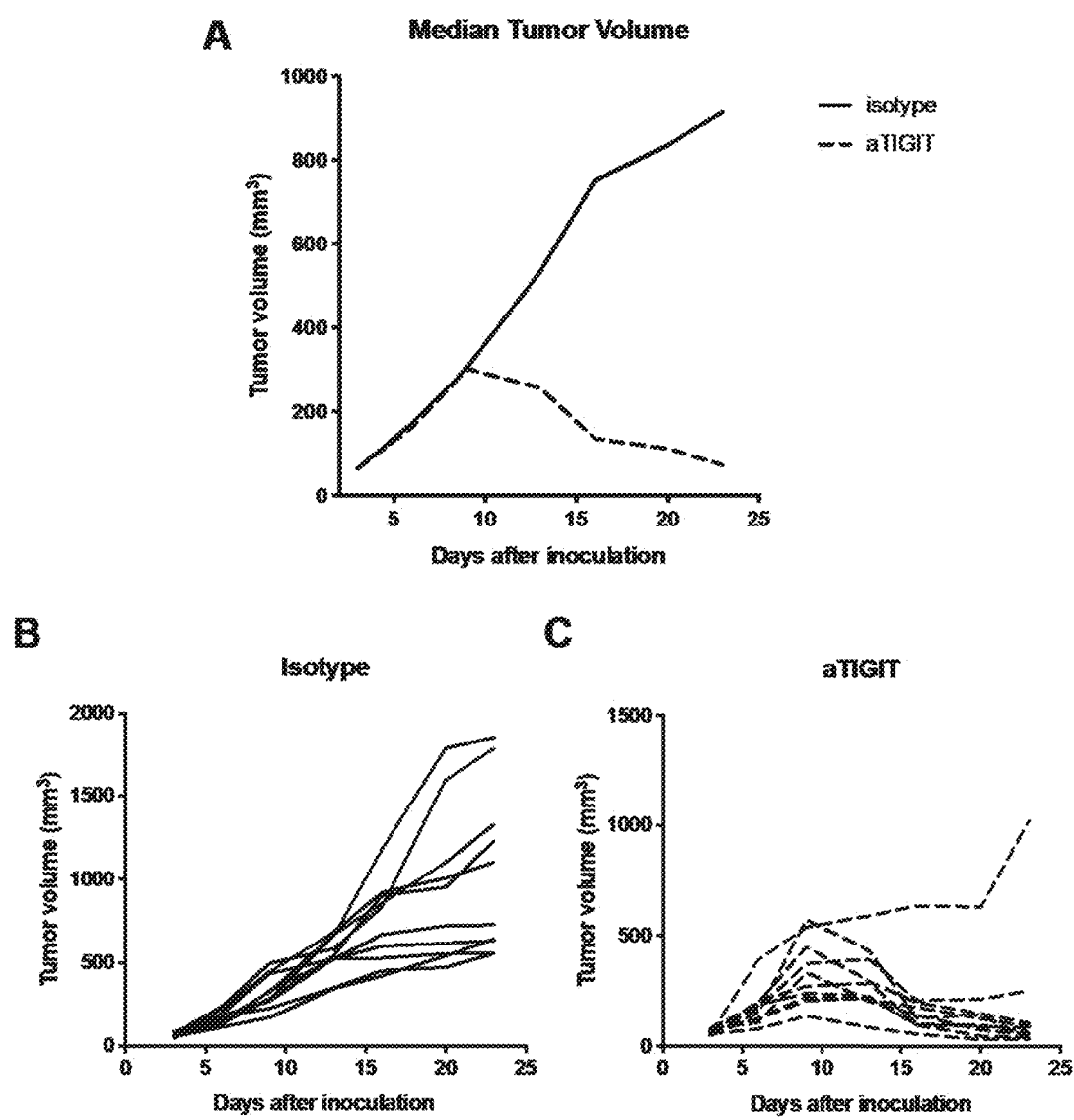

FIG. 35 Graph showing the anti-tumor efficacy of a-TIGIT mAb in monotherapy in a hepatocellular carcinoma mouse model. Data are represented as (A) Median tumor growth and (B) individual curves.

FIG. 36 Graph showing the anti-tumor efficacy of a-TIGIT mAb in monotherapy and in combination with a-4-1BB mAb in a s.c. pancreatic adenocarcinoma mouse model. Data are represented as (A) Median tumor growth and (B) individual curves.

Figure 37:
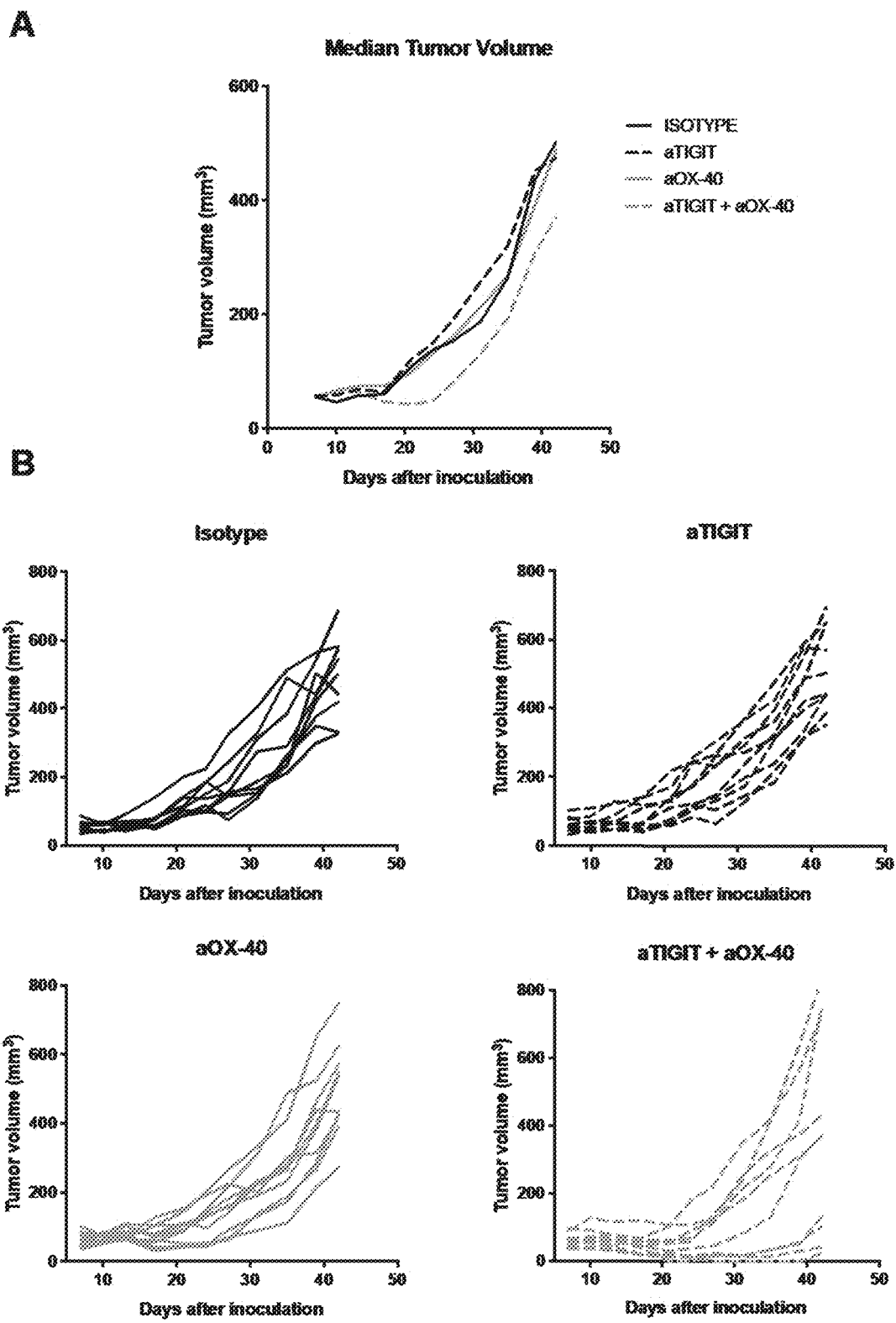

FIG. 37 Graph showing the anti-tumor efficacy of a-TIGIT mAb in monotherapy and in combination with a-OX40 mAb in a s.c. pancreatic adenocarcinoma mouse model. Data are represented as (A) Median tumor growth and (B) individual curves.

Figure 38:
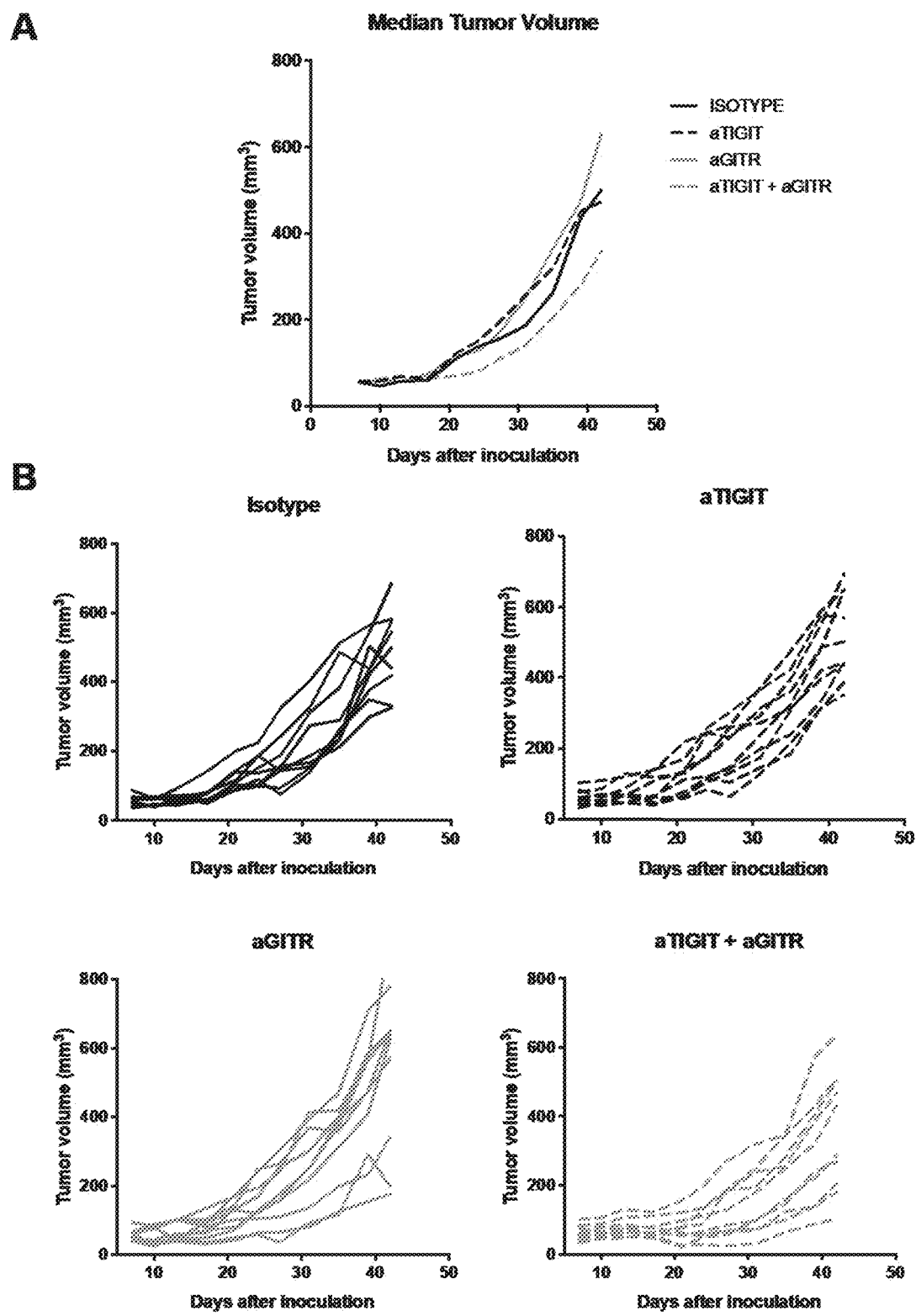

FIG. 38 Graph showing the anti-tumor efficacy of a-TIGIT mAb in monotherapy and in combination with a-GITR mAb in a s.c. pancreatic adenocarcinoma mouse model. Data are represented as (A) Median tumor growth and (B) individual curves.

Figure 39:
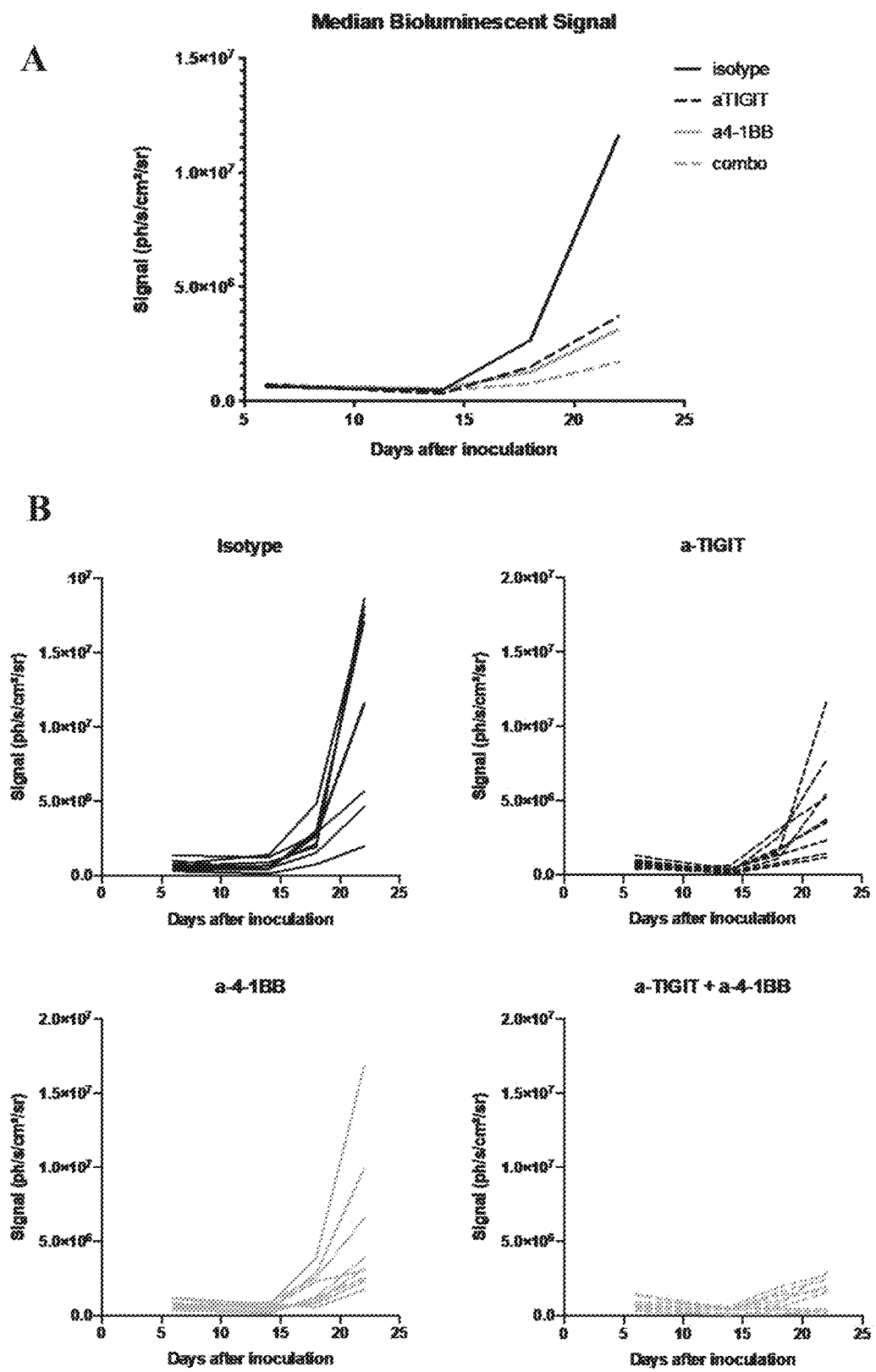
Figure 39:
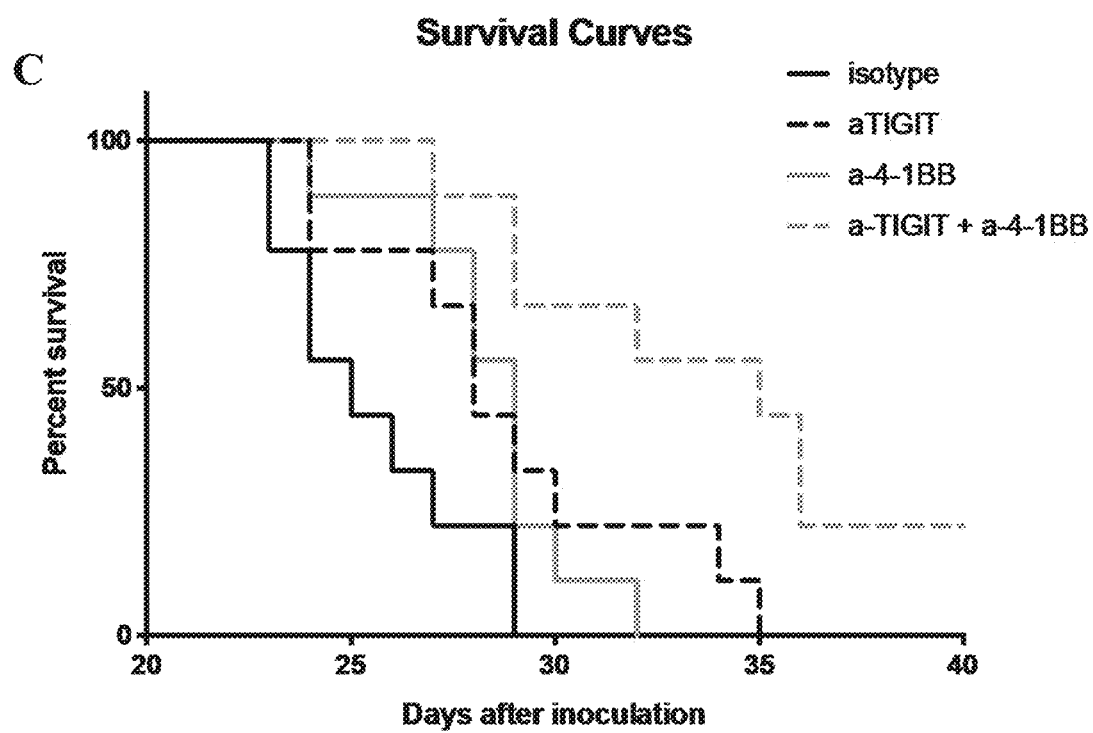

FIG. 39 Graph showing the anti-tumor efficacy of a-TIGIT mAb in monotherapy and in combination with a-4-1BB mAb in an orthotopic pancreatic adenocarcinoma mouse model. Data are represented as (A) Median bioluminescent signal, (B) individual curves and (C) survival curves.

FIG. 40 Graph showing the anti-tumor efficacy of a-TIGIT mAb in monotherapy in a humanized lung tumor model. A) Histogram plots showing the expression of CD155, CD112 and CD113 by human A549 lung tumor cell line. The effect of a-TIGIT mAb on tumor growth is shown as (A) Median tumor growth and (B) individual curves FIG. 41 Graph showing the activity of a-TIGIT mAb to increase IFNγ secretion by γδ T cells in a functional assay performed on total PBMC.

Figure 42:
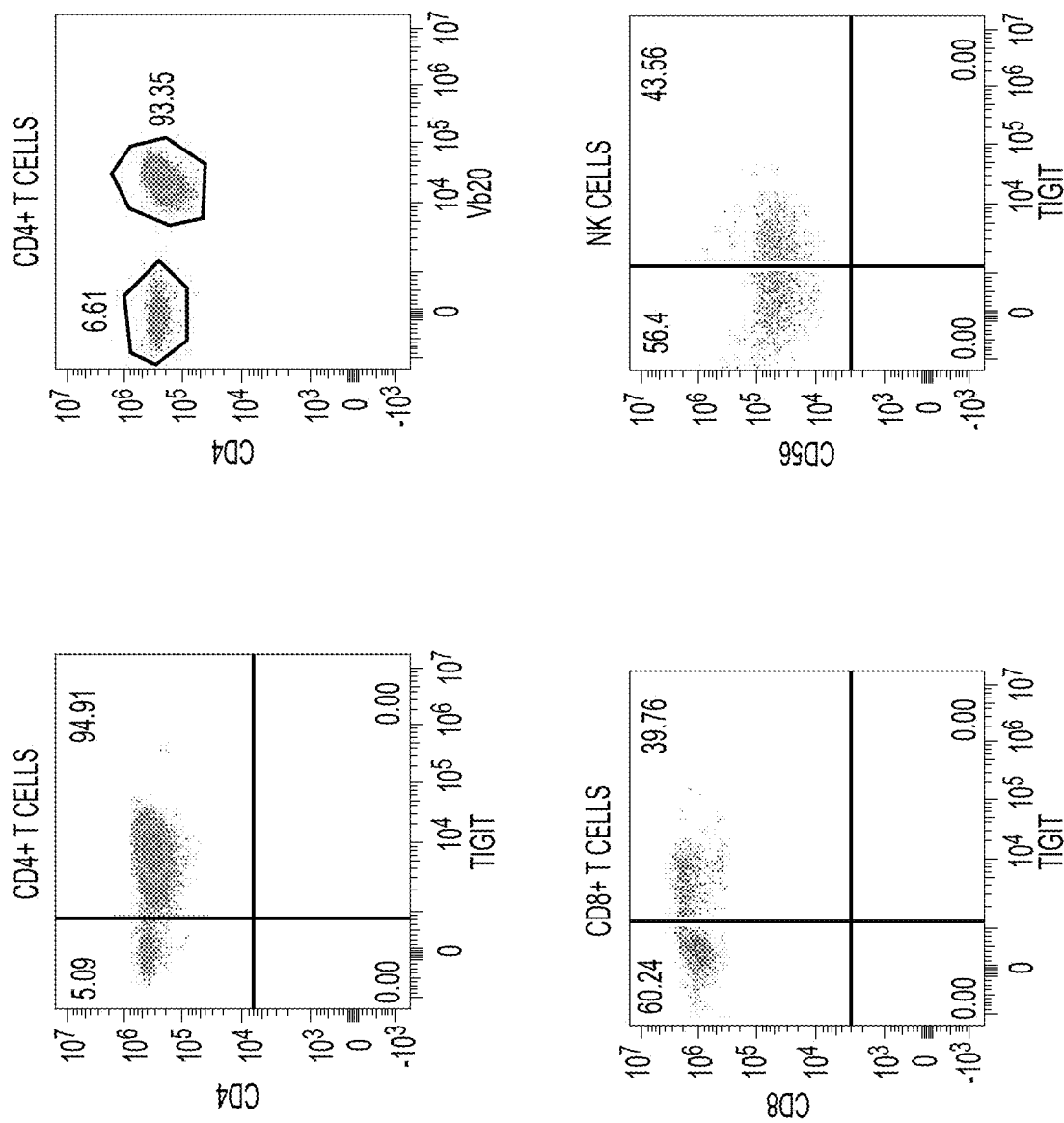
Figure 42:
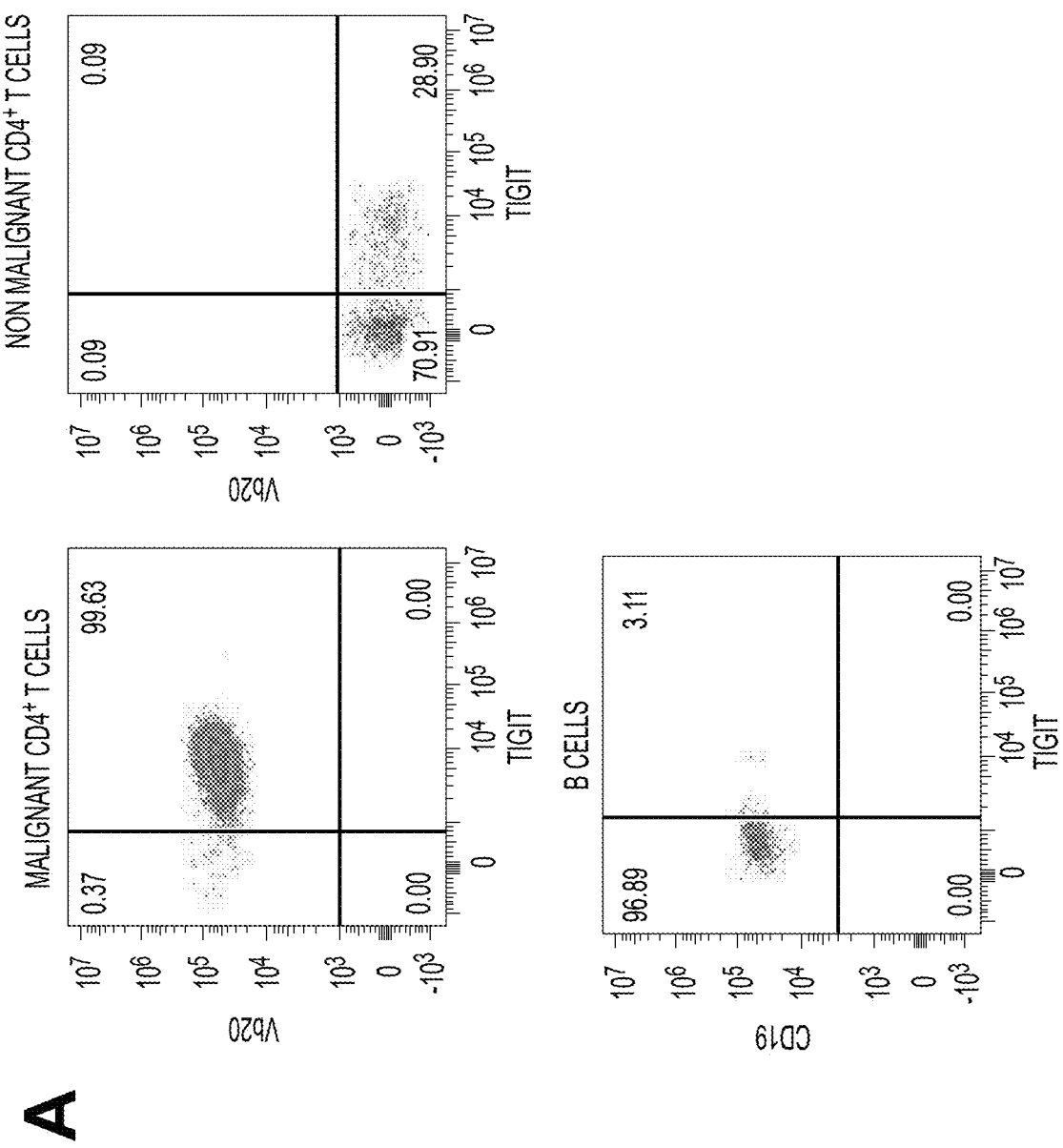

FIG. 42 Graph showing the in vitro cytotoxicity activity of a-TIGIT mAb in patient with Sezary Syndrome. (A) Gating strategy to separate malignant and normal $CD4^+$ T cells. (B) In vitro cytotoxicity activity of a-TIGIT mAb on malignant $CD4^+$, non-malignant $CD4^+$ and NK populations in PBMC from patient with Sezary Syndrome.

Figure 43:
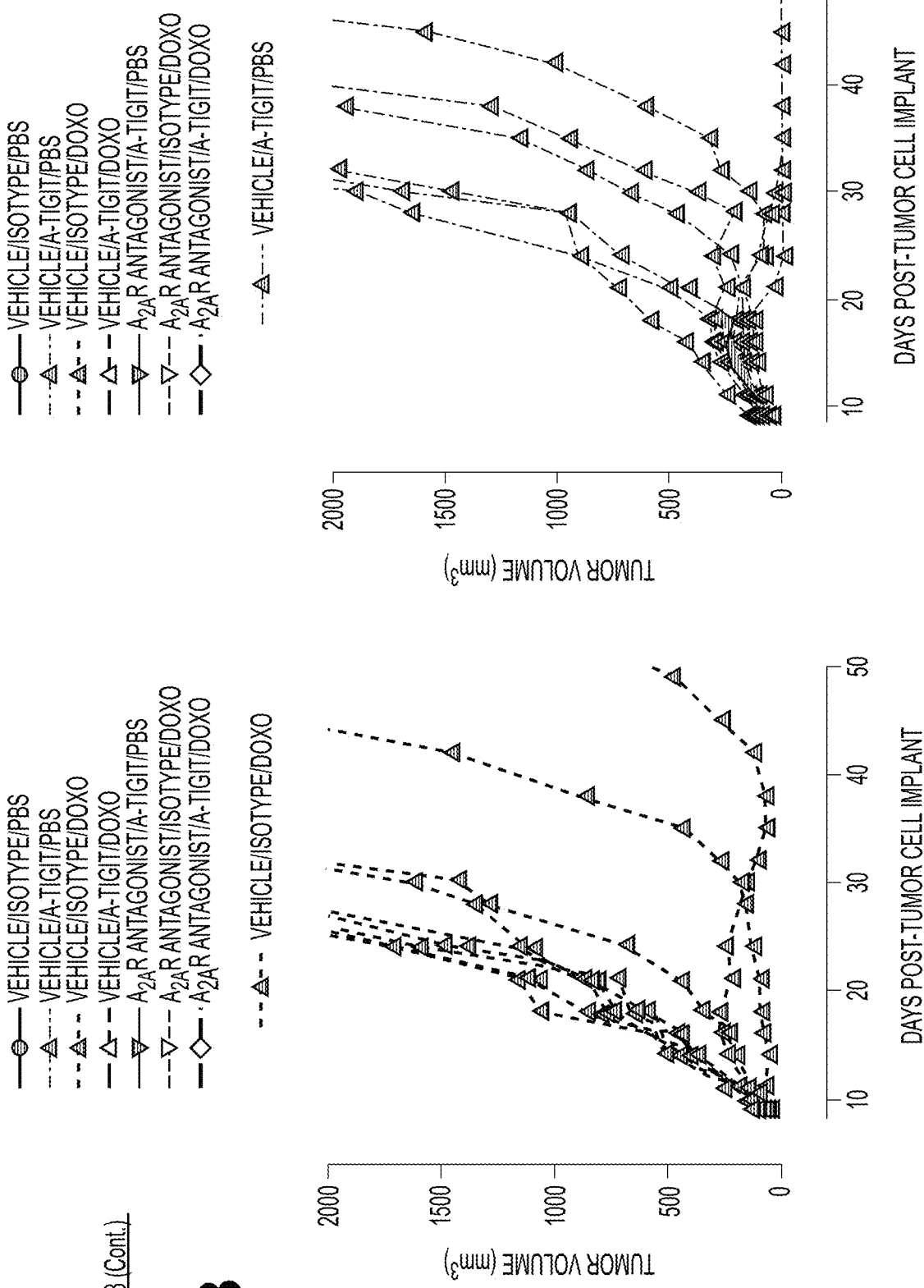
Figure 43:
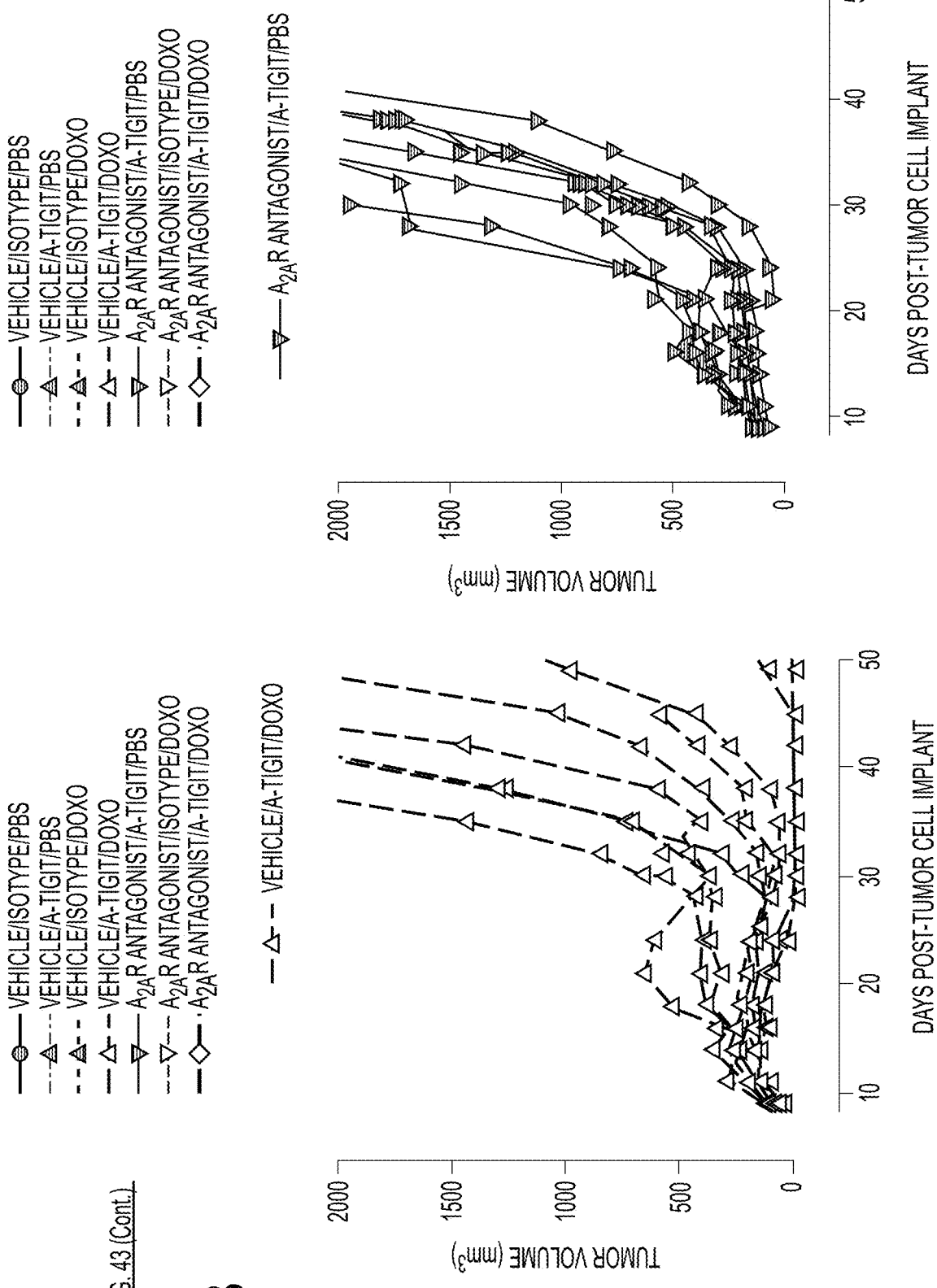

FIG. 43 Graphs showing the tumour growth curves in mice inoculated with CT26 tumours. (A) Median tumour growth curves for mice treated with anti-TIGIT, $A_{2A}R$ antagonist and/or doxorubicin. (B) Individual tumour growth curves for each treatment group.

Figure 44:
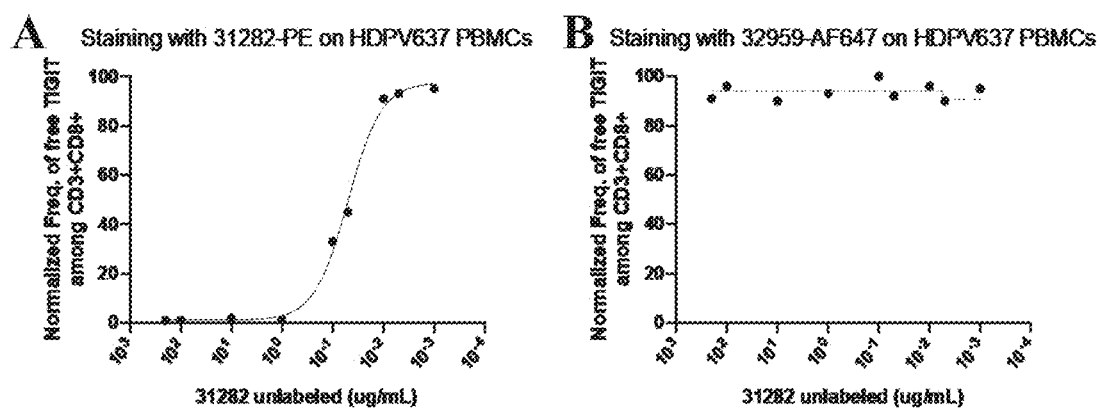

FIG. 44 Detection of $TIGIT^+$ population using clone 31282-PE or 32959-AF647 on cells previously incubated with a-TIGIT clone 31282. (A) Graph showing the normalized frequency of $TIGIT^+$ cells after incubation with a-TIGIT clone 31282 and detection with clone 31282-PE. (B) Graph showing the normalized frequency of $TIGIT^+$ cells after incubation with a-TIGIT clone 31282 and detection with clone 32959-AF647.

Figure 45:
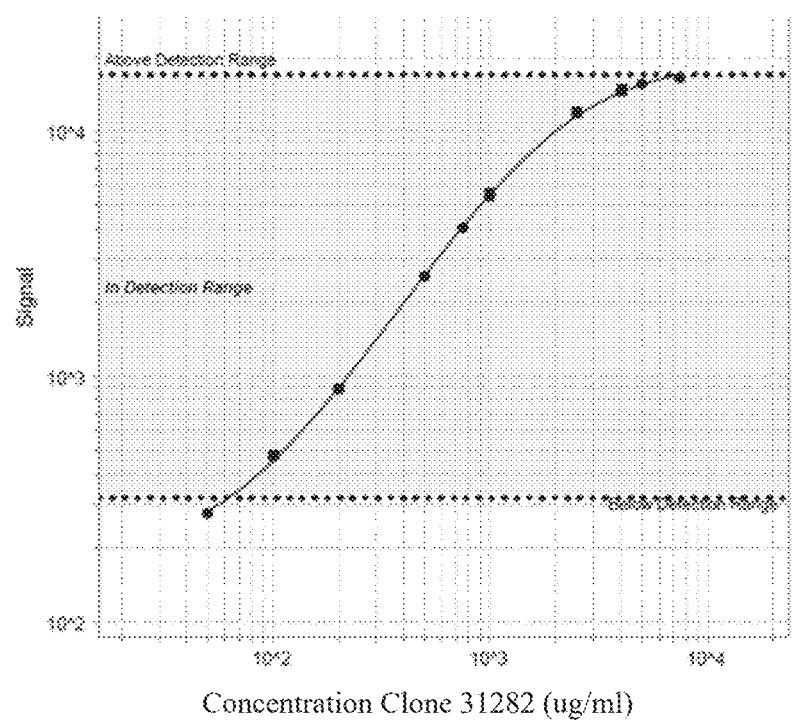

FIG. 45 Graph represents human serum samples spiked with different dilutions of clone 31282 and tested using the MSD ELISA developed with the anti-idiotypic antibody 32869. The light signal emitted is proportional to the concentration of clone 31282 in the serum samples.

DETAILED DESCRIPTION OF INVENTION

As used herein, the term "immunoglobulin" includes a polypeptide having a combination of two heavy and two light chains whether or not it possesses any relevant specific immunoreactivity. "Antibodies" refers to such assemblies which have significant known specific immunoreactive activity to an antigen of interest (e.g. TIGIT). The term "TIGIT antibodies" or "anti-TIGIT antibodies" are used herein to refer to antibodies which exhibit immunological specificity for TIGIT protein. Antibodies and immunoglobulins comprise light and heavy chains, with or without an interchain covalent linkage between them. Basic immunoglobulin structures in vertebrate systems are relatively well understood.

The generic term "immunoglobulin" comprises five distinct classes of antibody that can be distinguished biochemically. Although all five classes of antibodies are within the scope of the present invention, the following discussion will generally be directed to the IgG class of immunoglobulin molecules. With regard to IgG, immunoglobulins comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

The light chains of an antibody are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated by B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA, IgD or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernible to the skilled artisan in view of the instant disclosure and, accordingly, are within the scope of the instant invention.

As indicated above, the variable region of an antibody allows the antibody to selectively recognize and specifically bind epitopes on antigens. That is, the VL domain and VH domain of an antibody combine to form the variable region that defines a three dimensional antigen binding site. This quaternary antibody structure forms the antigen binding site present at the end of each arm of the Y. More specifically, the antigen binding site is defined by three complementary determining regions (CDRs) on each of the VH and VL chains.

As used herein, the terms "TIGIT protein" or "TIGIT antigen" or "TIGIT" are used interchangeably and refer to the human T-cell immunoreceptor (GenBank accession number: NM_173799) that binds the poliovirus receptor (PVR—also known as CD155). TIGIT is also known as VSIG9, VSTM3, or WUCAM. Reference to TIGIT includes the native human TIGIT protein naturally expressed in the human host and/or on the surface of human cultured cell lines, as well as recombinant forms and fragments thereof and also naturally occurring mutant forms.

As used herein, the term "binding site" comprises a region of a polypeptide which is responsible for selectively binding to a target antigen of interest (e.g. TIGIT). Binding domains comprise at least one binding site. Exemplary binding domains include an antibody variable domain. The antibody molecules of the invention may comprise a single binding site or multiple (e.g., two, three or four) binding sites.

As used herein the term "derived from" a designated protein (e.g. a TIGIT antibody or antigen-binding fragment thereof) refers to the origin of the polypeptide. In one embodiment, the polypeptide or amino acid sequence which is derived from a particular starting polypeptide is a CDR sequence or sequence related thereto. In one embodiment, the amino acid sequence which is derived from a particular starting polypeptide is not contiguous. For example, in one embodiment, one, two, three, four, five, or six CDRs are derived from a starting antibody. In one embodiment, the polypeptide or amino acid sequence which is derived from a particular starting polypeptide or amino acid sequence has an amino acid sequence that is essentially identical to that of the starting sequence, or a portion thereof wherein the portion consists of at least 3-5 amino acids, at least 5-10 amino acids, at least 10-20 amino acids, at least 20-30 amino acids, or at least 30-50 amino acids, or which is otherwise identifiable to one of ordinary skill in the art as having its origin in the starting sequence. In one embodiment, the one or more CDR sequences derived from the starting antibody are altered to produce variant CDR sequences, e.g. affinity variants, wherein the variant CDR sequences maintain TIGIT binding activity.

As used herein, a "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide may be replaced with another amino acid residue from the same side chain family. In another embodiment, a string of amino acids can be replaced with a structurally similar string that differs in order and/or composition of side chain family members.

As used herein, the term "heavy chain portion" includes amino acid sequences derived from the constant domains of an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. In one embodiment, an antibody or antigen binding fragment of the invention may comprise the Fc portion of an immunoglobulin heavy chain (e.g., a hinge portion, a CH2 domain, and a CH3 domain). In another embodiment, an antibody or antigen binding fragment of the invention may lack at least a portion of a constant domain (e.g., all or part of a CH2 domain). In certain embodiments, at least one, and preferably all, of the constant domains are derived from a human immunoglobulin heavy chain. For example, in one preferred embodiment, the heavy chain portion comprises a fully human hinge domain. In other preferred embodiments, the heavy chain portion comprises a fully human Fc portion (e.g., hinge, CH2 and CH3 domain sequences from a human immunoglobulin).

In certain embodiments, the constituent constant domains of the heavy chain portion are from different immunoglobulin molecules. For example, a heavy chain portion of a polypeptide may comprise a CH2 domain derived from an IgG1 molecule and a hinge region derived from an IgG3 or IgG4 molecule. In other embodiments, the constant domains are chimeric domains comprising portions of different immunoglobulin molecules. For example, a hinge may comprise a first portion from an IgG1 molecule and a second portion from an IgG3 or IgG4 molecule. As set forth above, it will be understood by one of ordinary skill in the art that the constant domains of the heavy chain portion may be modified such that they vary in amino acid sequence from the naturally occurring (wild-type) immunoglobulin molecule. That is, the polypeptides of the invention disclosed herein may comprise alterations or modifications to one or more of the heavy chain constant domains (CH1, hinge, CH2 or CH3) and/or to the light chain constant region domain (CL). Exemplary modifications include additions, deletions or substitutions of one or more amino acids in one or more domains.

As used herein, the terms "variable region" and "variable domain" are used interchangeably and are intended to have equivalent meaning. The term "variable" refers to the fact that certain portions of the variable domains VH and VL differ extensively in sequence among antibodies and are used in the binding and specificity of each particular antibody for its target antigen. However, the variability is not evenly distributed throughout the variable domains of antibodies. It is concentrated in three segments called "hypervariable loops" in each of the VL domain and the VH domain which form part of the antigen binding site. The first, second and third hypervariable loops of the $V_{Lambda}$ light chain domain are referred to herein as L1 (λ), L2(λ) and L3(λ) and may be defined as comprising residues 24-33 (L1(λ), consisting of 9, 10 or 11 amino acid residues), 49-53 (L2(λ), consisting of 3 residues) and 90-96 (L3(λ), consisting of 5 residues) in the VL domain (Morea et al., Methods 20, 267-279, 2000). The first, second and third hypervariable loops of the $V_{Kappa}$ light chain domain are referred to herein as L1((κ)), L2((κ)) and L3((κ)) and may be defined as comprising residues 25-33 (L1((κ)), consisting of 6, 7, 8, 11, 12 or 13 residues), 49-53 (L2((κ)), consisting of 3 residues) and 90-97 (L3((κ)), consisting of 6 residues) in the VL domain (Morea et al., Methods 20, 267-279, 2000). The first, second and third hypervariable loops of the VH domain are referred to herein as H1, H2 and H3 and may be defined as comprising residues 25-33 (H1, consisting of 7, 8 or 9 residues), 52-56 (H2, consisting of 3 or 4 residues) and 91-105 (H3, highly variable in length) in the VH domain (Morea et al., Methods 20, 267-279, 2000).

Unless otherwise indicated, the terms L1, L2 and L3 respectively refer to the first, second and third hypervariable loops of a VL domain, and encompass hypervariable loops obtained from both $V_{Kappa}$ and $V_{Lambda}$ isotypes. The terms H1, H2 and H3 respectively refer to the first, second and third hypervariable loops of the VH domain, and encompass hypervariable loops obtained from any of the known heavy chain isotypes, including γ, ε, δ, α or μ.

The hypervariable loops L1, L2, L3, H1, H2 and H3 may each comprise part of a "complementarity determining region" or "CDR", as defined below. The terms "hypervariable loop" and "complementarity determining region" are not strictly synonymous, since the hypervariable loops (HVs) are defined on the basis of structure, whereas complementarity determining regions (CDRs) are defined based on sequence variability (Kabat et al., Sequences of Proteins of Immunological Interest, 5th Ed. Public Health Service, National Institutes of Health, Bethesda, MD, 1991) and the limits of the HVs and the CDRs may be different in some VH and VL domains.

The CDRs of the VL and VH domains can typically be defined as comprising the following amino acids: residues 24-34 (LCDR1), 50-56 (LCDR2) and 89-97 (LCDR3) in the light chain variable domain, and residues 31-35 or 31-35b (HCDR1), 50-65 (HCDR2) and 95-102 (HCDR3) in the heavy chain variable domain; (Kabat et al., Sequences of Proteins of Immunological Interest, 5th Ed. Public Health Service, National Institutes of Health, Bethesda, MD, 1991). Thus, the HVs may be comprised within the corresponding CDRs and references herein to the "hypervariable loops" of VH and VL domains should be interpreted as also encompassing the corresponding CDRs, and vice versa, unless otherwise indicated.

The more highly conserved portions of variable domains are called the framework region (FR), as defined below. The variable domains of native heavy and light chains each comprise four FRs (FR1, FR2, FR3 and FR4, respectively), largely adopting a β-sheet configuration, connected by the three hypervariable loops. The hypervariable loops in each chain are held together in close proximity by the FRs and, with the hypervariable loops from the other chain, contribute to the formation of the antigen-binding site of antibodies. Structural analysis of antibodies revealed the relationship between the sequence and the shape of the binding site formed by the complementarity determining regions (Chothia et al., J. Mol. Biol. 227, 799-817, 1992; Tramontano et al., J. Mol. Biol, 215, 175-182, 1990). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

As used herein, the term "CDR" or "complementarity determining region" means the non-contiguous antigen combining sites found within the variable region of both heavy and light chain polypeptides. These particular regions have been described by Kabat et al., J. Biol. Chem. 252, 6609-6616, 1977, by Kabat et al., Sequences of Proteins of Immunological Interest, 5th Ed. Public Health Service, National Institutes of Health, Bethesda, MD, 1991, by Chothia et al., J. Mol. Biol. 196, 901-917, 1987, and by MacCallum et al., J. Mol. Biol. 262, 732-745, 1996, where the definitions include overlapping or subsets of amino acid residues when compared against each other. The amino acid residues which encompass the CDRs as defined by each of the above cited references are set forth for comparison. Preferably, the term "CDR" is a CDR as defined by Kabat based on sequence comparisons.

TABLE 1

CDR definitions.

| | CDR Definitions | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term "framework region" or "FR region" includes the amino acid residues that are part of the variable region, but are not part of the CDRs (e.g., using the Kabat definition of CDRs). Therefore, a variable region framework is between about 100-120 amino acids in length but includes only those amino acids outside of the CDRs. For the specific example of a heavy chain variable domain and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light claim variable region CDRs. Similarly, using the definition of CDRs by Chothia et al. or McCallum et al. the framework region boundaries are separated by the respective CDR termini as described above. In preferred embodiments the CDRs are as defined by Kabat.

In naturally-occurring antibodies, the six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

As used herein, the term "fragment" refers to a part or portion of an antibody or antibody chain comprising fewer amino acid residues than an intact or complete antibody or antibody chain. The term "antigen-binding fragment" refers to a polypeptide fragment of an immunoglobulin or antibody that binds antigen or competes with intact antibody (i.e., with the intact antibody from which they were derived) for antigen binding (i.e., specific binding to TIGIT). As used herein, the term "fragment" of an antibody molecule includes antigen-binding fragments of antibodies, for example, an antibody light chain variable domain (VL), an antibody heavy chain variable domain (VH), a single chain antibody (scFv), a F(ab')2 fragment, a Fab fragment, an Fd fragment, an Fv fragment, and a single domain antibody fragment (DAb). Fragments can be obtained, e.g., via chemical or enzymatic treatment of an intact or complete antibody or antibody chain or by recombinant means.

As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different ligands or different antigens, or different epitopes on the same antigen). The subject binding molecules have at least one binding site specific for TIGIT.

As used herein, the term "specificity" refers to the ability to bind (e.g., immunoreact with) a given target, e.g., TIGIT. A polypeptide may be monospecific and contain one or more binding sites which specifically bind a target or a polypeptide may be multispecific and contain two or more binding sites which specifically bind the same or different targets. In one embodiment, an antibody of the invention is specific for more than one target. For example, in one embodiment, a multispecific binding molecule of the invention binds TIGIT and a second target molecule. In this context, the second target molecule is a molecule other than TIGIT.

As used herein the term "synthetic" with respect to polypeptides includes polypeptides which comprise an amino acid sequence that is not naturally occurring. For example, non-naturally occurring polypeptides which are modified forms of naturally occurring polypeptides (e.g., comprising a mutation such as an addition, substitution or deletion) or which comprise a first amino acid sequence (which may or may not be naturally occurring) that is linked in a linear sequence of amino acids to a second amino acid sequence (which may or may not be naturally occurring) to which it is not naturally linked in nature.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques). Preferably, the antibodies of the invention have been engineered to improve one or more properties, such as antigen binding, stability/half-life or effector function.

As used herein, the term "modified antibody" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen; heavy chain molecules joined to scFv molecules and the like. ScFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen). In another embodiment, a modified antibody of the invention is a fusion protein comprising at least one heavy chain portion lacking a CH2 domain and comprising a binding domain of a polypeptide comprising the binding portion of one member of a receptor ligand pair.

The term "modified antibody" may also be used herein to refer to amino acid sequence variants of a TIGIT antibody of the invention. It will be understood by one of ordinary skill in the art that a TIGIT antibody of the invention may be modified to produce a variant TIGIT antibody which varies in amino acid sequence in comparison to the TIGIT antibody from which it was derived. For example, nucleotide or amino acid substitutions leading to conservative substitutions or changes at "non-essential" amino acid residues may be made (e.g., in CDR and/or framework residues). Amino acid substitutions can include replacement of one or more amino acids with a naturally occurring or non-natural amino acid.

"Antibody fragments" comprise a portion of a full length antibody, generally the antigen binding or variable domain thereof. Examples of antigen binding antibody fragments include Fab, Fab', F(ab')2, bi-specific Fab's, and Fv fragments, diabodies, linear antibodies, single-chain antibody molecules, a single chain variable fragment (scFv) and multispecific antibodies formed from antibody fragments (see Holliger and Hudson, Nature Biotechnol. 23:1126-1136, 2005, the contents of which are incorporated herein by reference).

As used herein, the term "affinity variant" refers to a variant antibody which exhibits one or more changes in amino acid sequence compared to a reference TIGIT antibody of the invention, wherein the affinity variant exhibits an altered affinity for TIGIT in comparison to the reference antibody. Preferably the affinity variant will exhibit improved affinity for TIGIT, as compared to the reference TIGIT antibody. The improvement may be apparent as a lower KD for TIGIT, or a slower off-rate for TIGIT. Affinity variants typically exhibit one or more changes in amino acid sequence in the CDRs, as compared to the reference TIGIT antibody. Such substitutions may result in replacement of the original amino acid present at a given position in the CDRs with a different amino acid residue, which may be a naturally occurring amino acid residue or a non-naturally occurring amino acid residue. The amino acid substitutions may be conservative or non-conservative.

As used herein, the term "affinity" or "binding affinity" should be understood based on the usual meaning in the art in the context of antibody binding, and reflects the strength and/or stability of binding between an antigen and a binding site on an antibody or antigen binding fragment thereof.

The anti-TIGIT antibodies provided herein are characterised by high affinity binding to human TIGIT. Binding affinity for TIGIT may be assessed using standard techniques known to persons of skill in the art.

Binding affinity may also be expressed as the dissociation constant for a particular antibody, or the $K_D$. The lesser the $K_D$ value, the stronger the binding interaction between an antibody and its target antigen. In one embodiment, binding affinity of a Fab clone comprising a defined VH/VL pairing may be assessed by using methods known in the art, for example by the ForteBio™ system, by MSD-solution equilibrium titration (SET), or by surface plasmon resonance, e.g. using the Biacore™ system as described in the accompanying examples. Fab fragments of the antibodies according to the invention typically exhibit a $K_D$ for TIGIT measured by ForteBio™ in the range of from $1\times10^{-10}$ to $5\times10^{-8}$ M, optionally $7\times10^{-10}$ to $4\times10^{-8}$ M. A $K_D$ within this range may be taken as an indication that the Fab, and a corresponding bivalent mAb, exhibit high affinity binding to hTIGIT. Bivalent mAbs comprising two Fabs that (individually) exhibit $K_D$ for hTIGIT within the stated ranges are also taken to exhibit high affinity binding to hTIGIT. A MSD $K_D$ in the range of from $1\times10^{-11}$ to $5\times10^{-9}$, optionally $2\times10^{-11}$ to $1\times10^{-9}$ may be taken as an indication of high affinity binding to hTIGIT. Fab fragments of the antibodies according to the invention typically exhibit a $K_D$ for TIGIT measured by Biacore™ in the range of from $1\times10^{-10}$ M to $1\times10^{-9}$ M, optionally from $1\times10^{-10}$ to $7\times10^{10}$, optionally $2\times10^{-10}$ to $7\times10^{-10}$ M. A $K_D$ within this range may be taken as an indication that the Fab, and a corresponding bivalent mAb, exhibit high affinity binding to hTIGIT.

Binding affinity to human TIGIT can also be assessed using a cell-based system as described in the accompanying examples, in which mAbs are tested for binding to mammalian cells (cell lines or ex vivo cells that express TIGIT), for example using ELISA or flow cytometry. High affinity for TIGIT may be indicated, for example, by an $EC_{50}$ of no more than 0.5 nM by flow cytometric (e.g. FACS) analysis such as that described in Example 10. In certain embodiments, antibodies of the invention exhibit a cell binding $EC_{50}$ of no more than 0.5 nM, optionally no more than 0.2 nM. Cell-based determination of affinity expressed as $EC_{50}$ is preferably determined using Jurkat cells expressing hTIGIT or primary CD8 T cells from human peripheral blood mononuclear cells (PBMCs).

As used herein "Treg cells", or simply "Tregs", refer to regulatory CD4+ T cells—that is, T cells that decrease the effector function(s) of conventional T cells (CD8 or CD4 T cells). Tregs can be identified according to methods known in the art, for example using flow cytometry to identify CD4 cells expressing high levels of CD25 and low levels or absence of CD127.

As summarised above, the invention relates, at least in part, to antibodies, and antigen binding fragments thereof, that bind to TIGIT. The properties and characteristics of the TIGIT antibodies, and antibody fragments, according to the invention will now be described in further detail.

Anti-Tigit Antibodies

In one aspect, the present invention provides an isolated antibody or antigen binding fragment thereof which binds to human TIGIT and which comprises a heavy chain variable domain comprising a heavy chain CDR1 (HCDR1), a heavy chain CDR2 (HCDR2), and a heavy chain CDR3 (HCDR3) selected from the HCDR1, HCDR2 and HCDR3 sequences shown in FIG. 1 and which further comprises a light chain variable domain comprising a light chain CDR1 (LCDR1), a light chain CDR2 (LCDR2), and a light chain CDR3 (LCDR3) selected from the LCDR1, LCDR2, and LCDR3 sequences shown in FIG. 2. That is, the invention provides an isolated antibody or antigen binding fragment thereof which binds to human TIGIT and which comprises a heavy chain variable domain comprising a heavy chain CDR1 (HCDR1), a heavy chain CDR2 (HCDR2), and a heavy chain CDR3 (HCDR3), wherein:
  (i) HCDR1 is selected from the group consisting of SEQ ID Nos: 1, 4, 7, 10, 13, 16, 19, 22, 25, 28, 31, 34, 37, 40, 43, 271, 274, and 277;
  (ii) HCDR2 is selected from the group consisting of SEQ ID Nos: 2, 5, 8, 11, 14, 17, 20, 23, 26, 29, 32, 35, 38, 41, 44, 272, 275, and 278;
  (iii) HCDR3 is selected from the group consisting of SEQ ID Nos: 3, 6, 9, 12, 15, 18, 21, 24, 27, 30, 33, 36, 39, 42, 45, 273, 276, and 279;
and which further comprises a light chain variable domain comprising a light chain CDR1 (LCDR1), a light chain CDR2 (LCDR2), and a light chain CDR3 (LCDR3), wherein
  (iv) LCDR1 is selected from the group consisting of SEQ ID Nos: 46, 49, 52, 55, 58, 61, 64, 67, 70, 73, 76, 79, 82, 85, 88, 283, 286, and 289;
  (v) LCDR2 is selected from the group consisting of SEQ ID Nos: 47, 50, 53, 56, 59, 62, 65, 68, 71, 74, 77, 80, 83, 86, 89, 284, 287, and 290; and
  (vi) LCDR3 is selected from the group consisting of SEQ ID Nos: 48, 51, 54, 57, 60, 63, 66, 69, 72, 75, 78, 81, 84, 87, 90, 285, 288, and 291.

Any given anti-TIGIT antibody or antigen binding fragment thereof comprising a VH domain paired with a VL domain to form a binding site for antigen (human TIGIT) will comprise a combination of 6 CDRs: variable heavy chain CDR3 (HCDR3), variable heavy chain CDR2 (HCDR2), variable heavy chain CDR1 (HCDR1), variable light chain CDR3 (LCDR3), variable light chain CDR2 (LCDR2) and variable light chain CDR1 (LCDR1). Although many different combinations of 6 CDRs selected from the CDR sequence groups listed above are permissible, and within the scope of the invention, certain combinations of 6 CDRs are particularly preferred; these being the "native" combinations within a single mAb exhibiting high affinity binding to human TIGIT. In certain embodiments the antibody or antigen binding fragment comprises a combination of HCDR1, HCDR2, HCDR3, LCDR1, LCDR2 and LCDR3, wherein the combination is selected from the group of combinations formed by the HCDRs from each antibody in FIG. 1 taken with the LCDRs from the corresponding antibody in FIG. 2.

That is, in certain embodiments the antibody or antigen binding fragment comprises a combination of HCDR1, HCDR2, HCDR3, LCDR1, LCDR2 and LCDR3, wherein the combination is selected from the group consisting of:

(i) HCDR1 comprising SEQ ID NO:1, HCDR2 comprising SEQ ID NO:2, HCDR3 comprising SEQ ID NO:3, LCDR1 comprising SEQ ID NO:46, LCDR2 comprising SEQ ID NO:47, and LCDR3 comprising SEQ ID NO:48;

(ii) HCDR1 comprising SEQ ID NO:4, HCDR2 comprising SEQ ID NO:5, HCDR3 comprising SEQ ID NO:6, LCDR1 comprising SEQ ID NO:49, LCDR2 comprising SEQ ID NO:50, and LCDR3 comprising SEQ ID NO:51;

(iii) HCDR1 comprising SEQ ID NO:7, HCDR2 comprising SEQ ID NO:8, HCDR3 comprising SEQ ID NO:9, LCDR1 comprising SEQ ID NO:52, LCDR2 comprising SEQ ID NO:53, and LCDR3 comprising SEQ ID NO:54;

(iv) HCDR1 comprising SEQ ID NO:10, HCDR2 comprising SEQ ID NO:11, HCDR3 comprising SEQ ID NO:12, LCDR1 comprising SEQ ID NO:55, LCDR2 comprising SEQ ID NO:56, and LCDR3 comprising SEQ ID NO:57;

(v) HCDR1 comprising SEQ ID NO:13, HCDR2 comprising SEQ ID NO:14, HCDR3 comprising SEQ ID NO:15, LCDR1 comprising SEQ ID NO:58, LCDR2 comprising SEQ ID NO:59, and LCDR3 comprising SEQ ID NO:60;

(vi) HCDR1 comprising SEQ ID NO:16, HCDR2 comprising SEQ ID NO:17, HCDR3 comprising SEQ ID NO:18, LCDR1 comprising SEQ ID NO:61, LCDR2 comprising SEQ ID NO:62, and LCDR3 comprising SEQ ID NO:63;

(vii) HCDR1 comprising SEQ ID NO:19, HCDR2 comprising SEQ ID NO:20, HCDR3 comprising SEQ ID NO:21, LCDR1 comprising SEQ ID NO:64, LCDR2 comprising SEQ ID NO:65, and LCDR3 comprising SEQ ID NO:66;

(viii) HCDR1 comprising SEQ ID NO:22, HCDR2 comprising SEQ ID NO:23, HCDR3 comprising SEQ ID NO:24, LCDR1 comprising SEQ ID NO:67, LCDR2 comprising SEQ ID NO:68, and LCDR3 comprising SEQ ID NO:69;

(ix) HCDR1 comprising SEQ ID NO:25, HCDR2 comprising SEQ ID NO:26, HCDR3 comprising SEQ ID NO:27, LCDR1 comprising SEQ ID NO:70, LCDR2 comprising SEQ ID NO:71, and LCDR3 comprising SEQ ID NO:72;

(x) HCDR1 comprising SEQ ID NO:28, HCDR2 comprising SEQ ID NO:29, HCDR3 comprising SEQ ID NO:30, LCDR1 comprising SEQ ID NO:73, LCDR2 comprising SEQ ID NO:74, and LCDR3 comprising SEQ ID NO:75;

(xi) HCDR1 comprising SEQ ID NO:31, HCDR2 comprising SEQ ID NO:32, HCDR3 comprising SEQ ID NO:33, LCDR1 comprising SEQ ID NO:76, LCDR2 comprising SEQ ID NO:77, and LCDR3 comprising SEQ ID NO:78;

(xii) HCDR1 comprising SEQ ID NO:34, HCDR2 comprising SEQ ID NO:35, HCDR3 comprising SEQ ID NO:36, LCDR1 comprising SEQ ID NO:79, LCDR2 comprising SEQ ID NO:80, and LCDR3 comprising SEQ ID NO:81;

(xiii) HCDR1 comprising SEQ ID NO:37, HCDR2 comprising SEQ ID NO:38, HCDR3 comprising SEQ ID NO:39, LCDR1 comprising SEQ ID NO:82, LCDR2 comprising SEQ ID NO:83, and LCDR3 comprising SEQ ID NO:84;

(xiv) HCDR1 comprising SEQ ID NO:40, HCDR2 comprising SEQ ID NO:41, HCDR3 comprising SEQ ID NO:42, LCDR1 comprising SEQ ID NO:85, LCDR2 comprising SEQ ID NO:86, and LCDR3 comprising SEQ ID NO:87;

(xv) HCDR1 comprising SEQ ID NO:43, HCDR2 comprising SEQ ID NO:44, HCDR3 comprising SEQ ID NO:45, LCDR1 comprising SEQ ID NO:88, LCDR2 comprising SEQ ID NO:89, and LCDR3 comprising SEQ ID NO:90;

(xvi) HCDR1 comprising SEQ ID NO:271, HCDR2 comprising SEQ ID NO:272, HCDR3 comprising SEQ ID NO:273, LCDR1 comprising SEQ ID NO:283, LCDR2 comprising SEQ ID NO:284, and LCDR3 comprising SEQ ID NO:285;

(xvii) HCDR1 comprising SEQ ID NO:274, HCDR2 comprising SEQ ID NO:275, HCDR3 comprising SEQ ID NO:276, LCDR1 comprising SEQ ID NO:286, LCDR2 comprising SEQ ID NO:287, and LCDR3 comprising SEQ ID NO:288;

(xviii) HCDR1 comprising SEQ ID NO:277, HCDR2 comprising SEQ ID NO:278, HCDR3 comprising SEQ ID NO:279, LCDR1 comprising SEQ ID NO:289, LCDR2 comprising SEQ ID NO:290, and LCDR3 comprising SEQ ID NO:291.

In certain embodiments the antibody or antigen binding fragment comprises a heavy chain variable domain having an amino acid sequence selected from the group consisting of: SEQ ID Nos: 211, 213, 215, 217, 219, 221, 223, 225, 227, 229, 231, 233, 235, 237, 239, 327, 329, and 331 and amino acid sequences exhibiting at least 90%, 95%, 97%, 98% or 99% sequence identity thereto; and optionally comprising a light chain variable domain having an amino acid sequence selected from the group consisting of: the amino acid sequences of SEQ ID Nos: 212, 214, 216, 218, 220, 222, 224, 226, 228, 230, 232, 234, 236, 238, 240, 328, 330, and 332 and amino acid sequences exhibiting at least 90%, 95%, 97%, 98% or 99% sequence identity thereto.

Although all possible pairings of VH domains and VL domains selected from the VH and VL domain sequence groups listed above are permissible, and within the scope of the invention, certain combinations VH and VL are particularly preferred; these being the "native" combinations within a single mAb exhibiting high affinity binding to human TIGIT.

In certain embodiments the antibody or antigen binding fragment comprises a combination of a heavy chain variable domain and a light chain variable domain, wherein the combination is selected from the group of combinations formed by the VH from each antibody in FIG. 5, or an amino acid sequence exhibiting at least 90%, 95%, 97%, 98% or 99% sequence identity thereto, taken with the VL from the same antibody in FIG. 5, or an amino acid sequence exhibiting at least 90%, 95%, 97%, 98% or 99% sequence identity thereto. In certain embodiments the antibody or antigen binding fragment comprises a combination of a heavy chain variable domain and a light chain variable domain, wherein the combination is selected from the group consisting of:

(i) a heavy chain variable domain comprising the amino acid sequence of SEQ ID NO:211 and a light chain variable domain comprising the amino acid sequence of SEQ ID NO:212;

(ii) a heavy chain variable domain comprising the amino acid sequence of SEQ ID NO:213 and a light chain variable domain comprising the amino acid sequence of SEQ ID NO:214;
(iii) a heavy chain variable domain comprising the amino acid sequence of SEQ ID NO:215 and a light chain variable domain comprising the amino acid sequence of SEQ ID NO:216;
(iv) a heavy chain variable domain comprising the amino acid sequence of SEQ ID NO:217 and a light chain variable domain comprising the amino acid sequence of SEQ ID NO:218;
(v) a heavy chain variable domain comprising the amino acid sequence of SEQ ID NO:219 and a light chain variable domain comprising the amino acid sequence of SEQ ID NO:220;
(vi) a heavy chain variable domain comprising the amino acid sequence of SEQ ID NO:221 and a light chain variable domain comprising the amino acid sequence of SEQ ID NO:222;
(vii) a heavy chain variable domain comprising the amino acid sequence of SEQ ID NO:223 and a light chain variable domain comprising the amino acid sequence of SEQ ID NO:224;
(viii) a heavy chain variable domain comprising the amino acid sequence of SEQ ID NO:225 and a light chain variable domain comprising the amino acid sequence of SEQ ID NO:226;
(ix) a heavy chain variable domain comprising the amino acid sequence of SEQ ID NO:227 and a light chain variable domain comprising the amino acid sequence of SEQ ID NO:228;
(x) a heavy chain variable domain comprising the amino acid sequence of SEQ ID NO:229 and a light chain variable domain comprising the amino acid sequence of SEQ ID NO:230;
(xi) a heavy chain variable domain comprising the amino acid sequence of SEQ ID NO:231 and a light chain variable domain comprising the amino acid sequence of SEQ ID NO:232;
(xii) a heavy chain variable domain comprising the amino acid sequence of SEQ ID NO:233 and a light chain variable domain comprising the amino acid sequence of SEQ ID NO:234;
(xiii) a heavy chain variable domain comprising the amino acid sequence of SEQ ID NO:235 and a light chain variable domain comprising the amino acid sequence of SEQ ID NO:236;
(xiv) a heavy chain variable domain comprising the amino acid sequence of SEQ ID NO:237 and a light chain variable domain comprising the amino acid sequence of SEQ ID NO:238;
(xv) a heavy chain variable domain comprising the amino acid sequence of SEQ ID NO:239 and a light chain variable domain comprising the amino acid sequence of SEQ ID NO:240;
(xvi) a heavy chain variable domain comprising the amino acid sequence of SEQ ID NO:327 or an amino acid sequence at least 90% identical thereto and a light chain variable domain comprising the amino acid sequence of SEQ ID NO:328 or an amino acid sequence at least 90% identical thereto;
(xvii) a heavy chain variable domain comprising the amino acid sequence of SEQ ID NO:329 or an amino acid sequence at least 90% identical thereto and a light chain variable domain comprising the amino acid sequence of SEQ ID NO:330 or an amino acid sequence at least 90% identical thereto; and
(xviii) a heavy chain variable domain comprising the amino acid sequence of SEQ ID NO:331 or an amino acid sequence at least 90% identical thereto and a light chain variable domain comprising the amino acid sequence of SEQ ID NO:332 or an amino acid sequence at least 90% identical thereto.

For each of the specific VH/VL combinations listed above, it is also permissible, and within the scope of the invention, to combine a VH domain having an amino acid sequence at least 90%, 92%, 95%, 97% or 99% identical to the recited VH domain sequence with a VL domain having an amino acid sequence at least 90%, 92%, 95%, 97% or 99% identical to the recited VL domain sequence. Embodiments wherein the amino acid sequence of the VH domain exhibits less than 100% sequence identity with a given reference VH sequence may nevertheless comprise heavy chain CDRs which are identical to HCDR1, HCDR2 and HCDR3 of the reference sequence whilst exhibiting amino acid sequence variation within the framework regions. Likewise, embodiments wherein the amino acid sequence of the VL domain exhibits less than 100% sequence identity with a given reference sequence may nevertheless comprise light chain CDRs which are identical to LCDR1, LCDR2 and LCDR3 of the reference sequence whilst exhibiting amino acid sequence variation within the framework regions.

In the preceding paragraph, and elsewhere herein, the structure of the antibodies/antigen binding fragments is defined on the basis of % sequence identity with a recited reference sequence (with a given SEQ ID NO). In this context, % sequence identity between two amino acid sequences may be determined by comparing these two sequences aligned in an optimum manner and in which the amino acid sequence to be compared can comprise additions or deletions with respect to the reference sequence for an optimum alignment between these two sequences. The percentage of identity is calculated by determining the number of identical positions for which the amino acid residue is identical between the two sequences, by dividing this number of identical positions by the total number of positions in the comparison window and by multiplying the result obtained by 100 in order to obtain the percentage of identity between these two sequences. Typically, the comparison window with correspond to the full length of the sequence being compared. For example, it is possible to use the BLAST program, "BLAST 2 sequences" (Tatusova et al, "Blast 2 sequences—a new tool for comparing protein and nucleotide sequences", FEMS Microbiol Lett. 174:247-250), the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program. Determining sequence identity of a query sequence to a reference sequence is within the ability of the skilled person and can be performed using commercially available analysis software such as BLAST™.

In certain preferred embodiments of all aspects of the invention, the antibody or antigen binding fragment may comprise a heavy chain variable domain and a light chain variable domain wherein HCDR1 comprises SEQ ID NO: 16, HCDR2 comprises SEQ ID NO: 17, HCDR3 comprises SEQ ID NO: 18, and LCDR1 comprises SEQ ID NO: 61, LCDR2 comprises SEQ ID NO: 62, and LCDR3 comprises SEQ ID NO: 63.

In certain such embodiments, the heavy chain variable domain may comprise the amino acid sequence shown as SEQ ID NO: 221 or an amino acid sequence exhibiting at least 90%, 95%, 97%, 98% or 99% sequence identity thereto, and the light chain variable domain may comprise the amino acid sequence shown as SEQ ID NO: 222 or an amino acid sequence exhibiting at least 90%, 95%, 97%, 98% or 99% sequence identity thereto. In certain such embodiments, the heavy chain variable domain and light chain variable domain are the VH and VL domain of antibody 31282 provided herein.

Antibody 31282 provided herein is derived from antibody 29489. Antibody 31282 was produced from 29489 by an M-T substitution at amino acid 116 in VH FR4 region. This substitution is understood to remove a potential oxidation site of the antibody and thereby improve stability without affecting function. Antibodies 31282 and 29489 thus share identical HCDR1, HCDR2, HCDR3, LCDR1, LCDR2 and LCDR3 sequences, differing only in the framework.

Accordingly, in certain embodiments of the antibodies or antigen binding fragments of the invention, the heavy chain variable domain may comprise the amino acid sequence shown as SEQ ID NO: 219 or an amino acid sequence exhibiting at least 90%, 95%, 97%, 98% or 99% sequence identity thereto, and the light chain variable domain may comprise the amino acid sequence shown as SEQ ID NO: 220 or an amino acid sequence exhibiting at least 90%, 95%, 97%, 98% or 99% sequence identity thereto. In certain such embodiments, the heavy chain variable domain and light chain variable domain are the VH and VL domain of antibody 29489 provided herein.

Embodiments wherein the amino acid sequence of the VH domain exhibits less than 100% sequence identity with the sequence shown as SEQ ID NO: 221 or 219 may nevertheless comprise heavy chain CDRs which are identical to HCDR1, HCDR2 and HCDR3 of SEQ ID NO:221 and 219 (SEQ ID NOs:16, 17 and 18, respectively) whilst exhibiting amino acid sequence variation within the framework regions. Likewise, embodiments wherein the amino acid sequence of the VL domain exhibits less than 100% sequence identity with the sequence shown as SEQ ID NO: 222 or 220 may nevertheless comprise light chain CDRs which are identical to LCDR1, LCDR2 and LCDR3 of SEQ ID NO:222 and 220 (SEQ ID NOs:61, 62 and 63, respectively) whilst exhibiting amino acid sequence variation within the framework regions.

TABLE 2

| Antibody clone | VH CDR3 Lineage | Optimization Method | VH Germline |
|---|---|---|---|
| 26518 | 26518 | Parent | VH3-07 |
| 29478 | 26518 | H1/H2/H3 | VH3-30 |
| 26452 | 26452 | Parent | VH1-46 |
| 29487 | 26452 | H1/H2/H3 | VH1-46 |
| 29489 | 26452 | H1/H2/H3 | VH1-46 |
| 31282 | 29489 | M116T amino acid mutation | VH1-46 |
| 26486 | 26486 | Parent | VH4-0B |
| 29499 | 26486 | H1/H2/H3 | VH4-39 |
| 29494 | 26486 | H1/H2/H3 | VH4-39 |
| 31288 | 29494 | Germline reversion + M116T amino acid mutation | VH4-39 |
| 32919 | 31288 | L1/L2/L3 | VH4-39 |
| 32931 | 31288 | L1/L2/L3 | VH4-39 |
| 26521 | 26521 | Parent | VH1-69 |
| 29513 | 26521 | H1/H2/H3 | VH1-69 |
| 26493 | 26493 | Parent | VH3-09 |

TABLE 2-continued

| Antibody clone | VH CDR3 Lineage | Optimization Method | VH Germline |
|---|---|---|---|
| 29520 | 26493 | H1/H2/H3 | VH3-09 |
| 29523 | 26493 | H1/H2/H3 | VH3-33 |
| 29527 | 26493 | H1/H2/H3 | VH3-30 |
| 26432 | 26432 | Parent | VH1-69 |
| 32959 | 26432 | H1/H2/H3 | VH1-69 |

Exemplary TIGIT antibodies described herein and having the sequences set out in FIG. 1-5 were developed from 5 parent antibody clones. Table 2 summarises the lineage of the antibodies described herein. Naïve parent human anti-TIGIT antibodies were expressed in yeast and those exhibiting high functional activity against TIGIT were selected (grey rows, named 26 . . . ), and underwent affinity maturation. Selected affinity-matured antibodies then were expressed in mammalian cells (white rows beneath each parent, named 29 . . . or 3 . . . ). In addition, antibody 31282 was produced from 29489 by an M-T substitution at amino acid 116 in VH FR4 region. This substitution is understood to remove a potential oxidation site of the antibody and thereby improve stability without affecting function. In addition, antibody 31288 was produced from 29494 by a V-L substitution at amino acid 2 in VH FR1 region and by an M-T substitution at amino acid 120 in VH FR4 region. The V-L substitution is understood to restore the sequence of VH4-39 germline and the M-T substitution to remove a potential oxidation site of the antibody and thereby improve stability without affecting function.

The second generation antibodies exhibit higher affinity than the respective parent antibodies.

In certain embodiments, the invention provides anti-TIGIT antibodies or antigen binding fragments thereof wherein the VH domain is derived from a human V region germline sequence selected from: VH3-07, VH3-30, VH1-46, VH4-0B, VH4-39, VH1-69, VH3-09, VH3-33, VH3-30. In certain preferred embodiments, the antibody or antigen binding fragment thereof comprises a VH domain derived from human V region germline VH1-46.

A VH domain is "derived from" a particular V region germline sequence if the sequence of the heavy chain variable region is more likely derived from the given germline than from any other.

TIGIT Epitope

The invention also provides an antibody or antigen binding fragment thereof which binds to human TIGIT at an epitope comprising residues Q56 and I109. In certain embodiments, the antibody or antigen binding fragment thereof binds human TIGIT at least at residues Q56, N58 and I109. In certain embodiments, the antibody or antigen binding fragment thereof binds human TIGIT at an epitope comprising residues Q56, N58 and I109 and optionally one or more of residues E60, I68, L73 and H76. In certain embodiments, the antibody or antigen binding fragment thereof binds human TIGIT at an epitope comprising residues Q56, N58, E60, I68, L73, H76, and I109.

In certain embodiments, the antibody or antigen binding fragment thereof binds to human TIGIT at an epitope consisting of TIGIT residues Q56, N58, E60, I68, L73, H76, and I109. In certain embodiments, the antibody or antigen binding fragment thereof binds the same epitope as antibody 31282.

Where the antibody or antigen binding fragment binds an epitope of human TIGIT comprising the indicated TIGIT residues, the antibody binds each of these residues and optionally other residues of TIGIT. Where the antibody or antigen binding fragment binds an epitope of human TIGIT consisting of TIGIT residues Q56, N58, E60, I68, L73, H76, and I109, the antibody binds each of these residues and no other residues of TIGIT.

An antibody or antigen binding fragment binds to human TIGIT at a given epitope if it contacts the indicated TIGIT amino acid residue(s) when bound to TIGIT. As used herein, an antibody contacts a TIGIT residue if, when in the protein complex formed by antibody-TIGIT binding, the residue meets each of the following criteria: (i) it has a calculated binding free energy contribution greater than 0.3 kcal/mol, (ii) it has an experimental averaged B-factor lower than the mean B-factor of all residues in the X-ray structure, (iii) it makes at least 3 pairs of heavy-atom interatomic contacts with antibody atoms at a distance less than or equal to 4.0 Angstroms, (iv) it does not make only solvent-exposed hydrogen bond or ionic interactions, (v) if it is a non-aromatic polar residue (Asn, Gin, Ser, Thr, Asp, Glu, Lys, or Arg), it makes at least one hydrogen bond or ionic interaction with the antibody. Calculation of binding free energy would be within the abilities of the skilled person. Preferably binding free energy is calculated using an empirical force field, preferably FoldX. FoldX would be familiar to the skilled person and is publicly available. Calculation of binding free energy using FoldX is also described in Guerois et al. J. Mol. Biol. 2002; 320(2):369-87, which is incorporated herein by reference. As would be familiar to the skilled person, heavy atoms are all non-hydrogen atoms (including C, N, O, S).

Accordingly, the invention also provides an antibody or antigen binding fragment thereof which contacts human TIGIT at least at residues Q56 and I109. In certain embodiments, the antibody or antigen binding fragment thereof contacts human TIGIT at least at residues Q56, N58 and I109. In certain embodiments, the antibody or antigen binding fragment thereof contacts human TIGIT at least at residues Q56, N58 and I109 and optionally one or more of residues E60, I68, L73 and H76. In certain embodiments, the antibody or antigen binding fragment thereof contacts human TIGIT at least at residues Q56, N58, E60, I68 L73, H76, and I109.

In certain such embodiments, the antibody or antigen binding fragment thereof contacts human TIGIT only at residues Q56, N58, E60, I68, L73, H76, and I109.

Means for determining which residues of TIGIT are contacted by an antibody or antigen-binding fragment are familiar to the skilled person, including X-Ray crystallography, such as that described in Example 23.

Also provided is an isolated antibody or antigen binding fragment thereof which binds to the same epitope as an antibody or antigen-binding fragment described herein.

Antibody Subtypes

TIGIT antibodies can take various different embodiments in which both a VH domain and a VL domain are present. The term "antibody" herein is used in the broadest sense and encompasses, but is not limited to, monoclonal antibodies (including full length monoclonal antibodies), polyclonal antibodies, multispecific antibodies (e.g., bispecific antibodies), so long as they exhibit the appropriate immunological specificity for a human TIGIT protein. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes) on the antigen, each monoclonal antibody is directed against a single determinant or epitope on the antigen.

In non-limiting embodiments, the TIGIT antibodies provided herein may comprise CH1 domains and/or CL domains, the amino acid sequence of which is fully or substantially human. If the TIGIT antibody is intended for human therapeutic use, it is typical for the entire constant region of the antibody, or at least a part thereof, to have fully or substantially human amino acid sequence. Therefore, one or more or any combination of the CH1 domain, hinge region, CH2 domain, CH3 domain and CL domain (and CH4 domain if present) may be fully or substantially human with respect to its amino acid sequence. Such antibodies may be of any human isotype, with human IgG4 and IgG1 being particularly preferred.

Advantageously, the CH1 domain, hinge region, CH2 domain, CH3 domain and CL domain (and CH4 domain if present) may all have fully or substantially human amino acid sequence. In the context of the constant region of a humanised or chimeric antibody, or an antibody fragment, the term "substantially human" refers to an amino acid sequence identity of at least 90%, or at least 92%, or at least 95%, or at least 97%, or at least 99% with a human constant region. The term "human amino acid sequence" in this context refers to an amino acid sequence which is encoded by a human immunoglobulin gene, which includes germline, rearranged and somatically mutated genes. Such antibodies may be of any human isotype, with human IgG4 and IgG1 being particularly preferred.

Also provided are TIGIT antibodies comprising constant domains of "human" sequence which have been altered, by one or more amino acid additions, deletions or substitutions with respect to the human sequence.

The TIGIT antibodies provided herein may be of any isotype. Antibodies intended for human therapeutic use will typically be of the IgA, IgD, IgE IgG, IgM type, often of the IgG type, in which case they can belong to any of the four sub-classes IgG1, IgG2a and b, IgG3 or IgG4. Within each of these sub-classes it is permitted to make one or more amino acid substitutions, insertions or deletions within the Fc portion, or to make other structural modifications, for example to enhance or reduce Fc-dependent functionalities.

In certain preferred embodiments, the TIGIT antibodies provided herein are IgG antibodies. In certain embodiments, antibodies according to the invention are IgG1 antibodies. In certain alternate embodiments, antibodies according to the invention are IgG4 antibodies.

IgG4 antibodies are known to undergo Fab arm exchange (FAE), which can result in unpredictable pharmacodynamic properties of an IgG4 antibody. FAE has been shown to be prevented by the S228P mutation in the hinge region (Silva et al. J Biol Chem. 2015 Feb. 27; 290(9): 5462-5469). Therefore, in certain such embodiments wherein an antibody according to the invention is an IgG4 antibody, the antibody comprises the mutation S228P—that is, a serine to proline mutation at position 228 (according to EU numbering).

In non-limiting embodiments, it is contemplated that one or more amino acid substitutions, insertions or deletions may be made within the constant region of the heavy and/or the light chain, particularly within the Fc region. Amino acid substitutions may result in replacement of the substituted amino acid with a different naturally occurring amino acid, or with a non-natural or modified amino acid. Other structural modifications are also permitted, such as for example changes in glycosylation pattern (e.g. by addition or deletion of N- or O-linked glycosylation sites). Depending on the intended use of the TIGIT antibody, it may be desirable to modify the antibody of the invention with respect to its binding properties to Fc receptors, for example to modulate effector function.

In certain embodiments, the TIGIT antibodies may comprise an Fc region of a given antibody isotype, for example human IgG1, which is modified in order to reduce or substantially eliminate one or more antibody effector functions naturally associated with that antibody isotype.

As demonstrated herein, antibodies with cell lytic effector functions can be effective at reducing Treg cell populations but, surprisingly, without adversely affecting conventional effector T cell populations. This selectivity can allow more potent inhibition of the regulatory effect of Tregs whilst retaining anti-tumour effector T cells.

Therefore, in certain alternative embodiments, the TIGIT antibodies retain one or more of the antibody effector functions naturally associated with that antibody isotype. For example, the TIGIT antibodies of the invention may be IgG1 antibodies that retain ADCC functionality. In further embodiments, the TIGIT antibodies may comprise an Fc region of a given antibody isotype, for example human IgG1, which is modified in order to enhance one or more antibody effector functions naturally associated with that antibody isotype. In this context, "antibody effector functions" include one or more or all of antibody-dependent cellular cytotoxicity (ADCC), complement-dependent cytotoxicity (CDC) and antibody-dependent cellular phagocytosis (ADCP).

In certain embodiments the anti-TIGIT antibody is a modified antibody.

In certain embodiments is provided a bispecific antibody comprising a first arm specific for TIGIT and a second arm specific for a second target. In preferred embodiments the second target is an immune checkpoint molecule. In certain embodiments, the second target is OX40. In certain embodiments, the second target is ICOS. In certain embodiments, the second target is GITR. In certain embodiments, the second target is 4-1BB. In certain embodiments, the second target is PD-1. In certain embodiments, the second target is PD-L1. In certain embodiments, the first arm specific of TIGIT comprises a combination of HCDR1, HCDR2, HCDR3, LCDR1, LCDR2 and LCDR3 sequences of an antibody according to the invention. In certain embodiments the first arm comprises comprise a heavy chain variable domain and a light chain variable domain wherein HCDR1 comprises SEQ ID NO: 16, HCDR2 comprises SEQ ID NO: 17, HCDR3 comprises SEQ ID NO: 18, and LCDR1 comprises SEQ ID NO: 61, LCDR2 comprises SEQ ID NO: 62, and LCDR3 comprises SEQ ID NO: 63.

Monoclonal antibodies or antigen-binding fragments thereof that "cross-compete" with the TIGIT antibodies disclosed herein are those that bind human TIGIT at site(s) that are identical to, or overlapping with, the site(s) at which the present TIGIT antibodies bind. Competing monoclonal antibodies or antigen-binding fragments thereof can be identified, for example, via an antibody competition assay. For example, a sample of purified or partially purified human TIGIT can be bound to a solid support. Then, an antibody compound or antigen binding fragment thereof of the present invention and a monoclonal antibody or antigen-binding fragment thereof suspected of being able to compete with such invention antibody compound are added. One of the two molecules is labelled. If the labelled compound and the unlabelled compound bind to separate and discrete sites on TIGIT, the labelled compound will bind to the same level whether or not the suspected competing compound is present. However, if the sites of interaction are identical or overlapping, the unlabelled compound will compete, and the amount of labelled compound bound to the antigen will be lowered. If the unlabelled compound is present in excess, very little, if any, labelled compound will bind.

For purposes of the present invention, competing monoclonal antibodies or antigen-binding fragments thereof are those that decrease the binding of the present antibody compounds to TIGIT by about 50%, about 60%, about 70%, about 80%, about 85%, about 90%, about 95%, or about 99%. Details of procedures for carrying out such competition assays are well known in the art and can be found, for example, in Harlow and Lane, Antibodies, A Laboratory Manual, Cold Spring Harbor Laboratory Press, Cold Spring Harbor, New York, 1988, 567-569, 1988, ISBN 0-87969-314-2. Such assays can be made quantitative by using purified antibodies. A standard curve is established by titrating one antibody against itself, i.e., the same antibody is used for both the label and the competitor. The capacity of an unlabelled competing monoclonal antibody or antigen-binding fragment thereof to inhibit the binding of the labelled molecule to the plate is titrated. The results are plotted, and the concentrations necessary to achieve the desired degree of binding inhibition are compared.

Antibodies of the Invention Exhibit High Affinity for Tigit and Compete with CD155

In certain embodiments, the antibodies or antigen binding fragments of the invention exhibit high affinity for human TIGIT. In certain embodiments, Fab fragments of the antibodies according to the invention exhibit a $K_D$ for TIGIT measured by ForteBio™ in the range of from $1\times10^{-10}$ to $5\times10^{-8}$ M, optionally $7\times10^{-10}$ to $4\times10^{-8}$ M. In certain embodiments antibodies according to the invention exhibit MSD $K_D$ in the range of from $1\times10^{-11}$ to $5\times10^{-9}$ M, optionally $2\times10^{11}$ to $1\times10^{-9}$. In certain embodiments, Fab fragments of the antibodies according to the invention exhibit a $K_D$ for TIGIT measured by Biacore™ in the range of from $1\times10^{-10}$ M to $1\times10^{-9}$ M, optionally $1\times10^{-10}$ to $7\times10^{-10}$ M, optionally $2\times10^{-10}$ to $7\times10^{-10}$ M.

TABLE 3

| Clone | ForteBio Fab KD Biotinylated Human TIGIT HIS (M) Monovalent | ForteBio Fab KD Mouse TIGIT-Fc (M) Monovalent | ForteBio Fab KD Cyno TIGIT-Fc (M) Monovalent | ForteBio IgG KD Human TIGIT-Fc (M) Avid | MSD-monovalent KD (M), human TIGIT-His | Biacore - monovalent KD (M), human TIGIT-His | Cell binding Jurkat Human TIGIT FON (Fold Over Negative) | Cell binding Jurkat Mouse TIGIT FON (Fold Over Negative) |
|---|---|---|---|---|---|---|---|---|
| 26518 | 1.24E−09 | N.B. | 4.47E−09 | 6.30E−10 | | | 154 | 233 |
| 29478 | 7.03E−10 | 9.18E−08 | 1.26E−09 | 5.27E−10 | | | 182 | 500 |
| 26452 | 5.08E−09 | N.B. | N.B. | 4.74E−10 | | | 164 | 47 |
| 29487 | 2.08E−09 | N.B. | 1.55E−07 | 3.96E−10 | | | 161 | 95 |

TABLE 3-continued

| Clone | ForteBio Fab KD Biotinylated Human TIGIT HIS (M) Monovalent | ForteBio Fab KD Mouse TIGIT-Fc (M) Monovalent | ForteBio Fab KD Cyno TIGIT-Fc (M) Monovalent | ForteBio IgG KD Human TIGIT-Fc (M) Avid | MSD- monovalent KD (M), human TIGIT-His | Biacore - monovalent KD (M), human TIGIT-His | Cell binding Jurkat Human TIGIT FON (Fold Over Negative) | Cell binding Jurkat Mouse TIGIT FON (Fold Over Negative) |
|---|---|---|---|---|---|---|---|---|
| 29489 | 8.81E−10 | N.B. | 3.52E−08 | 3.53E−10 | 1.1E−10 | 2.48E−10 | 162 | 187 |
| 31282 | 1.34E−09 | N.B. | 3.77E−08 | | | 2.94E−10 | | |
| 26486 | 2.19E−08 | N.B. | N.B. | 5.89E−10 | | | 143 | 199 |
| 29499 | 1.66E−09 | 2.55E−08 | 1.45E−08 | 3.19E−10 | 1.9E−11 | | 164 | 541 |
| 29494 | 1.66E−09 | 5.36E−08 | 1.86E−08 | 3.76E−10 | 7.0E−11 | 2.70E−10 | 164 | 511 |
| 31288 | 2.09E−09 | | 2.51E−08 | | | 1.92E−10 | | |
| 32919 | 1.42E−09 | | 6.57E−09 | | | | 680 | |
| 32931 | 1.18E−09 | | 1.97E−09 | | | | 741 | |
| 29499 | 1.66E−09 | 2.55E−08 | 1.45E−08 | 3.19E−10 | 1.9E−11 | | 164 | 541 |
| 26521 | 9.87E−09 | N.B. | 1.49E−07 | 5.41E−10 | | | 146 | 218 |
| 29513 | 7.74E−10 | 8.55E−08 | 9.56E−09 | 3.92E−10 | 2.5E−11 | | 156 | 406 |
| 26493 | 4.06E−08 | 2.67E−08 | N.B. | 1.49E−09 | | | 80 | 463 |
| 29520 | 1.31E−09 | 1.95E−09 | 2.68E−09 | 3.84E−10 | 2.1E−10 | 7.16E−10 | 166 | 535 |
| 29523 | 3.84E−09 | 1.89E−08 | 2.79E−08 | 5.31E−10 | 1.7E−09 | | 150 | 502 |
| 29527 | 1.33E−09 | 2.02E−08 | 1.76E−08 | 3.50E−10 | 6.4E−10 | | 142 | 414 |
| 26432 | 1.31E−08 | N.B. | N.B. | 4.62E−09 | | | | |

As demonstrated in the Examples, antibody 31282 exhibits surprisingly high affinity for TIGIT expressed on transgenic cells. Accordingly, in certain embodiments, an anti-TIGIT antibody or antigen binding fragment provided herein exhibits a binding $EC_{50}$ for human TIGIT of less than 0.5 nM. In preferred such embodiments, the antibody or antigen binding fragment exhibits a binding $EC_{50}$ of from about 0.05 to about 0.4 nM, preferably from about 0.05 to about 0.3 nM, preferably from about 0.05 to about 0.2 nM, preferably from about 0.05 to about 0.15 nM. In certain preferred embodiments, the antibody or antigen binding fragment exhibits a binding $EC_{50}$ for human TIGIT of about 0.1 nM. In preferred embodiments, the antibody comprises the CDRs of antibody 31282. Preferably the $EC_{50}$ is determined using Jurkat cells expressing human TIGIT, as described in Example 18. In certain embodiments, antibodies or antigen binding fragments of the invention cross-react with mouse TIGIT and/or cynomolgus TIGIT.

Since the "29 . . . " second generation antibodies are affinity matured progeny of the highly functional parent antibodies, it is expected that they will exhibit at least similar or equivalent functional properties as the parent antibodies, and vice versa.

As described herein, in certain embodiments an antibody or antigen binding fragment of the invention has equivalent affinity for TIGIT expressed by CD8 T cells and expressed by Treg cells. As used herein, an antibody or antigen binding fragment has "equivalent affinity" for CD8 T cells and Treg cells if the affinity for CD8 T cells is in the range of 0.5-1.5 times that of the affinity for Treg cells. For example, an antibody having equivalent affinity for CD8 T cells and Treg cells which exhibits an affinity for Treg cells of 0.03 nM would exhibit an affinity for CD8 T cells in the range of 0.015-0.045 nM.

Table 3 provides a summary of the affinity properties of the anti-TIGIT antibodies of the invention, with grey cells indicating parent antibody clones, with second and third generation antibodies of each lineage shown immediately below the respective parent antibody (see also Table 2).

As demonstrated in the Examples, antibody 31282 exhibits surprisingly high affinity for TIGIT expressed on human primary CD8+ T cells. Accordingly, in certain embodiments, an anti-TIGIT antibody or antigen binding fragment provided herein exhibits a binding $EC_{50}$ for human TIGIT of less than 0.5 nM. In preferred such embodiments, the antibody or antigen binding fragment exhibits a binding $EC_{50}$ of from about 0.05 to about 0.4 nM, preferably from about 0.1 to about 0.3 nM. In certain preferred embodiments, the antibody or antigen binding fragment exhibits a binding $EC_{50}$ for human TIGIT of about 0.2 nM. In preferred embodiments, the antibody or antigen binding fragment comprises the CDRs of antibody 31282. Preferably the $EC_{50}$ is determined using CD8+ T cells from human PBMCs, preferably from a healthy individual, as described in Example 18.

As demonstrated in the accompanying examples, in certain embodiments antibodies or antigen binding fragment of the invention exhibit high affinity for TIGIT-expressing CD8 T cells and high affinity for TIGIT-expressing Treg cells. In certain embodiments, antibodies or antigen binding fragment of the invention exhibit an affinity for TIGIT-expressing CD8 T cells and TIGIT-expressing Treg cells characterised by an $EC_{50}$ less than 0.5 nM, preferably less than 0.3 nM, preferably less than 0.2 nM. In certain embodiments, the antibodies or antigen binding fragment of the invention exhibit equivalent affinity for TIGIT-expressing CD8 T cells and for TIGIT-expressing Treg cells.

Antibodies according to the invention (e.g. antibody 31282) exhibit surprisingly high affinity for CD8+ T cells from cancer patients. This is particularly advantageous, since increasing effector activity of T cells from cancer patients by inhibition of TIGIT signalling can lead to more effective tumour control. Accordingly, in certain embodiments, an anti-TIGIT antibody or antigen binding fragment provided herein exhibits a binding $EC_{50}$ of less than 0.5 nM for human TIGIT on human CD8+ T cells from cancer patients. In preferred such embodiments, the antibody or antigen binding fragment exhibits a binding $EC_{50}$ of from about 0.05 to about 0.4 nM, preferably from about 0.1 to about 0.3 nM. In certain preferred embodiments, the antibody or antigen binding fragment exhibits an $EC_{50}$ for human TIGIT of from about 0.1 nM to about 0.2 nM. In preferred embodiments, the antibody or antigen binding fragment comprises the CDRs of antibody 31282. Preferably the $EC_{50}$ is determined using CD8+ T cells from PBMCs taken from a patient with cancer, as described in Example 18.

As demonstrated in the accompanying Examples, in certain embodiments antibodies or antigen binding fragments of the invention compete with CD155/PVR for TIGIT binding. In certain embodiments, an antibody or antigen binding fragment of the invention exhibits competition with CD155 characterised by an $IC_{50}$ of 0.2 nM or less, preferably 0.1 nM or less. In certain embodiments, the antibody or antigen binding fragment exhibits competition with CD155 characterised by an $IC_{50}$ of about 0.05 nM or less. In certain preferred embodiments, the exhibited $IC_{50}$ is about 0.05 nM. Without wishing to be bound by theory, competition of antibodies with CD155 for TIGIT binding is expected to decrease levels of CD155-induced TIGIT-mediated signalling, thereby increasing levels of effector T cell activation.

The invention further provides "affinity variants" of the antibodies described herein.

The invention also provides an isolated antibody or antigen binding fragment thereof which cross-competes for binding to human TIGIT with an antibody or antigen-binding fragment described herein.

Antibodies of the Invention Promote Pro-Inflammatory T Cell Activity

Antibodies according to the invention (e.g. antibody 31282) are surprisingly effective at promoting pro-inflammatory activity of CD8+ T cells. As demonstrated in the Examples, antibodies or antigen binding fragments according to the invention (especially 31282) are more effective at promoting pro-inflammatory CD8+ T cell activity (indicated by IFNg release) than comparator anti-TIGIT antibodies (see FIG. 24). This improved efficacy versus comparator antibodies was demonstrated in TIGIT-expressing transgenic Jurkat reporter cells and in primary CD8 T cells. Accordingly, in certain embodiments, an anti-TIGIT antibody or antigen binding fragment provided herein exhibits an activation $EC_{50}$ of less than 5 nM for human TIGIT expressed by Jurkat reporter cells as described in Example 19. In preferred such embodiments, the antibody or antigen binding fragment exhibits an $EC_{50}$ of from about 1 nM to about 4 nM, preferably from about 2 nM to about 4 nM.

In certain embodiments, an anti-TIGIT antibody or antigen binding fragment provided herein exhibits an activation $EC_{50}$ of less than 0.4 nM for CD8 T cells from healthy individuals as described in Example 19. CD8 T cell activity (i.e. pro-inflammatory activity) may be measured by inflammatory cytokine (e.g. IFNg) production. In preferred such embodiments, the antibody or antigen binding fragment exhibits an $EC_{50}$ of from about 0.05 nM to about 0.4 nM, preferably from about 0.1 nM to about 0.2 nM. Preferably the $EC_{50}$ is determined using CD8+ T cells from PBMCs taken from a healthy individual, as described in Example 19.

It is additionally and surprisingly demonstrated in the accompanying Examples that the provided anti-TIGIT antibodies are effective at increasing the activity of gamma-delta (γδ, or g/d) T cells (i.e. T cells expressing the γδ TCR subunits, as opposed to the conventional αβ TCR subunits). Such γδ T cells form a distinct and important component of the immune system and the ability of the antibodies provided herein to promote activity of these cells highlights the utility of the antibodies.

Accordingly, also provided herein is a method of promoting γδ T cell activity comprising contacting a population of γδ T cells with an anti-TIGIT antibody. In certain embodiments the method is performed in vitro. In certain embodiments the method is performed in vivo in a human subject. In certain such embodiments the human subject has cancer. In certain embodiments the anti-TIGIT antibody or antigen binding fragment comprises a combination of HCDR1, HCDR2, HCDR3, LCDR1, LCDR2 and LCDR3 sequences of an antibody according to the invention. In certain embodiments the anti-TIGIT antibody comprises a heavy chain variable domain and a light chain variable domain wherein HCDR1 comprises SEQ ID NO: 16, HCDR2 comprises SEQ ID NO: 17, HCDR3 comprises SEQ ID NO: 18, and LCDR1 comprises SEQ ID NO: 61, LCDR2 comprises SEQ ID NO: 62, and LCDR3 comprises SEQ ID NO: 63.

Selective Depletion of T-Reg Cells

As demonstrated herein, anti-TIGIT antibodies are able to selectively deplete TIGIT-expressing Treg cells. That is, anti-TIGIT antibodies reduce the proportion of TIGIT-expressing Treg cells relative to the total population of T cells to a greater extent than they reduce the proportion of effector or memory CD4 or CD8 T cells.

In certain embodiments, the antibody or antigen binding fragment thereof selectively depletes TIGIT-expressing Treg cells.

Figure 25:
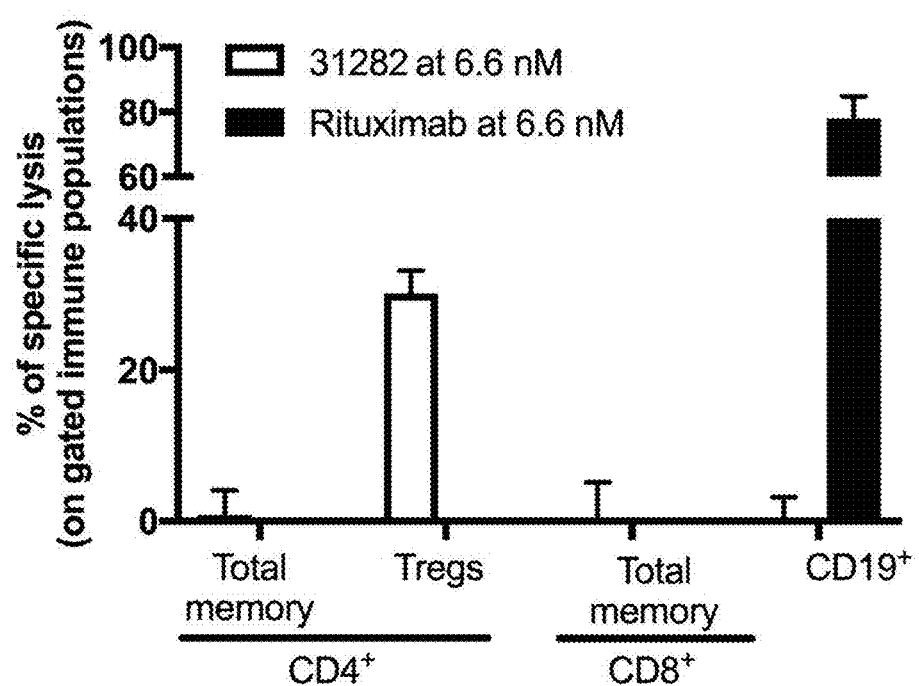
FIG. 25 Cytotoxic activity of a-TIGIT clone 31282 on total memory $CD4^+$ or $CD8^+$ T cells and Treg populations in PBMC from cancer patient FIG. 26 Graph showing the characterization of TIGIT expression on immune populations from cancer patients. (A)

This selective depletion of TIGIT-expressing Treg cells can be mediated via selective lysis of the TIGIT-expressing Tregs (e.g. by ADCC or CDC (see FIGS. 20, 21, and 25). TIGIT-expressing Tregs are understood to be the more potent regulatory cells than Tregs not expressing TIGIT. Without wishing to be bound by theory, selective depletion by lysis of TIGIT-expressing Treg cells is expected to increase T cell effector function (e.g. T-cell mediated cytotoxicity, pro-inflammatory cytokine release) by depleting the overall number of Treg cells but also depleting those Treg cells exhibiting the more potent regulatory function. This increased T cell effector function is demonstrated in FIG. 24.

Therefore, in certain embodiments, antibodies or antigen binding fragments of the invention selectively lyse TIGIT-expressing Treg cells.

Selective depletion of Treg cells expressing TIGIT can also be mediated by inducing internalisation of the TIGIT receptor such that it is no longer expressed at the cell membrane. Without wishing to be bound by theory, by inducing TIGIT internalisation such that TIGIT+ Treg cells become TIGIT− Treg cells, the regulatory function of these cells is expected to become less potent (since TIGIT+ Tregs are more potent regulatory cells). As a result of the receptor internalisation and subsequent drop in regulatory potency of these Tregs, T cell effector function is expected to increase. Therefore, in certain embodiments, antibodies or antigen binding fragments of the invention inhibit suppressive activity of TIGIT-expressing Treg cells, preferably by inducing internalisation of TIGIT by TIGIT-expressing Treg cells.

It is particularly advantageous for anti-TIGIT antibodies according to the invention to exhibit high affinity for CD8 T cells and Treg cells and also to exhibit selective depletion of Treg cells, thereby promoting T cell effector function via two mechanisms. Retention of antibody effector function (e.g. ADCC, CDC) results in effective depletion of the Tregs and the selectivity means the antibody effector function does not result in unwanted depletion of effector T cells. The selectivity is particularly surprising since previous attempts to produce an anti-TIGIT antibody have sought to eliminate antibody effector function in order to avoid lysis of effector T cells expressing TIGIT. Moreover, because TIGIT antibodies of the invention exhibit affinity for effector T cells (e.g. CD8 T cells), TIGIT-mediated signalling in these cells can be inhibited by competition for CD155 binding and/or inducing internalisation of TIGIT on effector T cells. In combination, these effects of the antibodies of the invention can result in significant upregulation of T cell effector function.

In a further aspect is provided a method for selectively depleting Treg cells from a population of T cells, comprising contacting the population of T cells with an anti-TIGIT antibody or antigen binding fragment thereof, whereby the anti-TIGIT antibody selectively depletes the population of Treg cells. In certain embodiments the method is performed in vitro. In certain embodiments the method is performed in vivo in a human subject. In certain such embodiments the human subject has cancer. In certain embodiments the anti-TIGIT antibody or antigen binding fragment comprises a combination of HCDR1, HCDR2, HCDR3, LCDR1, LCDR2 and LCDR3 sequences of an antibody according to the invention. In certain embodiments the anti-TIGIT antibody comprises a heavy chain variable domain and a light chain variable domain wherein HCDR1 comprises SEQ ID NO: 16, HCDR2 comprises SEQ ID NO: 17, HCDR3 comprises SEQ ID NO: 18, and LCDR1 comprises SEQ ID NO: 61, LCDR2 comprises SEQ ID NO: 62, and LCDR3 comprises SEQ ID NO: 63.

Further Advantageous Properties

Further surprising advantageous properties exhibited by antibodies and antigen binding fragments according to the invention include increasing the T cell effector function (e.g. release of proinflammatory cytokines) of tumour infiltrating lymphocytes (TILs). Exposure to the tumour microenvironment can lead to TILs exhibiting anergic or so-called "exhausted" phenotypes, possibly due to antigen over-exposure and/or an immunosuppressive tumour microenvironment. Enhancing the effector function of TILs is desirable as it is these cells that are infiltrating the tumour itself and thus positioned at a locus best-suited to reduce tumour size or growth; however due to the anergic or exhausted phenotype of many TILs, it is expected to be difficult to potentiate their effector function. The increase in proinflammatory response from TILs following exposure to antibodies of the invention is therefore surprising and indicates the antibodies may be particularly effective therapeutic agents.

Still further surprising advantageous properties exhibited by antibodies and antigen binding fragments include the ability to increase the pro-inflammatory activity of gamma-delta (γδ) T cells. The ability to promote activity of non-conventional T cells such as γδ T cells has not previously been reported for an anti-TIGIT antibody and offers the potential to treat diseases other than cancer in which γδ T cells are known to be important. For example, γδ T cells have been reported to be involved in the response to pathogenic infection (bacterial, viral (e.g. CMV), fungal) as well as to have a role in protecting from autoimmune diseases. In addition, the surprising ability to promote activity of non-conventional T cells provides further potency to the anti-tumour effects of the antibodies.

Still further surprising advantageous properties exhibited by antibodies and antigen binding fragments include the ability to selectively deplete malignant T cells while sparing normal T cells. Antibodies of the invention (e.g. 31282) can selectively deplete malignant T cells (e.g. CD4+ T cells), most-likely via ADCC. However there is limited impact on healthy T cells. This points to the antibodies of the invention being particularly useful in the treatment of T cell diseases such as T cell lymphoma (e.g. Sezary syndrome).

Tigit Antibodies that do not Compete with CD155

As demonstrated in the accompanying examples, the present invention also provides anti-TIGIT antibodies that do not compete with CD155/PVR for TIGIT binding. Therefore, in a further aspect, the invention provides a human TIGIT antibody or antigen binding fragment thereof that does not compete with CD155/PVR for human TIGIT binding. In certain such embodiments, Fab fragments of the CD155 non-competitive anti-TIGIT antibodies according to the invention exhibit a $K_D$ for TIGIT measured by ForteBio™ in the range of from $5 \times 10^9$ to $5 \times 10^{-8}$ M, optionally $1 \times 10^{-8}$ to $3 \times 10^{-8}$ M.

In certain preferred embodiments, the antibody may comprise a heavy chain variable domain and a light chain variable domain wherein HCDR1 comprises SEQ ID NO: 280, HCDR2 comprises SEQ ID NO: 281, HCDR3 comprises SEQ ID NO: 282, and LCDR1 comprises SEQ ID NO: 292, LCDR2 comprises SEQ ID NO: 293, and LCDR3 comprises SEQ ID NO: 294. In certain such embodiments, the heavy chain variable domain may comprise the amino acid sequence shown as SEQ ID NO: 333 or an amino acid sequence exhibiting at least 90%, 95%, 97%, 98% or 99% sequence identity thereto, and the light chain variable domain may comprise the amino acid sequence shown as SEQ ID NO: 334 or an amino acid sequence exhibiting at least 90%, 95%, 97%, 98% or 99% sequence identity thereto.

Embodiments wherein the amino acid sequence of the VH domain exhibits less than 100% sequence identity with the sequence shown as SEQ ID NO: 333 may nevertheless comprise heavy chain CDRs which are identical to HCDR1, HCDR2 and HCDR3 of SEQ ID NO:333 (SEQ ID NOs:280, 281 and 282, respectively) whilst exhibiting amino acid sequence variation within the framework regions. Likewise, embodiments wherein the amino acid sequence of the VL domain exhibits less than 100% sequence identity with the sequence shown as SEQ ID NO: 334 may nevertheless comprise light chain CDRs which are identical to LCDR1, LCDR2 and LCDR3 of SEQ ID NO:334 (SEQ ID NOs:292, 293 and 294, respectively) whilst exhibiting amino acid sequence variation within the framework regions.

In certain preferred embodiments, the antibody may comprise a heavy chain variable domain and a light chain variable domain wherein HCDR1 comprises SEQ ID NO: 353, HCDR2 comprises SEQ ID NO: 354, HCDR3 comprises SEQ ID NO: 355, and LCDR1 comprises SEQ ID NO: 356, LCDR2 comprises SEQ ID NO: 357, and LCDR3 comprises SEQ ID NO: 358. In certain such embodiments, the heavy chain variable domain may comprise the amino acid sequence shown as SEQ ID NO: 367 or an amino acid sequence exhibiting at least 90%, 95%, 97%, 98% or 99% sequence identity thereto, and the light chain variable domain may comprise the amino acid sequence shown as SEQ ID NO: 368 or an amino acid sequence exhibiting at least 90%, 95%, 97%, 98% or 99% sequence identity thereto.

Embodiments wherein the amino acid sequence of the VH domain exhibits less than 100% sequence identity with the sequence shown as SEQ ID NO: 367 may nevertheless comprise heavy chain CDRs which are identical to HCDR1, HCDR2 and HCDR3 of SEQ ID NO:367 (SEQ ID NOs:353, 354 and 355, respectively) whilst exhibiting amino acid sequence variation within the framework regions. Likewise, embodiments wherein the amino acid sequence of the VL domain exhibits less than 100% sequence identity with the sequence shown as SEQ ID NO: 368 may nevertheless comprise light chain CDRs which are identical to LCDR1, LCDR2 and LCDR3 of SEQ ID NO:368 (SEQ ID NOs:356, 357 and 358, respectively) whilst exhibiting amino acid sequence variation within the framework regions.

Polynucleotides, Vectors and Expression Systems

The invention also provides polynucleotide molecules encoding the TIGIT antibodies of the invention, also expression vectors containing a nucleotide sequences which encode the TIGIT antibodies of the invention operably linked to regulatory sequences which permit expression of the antigen binding polypeptide in a host cell or cell-free expression system, and a host cell or cell-free expression system containing this expression vector.

Polynucleotide molecules encoding the TIGIT antibodies of the invention include, for example, recombinant DNA molecules. The terms "nucleic acid", "polynucleotide" or a "polynucleotide molecule" as used herein interchangeably and refer to any DNA or RNA molecule, either single- or double-stranded and, if single-stranded, the molecule of its complementary sequence. In discussing nucleic acid molecules, a sequence or structure of a particular nucleic acid molecule may be described herein according to the normal convention of providing the sequence in the 5' to 3' direction. In some embodiments of the invention, nucleic acids or polynucleotides are "isolated". This term, when applied to a nucleic acid molecule, refers to a nucleic acid molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or non-human host organism. When applied to RNA, the term "isolated polynucleotide" refers primarily to an RNA molecule encoded by an isolated DNA molecule as defined above. Alternatively, the term may refer to an RNA molecule that has been purified/separated from other nucleic acids with which it would be associated in its natural state (i.e., in cells or tissues). An isolated polynucleotide (either DNA or RNA) may further represent a molecule produced directly by biological or synthetic means and separated from other components present during its production.

For recombinant production of a TIGIT antibody according to the invention, a recombinant polynucleotide encoding it may be prepared (using standard molecular biology techniques) and inserted into a replicable vector for expression in a chosen host cell, or a cell-free expression system. Suitable host cells may be prokaryote, yeast, or higher eukaryote cells, specifically mammalian cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen. Virol. 36:59-74, 1977); baby hamster kidney cells (BHK, ATCC CCL 10); Chinese hamster ovary cells/-DHFR (CHO, Urlaub et al., Proc. Natl. Acad. Sci. USA 77:4216, 1980; or CHO derived clones like CHO-K1, ATCC CCL-61, Kao and Puck, Genetics of somatic mammalian cells, VII. Induction and isolation of nutritional mutants in Chinese hamster cells, Proc. Natl. Acad. Sci. 60:1275-1281, 1968); mouse sertoli cells (TM4; Mather, Biol. Reprod. 23:243-252, 1980); mouse myeloma cells SP2/0-AG14 (ATCC CRL 1581; ATCC CRL 8287) or NSO (HPA culture collections no. 85110503); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumour (MMT 060562, ATCC CCL51); TRI cells (Mather et al., Annals N.Y. Acad. Sci. 383:44-68, 1982); MRC 5 cells; FS4 cells; and a human hepatoma line (Hep G2), as well as DSM's PERC-6 cell line. Expression vectors suitable for use in each of these host cells are also generally known in the art.

It should be noted that the term "host cell" generally refers to a cultured cell line. Whole human beings into which an expression vector encoding an antigen binding polypeptide according to the invention has been introduced are explicitly excluded from the definition of a "host cell".

In an important aspect, the invention also provides a method of producing a TIGIT antibody of the invention which comprises culturing a host cell (or cell free expression system) containing polynucleotide (e.g. an expression vector) encoding the TIGIT antibody under conditions which permit expression of the TIGIT antibody, and recovering the expressed TIGIT antibody. This recombinant expression process can be used for large scale production of TIGIT antibodies according to the invention, including monoclonal antibodies intended for human therapeutic use. Suitable vectors, cell lines and production processes for large scale manufacture of recombinant antibodies suitable for in vivo therapeutic use are generally available in the art and will be well known to the skilled person.

Therefore, in accordance with the invention is provided an isolated polynucleotide or combination of isolated polynucleotides encoding an antibody or antigen binding fragment comprising a combination of HCDR1, HCDR2, HCDR3, LCDR1, LCDR2 and LCDR3, wherein the combination is selected from the group consisting of:

(i) HCDR1 comprising SEQ ID NO: 16, HCDR2 comprising SEQ ID NO: 17, HCDR3 comprising SEQ ID NO:18, LCDR1 comprising SEQ ID NO:61, LCDR2 comprising SEQ ID NO:62, and LCDR3 comprising SEQ ID NO:63;

(ii) HCDR1 comprising SEQ ID NO:4, HCDR2 comprising SEQ ID NO:5, HCDR3 comprising SEQ ID NO:6, LCDR1 comprising SEQ ID NO:49, LCDR2 comprising SEQ ID NO:50, and LCDR3 comprising SEQ ID NO:51;

(iii) HCDR1 comprising SEQ ID NO:7, HCDR2 comprising SEQ ID NO:8, HCDR3 comprising SEQ ID NO:9, LCDR1 comprising SEQ ID NO:52, LCDR2 comprising SEQ ID NO:53, and LCDR3 comprising SEQ ID NO:54;

(iv) HCDR1 comprising SEQ ID NO:10, HCDR2 comprising SEQ ID NO:11, HCDR3 comprising SEQ ID NO:12, LCDR1 comprising SEQ ID NO:55, LCDR2 comprising SEQ ID NO:56, and LCDR3 comprising SEQ ID NO:57;

(v) HCDR1 comprising SEQ ID NO:13, HCDR2 comprising SEQ ID NO:14, HCDR3 comprising SEQ ID NO:15, LCDR1 comprising SEQ ID NO:58, LCDR2 comprising SEQ ID NO:59, and LCDR3 comprising SEQ ID NO:60;

(vi) HCDR1 comprising SEQ ID NO:1, HCDR2 comprising SEQ ID NO:2, HCDR3 comprising SEQ ID NO:3, LCDR1 comprising SEQ ID NO:46, LCDR2 comprising SEQ ID NO:47, and LCDR3 comprising SEQ ID NO:48;

(vii) HCDR1 comprising SEQ ID NO:19, HCDR2 comprising SEQ ID NO:20, HCDR3 comprising SEQ ID NO:21, LCDR1 comprising SEQ ID NO:64, LCDR2 comprising SEQ ID NO:65, and LCDR3 comprising SEQ ID NO:66;

(viii) HCDR1 comprising SEQ ID NO:22, HCDR2 comprising SEQ ID NO:23, HCDR3 comprising SEQ ID NO:24, LCDR1 comprising SEQ ID NO:67, LCDR2 comprising SEQ ID NO:68, and LCDR3 comprising SEQ ID NO:69;
(ix) HCDR1 comprising SEQ ID NO:25, HCDR2 comprising SEQ ID NO:26, HCDR3 comprising SEQ ID NO:27, LCDR1 comprising SEQ ID NO:70, LCDR2 comprising SEQ ID NO:71, and LCDR3 comprising SEQ ID NO:72;
(x) HCDR1 comprising SEQ ID NO:28, HCDR2 comprising SEQ ID NO:29, HCDR3 comprising SEQ ID NO:30, LCDR1 comprising SEQ ID NO:73, LCDR2 comprising SEQ ID NO:74, and LCDR3 comprising SEQ ID NO:75;
(xi) HCDR1 comprising SEQ ID NO:31, HCDR2 comprising SEQ ID NO:32, HCDR3 comprising SEQ ID NO:33, LCDR1 comprising SEQ ID NO:76, LCDR2 comprising SEQ ID NO:77, and LCDR3 comprising SEQ ID NO:78;
(xii) HCDR1 comprising SEQ ID NO:34, HCDR2 comprising SEQ ID NO:35, HCDR3 comprising SEQ ID NO:36, LCDR1 comprising SEQ ID NO:79, LCDR2 comprising SEQ ID NO:80, and LCDR3 comprising SEQ ID NO:81;
(xiii) HCDR1 comprising SEQ ID NO:37, HCDR2 comprising SEQ ID NO:38, HCDR3 comprising SEQ ID NO:39, LCDR1 comprising SEQ ID NO:82, LCDR2 comprising SEQ ID NO:83, and LCDR3 comprising SEQ ID NO:84;
(xiv) HCDR1 comprising SEQ ID NO:40, HCDR2 comprising SEQ ID NO:41, HCDR3 comprising SEQ ID NO:42, LCDR1 comprising SEQ ID NO:85, LCDR2 comprising SEQ ID NO:86, and LCDR3 comprising SEQ ID NO:87;
(xv) HCDR1 comprising SEQ ID NO:43, HCDR2 comprising SEQ ID NO:44, HCDR3 comprising SEQ ID NO:45, LCDR1 comprising SEQ ID NO:88, LCDR2 comprising SEQ ID NO:89, and LCDR3 comprising SEQ ID NO:90;
(xvi) HCDR1 comprising SEQ ID NO:271, HCDR2 comprising SEQ ID NO:272, HCDR3 comprising SEQ ID NO:273, LCDR1 comprising SEQ ID NO:283, LCDR2 comprising SEQ ID NO:284, and LCDR3 comprising SEQ ID NO:285;
(xvii) HCDR1 comprising SEQ ID NO:274, HCDR2 comprising SEQ ID NO:275, HCDR3 comprising SEQ ID NO:276, LCDR1 comprising SEQ ID NO:286, LCDR2 comprising SEQ ID NO:287, and LCDR3 comprising SEQ ID NO:288;
(xviii) HCDR1 comprising SEQ ID NO:277, HCDR2 comprising SEQ ID NO:278, HCDR3 comprising SEQ ID NO:279, LCDR1 comprising SEQ ID NO:289, LCDR2 comprising SEQ ID NO:290, and LCDR3 comprising SEQ ID NO:291.

In certain embodiments is provided an isolated polynucleotide or combination of isolated polynucleotides encoding an antibody or antigen binding fragment comprising a combination of HCDR1, HCDR2, HCDR3, LCDR1, LCDR2 and LCDR3 wherein:
(i) HCDR1 comprises or consists of SEQ ID NO: 16, HCDR2 comprises or consists of SEQ ID NO: 17, HCDR3 comprises or consists of SEQ ID NO:18, LCDR1 comprises or consists of SEQ ID NO:61, LCDR2 comprises or consists of SEQ ID NO:62, and LCDR3 comprises or consists of SEQ ID NO:63.

Also in accordance with the invention there is provided an isolated polynucleotide or combination of isolated polynucleotides encoding an antibody or antigen binding fragment described herein. In certain embodiments is provided an isolated polynucleotide encoding antibody 31282 provided herein, or an antigen binding fragment thereof.

Also, in accordance with the invention there is provided an isolated polynucleotide encoding a VH and/or a VL domain of an anti-TIGIT antibody, wherein the polynucleotide comprises one or more sequences selected from the group consisting of SEQ ID Nos: 241-270, 335-342 and 369-370. In certain embodiments, the isolated polynucleotide comprises a sequence according to SEQ ID NO: 251 and/or a sequence according to SEQ ID NO: 252. In certain embodiments where the polynucleotide comprises a sequence according to SEQ ID NO: 251 and a sequence according to SEQ ID NO: 252, the sequences are contiguous. In certain embodiments where the polynucleotide comprises a sequence according to SEQ ID NO: 251 and a sequence according to SEQ ID NO: 252, the sequences are not contiguous.

Also, in accordance with the invention there is provided an expression vector comprising a polynucleotide according to the invention operably linked to regulatory sequences which permit expression of the antigen binding polypeptide in a host cell or cell-free expression system.

Also, in accordance with the invention there is provided a host cell or cell-free expression system containing an expression vector according to the invention.

Also, in accordance with the invention there is provided a method of producing a recombinant antibody or antigen binding fragment thereof which comprises culturing the host cell or cell free expression system according to the invention under conditions which permit expression of the antibody or antigen binding fragment and recovering the expressed antibody or antigen binding fragment.

Pharmaceutical Compositions

Also provided herein are pharmaceutical compositions comprising an antibody or antigen binding fragment according to the invention formulated with one or more a pharmaceutically acceptable carriers or excipients. Such compositions may include one or a combination of (e.g., two or more different) TIGIT antibodies. Techniques for formulating antibodies for human therapeutic use are well known in the art and are reviewed, for example, in Wang et al., Journal of Pharmaceutical Sciences, Vol. 96, pp 1-26, 2007.

The TIGIT antibodies and pharmaceutical compositions provided herein have utility in therapy, in particular the therapeutic treatment of disease, in particular conditions that benefit from inhibition of TIGIT function.

Combination Products

As demonstrated herein, the antibodies of the invention or antigen binding fragments thereof are particularly effective when administered in combination with additional therapeutic agents. For example, the antibodies of the invention or antigen binding fragments thereof are particularly effective when administered in combination with immune checkpoint inhibitors—specifically anti-ICOS antagonist antibodies or anti-PD-1 antibodies (that is, antagonist antibodies specific for human immunoregulatory molecule PD-1). Administration of anti-TIGIT antibodies in combination with an anti-ICOS or anti-PD-1 antibody results in a synergistic reduction in tumour growth compared to either antibody alone. Similar effects are expected to be observed using a combination of an anti-TIGIT antibody according to the invention and an anti-PD-L1 antibody.

It is further demonstrated herein that antibodies of the invention or antigen binding fragments thereof are particularly effective when administered in combination with an agonist antibody specific to an immune checkpoint co-stimulatory molecule—specifically anti-4-1BB, anti-OX40 or anti-GITR agonist antibodies. Administration of anti-TIGIT antibodies in combination with an anti-4-1BB, anti-OX40 or anti-GITR agonist antibody results in a synergistic reduction in tumour growth compared to either antibody alone.

In a further aspect is provided a combination product comprising an anti-TIGIT antibody or antigen binding fragment thereof and one or more of a chemotherapeutic agent, an anti-PD1 antibody, an anti-PD-L1 antibody, an anti-41 BB antibody, an anti-OX40 antibody, an anti-GITR antibody, and an anti-ICOS antibody.

It is also demonstrated herein that a combination of an anti-TIGIT antibody or antigen binding fragment thereof according to the invention (e.g. 31282) and a chemotherapeutic agent (e.g. doxorubicin) is particularly effective at treating cancer, such that the combination reduced tumour volume significantly more than either therapy alone, pointing towards a synergistic effect (Example 35).

Furthermore, it is also demonstrated herein that a combination of an anti-TIGIT antibody or antigen binding fragment thereof according to the invention (e.g. 31282), a chemotherapeutic agent (e.g. doxorubicin), and an A2A receptor (A2AR) antagonist results in significantly effective therapy, to the extent that complete remission was induced in the majority of cases. Notably, a combination of anti-TIGIT antibody and A2AR antagonist alone did not improve efficacy over the monotherapies. The efficacy of the combinations of the invention is thus particularly unexpected.

Thus, in a further aspect is provided combination comprising an anti-TIGIT antibody or antigen binding fragment thereof according to the invention, and a chemotherapeutic agent. In a preferred embodiment the chemotherapeutic agent comprises doxorubicin.

In a preferred embodiment, the combination further comprises an adenosine A2A receptor (A2AR) antagonist. Exemplary A2AR antagonists are provided in PCT/EP2019/074208, which is incorporated herein by reference.

In certain preferred embodiments, the anti-TIGIT antibody or antigen binding fragment is an antibody or antigen binding fragment provided in accordance with the invention. In a most preferred embodiment, the anti-TIGIT antibody or antigen binding fragment comprises a combination of HCDR1, HCDR2, HCDR3, LCDR1, LCDR2 and LCDR3, wherein:

```
HCDR1 comprises SEQ ID NO: 16
(YTFTSYYMH),

HCDR2 comprises SEQ ID NO: 17
(VIGPSGASTSYAQKFQG),

HCDR3 comprises SEQ ID NO: 18
(ARDHSDYWSGIMEV),

LCDR1 comprises SEQ ID NO: 61
(RASQSVRSSYLA),

LCDR2 comprises SEQ ID NO: 62
(GASSRAT),
and

LCDR3 comprises SEQ ID NO: 63
(QQYFSPPWT).
```

Also provided is a combination as provided herein for use in a method of treating cancer or viral infection, optionally wherein the viral infection is CMV infection. Further provided is a combination as provided herein for use in a method provided herein.

As used herein, where two or more active agents are provided as a "combination", "therapeutic combination" or "combination therapy" (the terms are used interchangeably), this does not require or exclude that the active agents are formulated into a single composition. A combination therapy is given its conventional interpretation of two or more active agents to be administered such that the patient can derive a benefit from each agent. "Combination therapy" does not necessitate co-formulation, co-administration, simultaneous administration or fixed dose formulation.

Therapeutic Methods

The TIGIT antibodies, or antigen binding fragments thereof, pharmaceutical compositions and combinations provided herein can be used to inhibit the growth of cancerous tumour cells in vivo and are therefore useful in the treatment of tumours.

Accordingly, further aspects of the invention relate to methods of inhibiting tumour cell growth in a human patient, and also methods of treating or preventing cancer, which comprise administering to a patient in need thereof an effective amount of a TIGIT antibody or antigen binding fragment as described herein, a pharmaceutical composition as described herein, or a combination as described herein.

Another aspect of the invention provides a TIGIT antibody or antigen binding fragment as described herein for use in inhibiting the growth of tumour cells in a human patient. A still further aspect of the invention provides a TIGIT antibody or antigen binding fragment as described herein for use treating or preventing cancer in a human patient.

In another aspect the invention provides a method of selectively depleting Treg cells in a cancer patient, the method comprising administering an anti-TIGIT antibody or antigen-binding fragment thereof to the patient. In certain embodiments, the anti-TIGIT antibody binds at an epitope on human TIGIT comprising residues Q56, N58, E60, I68 L73, H76, and I109, preferably consisting of residues Q56, N58, E60, I68 L73, H76, and I109. In certain embodiments, the anti-TIGIT antibody is an anti-TIGIT antibody provided herein.

In certain embodiments, the anti-TIGIT antibody comprises a combination of HCDR1, HCDR2, HCDR3, LCDR1, LCDR2 and LCDR3, wherein:

```
HCDR1 comprises or consists of SEQ ID NO: 16
(YTFTSYYMH),

HCDR2 comprises or consists of SEQ ID NO: 17
(VIGPSGASTSYAQKFQG),

HCDR3 comprises or consists of SEQ ID NO: 18
(ARDHSDYWSGIMEV),

LCDR1 comprises or consists of SEQ ID NO: 61
(RASQSVRSSYLA),

LCDR2 comprises or consists of SEQ ID NO: 62
(GASSRAT),
and

LCDR3 comprises or consists of SEQ ID NO: 63
(QQYFSPPWT).
```

In certain preferred embodiments, the patient to be treated has a cancer selected from: renal cancer (e.g., renal cell carcinoma), breast cancer, brain tumours, chronic or acute leukaemias including acute myeloid leukaemia, chronic myeloid leukaemia, acute lymphoblastic leukaemia, chronic lymphocytic leukaemia, lymphomas (e.g., Hodgkin's and non-Hodgkin's lymphoma, lymphocytic lymphoma, primary CNS lymphoma, B-cell lymphoma (e.g. CLL), T-cell lymphoma (e.g. Sezary Syndrome)), nasopharyngeal carcinomas, melanoma (e.g., metastatic malignant melanoma), prostate cancer, colon cancer, lung cancer, bone cancer, pancreatic cancer, skin cancer, cancer of the head or neck (e.g. head and neck squamous cell carcinoma (HNSCC)), cutaneous carcinoma, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the oesophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumours of childhood, cancer of the bladder, cancer of the kidney or ureter, cancer of the renal pelvis, neoplasm of the central nervous system (CNS), tumour angiogenesis, spinal axis tumour, brain stem glioma, pituitary adenoma, Kaposi's sarcoma, epidermoid cancer, squamous cell cancer, mesothelioma. In certain embodiments, the cancer inhibited is lung cancer, bladder cancer, breast cancer, kidney cancer (for example kidney carcinoma), head and neck cancer (e.g. HNSCC), or colon cancer (for example colon adenocarcinoma). In certain embodiments, the cancer is colon cancer (for example colon adenocarcinoma) or lung cancer. In certain embodiments, the cancer is a blood cancer. In certain such embodiments, the cancer is lymphoma. In certain embodiments the cancer is T cell lymphoma or B cell lymphoma.

In certain embodiments the cancer treated is selected from colon adenocarcinoma, hepatic carcinoma, pancreatic carcinoma, lung cancer and T cell lymphoma (e.g. Sezary Syndrome). In certain embodiments the cancer treated is colon adenocarcinoma. In certain embodiments the cancer treated is hepatic carcinoma. In certain embodiments the cancer treated is pancreatic carcinoma. In certain embodiments the cancer treated is lung cancer, for example lung carcinoma. In certain embodiments the cancer treated is T cell lymphoma, for example Sezary Syndrome.

In certain embodiments, the method of treating cancer further comprises administration of an additional therapeutic agent, for example a chemotherapeutic agent.

In certain preferred embodiments, the method of treating cancer comprises administration of a combination according to the invention comprising an anti-TIGIT antibody or antigen binding fragment thereof, a chemotherapeutic agent and optionally a A2AR antagonist.

Also provided is a combination according to the invention comprising an anti-TIGIT antibody or antigen binding fragment thereof, a chemotherapeutic agent and optionally a A2AR antagonist, for use in therapy, optionally for use in treating cancer. Preferably the cancer is colon adenocarcinoma.

Also provided is an anti-TIGIT antibody or antigen binding fragment thereof according to the invention, for use in a method of treating cancer, wherein the method comprises administering the antibody in combination with a chemotherapeutic agent. Preferably the chemotherapeutic agent is doxorubicin.

In certain preferred embodiments, the method further comprises administering an A2AR antagonist, wherein the antibody or antigen binding fragment, the chemotherapeutic agent, and the A2AR antagonist are administered as a combination.

As demonstrated herein, the antibodies of the invention or antigen binding fragments thereof are particularly effective when administered in combination with immune checkpoint inhibitors—specifically anti-ICOS antagonist antibodies or anti-PD-1 antibodies (that is, antagonist antibodies specific for human immunoregulatory molecule PD-1). Administration of anti-TIGIT antibodies in combination with an anti-ICOS or anti-PD-1 antibody results in a synergistic reduction in tumour growth compared to either antibody alone. Similar effects are expected to be observed using a combination of an anti-TIGIT antibody according to the invention and an anti-PD-L1 antibody.

It is further demonstrated herein that antibodies of the invention or antigen binding fragments thereof are particularly effective when administered in combination with an agonist antibody specific to an immune checkpoint co-stimulatory molecule—specifically anti-4-1BB, anti-OX40 or anti-GITR agonist antibodies. Administration of anti-TIGIT antibodies in combination with an anti-4-1BB, anti-OX40 or anti-GITR agonist antibody results in a synergistic reduction in tumour growth compared to either antibody alone.

Therefore, also provided herein is a method of treating cancer in a subject comprising administering to the subject an effective amount of an anti-TIGIT antibody or antigen binding fragment thereof according to the invention and also administering an effective amount of an anti-PD-1 antibody, an anti-PD-L1 antibody, an anti-41BB antibody, an anti-OX40 antibody, and anti GITR antibody, or an anti-ICOS antibody.

In addition, the data provided herein demonstrating that anti-TIGIT antibodies can increase the activity of γδ cells as well as conventional T cells indicates that anti-TIGIT antibodies can be used to treat conditions other than cancer. In particular, γδ T cells are known to be important in the response to infection, for example bacterial, fungal or viral infection. As shown in Example 29, when contacted with an anti-TIGIT antibody, γδ T cells from CMV seropositive subjects exhibit markedly increased activation, characterised by an increase in IFNg section. The ability to promote activation of γδ T cells in CMV patients in this manner indicates that administration of an anti-TIGIT antibody will promote the antiviral activity of the γδ T cells.

Accordingly, provided herein is a method of treating viral infection in a subject comprising administering an effective amount of an anti-TIGIT antibody or antigen-binding fragment thereof. Also provided is a method of treating viral infection in a subject comprising administering an effective amount of an anti-TIGIT antibody or antigen-binding fragment or a pharmaceutical composition provided herein to the subject, thereby treating the viral infection. In preferred embodiments, the viral infection is CMV infection.

In certain embodiments, the method further comprises administration of one or more additional therapeutic agents. In certain embodiments, the one or more therapeutic agents are selected from: an anti-PD1 antibody, an anti-PD-L1 antibody, an anti-41BB antibody, an anti-OX40 antibody, an anti GITR antibody, and an anti-ICOS antibody.

As demonstrated in the Examples, the anti-TIGIT antibodies disclosed herein are effective at promoting T cell activity, especially pro-inflammatory T cell activity. T ell activity can be measured by methods familiar to those of skill in the art, for example by measuring IFNg production as described in the Examples.

Accordingly, also provided herein is a method of promoting T cell activity comprising contacting a population of T cells with an antibody or antigen binding fragment as described herein.

In certain embodiments, the method of promoting T cell activity is performed in vitro. In certain embodiments, the method of promoting T cell activity is performed in vivo in a human subject. In certain such embodiments, the human subject has cancer. In certain embodiments, the human subject has a viral infection, for example CMV infection.

In certain embodiments, the method promotes conventional αβ T cell activity. In certain embodiments, the method promotes CD4 T cell activity. In certain embodiments, the method promotes CD8 T cell activity. In certain embodiments, the method promotes γδ (gamma-delta) T cell activity.

It is further demonstrated in the Examples that the anti-TIGIT antibodies disclosed herein will be especially effective at promoting T cell activity when used in combination with an anti-PD1 antibody, an anti-PD-L1 antibody, an anti-41BB antibody, an anti-OX40 antibody, an anti GITR antibody, or an anti-ICOS antibody. Significantly, the combination provides a synergistic (i.e. greater than additive) increase in T cell activity.

Accordingly, in certain embodiments, the method of promoting T cell activity further comprises contacting the population of T cells with one or more of: an anti-PD1 antibody, an anti-PD-L1 antibody, an anti-41BB antibody, an anti-OX40 antibody, an anti GITR antibody, and an anti-ICOS antibody.

Variants and equivalents of the embodiments of the invention described herein but not departing from the spirit and scope of the invention will be familiar to the skilled person. The invention will be further understood with reference to the following non-limiting Examples.

EXAMPLES

Example 1: Selection of TIGIT Antigen-Binding Proteins

TIGIT ABPs were selected from a synthetic library of human antibodies expressed and presented on the surface of yeast cells in IgG format generally as described, e.g., in WO2009036379; WO2010105256; WO2012009568; and Xu et al., *Protein Eng Des Sel.*, Vol. 26(10), pp. 663-670 (2013)), and more specifically as provided below. The sequences and characteristics of the ABPs isolated from the recombinant library are provided in FIGS. 1 to 6.

Eight naïve human synthetic yeast libraries each of ~$10^9$ diversity were propagated as described previously (see, e.g.: Xu et al, 2013; WO2009036379; WO2010105256; and WO2012009568). For the first two rounds of selection, a magnetic bead sorting technique utilizing the Miltenyi MACS system was performed, as described (see, e.g., Siegel et al., 2004). Briefly, yeast cells (~$10^{10}$ cells/library) were incubated with biotinylated TIGIT-Fc antigen (Creative Biomart) in FACS wash buffer (phosphate-buffered saline (PBS)/0.1% bovine serum albumin (BSA)). After washing once with 50 ml ice-cold wash buffer, the cell pellet was resuspended in 40 mL wash buffer, and Streptavidin MicroBeads (500 µl) were added to the yeast and incubated for 15 min at 4° C. Next, the yeast were pelleted, resuspended in 5 mL wash buffer, and loaded onto a Miltenyi LS column. After the 5 mL was loaded, the column was washed 3 times with 3 ml FACS wash buffer. The column was then removed from the magnetic field, and the yeast were eluted with 5 mL of growth media and then grown overnight. The following rounds of sorting were performed using flow cytometry. Approximately $1×10^8$ yeast were pelleted, washed three times with wash buffer, and incubated with biotinylated TIGIT-Fc fusion antigen (10 nM) under equilibrium conditions at room temperature. Yeast were then washed twice and stained with LC-FITC (diluted 1:100) and either SA-633 (diluted 1:500) or EA-PE (diluted 1:50) secondary reagents for 15 min at 4° C. After washing twice with ice-cold wash buffer, the cell pellets were resuspended in 0.4 mL wash buffer and transferred to strainer-capped sort tubes. Sorting was performed using a FACS ARIA sorter (BD Biosciences) and sort gates were assigned to select for specific binders relative to a background control. Subsequent rounds of selection were employed in order to reduce the number of non-specific binders utilizing soluble membrane proteins from CHO cells (See, e.g., WO2014179363 and Xu et al., *Protein Eng Des Sel*, Vol. 26(10), pp. 663-670 (2013)), and identify binders with improved affinity to TIGIT using the TIGIT-Fc antigen. After the final round of sorting, yeast were plated and individual colonies were picked for characterization and for nomination of clones for affinity maturation. 63 clones were screened for functional activity. From the screening, clones 26518, 26452, 26486, 26521 and 26493 had the best functional activity and were selected for further optimization.

Example 2: Antibody Optimization

Optimization of naïve clones was carried out utilizing three maturation strategies: light chain diversification; diversification of HCDR1 and HCDR2; and diversification of HCDR3 within the selected HCDR1 and HCDR2 diversity pools.

Light chain diversification: Heavy chain variable regions were extracted from naïve outputs (described above) and transformed into a light chain library with a diversity of $1×10^6$. Selections were performed as described above with one round of MACS sorting and three rounds of FACS sorting using 10 nM or 1 nM biotinylated TIGIT-HIS antigen (Creative Biomart) for respective rounds.

HCDR1 and HCDR2 selection: The HCDR3s from clones selected from the light chain diversification procedure were recombined into a premade library with HCDR1 and HCDR2 variants of a diversity of $1×10^8$ and selections were performed using monomeric HIS-TIGIT antigen. Affinity pressures were applied by using decreasing concentrations of biotinylated HIS-TIGIT antigen (100 to 1 nM) under equilibrium conditions at room temperature.

HCDR3/HCDR1/HCDR2 selections: Oligos were ordered from IDT which comprised the HCDR3 as well as a homologous flanking region on either side of the HCDR3. Amino acid positions in the HCDR3 were variegated via NNK diversity at two positions per oligo across the entire HCHR3. The HCDR3 oligos were double-stranded using primers which annealed to the flanking region of the HCDR3. The remaining FWR1 to FWR3 of the heavy chain variable region was amplified from pools of antibodies with improved affinity that were isolated from the HCDR1 and HCDR2 diversities selected above. The library was then created by transforming the double stranded HCDR3 oligo, the FWR1 to FWR3 pooled fragments, and the heavy chain expression vector into yeast already containing the light chain of the original naïve parent. Selections were performed as during previous cycles using FACS sorting for four rounds. For each FACS round the libraries were assessed for PSR binding, species cross-reactivity, and affinity pressure, and sorting was performed to obtain populations with the desired characteristics. Affinity pressures for these selections were performed as described above in the HCDR1 and HCDR2 selection.

Example 3: Antibody Production and Purification

A. Production in Yeast

In order to produce sufficient amounts of optimized and non-optimized selected antibodies for further characterization, the yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0. Fab fragments were generated by papain digestion and purified in a two steps process over Protein A (GE LifeSciences) and KappaSelect (GE Healthcare LifeSciences).

B. Production in Mammalian Cells

In order to produce sufficient amounts of optimized and non-optimized selected antibodies for further characterization, DNA vector coding for specific antibody clones were generated and transduced into HEK cells. Human codon optimized synthetic DNA fragments for antibody variable domains were ordered at Geneart. Variable domain sequences were seamlessly ligated into pUPE expression vectors containing the mouse IgKappa signal sequence and constant regions of the respective antibody class. Expression vectors were verified by restriction analysis and DNA sequencing. For transient transfection Endotoxin free DNA maxipreps (Sigma) were produced and heavy and light chain vectors were co-transfected to HEK293EBNA1 cells, in Freestyle medium (ThermoFisherScientific), according to established protocols. Primatone (0.55% final volume) was added 24 hour post-transfection. Conditioned medium was harvested 6 days post transfection. Antibodies were purified batch wise by Mabselect sureLX (GE Healthcare) affinity chromatography. Bound antibodies were washed in 2 steps with PBS containing 1M NaCl and PBS. Antibodies were eluted with 20 mM Citrate 150 mM NaCl pH3 and neutralized to approximately pH7 with 1/6 volume of 1M K2HPO4/KH2PO4 pH8.

Next the antibodies were further purified by gel-filtration using a Superdex200 column, equilibrated in PBS. Fractions were analysed by NuPAGE and antibody containing fractions were pooled. The final products were sterilized over a 0.22 µM syringe filter. The product was analysed by NuPAGE and endotoxin levels were measured by LAL-assay.

Example 4: Affinity Determination for Binding of Anti-TIGIT Antibodies to Recombinant Human TIGIT Protein A. ForteBio $K_D$ Measurements ForteBio affinity measurements of selected antibodies were performed generally as previously described (see, e.g., Estep et al., Mabs, Vol. 5(2), pp. 270-278 (2013)). Briefly, ForteBio affinity measurements were performed by loading IgGs on-line onto AHQ sensors. Sensors were equilibrated off-line in assay buffer for 30 min and then monitored on-line for 60 seconds for baseline establishment. Sensors with loaded IgGs were exposed to 100 nM antigen (human TIGIT-Fc, human TIGIT-His or cyno TIGIT-Fc) for 5 minutes, afterwards they were transferred to assay buffer for 5 min for off-rate measurement. Kinetics were analyzed using the 1:1 binding model. More than 90 antibodies were tested for affinity by ForteBio and Table 3 provides data for 15 selected anti-TIGIT antibodies demonstrating strong binding to recombinant TIGIT protein.

B. MSD-SET $K_D$ Measurements

Equilibrium affinity measurements of selected antibodies were performed generally as previously described (Estep et al., Mabs, Vol. 5(2), pp. 270-278 (2013)). Briefly, solution equilibrium titrations (SET) were performed in PBS+0.1% IgG-Free BSA (PBSF) with antigen (TIGIT-His monomer) held constant at 10-100 µM and incubated with 3- to 5-fold serial dilutions of Fab or mAbs starting at 10 µM-10 nM. Antibodies (20 nM in PBS) were coated onto standard bind MSD-ECL plates overnight at 4° C. or at room temperature for 30 min. Plates were then blocked by BSA for 30 min with shaking at 700 rpm, followed by three washes with wash buffer (PBSF+0.05% Tween 20). SET samples were applied and incubated on the plates for 150 s with shaking at 700 rpm followed by one wash. Antigen captured on a plate was detected with 250 ng/mL sulfotag-labeled streptavidin in PBSF by incubation on the plate for 3 min. The plates were washed three times with wash buffer and then read on the MSD Sector Imager 2400 instrument using 1× Read Buffer T with surfactant. The percent free antigen was plotted as a function of titrated antibody in Prism and fit to a quadratic equation to extract the $K_D$. To improve throughput, liquid handling robots were used throughout MSD-SET experiments, including SET sample preparation. Selected antibodies were tested for affinity by MSD and Table 4 provides data for 7 anti-TIGIT clones demonstrating strong binding to recombinant TIGIT protein.

TABLE 4

MSD analysis of affinity for selected anti-TIGIT antibodies

| Clone | MSD Affinity Monovalent KD (M) Human TIGIT-His |
|---|---|
| 29489 | 1.1E-10 |
| 29494 | 7.0E-11 |
| 29499 | 1.9E-11 |
| 29513 | 2.5E-11 |
| 29520 | 2.1E-10 |
| 29523 | 1.7E-09 |
| 29527 | 6.4E-10 |

C. Biacore Measurement

Biosensor analysis was conducted at 25° C. in a HBS-EP buffer system (10 mM HEPES pH 7.3, 150 mM NaCl, 3 mM EDTA, 0.05% Surfactant P20) using a Biacore 8K optical biosensor docked with a CM5 sensor chip (GE Healthcare, Marlboro, MA). The sample hotel was maintained at 8° C. Goat anti-human IgG capture antibody (Fcγ fragment specific, Jackson ImmunoResearch Laboratories, Inc., West Grove, PA; 109-005-098) was immobilized (11700+/−200 RU) to both flow cells of the sensor chip using standard amine coupling chemistry. This surface type provided a format for reproducibly capturing fresh analysis antibody after each regeneration step. Flow cell 2 was used to analyze captured antibody (60-90 RU) while flow cell 1 was used as a reference flow cell. Antigen concentrations ranging from 30 to 0.123 nM (3-fold dilutions) were prepared in running buffer. Each of the antigen sample concentrations were run as a single replicate. Two blank (buffer) injections also were run and used to assess and subtract system artefacts. The association (300 s) and dissociation (600 s) phases for all antigen concentrations were performed at a flow rate of 30 uL/min. The surface was regenerated with three sequential injections (15 s, 15 s and 60 s) of 10 mM glycine, pH 1.5 at a flow rate of 30 uL/min. The data was aligned, double referenced, and fit to a 1:1 binding model using Biacore 8K Evaluation Software, version 1.0. Selected antibodies were tested for affinity by Biacore and Table 5 provides data for 5 anti-TIGIT clones demonstrating strong binding to recombinant TIGIT protein.

TABLE 5

Biacore analysis of affinity for selected anti-TIGIT antibodies

| Clone | Biacore: Monovalent KD (M) (IgG on CM5 chip, Human TIGIT-HIS in solution (Starting concentration 25 nM, 3x dilution) |
|---|---|
| 29489 | 2.48E−10 |
| 31282 | 2.94E−10 |
| 29494 | 2.70E−10 |
| 29520 | 7.16E−10 |
| 29527 | 1.20E−09 |
| 31288 | 1.92E−10 |

Example 5: Competition Assay Between Anti-TIGIT Antagonistic Antibodies and TIGIT Natural Ligands A. Octet Red384 Epitope Binning/Ligand Blocking Epitope binning/ligand blocking of selected antibodies was performed using a standard sandwich format cross-blocking assay. Control anti-target IgG was loaded onto AHQ sensors and unoccupied Fc-binding sites on the sensor were blocked with an irrelevant human IgG1 antibody. The sensors were then exposed to 100 nM target antigen (hTIGIT, Creative Biomart) followed by a second anti-target antibody or ligand (anti-TIGIT antibody and CD155 or CD113 or CD112). Data was processed using ForteBio's Data Analysis Software 7.0. Additional binding by the second antibody or ligand after antigen association indicates an unoccupied epitope (non-competitor), while no binding indicates epitope blocking (competitor or ligand blocking). Parental antibodies (before optimization) were tested for competition with natural ligands and Table 6 summarizes the data obtained for competition against CD155, CD112 and CD113. Parental clone 26432 was found not to compete with CD155 for TIGIT binding. All other selected anti-TIGIT antibodies compete with natural ligand for binding to recombinant human TIGIT protein.

TABLE 6

Binning analysis against TIGIT natural ligands for non-optimized anti-TIGIT antibodies

| Clone | CD155 competition | CD112 competition | CD113 competition |
|---|---|---|---|
| 26518 | Yes | Yes | Yes |
| 26452 | Yes | Yes | Yes |
| 26486 | Yes | Yes | Yes |
| 26521 | Yes | Yes | Yes |
| 26493 | Yes | Yes | Yes |
| 26432 | No | | |

B. Competition of Anti-TIGIT Antagonistic Antibodies with CD155 on Jurkat-hTIGIT Jurkat cells overexpressing human TIGIT (Jurkat-hTIGIT) were collected and distributed at $10^5$ cells/well and incubated with anti-human TIGIT antibodies at the following concentrations: 166.6; 53.24; 17.01; 5.43; 1.73; 0.55; 0.17; 0.05; 0.01; $5.78 \times 10^{-3}$; $1.85 \times 10^{-3}$; $5.9 \times 10^{-3}$ nM in complete medium during 45 min at 37° C. Excess of antibody was washed, and then the cells were incubated with CD155-His at 5 µg/ml (Creative Biomart, PVR-3141H) for 45 min at 37° C. Then, bound CD155-His was detected using anti-His tag-PE (Biolegend, 362603, at 2 µl per test), incubated for 30 min at 4° C. Cells were analysed by FACS using BD LSRFortessa and the half concentration ($IC_{50}$) that prevents CD155 binding was calculated on the basis of the geometric mean fluorescence.

The results were as follows: 0,101 nM for clone 29489; 0.07 nM for clone 29494; 0, 102 nM for clone 29520 and 0,078 nM for clone 29527, for the results illustrated in FIG. 7. The values of other tested antibodies are summarized in the Table 7 below. Overall, the results demonstrate a strong competition by the tested antagonistic anti-TIGIT antibodies with CD155 for binding to membrane expressed TIGIT.

TABLE 7

$IC_{50}$ data for CD155 competition on human TIGIT

| Clone | IC50 of CD155 competition for TIGIT binding (in nM) |
|---|---|
| 29489 | 0.101 |
| 29494 | 0.070 |
| 29499 | 0.103 |
| 29513 | 0.094 |
| 29520 | 0.102 |
| 29523 | 0.079 |
| 29527 | 0.078 |

Example 6: Characterization of Hydrophobic Interaction Chromatography (*MAbs*. 2015 May-June; 7(3):553-561.)

Anti-TIGIT IgG1 antibody samples were buffer exchanged into M ammonium sulfate and 0.1 M sodium phosphate at pH 6.5 using a Zeba 40 kDa 0.5 mL spin column (Thermo Pierce, cat #87766). A salt gradient was established on a Dionex ProPac HIC-10 column from 1.8 M ammonium sulfate, 0.1 M sodium phosphate at pH 6.5 to the same condition without ammonium sulfate. The gradient ran for 17 min at a flow rate of 0.75 ml/min. An acetonitrile wash step was added at the end of the run to remove any remaining protein and the column was re-equilibrated over 7 column volumes before the next injection cycle. Peak retention times were monitored at A280 absorbance and concentrations of ammonium sulfate at elution were calculated based on gradient and flow rate. Table 8 summarizes the results obtained for 15 selected anti-TIGIT antibodies.

TABLE 8

Analysis of Hydrophobic Interaction Chromatography for selected anti-TIGIT antibodies

| Clone | Hydrophobic Interaction Chromatography (HIC) Retention Time (min) |
|---|---|
| 26518 | 10.4 |
| 29478 | 12.7 |
| 26452 | 9.3 |
| 29487 | 9.9 |
| 29489 | 10.6 |
| 26486 | 11.0 |
| 29494 | 9.7 |
| 29499 | 9.1 |
| 26521 | 12.4 |
| 29513 | 12.5 |
| 26493 | 8.8 |
| 29520 | 9.6 |
| 29523 | 8.7 |

TABLE 8-continued

Analysis of Hydrophobic Interaction Chromatography for selected anti-TIGIT antibodies

| Clone | Hydrophobic Interaction Chromatography (HIC) Retention Time (min) |
|---|---|
| 29527 | 8.6 |
| 26432 | 11.1 |
| 32919 | 9.0 |
| 32931 | 9.3 |
| 32959 | 12.0 |

Example 7: Characterization of PSR Preparation Polyspecificity Reagent

A. Preparation of Polyspecificity Reagent:

Polyspecificity reagent (PSR) was prepared according to Xu et. al, *mAbs* 2013. In brief, 2.5 liters CHO-S cells were used as starting material. The cells were pelleted at 2,400×g for 5 min in 500 mL centrifuge bottles filled to 400 mL. Cell pellets were combined and then resuspended in 25 ml Buffer B and pelleted at 2,400×g for 3 min. The buffer was decanted and the wash repeated one time. Cell pellets were resuspended in 3× the pellet volume of Buffer B containing 1×protease inhibitors (Roche, cOmplete, EDTA-free) using a polytron homogenizer with the cells maintained on ice. The homogenate was then centrifuged at 2,400×g for 5 min and the supernatant retained and pelleted one additional time (2,400×g/5 min) to ensure the removal of unbroken cells, cell debris and nuclei; the resultant supernatant is the total protein preparation. The supernatant was then transferred into two Nalgene Oak Ridge 45 mL centrifuge tubes and pelleted at 40,000×g for 40 min at 4° C. The supernatants containing the Separated Cytosolic Proteins (SCPs) were then transferred into clean Oak Ridge tubes, and centrifuged at 40,000×g one more time. In parallel, the pellets containing the membrane fraction (EMF) were retained and centrifuged at 40,000 for 20 min to remove residual supernatant. The EMF pellets were then rinsed with Buffer B. 8 mL Buffer B was then added to the membrane pellets to dislodge the pellets and transfer into a Dounce Homogenizer. After the pellets were homogenized, they were transferred to a 50 mL conical tube and represented the final EMF preparation.

One billion mammalian cells (e.g. CHO, HEK293, Sf9) at ~$10^6$-$10^7$ cells/mL were transferred from tissue culture environment into 4×250 mL conical tubes and pelleted at 550×g for 3 min. All subsequent steps were performed at 4° C. or on ice with ice-cold buffers. Cells were washed with 100 mL of PBSF (1×PBS+1 mg/mL BSA) and combined into one conical tube. After removing the supernatant, the cell pellet was then re-suspended in 30 mL Buffer B (50 mM HEPES, 0.15 M NaCl, 2 mM CaCl2, 5 mM KCl, 5 mM MgCl2, 10% Glycerol, pH 7.2) and pelleted at 550×g for 3 min. Buffer B supernatant was decanted and cells re-suspended in 3× pellet volume of Buffer B plus 2.5× protease inhibitor (Roche, cOmplete, EDTA-free). Protease inhibitors in Buffer B were included from here on forward. Cells were homogenized four times for 30 sec pulses (Polyton homogenizer, PT1200E) and the membrane fraction was pelleted at 40,000×g for 1 hour at 4 C. The pellet is rinsed with 1 mL Buffer B; the supernatant is retained and represents the s. The pellet is transferred into a Dounce homogenizer with 3 mL of Buffer B and re-suspended by moving the pestle slowly up and down for 30-35 strokes. The enriched membrane fraction (EMF) is moved into a new collection tube, rinsing the pestle to collect all potential protein. Determine the protein concentration of the purified EMF using the Dc-protein assay kit (BioRad). To solubilize the EMF, transfer into Solubilization Buffer (50 mM HEPES, 0.15 M NaCl, 2 mM CaCl2, 5 mM KCl, 5 mM MgCl2, 1% n-Do-decyl-b-D-Maltopyranoside (DDM), 1× protease inhibitor, pH 7.2) to a final concentration of 1 mg/mL. Rotate the mixture overnight at 4° C. rotating followed by centrifugation in a 50 mL Oak Ridge tube (Fisher Scientific, 050529-ID) at 40,000×g for 1 hour. The supernatant, which represents the soluble membrane proteins (SMPs), was collected and the protein yield quantified as described above.

For biotinylation, prepare the NHS-LC-Biotin stock solution according to manufacturer's protocol (Pierce, Thermo Fisher). In brief, 20 ul of biotin reagent is added for every 1 mg of EMF sample and incubated at 4° C. for 3 hours with gentle agitation. Adjust the volume to 25 mL with Buffer B and transfer to an Oak Ridge centrifuge tube. Pellet the biotinylated EMF (b-EMF) at 40,000×g for 1 hour, and rinse two times with 3 mL of Buffer C (Buffer B minus the glycerol) without disturbing the pellet. Remove the residual solution. The pellet was re-suspended with a Dounce homogenizer in 3 mL of Buffer C as described previously. The re-suspended pellet now represents biotinylated EMF (b-EMF) and is solubilized as described above to prepare b-SMPs.

B. PSR Binding Analyses

PSR analyses were carried out generally as described in WO2014/179363. Briefly, to characterize the PSR profile of monoclonal antibodies presented on yeast, two million IgG-presenting yeast were transferred into a 96-well assay plate and pellet at 3000×g for 3 min to remove supernatant. Re-suspend the pellet in 50 ul of freshly prepared 1:10 dilution of stock b-PSRs and incubate on ice for 20 minutes. Wash the cells twice with 200 ul of cold PBSF and pellet re-suspended in 50 ul of secondary labeling mix (Extravidin-R-PE, anti-human LC-FITC, and propidium iodide). Incubate the mix on ice for 20 minutes followed by two washes with 200 ul ice-cold PBSF. Re-suspend the cells in 100 ul of ice-cold PBSF and run the plate on a FACS Canto (BD Biosciences) using HTS sample injector. Flow cytometry data was analyzed for mean fluorescence intensity in the R-PE channel and normalized to proper controls in order to assess non-specific binding. Table 9 summarizes the results of Poly-specificity Reagent binding obtained for 15 selected anti-TIGIT antibodies which confirm low score for most of the clones.

TABLE 9

Analysis of Polyspecificity Reagent

| Clone | Polyspecificity Reagent (PSR) Score (0-1) |
|---|---|
| 26518 | 0.00 |
| 29478 | 0.01 |
| 26452 | 0.00 |
| 29487 | 0.01 |
| 29489 | 0.01 |
| 26486 | 0.00 |
| 29494 | 0.00 |
| 29499 | 0.10 |
| 26521 | 0.00 |
| 29513 | 0.01 |
| 26493 | 0.00 |
| 29520 | 0.32 |
| 29523 | 0.12 |
| 29527 | 0.12 |
| 26432 | 0.00 |
| 31288 | 0.00 |
| 32919 | 0.00 |

TABLE 9-continued

Analysis of Polyspecificity Reagent

| Clone | Polyspecificity Reagent (PSR) Score (0-1) |
|---|---|
| 32931 | 0.00 |
| 32959 | 0.1 |

Example 8: Characterization of TIGIT Expression on Immune Populations from Healthy Human PBMC A. TIGIT Expression Profile on T Cell Subsets Flow cytometry analyses were performed to assess the expression of TIGIT on immune cell subsets in PBMC freshly isolated from healthy individuals. Conjugated antibodies were purchased from Ebioscience/Thermo Fisher Scientific, BioLegend or BD Biosciences. Cells were stained per manufacturer's instruction using filtered FACS buffer (PBS+2 mM EDTA+0.1% BSA) and Brilliant Stain buffer (BD #563794). Cells were blocked with appropriate Human FcBlock (BD #564220) prior to staining and were fixed using IC fixation buffer (eBioscience #00-8222-49) prior acquisition. Acquisition was performed on a FACS Fortessa (BD Biosciences) and analyzed with FlowJo software (FlowJo, LLC). Viable cells were gated on Forward and Side scatter. Various Immune cells subsets were gated as followed: $CD19^+$ (B cells), $CD3^- CD19^- CD14^+$ (Monocytes), $CD3^+ TCRab^-$ (TCRgd T cells), $CD3^+ TCRab^+$ (TCRab T cells), $CD3^- CD19^- CD14^- HLA-DR^- CD56^{low/high}$ (NK cells), $CD3^- CD19^- CD14^- HLA-DR^+$ (Dendritic cells), $CD3^+ TCRab^+ CD4^+ CD127^{low} CD25^+$ (regulatory T cells), $CD3^+ TCRab^+ CD4^+$ or $CD8^+ CD45RO^- CCR7^+$ (CD4 or CD8 naïve T cells), $CD3^+ TCRab^+ CD4^+$ or $CD8^+ CD45RO^+$ (memory T cells) and $CD45RO^- CD62L^-$ (effector T cells), As shown in FIGS. 8A and 8B, TIGIT is preferentially expressed on NK cells, regulatory T cells and CD8 memory T cells. It is present to a lesser extent on other T cells subsets with a low proportion of naïve T cells showing TIGIT expression. In addition, TIGIT is not expressed on monocytes, dendritic cells and B cells (FIG. 8B). This set of data is in agreement with published data (Yu et al. NI 2008 and Wang et al. EJI 2015).

Example 9: Cellular Binding of Anti-TIGIT Antagonistic Antibodies

A. Binding of Anti-TIGIT Antibodies to Jurkat-hTIGIT and Jurkat-mTIGIT

The affinity of human anti-TIGIT antibodies has been measured using Jurkat E6.1 cells transduced with human-TIGIT (Jurkat hTIGIT) or mouse TIGIT (Jurkat-mTIGIT). To analyse the affinity of the selected antibodies for hTIGIT or mTIGIT, $10^5$ cells were distributed per well and incubated with anti-TIGIT antibody at a single dose of 100 nM (Table 3) or with decreasing concentration (166.6; 53.24; 17.01; 5.43; 1.73; 0.55; 0.17; 0.05; 0.01; $5.78 \times 10^{-3}$; $1.85 \times 10^{-3}$; $5.9 \times 10^3$ nM) of selected antibodies (FIG. 9). Antibodies were incubated with the cells for 20 min at 4° C. in FACS buffer. After washing, cells were incubated with anti-human Ig (Fc gamma specific)-PE (eBioscience, 12-4998-82, at 2.5 µg/ml) for 20 min on ice and washed twice. Geometric mean fluorescence intensity was analysed using LSR BD Fortessa. Cell binding was recorded as the median florescence intensity of PE on the transfected line compared to the untransfected line for each antibody (Table 3). For calculation of $EC_{50}$ binding, the half-maximal concentration of binding ($EC_{50}$) to hTIGIT-Jurkat was calculated using a four-variable curve-fit equation in Prism, and the obtained values were the following ones: 0,082 nM for clone 29489; 0.07 nM for clone 29494; 0.119 nM for clone 29520 and 0.05 nM for clone 29527 for the data illustrated in FIG. 9. The results demonstrate a strong binding to membrane expressed human TIGIT for the tested anti-TIGIT antibodies.

B. Binding of Anti-TIGIT Antagonistic Antibodies to Human Primary T Cells

Isolated human PBMCs from healthy volunteers were analysed for binding by antagonistic anti-TIGIT antibodies. Cells were distributed at $5 \times 10^5$ cells per well. Cells were incubated with anti-CD16 (Clone 3G8, BioLegend 302002), CD32 (Clone FL18.26, BD Bioscience 557333) and CD64 (BD Bioscience 555525) at room temperature for 10 min, and the indicated anti-human TIGIT antibodies were directly added at a final concentration of: 12.65; 4; 1.26; 0.40; 0.126; 0.040; 0.12 and $4 \times 10^{-3}$ nM in FACS buffer and incubated for 20 min at 4° C. After washing, cells were incubated with anti-human Ig (Fc gamma specific)-PE (eBioscience, 12-4998-82, at 2.5 µg/ml) for 20 min at 4° C. Then, cells were washed and incubated with the following antibodies and LVD mix for results of FIGS. 10A and 10B: anti-CD4–PercP-Cy5.5 (clone A161A1, BioLegend 357414); anti-CD8– BV510 (clone SK1, BD Bioscience 563919) and LVD efluor 520 (eBioscience 65-0867-14). For FIG. 10C, cells were washed and incubated with the following antibodies and LVD mix: LVD efluor 520 (eBioscience 65-0867-14), anti-TCRab-PercP-Cy5.5 (Clone IP26, Biolegend 306723), anti-CD4-BV510 (Clone SK3, BD Horizon 562970), anti-CD8-APC-Cy7 (Clone SK1, Biolegend 344714), anti-CD25-BV605 (Clone 2A3, Biolegend 562660), anti-CD127-APC (A019D5, Biolegend 351316), anti-CCR7-BV421 (Clone G043H7, Biolegend 353207) and anti-CD45RO-PE-Cy7 (Clone UCHL1, Biolegend 304229).

The $EC_{50}$ value for binding to $CD8^+$ human primary T cells was calculated using the % of positive TIGIT stained cells on gated $LVD-CD8^+T$ cells (FIGS. 10A and 10B). The $EC_{50}$ value for binding to human memory $CD8^+$ or Treg primary T cells was calculated using the % of positive TIGIT stained cells on gated $LVD^-TCRab^+CD45RO^+CD8^+T$ cells (for memory $CD8^+$ T cells) or on gated $LVD-TCRab^+ CD127^{lo}CD25^{hi}CD4^+$ T cells (for Tregs) and are illustrated in FIG. 10C.

As shown in FIG. 10A, the $EC_{50}$ value for binding to total human $CD8^+$ T cells are 0,123 nM for clone 29489; 0.181 nM, for clone 29520 and 0,253 nM for clone 29527. Direct comparison between 29489 and 31282 (the 29489 mutant with a M to T mutation on residue 116) was performed, and the $EC_{50}$ value was 0,057 nM and 0,086 nM respectively, demonstrating strong and similar binding efficacy to human primary $CD8^+$ T cells for the 2 clones (FIG. 10B). The $EC_{50}$ values obtained for binding to memory $CD8^+$ T cells and Treg were 0,039 nM and 0.03 nM respectively, demonstrating a strong and similar affinity for both populations (FIG. 10C).

C. Binding of Anti-TIGIT Antagonistic Antibodies to Cynomolgus Primary T Cells

Isolated PBMCs from *Macaca fascicularis* were obtained from BioPRIM. Cells were thawed and stimulated using the T cell activation/expansion kit for non-human primate (Miltenyi Biotec) at 1:2 (bead:cell ratio) following the manufacturer's specifications. The next day, cells were collected, counted and distributed at $5 \times 10^4$ cells per well. Cells were incubated with anti-CD16 (Clone 3G8, BioLegend 302002), CD32 (Clone FL18.26, BD Bioscience 557333) and CD64 (BD Bioscience 555525) at room temperature for 10 min, and selected anti-human TIGIT antibodies were directly added at a final concentration of: 12.65; 4; 1.26; 0.40; 0.126; 0.040; 0.12 and 4×10$^{-3}$ nM in FACS buffer and incubated for 20 min at 4° C. After washing, cells were incubated with anti-human Ig (Fc gamma specific)-PE (eBioscience, 12-4998-82, at 2.5 µg/ml) for 20 min at 4° C. Then, cells were washed and incubated with the following antibodies and LVD mix for data illustrated in FIGS. 11A and 11B: anti-CD4– PercP-Cy5.5 (clone A161A1, BioLegend 357414); anti-CD8– BV510 (clone SK1, BD Bioscience 563919), CD69-APC-Cy7 (Clone FN50, BioLegend, 310914) and LVD efluor 520 (eBioscience 65-0867-14). Stained cells were analysed by FACS using BD LSR Fortessa. The EC$_{50}$ value of binding was calculated using the % of positive TIGIT stained cells gated on LVD-CD69$^{+}$ CD8$^{+}$ T cells. As shown in FIG. 11, the EC$_{50}$ values for binding to cynomolgus CD8$^{+}$ T cells were 0,487 nM for clone 29489, 1.73 nM for clone 29520 and 0,378 nM for clone 29527. Clones 29489 and 31282 (the 29489 mutant with a M to T mutation on residue 116) were compared as well, and the EC$_{50}$ values were 0.25 nM and 0.26 nM respectively for the example shown in FIG. 11B, demonstrating a similar and strong affinity for cynomolgus primary CD8$^{+}$ T cells for the 2 clones.

Example 10: In Vitro Functional Characterization of Antagonistic Anti-TIGIT Activity A. TIGIT Bioassay on CHO-TCR-CD155 and Jurkat-hTIGIT Co-Culture To characterize the functional consequence of blocking human TIGIT receptor, we co-cultured Jurkat cells, that express hTIGIT and a luciferase reporter activated upon TCR engagement (Thaw-and-Use TIGIT Effector cells from Promega), with CHO-K1 cell line engineered to express human CD155 and TCR activator (Thaw-and-Use CD155 aAPC/CHO-K1 from Promega). The activation of TIGIT-overexpressing Jurkat cells can be induced by contact with CD155-expressing CHO-K1 cells upon TCR engagement on Jurkat cells and can be increased in presence of antagonistic anti-TIGIT antibody. To compare the potency of the different antibodies to increase Jurkat cell activation, the experiment was conducted in presence of increasing antibody concentrations and the EC$_{50}$ values were calculated.

Thaw-and-Use CD155 aAPC/CHO-K1 (Promega, CS198811) cells were seeded according to manufacturer's recommendations and incubated at 37° C., 5% CO2 incubator O/N. The day after, Thaw-and-Use TIGIT Effector cells (Promega, CS198811) were added according to manufacturer's recommendations to the CD155 aAPC/CHO-K1 cell plates containing fresh full medium with anti-TIGIT antibody at 133 nM (FIG. 12A) or increasing concentrations (0.22; 0.54; 1.36; 3.41; 8.53; 21.3; 53.3; 133.33; and 333 nM) of anti-TIGIT antibody (FIG. 12B) and incubated at 37° C., 5% CO2 during 6 hours.

After the 6 hours of incubation, activation of TIGIT Effector cell was assessed by measuring the luciferase activity by using Bio-Glo™ Luciferase Assay System (Promega, G7941).

Figure 12:
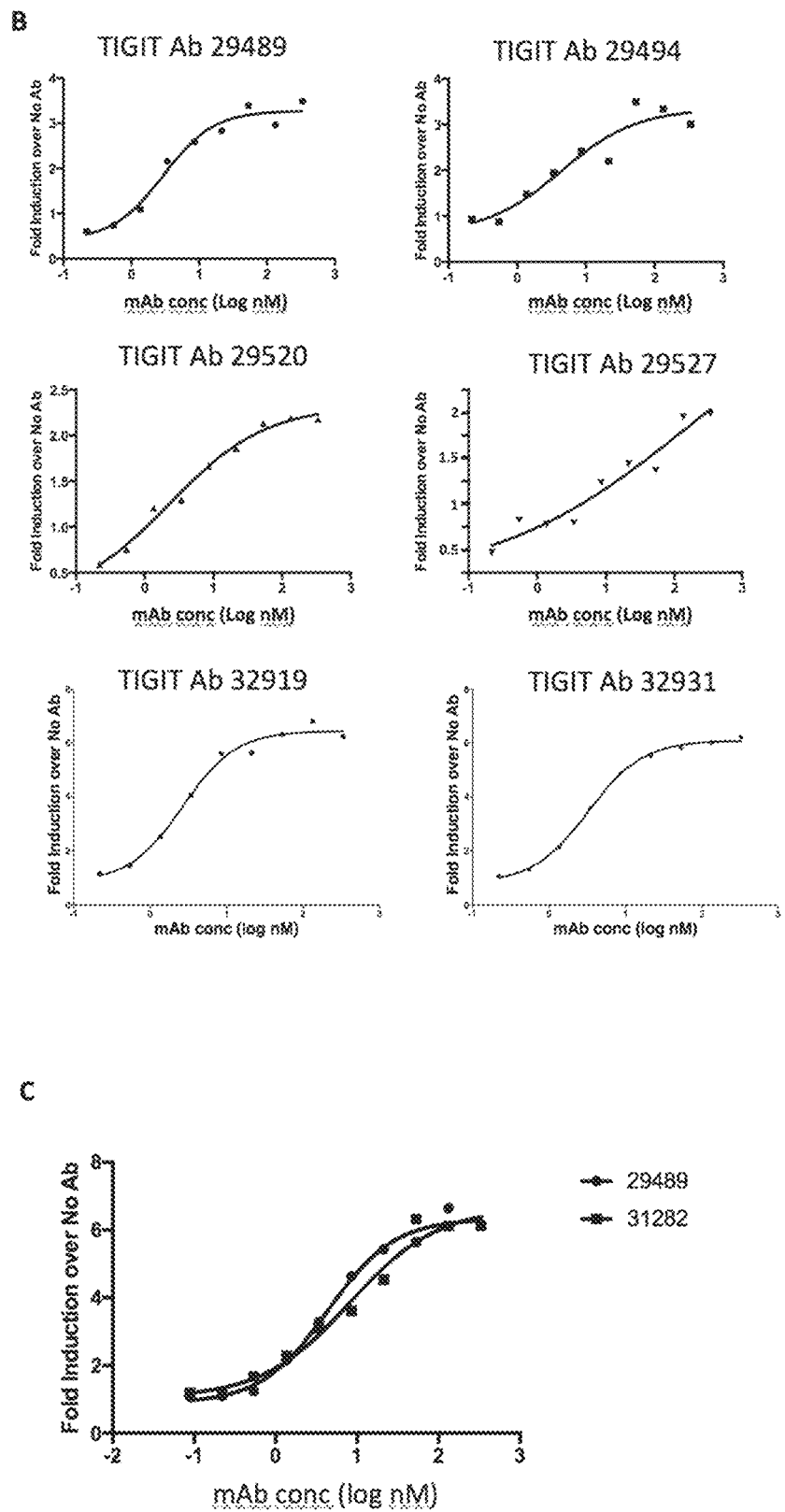

FIG. 12A shows the effect of the addition of the selected clones on Luciferase signal as compared to isotype control. The data demonstrates the antagonistic activity of those antibodies that resulted in a stronger activation of Jurkat-hTIGIT cells. Table 10 summarizes the fold change induction in luciferase expression obtained for the different anti-TIGIT antibodies over the isotype control clone (03847).

TABLE 10

| Fold change induction over isotype control | |
|---|---|
| Clone name | Induction over Isotype control (fold change) |
| 26518 | 2.89 |
| 29478 | 3.57 |
| 26452 | 2.9 |
| 29487 | 3.22 |
| 29489 | 4.08 |
| 26486 | 1.9 |
| 29494 | 3.42 |
| 29499 | 3.68 |
| 26521 | 2.66 |
| 29513 | 3.26 |
| 26493 | 0.96 |
| 29520 | 2.52 |
| 29523 | 2.4 |
| 29527 | 2.96 |
| 03847 | 1 |

As shown in FIG. 12B, Jurkat-hTIGIT cell activation was assessed with anti-TIGIT antibody between 0.22 nM and 333 nM and gave an EC$_{50}$ value of 3.0 nM for clone 29489; 4.4 nM for clone 29494; 2.3 nM for clone 29520 and 32 nM for clone 29527; 2.7 nM for clone 32919 and 3.2 nM for clone 32931 demonstrating a strong functional activity consecutive to blocking TIGIT inhibitory signalling. Clones 29489 and 31282 (the 29489 mutant with a M to T mutation on residue 116) were compared as well, and the EC$_{50}$ values were respectively of 4.3 nM and 8.1 nM for the example shown in FIG. 12C, demonstrating a similar functional activity for the 2 clones.

B. Human Primary CD8$^{+}$ T Cell-Based Functional Assay

To characterize the functional consequence of blocking human TIGIT receptor, we co-cultured human primary CD8$^{+}$ T cells from PBMC of healthy human donors with CHO-K1 cell line engineered to express human CD155 and to activate human T cells. We observed that the release of IFNg by CD8$^{+}$ T cells in the presence of engineered CD155-expressing CHO-K1 cells could be increased by blocking hTIGIT with anti-TIGIT antagonistic antibodies. To compare the potency of these antibodies to increase IFNg release, the experiment was conducted in presence of increasing antibody concentrations and the EC$_{50}$ values were calculated.

Thaw-and-Use CD155 aAPC/CHO-K1 (Promega, CS198811) cells were seeded in U-bottom 96-well plates according to manufacturer's recommendations and incubated at 37° C., 5% CO2 incubator O/N. The next day, CD8$^{+}$ T cells were purified according to manufacturer's recommendations by using negative selection kit (Stemcell Technologies, 17953) from frozen human peripheral blood mononuclear cells isolated from total blood of healthy donors (Immunehealth). Purified CD8 T cells were then incubated with increasing concentrations (0.11 nM, 0.33 nM, 1.06 nM, 3.3 nM, 10.6 nM, 33.3 nM, 105.5 nM and 333 nM) of antibodies (100,000 CD8 T cells/100 ul of full medium containing antibody) during 1 hour. After that, the antibody-CD8 mix was added to the CD155 aAPC/CHO-K1 cell plates containing 50 µl of fresh full medium and incubated at 37° C., 5% CO2 during 5 days. Finally, IFNg concentrations were assessed in cell supernatant using an ELISA assay (Affymetrix eBioscience, 88-7316-86) that was run according to manufacturer's recommendations.

As shown in FIG. 13A, all the anti-TIGIT antibodies increased IFNg secretion over isotype control. The highest increase was observed with clone 29489 (6.4 fold) followed by 29494 (5.8 fold), 29520 (5.4 fold), 29499 (5.2 fold), 29527 (4.5 fold) and 29513 (3.2 fold).

Dose range study (between 0.22 nM and 333 nM of anti-TIGIT antibody) was also conducted to evaluate the $EC_{50}$ value for increase in IFNg secretion by human primary CD8 T cells. As shown in FIG. 13B, anti-TIGIT antibody 29489 showed the best activity with an $EC_{50}$ of 3.5 nM followed by clone 29527 $EC_{50}$=5.1 nM), clone 29494 ($EC_{50}$=6.1 nM) and clone 29520 ($EC_{50}$=11.1 nM). Finally, clone 29489 and its mutant 31282 were tested in parallel and demonstrated a similar activity with a respective $EC_{50}$ value of 0.49 nM and 0.50 nM (FIG. 13C). Altogether these data demonstrate a strong functional activity of antagonistic anti-TIGIT antibodies to block TIGIT inhibitory signal in $CD8^+$ human T cells and to increase effector functions, as characterized by a strong increase in IFNg production.

C. Human TIL Functional Assay

To characterize the functional consequence of blocking human TIGIT receptor on Tumour Infiltrating Lymphocytes (TILS) from cancer patients, we co-cultured human primary $CD8^+$ T cells from TILs of ovarian ascites patient with CHO-K1 cell line engineered to express human CD155 and to activate human T cells. We observed that the release of IFNg by CD8W T cells in presence of engineered CD155-expressing CHO-K1 cells can be increased by blocking hTIGIT with anti-TIGIT antagonistic antibodies.

Thaw-and-Use CD155 aAPC/CHO-K1 (Promega, CS198811) cells were seeded in U-bottom 96-well plates according to manufacturer's recommendations and incubated at 37° C., 5% CO2 incubator O/N.

The next day, CD8 T cells were purified according to manufacturer's recommendations by using negative selection kit (Stemcell Technologies, 17953) from frozen human TILs isolated from ovarian ascites (Immunehealth). Purified $CD8^+$ T cells were then incubated with anti-TIGIT antibody clone 26452, the non-optimized parent of clones 29489 and 31282 (100,000 $CD8^+$ T cells/100 μl of full medium containing antibody) during 1 hour. After that, the antibody-CD8 mix was added to the CD155 aAPC/CHO-K1 cell plates containing 50 ul of fresh full medium and incubated at 37° C., 5% CO2 during 5 days.

Finally, IFNg concentrations were assessed in cell supernatant using an ELISA assay (Affymetrix eBioscience, 88-7316-86) that was run according to manufacturer's recommendations. As seen in FIG. 14, IFNg secretion was increased by almost 2 folds when anti-TIGIT antibody was added to the co-culture. These data demonstrate a strong functional activity of antagonistic anti-TIGIT antibodies to block TIGIT inhibitory signal in $CD8^+$ human TILs and to increase effector functions of T cells in a tumour setting.

Example 11: Characterization of Anti-TIGIT Antagonistic Antibody with Functional Activity in Mouse A. Mouse CD155 Competition Assay for Surrogate Anti-TIGIT Antagonistic Antibody For this assay, Jurkat cells (clone E6-1, ATCC TIB-152) engineered to overexpress mouse TIGIT (Jurkat-mTIGIT) were used. Anti-TIGIT antibody 26493 was used as a surrogate as this antibody showed cross-reactivity for mouse TIGIT as well as binding to human TIGIT. Cells were pre-incubated for 45 min at 37° C. with different concentrations of anti-TIGIT antibody clone 26493 (0.03 to 10 μg/ml) in 25 μl of complete medium (RPMI+10% FBS). Cells were washed once and incubated with 4 μg/ml mouse CD155-His-Fc tag protein (Thermo Fisher, 50259M03H50) in 50 μl of complete medium for 45 min in incubator. Cells were washed once, and stained with PE-anti-His antibody (Biolegend, 362603) during 30 min at 4° C. The median fluorescence intensity (MFI) measured by FACS was used as a measure of binding of CD155 to Jurkat-mTIGIT. FIG. 15A shows the dose-response curve of anti-TIGIT clone 26493 for CD155 competition identifying 2.3 nM as $IC_{50}$ (upper dotted line represent signal from isotype, bottom dotted line signal from cells without CD155). These results demonstrate the functional efficacy of anti-TIGIT antibody to compete with CD155 ligand for mouse TIGIT.

B. Mouse Functional In Vitro Assay: Antigen-Specific Cytotoxicity (OT-I)

To assess the antigen-specific cytotoxic activity of OT-1 $CD8^+$ T cells towards OVA-pulsed target cells and the effect of anti-TIGIT antibody in this assay, OT1 cells were isolated from the spleens of C57BL/6-Tg$^{(TrcaTcrb)}$1100Mjb/Crl mice (Charles River) by mechanical dissociation followed by negative selection for mouse T cells using EasySep™ Mouse T Cell Isolation Kit (Stemcell, Catalog #19851). As antigen-presenting cells, PanO2 cancer cells that naturally express CD155, were treated with Mitomycin C (25 μg/ml) and subsequently pulsed with OVA-peptide (S7951-1 MG, Sigma Aldrich, 1 μg/ml, 1 h at 37° C.). $CD8^+$ T cells and PanO2 were co-cultured for 3 days in the presence of anti-TIGIT clone 26493 or isotype control at 133 nM. At day 3, supernatant was collected for detection of IFNg by ELISA (FIG. 15B) and T cells for the cytotoxicity assay (FIG. 15C). As target cells, OVA-pulsed PanO2 were used. Target cells and non-pulsed PanO2 cells (non-target internal control), $1\times10^6$ each, were labelled with CFSE (C1157, ThermoFisher) and CellTrace™ Far Red Cell Proliferation Kit (C34564, ThermoFisher) respectively, according to manufacturer instructions. These cells were mixed (1:1 ratio) and plated at $2\times10^4$ cells per well. The stimulated OT-1 $CD8^+$ T cells were added at $1\times10^5$ cells/well (effector cells) resulting in 10:1 effector to target ratio in the presence of anti-TIGIT clone 26493 or isotype control at 133 nM. After 24 hrs cells were washed with PBS and lifted by trypsinization. Cells were then stained with Live/dead fixable violet dead cell staining kit (Molecular Probes, L34955). Cytotoxic killing of target cells was then measured by monitoring the change in the ratio of living target cells to non-target cells by flow-cytometry.

FIG. 15B shows that anti-TIGIT antibody increases IFNg production by almost 2 folds while FIG. 15C shows an increased cytotoxic activity of mouse OT-1 $CD8^+$ T cells of around 60%. Altogether, these results confirm the functional activity of anti-TIGIT antibody to increase mouse $CD8^+$ T cell effector function.

Example 12: Anti-Tumour Activity of Anti-TIGIT Antagonistic Antibody in Monotherapy and in Combination with Anti-PD1 Antibodies in Mouse Model A. In Vivo Anti-Tumor Activity of Anti-TIGIT Antagonistic Antibody in Monotherapy For this experiment, anti-TIGIT clone 26493 was produced in mammalian cells on a mouse IgG2a isotype. Female Balb/c mice of 8 weeks were inoculated with 500.000 CT26 colon cancer cells (ATCC® CRL-2638 ™) subcutaneously. On day 9 after inoculation, when tumor volumes were on average around 45 mm$^3$, mice were randomized in treatment groups with equal tumor volume (n=8 per group). Mice were treated with 200 µg of anti-TIGIT or with isotype control (mIgG2a, BioXcell) or with 200 µg of anti-PD-1 (RMP1-14, BioXcell) and 200 µg of isotype control (mIgG2a, BioXcell) or with 200 µg of anti-PD-1 (RMP1-14, BioXcell) and different concentrations of anti-TIGIT (200 µg, 60 µg, 20 µg) by intraperitoneal injections on day 9, day 12 and day 15. Tumor growth was monitored and tumor volumes were measured with electronic calipers three times a week from day 9 until day 36. Mice were sacrificed when tumor volume exceeded 2000 mm³. Tumor growth curves were statistically analyzed by a linear mixed model. Differences between treatment groups were evaluated by testing the interaction of time*treatment group. To test for a synergistic effect between anti-TIGIT and anti-PD-1, treatment groups were recoded by a combination of two variables; anti-TIGIT (yes/no) and anti-PD-1 (yes/no). A synergistic effect, on top of the additive effect of each treatment (anti-TIGIT*time and anti-PD-1*time) was evaluated by testing the interaction term anti-TIGIT*anti-PD-1*time.

FIG. 16A shows median tumor growth curves per group as well as individual growth curves for mice treated with anti-TIGIT antibody in monotherapy. Whereas in the control group, no mice had regression of the tumor, 2/8 mice treated with anti-TIGIT had a complete response. In the remaining mice, a clear tumor growth delay was present. In the control group, no mice survived beyond 30 days, whereas in the treated group, 7/8 mice survived beyond 30 days.

FIG. 16B shows median tumor growth curves per group as well as individual growth curves for mice treated by anti-PD1 in monotherapy or in combination with anti-TIGIT. There was significant suppression of tumor growth in mice treated with anti-TIGIT+anti-PD-1 compared to anti-PD-1 monotherapy (p<0.0001). The combination of anti-TIGIT+anti-PD-1 achieved synergistic anti-tumor efficacy that was more than the additive effect of both monotherapy treatments (p=0.02). The combination of anti-TIGIT (at 200 ug) and anti-PD1 antibodies resulted in 7/8 mice showing a complete response. The anti-tumor efficacy was maintained with combination of anti-PD1 and lower doses of anti-TIGIT that achieve complete response for 8/8 mice when anti-TIGIT antibody was decreased to 60 µg and 5/8 mice when anti-TIGIT antibody was decreased further to 20 µg (FIG. 16C). These data demonstrate the significant anti-tumor efficacy of anti-TIGIT therapy in monotherapy (p<0.0001) or in combination with an anti-PD1 antibody (p<0.0001) for treatment of pre-established tumours.

Example 13: Isotype-Dependent Anti-Tumour Activity of Anti-TIGIT Antagonistic Antibody in Monotherapy and Combination with Anti-PD1 Antibodies in Mouse Model For this experiment, anti-TIGIT clone 26493 was produced in mammalian cells on a mouse IgG2a and mouse IgG1 isotype. Female Balb/c mice of 8 weeks were inoculated with 500.000 CT26 colon cancer cells (ATCC® CRL-2638™) subcutaneously. On day 10 after inoculation, when tumor volumes were on average around 100 mm³, mice were randomized in treatment groups with equal tumor volume (n=10 per group). For evaluation of monotherapy, mice were treated with 200 µg of anti-TIGIT or isotype control (mIgG2a, BioXcell) by intraperitoneal injections on day 10, day 13 and day 16. For evaluation of combination with anti-PD-1, mice were treated with 200 µg of anti-PD-1 (RMP1-14, BioXcell) and 200 µg of isotype control (mIgG2a, BioXcell) or by combination of 200 µg of anti-PD-1 (RMP1-14, BioXcell) and 200 µg of anti-TIGIT by intraperitoneal injections on day 10, day 13 and day 16. Tumor growth was monitored and tumor volumes were measured with electronic calipers three times a week from day 10 until day 33. Mice were sacrificed when tumor volume exceeded 2000 mm³.

FIG. 17A shows median tumor growth curves per group as well as individual growth curves for monotherapy with anti-TIGIT antibody and FIG. 17B for combination therapy with anti-TIGIT and anti-PD1 antibodies. Both in monotherapy and in combination with anti-PD-1, treatment with anti-TIGIT antibody resulted in significant anti-tumor efficacy when administered as a mouse IgG2a isotype (p=0.0001 and p=0.009 respectively). However, no anti-tumor efficacy could be observed with anti-TIGIT as a mouse IgG1 isotype, suggesting that interaction of Fc receptor with mIgG2a is important for the anti-tumor activity of anti-TIGIT antagonistic antibodies in the murine CT26 model. These data demonstrate the isotype-dependant anti-tumor efficacy of anti-TIGIT therapy in monotherapy or combination for treatment of pre-established tumours.

Example 14: Characterization of the Mechanism of Action of In Vivo Anti-Tumour Activity of Anti-TIGIT Antagonistic Antibody A. Flow Cytometry Analysis of Spleen and Tumor To investigate the in vivo mode of action of antagonistic anti-TIGIT antibody, tumours were analysed by flow cytometry for the immune cell infiltrate following treatment with anti-TIGIT antibody 26493 (IgG2a), in monotherapy and in combination with anti-PD-1. Mice were inoculated and treated as described in example 12. Two days after the second treatment, mice (8 mice per group) were sacrificed and tumours harvested. Tumours were dissociated with a tumour dissociation kit (Miltenyi Biotec). For direct ex-vivo staining, cells were stained with anti-CD45, anti-CD4, anti-CD8 and anti-FoxP3 (all from eBioscience) after staining with a viability dye (Molecular Probes, L34955) and Fc-block. For ex vivo stimulation, cells were incubated with cell stimulation cocktail (eBioscience) and protein transport inhibitor (eBioscience) for 3 hours. This was followed by staining with anti-CD4 and anti-CD8 antibodies and Fc-block. After fixation and permeabilization with commercial buffers (IC fixation buffer and permeabilization buffer), cells were stained with anti-IL-10 and anti-IFNg (all from eBioscience). In all the figures, the percentage change compared to the relevant control group (isotype control for monotherapy, anti-PD-1 for combination) is shown, with a negative value representing a decrease and a positive value an increase compared to the control group.

FIG. 18A shows that in vivo treatment of tumour with anti-TIGIT mIgG2a antibody results in a decrease in proportion of regulatory T cells within CD4$^+$ TILs population of 28% compared to the control group, which is not observed after treatment with anti-TIGIT mIgG1. This shows that there is a depletion of TIGIT$^+$ Treg cells, possibly explaining the differential efficacy of the two isotypes as discussed in example 14. FIG. 18B shows that there is no depletion of CD8$^+$ TILs, but instead a small increase is observed for the two isotypes (a 17% increase compared to control for mIgG1 and 16% for mIgG2a). These findings together result in an increase of more than 50% of the CD8/Treg ratio in tumor treated with anti-TIGIT mIgG2a (FIG. 18C). Functionality of intratumoral T cells is also improved for the group treated with anti-TIGIT mIgG2a antibody, with a strong increase in IFNg production of both CD4+ (FIG. 18D) and CD8+ TILs (FIG. 18E). This resulted in a strong increase of the ratio IFN-g producing cells/IL-10 producing cells after ex vivo stimulation in the CD4+ TILs/CD8+ population (FIG. 18F).

FIG. 18G shows that combining anti-TIGIT mIgG2a with anti-PD-1 results in regulatory T cells being decreased by 33% compared to anti-PD-1 monotherapy. Again, for CD8+ T cells the opposite is true, with 22% and 28% increase in CD8+ T cell infiltration, respectively for mIgG1 and mIgG2a isotypes, compared to anti-PD-1 monotherapy (FIG. 18H). Together, this results in more than two-fold increase in the CD8+ TILs to Treg ratio in the tumor for the combination with anti-TIGIT mIgG2a (FIG. 18I). Additionally, treatment with anti-TIGIT antibody mIgG2a combined with anti-PD-1 demonstrates a shift in Th1 versus Th2 phenotype for intratumor CD4+ T cells, with a marked increase in IFNg producing CD4 cells (FIG. 18J) and a decrease in IL-10 producing CD4 cells (FIG. 18K). This resulted in a strong increase in IFNg/IL-10 producing cells after ex vivo stimulation in the CD4+ TILs population compared to mice treated with anti-PD-1 in monotherapy (FIG. 18L).

TABLE 11

Differentially expressed genes between anti-TIGIT mIgG2a and vehicle treated mice

| Gene symbol | Log2 fold change | Corrected p-value |
| --- | --- | --- |
| Ccr2 | −1.29 | 0.0000668 |
| Prf1 | 1.79 | 0.0000668 |
| Ctsg | 2.13 | 0.0000668 |
| Ctla4 | 1.72 | 0.00309 |
| Gzmb | 1.51 | 0.00309 |
| Ccl2 | 0.56 | 0.0174 |
| Il2ra | 1.61 | 0.0174 |
| Cd55 | 1.64 | 0.0213 |
| Il2rb | 0.872 | 0.0379 |
| Cd274 | 0.982 | 0.0385 |
| Klrg1 | 1.3 | 0.0402 |
| Icos | 1.26 | 0.0402 |
| Il1rn | 0.87 | 0.0402 |
| Cx3cr1 | −0.82 | 0.0428 |
| C1ra | 0.896 | 0.0428 |
| Cd33 | −0.906 | 0.0479 |
| Ccl4 | 0.886 | 0.0518 |

TABLE 12

Differentially expressed genes between anti-TIGIT mIgG2a + anti-PD-1 and anti-PD1 treated mice

| Gene symbol | Log2 fold change | Corrected p-value |
| --- | --- | --- |
| Ctsg | 2.34 | 0.0000375 |
| Prf1 | 1.69 | 0.000255 |
| Gzmb | 1.71 | 0.000766 |
| Cd55 | 2.08 | 0.00131 |
| Entpd1 | 0.839 | 0.00131 |
| Klrg1 | 1.76 | 0.00132 |
| Itga1 | 0.874 | 0.0017 |
| Ctla4 | 1.72 | 0.00173 |
| Il2ra | 1.82 | 0.00237 |
| Itgb3 | 0.863 | 0.00237 |
| Slc11a1 | 0.849 | 0.00329 |
| Cd36 | 1.44 | 0.0049 |
| Cd180 | 0.899 | 0.00602 |
| Icam1 | 0.893 | 0.00802 |
| Cd274 | 1.06 | 0.00993 |
| Cd40 | 0.926 | 0.0113 |
| Eomes | 1.28 | 0.0113 |
| Abcg1 | 0.869 | 0.0113 |
| Ccr2 | −0.781 | 0.0122 |
| Thy1 | 0.868 | 0.0165 |

TABLE 12-continued

Differentially expressed genes between anti-TIGIT mIgG2a + anti-PD-1 and anti-PD1 treated mice

| Gene symbol | Log2 fold change | Corrected p-value |
| --- | --- | --- |
| Ccl2 | 0.501 | 0.0203 |
| Gbp5 | 1.12 | 0.0216 |
| Icos | 1.24 | 0.0263 |
| Tgfbr2 | 0.458 | 0.0278 |
| H2 K1 | 0.292 | 0.0307 |
| Sh2d1a | 0.999 | 0.0307 |
| Il2rb | 0.808 | 0.0307 |
| Selplg | 0.64 | 0.031 |
| Bst1 | 0.702 | 0.0317 |
| Cd247 | 1 | 0.032 |
| Irf8 | 0.699 | 0.0365 |
| Il21r | 0.899 | 0.0392 |
| Gbp2b | 1.11 | 0.0392 |
| Stat1 | 0.865 | 0.0427 |
| C4b | 0.922 | 0.0428 |
| Abca1 | 0.537 | 0.044 |
| Trem2 | 0.482 | 0.0454 |

B. Transcriptomics Analysis of Tumor by NanoString

To investigate the in vivo mode of action of anti-TIGIT antibody, the immune cell infiltrate of tumours treated with anti-TIGIT, in monotherapy and in combination with anti-PD-1, was analysed by transcriptomic analysis (Nanostring). Mice were inoculated and treated as described in Example 12. Two days after the third treatment with anti-TIGIT and/or anti-PD1 antibodies, mice were sacrificed and tumors harvested. RNA was extracted and the expression of a selection of 770 genes involved in cancer immunology was directly quantified with the nCounter technology (PanCancer Immune Profiling panel, Nanostring; performed by VIB Nucleomics Core). Data were analyzed with nSolver software (Nanostring).

FIG. 19A shows a volcano plot of the genes that are differentially regulated between vehicle treated mice and anti-TIGIT mIgG2a treated mice. Highly statistically significant genes fall at the top of the plot, and highly differentially expressed genes fall to either side (left: downregulated in anti-TIGIT treated mice, right: upregulated in anti-TIGIT treated mice). Examples of highly upregulated genes include perforin, granzyme B and CTLA-4. The solid line represents a non-corrected p-value of 0.01, the dotted line a corrected p-value of 0.05 (Benjamini-Hochberg correction). Table 11 and Table 12 show the genes that were significantly differentially expressed for anti-TIGIT mIgG2a compared with vehicle and aPD-1+anti-TIGIT mIgG2a versus anti-PD1 respectively. When multiple genes were summarized in scores for functional subsets of immune cells, the most striking finding was an increase in cytotoxic cell and CD8+ T cell score (FIG. 19B). The same changes were present in mice treated with anti-PD-1+anti-TIGIT mIgG2a compared to anti-PD-1 alone. No changes were observed in mice treated with anti-TIGIT mIgG1, in monotherapy or in combination with anti-PD-1.

Altogether, these results demonstrate that the anti-tumour efficacy observed after in vivo treatment with anti-TIGIT antibody is mediated by a decreased Treg infiltrate in the tumour while CD8+ effector T cell population is increased. In addition, effector function of CD4+ and CD8+ TILs are increased as shown by the higher proportion of IFNg producing cells, the shift towards Th1 response and the increased expression of genes important for T cell cytotoxic functions.

Example 15: Antibody Dependent Cellular Toxicity (ADCC) Activity Induced by Anti-TIGIT Antagonistic Antibodies A. In Vitro ADCC on Human PBMC from Healthy Donors Isolated PBMCs from healthy human donors were resuspended in complete RPMI medium (supplemented with 10% FBS heat inactivated+50 U Penicilin+50 U Streptomycin, and supplemented with 200 IU IL-2/ml). $2.5 \times 10^5$ human PBMCs were distributed per well in 96 U well plate. Anti-human TIGIT antibody clone 26452 produced in mammalian cells or IgG1 isotype control (Biolegend, 403102) were added at a final concentration of 66.6; 0.66 and 0,006 nM to each corresponding well. Cells were incubated for 20 h at 37° C. with 5% CO2. Then cells were collected and stained with the following antibody panel: LVD efluor 520 (eBioscience 65-0867-14), ant-TCRab-PercP-Cy5.5 (Clone IP26, Biolegend 306723), anti-CD4-BV510 (Clone SK3, BD Horizon 562970), anti-CD8-APC-Cy7 (Clone SK1, Biolegend 344714), anti-CD25-BV605 (Clone 2A3, Biolegend 562660), anti-CD127-APC (A019D5, Biolegend 351316), anti-CCR7-BV421 (Clone G043H7, Biolegend 353207) and anti-CD45RO-PE-Cy7 (Clone UCHL1, Biolegend 304229). Results are presented on gated live cells. $CD45^+CD4^+$ or $CD45^+CD8^+$ represent the total $CD4^+$ or $CD8^+$ T cells. $CD45^+RO^+CD4^+$ or $CD45^+RO^+CD8^+$ cells represent the memory $CD4^+$ or $CD8^+$ T cells while $CD25^{hi}CD127^{low}CD4^+$ represent Treg cells. The proportion of $TIGIT^+$ cells on gated Tregs is higher than on gated memory $CD8^+$ T cells and $CD4^+$ T cells, as shown in FIG. 20A.

Absolute quantification is done using AccuCheck Counting beads (Life technologies) following manufacturer's specifications. After calculation of absolute cell numbers per µl, % of specific lysis is calculated using the following formula=(1−(absolute number of cells per µl on 26452 TIGIT antibody treated sample/average of triplicate of no antibody treatment))×100. As shown in FIG. 20B anti-TIGIT 26452 hIgG1 antibody triggers higher specific lysis on Tregs (62.22%) than on total $CD8^+$ T cells (12.2%) or total $CD4^+$ T cells (16.36%).

B. Ex-Vivo ADCC on Mouse Tumor

To confirm that anti-TIGIT mouse IgG2a antibody can deplete $TIGIT^+$ regulatory T cells, an ex-vivo ADCC assay was set-up. Female Balb/c mice of 8 weeks were inoculated with 500.000 CT26 colon cancer cells (ATCC® CRL-2638™) subcutaneously. Three weeks after inoculation, tumors were harvested and dissociated with a tumor dissociation kit (Miltenyi Biotec). The single cell suspension was incubated with 133 nM anti-TIGIT antibody 26493 (mIgG1 or mIgG2a isotype) for 20 h (1 million cells/200 µl in RPMI+10% FBS). After 20 h, cells were stained with anti-CD4, anti-TIGIT, anti-CD8 and anti-FoxP3 antibodies (all from eBioscience) after staining with a viability dye (Molecular Probes, L34955) and Fc-block.

FIG. 21 shows the % decrease in absolute $TIGIT^+$ cell counts compared to treatment with isotype control for the different $TIGIT^+$ immune subsets. The strongest decrease after anti-TIGIT mIgG2a antibody treatment is evident in regulatory T cells (around 40% decrease), suggesting that these cells are more susceptible to ADCC than conventional $CD4^+$ or $CD8^+$ T cells.

Overall, these results demonstrate the efficacy of anti-TIGIT hIgG1 or mIgG2a to deplete $TIGIT^+$ immune cells with a stronger activity demonstrated on Treg population.

Example 16: Immunogenicity Prediction Using in Silico Analysis

Immunogenic potential of clones 29494 and 29489 as well as its variant 31282 was assessed by in silico prediction using EpiMatrix Protein Score (De Groot et al. (2009) Clinical Immunol. 131:189). To complete the analysis, the input sequences were parsed into overlapping 9-mer frames and each frame was evaluated with respect to a panel of eight common Class II HLA alleles. These alleles are "super-types". Each one is functionally equivalent to, or nearly equivalent to, many additional "family member" alleles. Taken collectively, these eight super-type alleles, along with their respective family members, "cover" well over 95% of the human population (Southwood et al. (1998) J. Immunol 160:3363). Each frame-by-allele "assessment" is a statement about predicted HLA binding affinity. EpiMatrix assessment scores range from approximately −3 to +3 and are normally distributed. EpiMatrix assessment scores above 1.64 are defined as "hits"; that is to say potentially immunogenic and worthy of further consideration.

All other factors being equal, the more HLA ligands (i.e. EpiMatrix hits) contained in a given protein, the more likely that protein is to induce an immune response. The EpiMatrix Protein Score is the difference between the number of predicted T cell epitopes expected to be found in a protein of a given size and the number of putative epitopes predicted by the EpiMatrix System. The EpiMatrix Protein Score is correlated with observed immunogenicity. EpiMatrix Protein Scores are "normalized" and can be plotted on a standardized scale. The EpiMatrix Protein Score of an "average" protein is zero. EpiMatrix Protein Scores above zero indicate the presence of excess MHC ligands and denote a higher potential for immunogenicity while scores below zero indicate the presence of fewer potential MHC ligands than expected and a lower potential for immunogenicity. Proteins scoring above +20 are considered to have a significant immunogenic potential.

Adjusting for the Presence of Regulatory T Cell Epitopes.

Antibodies are unique proteins in that the amino acid sequences of their variable domains, especially their Complementarity Determining Regions (CDRs), can vary to an extraordinary extent. It is this variability that allows antibodies to recognize a wide variety of antigens. However, the recombination and mutation events that control antibody maturation can also produce new or neo-T cell epitopes. These neo-epitopes can appear to be "foreign" to circulating T cells. The presence of neo-epitopes in antibody sequences can lead to the formation of a human-anti-human antibody response; also known as the HAHA response or ADA (Anti-Drug-Antibodies).

Regulatory T cells play an important role in suppressing immune responses to fully human proteins in the periphery, including those containing mutated and/or highly variable sequences such as antibody CDRs. Regulatory T cells are engaged and activated by regulatory T cell epitopes. The inherent risk associated with the presence of neo-epitopes in antibody sequences appears to be balanced by the presence of naturally occurring regulatory T cell epitopes.

By screening the sequences of many human antibody isolates, EpiVax has identified several highly conserved HLA ligands which are believed to have a regulatory potential. Experimental evidence suggests many of these peptides are, in fact, actively tolerogenic in most subjects. These highly conserved, regulatory, and promiscuous T cell epitopes are now known as Tregitopes (De Groot et al. (2008) Blood 112:3303)

In many cases, the immunogenic potential of neo-epitopes contained in humanized antibodies can be effectively controlled in the presence of significant numbers of Tregitopes. For the purposes of antibody immunogenicity analysis, EpiVax has developed a Tregitope-adjusted EpiMatrix Score and corresponding prediction of anti-therapeutic antibody response. To calculate the Tregitope-adjusted EpiMatrix Score, the scores of the Tregitopes are deducted from the EpiMatrix Protein Score. The Tregitope-adjusted scores have been shown to be well correlated with observed clinical immune response for a set of 23 commercial antibodies (De Groot et al. (2009) Clinical Immunol. 131:189).

Clones 29489, 29494 and 31282 antibody sequences score on the low end of EpiMatrix scale, indicating limited potential for immunogenicity. Regression analysis of licensed monoclonal antibodies predicts ADA response in ~0% of exposed patients for antibody clone 29489 and 31282. For clone 29494, analysis predicts ADA response in 2.78% of exposed patients for the baseline VH sequence, and 2.88% for the variant VH sequence. Data are summarized in Table 13, below.

TABLE 13

EpiMatrix and Tregitope adjusted EpiMatrix Scores

| Input Sequence | Length | Assessments | EpiMatrix Hits | EpiMatrix Score | Tregitope adjusted EpiMatrix Score |
|---|---|---|---|---|---|
| 29489_VH | 121 | 904 | 40 | −19.41 | −47.26 |
| 29489_VL | 108 | 800 | 39 | −17.58 | −51.75 |
| 31282_VH | 121 | 904 | 40 | −19.41 | −47.26 |
| 31282_VL | 108 | 800 | 39 | −17.58 | −51.75 |
| 29494_VH | 125 | 936 | 54 | 2.68 | −7.18 |
| 29494_VL | 107 | 792 | 40 | −12.2 | −38.83 |

Example 17: Affinity Determination for Binding of Anti-TIGIT Clones to Recombinant Human TIGIT Protein Antibody 31282 was compared against anti-TIGIT antibody clones described in other patent applications. Specifically, 31282 was compared with: 4.1D3.Q1E (also referred to as 4.1D3, from WO2017/053748); 22G2 (from WO2016106302); 31C6 (from WO2016/028656); 313M2 (from WO2016/191643); and TIG1 (from WO2017/152088). The references and sequences of the compared antibody clones are shown in Table 14 below:

TABLE 14

Sequences of VH and VL domains of comparative anti-TIGIT antibodies

| a-TIGIT clone | Reference | Sequence |
|---|---|---|
| 4.1D3.Q1E | VH: SEQ ID NO: 34 of WO2017/053748<br>VL: SEQ ID NO: 36 of WO2017/053748 | VH sequence:<br>EVQLQQSGPGLVKPSQTLSLTCAISGDSVSSNSAAWNWIRQSP<br>SRGLEWLGKTYYRFKWYSDYAVSVKGRITINPDTSKNQFSLQL<br>NSVTPEDTAVFYCTRESTTYDLLAGPFDYWGQGTLVTVSS<br>(SEQ ID NO: 343 herein)<br>VL sequence:<br>DIVMTQSPDSLAVSLGERATINCKSSQTVLYSSNNKKYLAWYQQ<br>KPGQPPNLLIYWASTRESGVPDRFSGSGSGTDFTLTISSLQAED<br>VAVYYCQQYYSTPFTFGPGTKVEIK (SEQ ID NO: 344 herein) |
| 22G2 | VH: SEQ ID NO: 7 of WO2016/106302<br>VL: SEQ ID NO: 9 of WO2016/106302 | VH sequence:<br>QVHLQESGPGLVKPSETLSLTCTVSGGSVSSGIYYWSWIRQPP<br>GKGLEWIGYIYYSGSTNYNPSLKSRVTISVDTSKNQFSLKLSSVT<br>AADTAVYYCARDYYVSGNYYNVDYYFFGVDVWGQGTTVTVSS<br>(SEQ ID NO: 345 herein)<br>VL sequence:<br>EIVLTQSPATLSLSPGERATLSCRASQSVSSYLAWYQQKPGQA<br>PRLLIYDASNRATGIPARFSGSGSGTDFTLTISSLEPEDFAVYYC<br>QQRSNWPPLFTFGPGTKVDIK (SEQ ID NO: 346 herein) |
| 31C6<br>(MEB125.31C<br>6.A1.205<br>VH4/VL1) | VH: SEQ ID NO: 127 of WO2016/028656<br>VL: SEQ ID NO: 130 of WO2016/028656 | VH sequence:<br>EVQLVQSGAEVKKPGASVKVSCKASGYTFSSYVMHWVRQAPG<br>QGLEWIGYIDPYNDGAKYAQKFQGRVTLTSDKSTSTVYMELSSL<br>RSEDTAVYYCARGGPYGWYFDVWGQGTTVTVSS (SEQ ID NO: 347 herein)<br>VL sequence:<br>DIQMTQSPSSLSASVGDRVTITCRASEHIYSYLSWYQQKPGKAP<br>KLLIYNAKTLAEGVPSRFSGSGSGTDFTLTISSLQPEDFATYYCQ<br>HHFGSPLTFGQGTRLEIK (SEQ ID NO: 348 herein) |

TABLE 14-continued

Sequences of VH and VL domains of comparative anti-TIGIT antibodies

| a-TIGIT clone | Reference | Sequence |
|---|---|---|
| 313M32 | VH: SEQ ID NO: 67 of WO2016/191643<br>VL: SEQ ID NO: 68 of WO2016/191643 | VH sequence:<br>QVQLQESGPGLVKPSETLSLTCAVSGYSITSDYAWNWIRQPPG<br>KGLEWIGYISYSGSTSYNPSLRSRVTISRDTSKNQFFLKLSSVTA<br>ADTAVYYCARRQVGLGFAYWGQGTLVTVSS (SEQ ID NO: 349 herein)<br>VL sequence:<br>DIQMTQSPSSLSASVGDRVTITCKASQDVSTAVAWYQQKPGKA<br>PKLLIYSASYRYTGVPSRFSGSGSGTDFTFTISSLQPEDIATYYC<br>QQHYSTPWTFG (SEQ ID NO: 350 herein) |
| TIG1 | VH: SEQ ID NO: 10 of WO2017/152088<br>VL: SEQ ID NO: 14 of WO2017/152088 | VH sequence:<br>DVQLVESGGGLVQPGGSRKLSCAASGFTFSNFGMHWVRQAPE<br>KGLEWVAFISSGSSSIYYADTVKGRFTISRDNPKNTLFLQMTSLR<br>SEDTAMYYCARMRLDYYAMDYWGQGTSVTVSS (SEQ ID NO: 351 herein)<br>VL sequence:<br>DVQITQSPSYLAASPGETITINCRASKSISKYLAWYQEKPGKTNK<br>LLIYSGSTLQSGIPSRFSGSGSGTDFTLTISSLEPEDFAMYYCQQ<br>HNEYPWTFGGGTKLEIK (SEQ ID NO: 352 herein) |

A. Production in Mammalian Cells

In order to produce sufficient amounts of selected a-TIGIT clones for further characterization, DNA vectors coding for specific antibody clones (clones 31282_up, 4.1D3, 22G2, 31C6, 313M32 and TIG1) were generated and transduced into HEK cells for production of human IgG1 isotype. Human codon optimized synthetic DNA fragments for antibody variable domains were ordered at Geneart. Variable domain sequences were seamlessly ligated into pUPE expression vectors containing the mouse IgKappa signal sequence and constant regions of the respective antibody class. Expression vectors were verified by restriction analysis and DNA sequencing. For transient transfection Endotoxin free DNA maxipreps (Sigma) were produced and heavy and light chain vectors were co-transfected to HEK293EBNA1 cells, in Freestyle medium (ThermoFisherScientific), according to established protocols. Primatone (0.55% final volume) was added 24 hours post-transfection. Conditioned medium was harvested 6 days post transfection. Antibodies were purified batch wise by Mabselect sureLX (GE Healthcare) affinity chromatography. Bound antibodies were washed in 2 steps with PBS containing 1M NaCl and PBS. Antibodies were eluted with 20 mM Citrate 150 mM NaCl pH3 and neutralized to approximately pH7 with 1/6 volume of 1 M K2HPO4/KH2PO4 pH8.

Next the antibodies were further purified by gel-filtration using a Superdex200 column, equilibrated in PBS. Fractions were analysed by NuPAGE and antibody containing fractions were pooled. The final products were sterilized over a 0.22 µM syringe filter. The product was analysed by NuPAGE and endotoxin levels were measured by LAL-assay.

Additionally, clone 31282 was also produced in CHO-K1 cell as follow (clone 31282_wu) on IgG1 or IgG4 isotype. DNA vectors coding for the antibodies were constructed and transfected into CHO-K1 cells. CHO codon optimized DNA fragments for antibody variable domains were synthesized, and ligated into expression vectors containing the signal sequence and constant regions of the respective antibody class. Expression vectors were verified by restriction analysis and DNA sequencing. Heavy and light chain vectors were co-transfected to CHO-K1 cells by electroporation (Bio-rad) according to established protocols. The transfected cultures were scaled up and inoculated into fed-batch cultures. Conditioned medium was harvested after 14 days of fed-batch cultures.

Harvested cell culture was firstly clarified by two stages of depth filtration with DOHC and A1HC (Millipore) connected in series. Then, the clarified harvest was firstly purified by affinity chromatography with MabSelect SuRe (GE Healthcare). Bound antibodies were washed in 2 steps with 50 mM NaAc-HAc (pH 5.5) containing 1 M NaCl and 50 mM NaAc-HAc (pH 5.5). Antibodies were then eluted with 50 mM NaAc-HAc (pH 3.5) and neutralized to approximately pH 5.5 with 1 M Tris-HCl (pH 9.0).

Next the neutralized intermediate was further polished by anion exchange chromatography (AEX) using POROS HQ50 (Life Tech) in flow-through mode. The column was equilibrated by 50 mM NaAc-HAc (pH 5.5) before loading. AEX flow through collected during loading and recovering step was further polished by cation exchange chromatography (CEX) in bind-elute mode using POROS XS (Life Tech.). The CEX column was equilibrated in 50 mM NaAc-HAc (pH 5.5), and the antibodies were eluted out by linear gradient elution (LGE) to reach 50 mM NaAc-HAc (pH 5.5) containing 0.5 M NaCl in 10 CV. The final ultrafiltration and dia-filtration (UF/DF) using Pellicon 3, ultracel 30 kD, type A (Millipore) was performed to concentrate the CEX eluate and exchange buffer into 20 mM His-HCl (pH 5.5). Afterwards, Polysorbate 80 (PS80) and sucrose was added into the dia-filtrated sample to obtain the final product of which the concentration was proximately 20 g/L, in the buffer of 20 mM His-HCl, 0.01% (w/w) PS 80, and 9% (w/v) sucrose (pH 5.5). The product had gone through all PQA tests. The SEC purity, Endotoxin level and other criteria had all met the requirement.

B. Biacore Measurement

Biosensor analysis was conducted at 25° C. in a HBS-EP buffer system (10 mM HEPES pH 7.3, 150 mM NaCl, 3 mM EDTA, 0.05% Tween20) using Biacore T200 technology, CM5 sensor chip (run at Novalix, France). The sample hotel was maintained at 8° C. Goat anti-human IgG capture antibody (Fcγ fragment specific, Jackson ImmunoResearch Laboratories) was immobilized (10000 RU) to both flow cells of the sensor chip using standard amine coupling chemistry. This surface type provided a format for reproducibly capturing fresh analysis antibody after each regeneration step. Flow cell 2 was used to analyse captured antibody while flow cell 1 was used as a reference flow cell. 6 different antigen concentrations ranging from 30 to 0.123 nM were prepared in running buffer. Each of the antigen sample concentrations were run as a single replicate, except 3.33 nM run in duplicate. Two blank (buffer) injections also were run and used to assess and subtract system artefacts. The association (300 s) and dissociation (600 s) phases for all antigen concentrations were performed at a flow rate of 30 uL/min. The surface was regenerated with three sequential injections (15 s, 15 s and 60 s) of 10 mM glycine-HCl, pH 1.5. The obtained sensorgrams were fitted globally to a 1:1 model (assuming the same kinetic values for all applied concentrations). Affinity was also determined from steady state for clone 313M32 as 1:1 kinetic model fitting was not reliable, showing equilibrium with human TIGIT at the end of the association time. Results obtained for the different a-TIGIT clones are reported in Table 15.

TABLE 15

Kinetic and affinity evaluation

| | Kinetic model 1:1 Binding | | | | Steady State Model | |
|---|---|---|---|---|---|---|
| Clone | Ka (1/s) | Kd (1/s) | $K_d$ (nM) | Rmax (RU) | $K_d$ (nM) | Rmax (RU) |
| 31282_wu | $3.86^{+06}$ | $4.62^{-04}$ | 0.120 | 16.7 | | |
| 31282_up | $3.70^{+06}$ | $4.75^{-04}$ | 0.128 | 15.3 | | |
| 4.1D3 | $1.07^{+06}$ | $4.72^{-05}$ | 0.044 | 14.4 | | |
| 22G2 | $2.51^{+06}$ | $1.78^{-04}$ | 0.071 | 11.1 | | |
| 31C6 | $3.10^{+06}$ | $2.09^{-04}$ | 0.067 | 16.7 | | |
| 313M32 | na | na | na | na | 10.1 | 17.2 |
| TIG1 | $5.24^{+06}$ | $1.31^{-02}$ | 2.49 | 11.1 | | |

Example 18: Cellular Binding of Anti-TIGIT Antagonistic Antibodies

A. Binding of Anti-TIGIT Clones to Jurkat-hTIGIT

The affinity of human anti-TIGIT antibodies has been measured using Jurkat E6.1 cells transduced with human-TIGIT (Jurkat hTIGIT). To analyse the affinity of the selected antibodies for hTIGIT, $10^5$ cells were distributed per well and incubated with decreasing concentration (8; 4; 2; 1; 0.5; 0.25; 0.125; 0.062; 0.031; 0.016; $8 \times 10^{-3}$ and $4 \times 10^{-3}$ nM) of various anti-TIGIT antagonist antibody clones (FIG. 2). Antibodies were incubated with the cells for 20 min at 4° C. in FACS buffer. After washing, cells were incubated with anti-human Ig (Fc gamma specific)-PE (eBioscience, 12-4998-82, at 2.5 µg/ml) for 20 min on ice and washed twice. Fluorescence intensity was analysed using LSR BD Fortessa and cell binding was recorded as the median fluorescence intensity of PE in cells expressing TIGIT at their surface.

The half-maximal concentration of binding ($EC_{50}$) to Jurkat-hTIGIT was calculated using a four-variable curve-fit equation in Prism. The results are illustrated in FIG. 22A and the values summarized in the Table 16 below. $EC_{50}$ values for binding Jurkat-hTIGIT are very close for clone 31282 with no marked difference between antibody produced in HEK cells (31282_up, 0.13 nM) or in CHO-K1 cells (31282-wu, 0.10 nM). Clone 31C6 and TIG1 also show $EC_{50}$ values below 0.2 nM while affinity for other clones (4.1 D3, 22G2 and 313M32) is lower and results show $EC_{50}$ values ranging from 0.267 to 0.445 nM. Results demonstrate a strong binding to membrane expressed human TIGIT in an engineered system for anti-TIGIT clones 31282, 31C6 and TIG1 while other clones have a lower affinity.

TABLE 16

$EC_{50}$ data and comparison of different a-TIGIT clones for binding to Jurkat-hTIGIT

| Clone | $EC_{50}$ binding to Jurkat-hTIGIT (in nM) | Fold change of $EC_{50}$ over $EC_{50}$ of best clone (31282_wu) |
|---|---|---|
| 31282_wu | 0.10 | 1 |
| 31282_up | 0.13 | 1.3 |
| 313M32 | 0.44 | 4.2 |
| 4.1D3 | 0.27 | 2.5 |
| 22G2 | 0.32 | 3.0 |
| 31C6 | 0.13 | 1.2 |
| TIG1 | 0.17 | 1.6 |

B. Binding of Anti-TIGIT Clones to Primary CD8+ T Cells from Healthy Human PBMCs Isolated human PBMCs from healthy volunteers were analysed for binding by antagonist anti-TIGIT antibodies. Cells were distributed at $1 \times 10^5$ cells per well. Cells were incubated with anti-CD16 (Clone 3G8, BioLegend 302002), CD32 (Clone FL18.26, BD Bioscience 557333) and CD64 (BD Bioscience 555525) at room temperature for 10 min, and the indicated anti-human TIGIT antibody clones were directly added at a final concentration of 8; 4; 2; 1; 0.5; 0.25; 0.125; 0.062; 0.031; 0.016; $8 \times 10^{-3}$ and $4 \times 10^{-3}$ nM in FACS buffer and incubated for 20 min at 4° C. After washing, cells were incubated with anti-human Ig (Fc gamma specific)-PE (eBioscience, 12-4998-82, at 2.5 µg/ml) for 20 min at 4° C. Then, cells were washed and incubated with the following antibodies and LVD mix: anti-CD4– PercP-Cy5.5 (clone A161A1, BioLegend 357414); anti-CD8– BV510 (clone SK1, BD Bioscience 563919) and LVD efluor 660 (eBioscience 65-0864-18).

The $EC_{50}$ values for binding to CD8+ human primary T cells were calculated using the MFI signal on living TIGIT+ CD8+T cells. The results are illustrated in FIG. 22B and the $EC_{50}$ concentrations summarized in the Table 17 below. $EC_{50}$ values for binding human primary CD8+ T cells are very close for clone 31282 with no marked difference between antibody produced in HEK cells (31282_up, 0.21 nM) or in CHO-K1 cells (31282-wu, 0.19 nM). Comparison between the different clones of antagonist a-TIGIT antibodies show the best $EC_{50}$ value for binding on human primary CD8+ T cells for clone 31282_wu (0.19 nM) and clone 31282_up (0.21 nM). Clones 31C6 and TIG1 show a difference in $EC_{50}$ of 2 fold while clone 22G2, 313M32 and 4.1D3 differs by a factor of 6.1 to 9.7 fold. Overall, 31282_wu and 31282_up show the best binding to membrane expressed TIGIT on human primary CD8+ T cells.

TABLE 17

$EC_{50}$ data and comparison of different a-TIGIT clones for binding to Human primary CD8+ T cells

| Clone | $EC_{50}$ concentration for binding to CD8+ T cells (in nM) | Fold change of $EC_{50}$ over $EC_{50}$ of best clone (31282_wu) |
|---|---|---|
| 31282_wu | 0.19 | 1 |
| 31282_up | 0.21 | 1.1 |
| 313M32 | 1.45 | 7.5 |
| 4.1D3 | 1.88 | 9.7 |

TABLE 17-continued

EC$_{50}$ data and comparison of different a-TIGIT clones
for binding to Human primary CD8$^+$ T cells

| Clone | EC$_{50}$ concentration for binding to CD8$^+$ T cells (in nM) | Fold change of EC$_{50}$ over EC$_{50}$ of best clone (31282_wu) |
|---|---|---|
| 22G2 | 1.17 | 6.1 |
| 31C6 | 0.39 | 2.0 |
| TIG1 | 0.38 | 2.0 |

C. Binding of Anti-TIGIT Clones to Primary CD8$^+$ T Cells from Cancer Patients PBMCs Isolated human PBMCs from cancer patients were analysed for binding by different antagonist anti-TIGIT antibody clones. Cells were distributed at 1×10$^5$ cells per well. Cells were incubated with anti-CD16 (Clone 3G8, BioLegend 302002), CD32 (Clone FLI8.26, BD Bioscience 557333) and CD64 (BD Bioscience 555525) at room temperature for 10 min, and the indicated anti-human TIGIT antibodies were directly added at a final concentration of: 8, 4, 2, 1, 0.5, 0.25, 0.125, 0.062 and 0.031 nM in FACS buffer and incubated for 20 min at 4° C. After washing, cells were incubated with anti-human Ig (Fc gamma specific)-PE (eBioscience, 12-4998-82, at 2.5 µg/ml) for 20 min at 4° C. Then, cells were washed and incubated with the following antibodies and life viability dye (LVD) mix: anti-CD4-PercP-Cy5.5 (clone A161A1, BioLegend 357414); anti-CD8− BV510 (clone SK1, BD Bioscience 563919) and LVD efluor 520 (eBioscience 65-0867-14). Cells were washed and fixed and surface staining was quantified using BD LSR Fortessa. Flow cytometry data was analysed using FlowJo V10.1. TIGIT MFI on gated LVD$^-$TIGIT$^+$CD8$^+$ cells was used to calculate EC$_{50}$ values. Nonlinear regression curves are shown on FIG. 22C and the values summarized in Table 18 below.

Clones 31282_wu and 31282_up show very close EC$_{50}$ value for binding on CD8$^+$ T cells from cancer patients with concentration of 0.14 and 0.12 nM, respectively. The rest of the clones show lower affinity with clone 31C6, TIG1 and 22G2 showing a 1.5, 2.7 and 3.1 fold lower affinity, respectively. Measured EC$_{50}$ value for clone 313M32 is 8.3 fold lower compared to clone 31282_up. Clone 4.1D3 shows the lowest affinity, binding with a difference of 9.5 fold to the best clone tested.

TABLE 18

EC$_{50}$ data and comparison of different a-TIGIT clones for
binding to Human primary CD8$^+$ T cells from cancer patients

| Clone | EC$_{50}$ value for CD8$^+$ T cells binding (in nM) | Fold change of EC$_{50}$ over EC$_{50}$ of best clone (31282) |
|---|---|---|
| 31282_wu | 0.14 | 1.2 |
| 31282_up | 0.12 | 1.0 |
| 313M32 | 1.0 | 8.3 |
| 4.1D3 | 1.15 | 9.5 |
| 22G2 | 0.37 | 3.1 |
| 31C6 | 0.18 | 1.5 |
| TIG1 | 0.33 | 2.7 |

Example 19: Competition Assay Between Anti-TIGIT Antagonist Antibody Clones and TIGIT Natural Ligand (CD155)

Jurkat cells overexpressing human TIGIT (Jurkat-hTIGIT) were collected and distributed at 5.10$^4$ cells/well and incubated with anti-human TIGIT antibodies at the following concentrations: 133.33; 42.20; 13.33; 4.22; 1.33; 0.422; 0.133; 0.042; 0.0133; 4.2×10$^{-3}$; 1.3×10$^{-3}$; 4.2×10$^{-4}$; 1.3×10$^{-4}$; 4.2×10$^{-5}$ nM in complete medium during 45 min at 37° C. Excess of antibody was washed, and then the cells were incubated with CD155-His at 15 µg/ml (Creative Biomart, PVR-3141H) for 45 min at 37° C. Then, bound CD155-His was detected using anti-His tag-PE (Biolegend, 362603, at 2 µl per test), incubated for 30 min at 4° C. Cells were analysed by FACS using BD LSRFortessa and the half concentration (IC$_{50}$) that prevents CD155 binding was calculated based on the median fluorescence intensity of PE in total cells.

Figure 23:
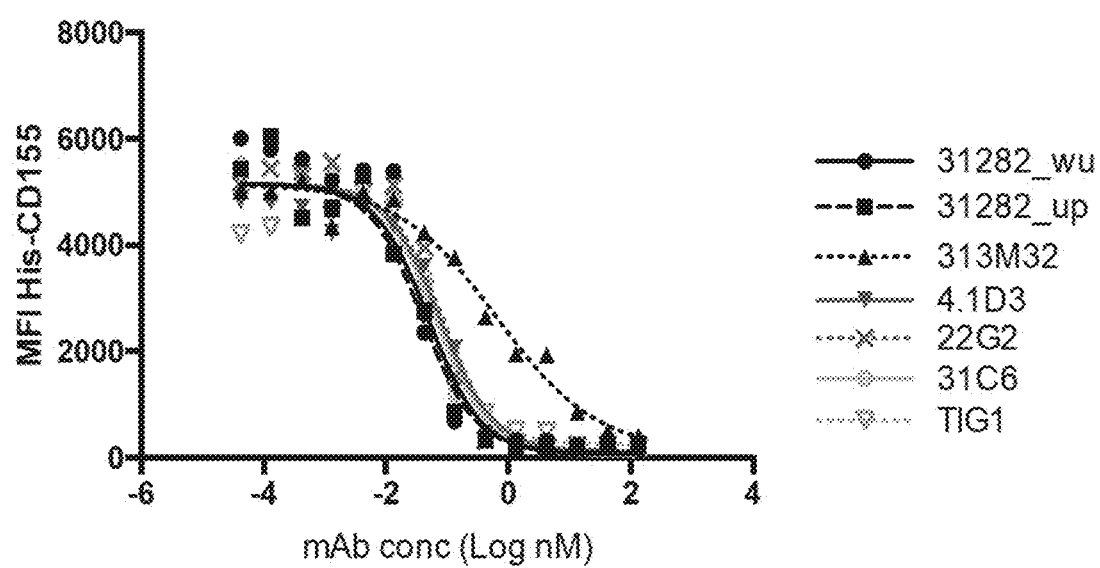
FIG. 23 Graph showing the results of a competition assay between human CD155 and anti-TIGIT antibody clones for binding to Jurkat-hTIGIT FIG. 24 Graph showing the functional characterization of antagonist a-TIGIT clones. (A) Graphs showing the effect of anti-TIGIT antibodies in a functional assay using Jurkat-hTIGIT effector cells (Luciferase reporter assay). (B) Graphs showing the effect of anti-TIGIT antibodies in a functional assay measuring IFNg secretion by human primary $CD8^+$ T cell from healthy volunteers. (C) Graph showing the effect of anti-TIGIT antibody clone 31282 in functional assay measuring IFNg secretion by cancer patient $CD3^+$ T cell from PBMC. (D) Graph showing the effect of anti-TIGIT antibody clone 31282 in functional assay measuring intracellular cytokine staining in cancer patient TILs or PBMCs.

The results are illustrated in FIG. 23 and the values summarized in the Table 19 below. Anti-TIGIT clones 31282_wu and 31282_up show the best IC$_{50}$ values for CD155 competition on Jurkat cells engineered to express hTIGIT with concentration of 0.05 and 0.04 nM respectively. Other clones (4.1D3, 22G2, 31C6, TIG1) have IC$_{50}$ values between 0.07 and 0.09 nM while clone 313M32 clone competes with CD155 for binding to TIGIT with a much lower efficiency (0.65 nM).

TABLE 19

IC$_{50}$ data and comparison of different a-TIGIT
clones for CD155 competition on human TIGIT

| Clone | IC$_{50}$ of CD155 competition for TIGIT binding (in nM) | Fold change of IC$_{50}$ over IC$_{50}$ of best clone (31282_up) |
|---|---|---|
| 31282_wu | 0.05 | 1.3 |
| 31282_up | 0.04 | 1 |
| 313M32 | 0.65 | 16.7 |
| 4.1D3 | 0.07 | 1.9 |
| 22G2 | 0.09 | 2.2 |
| 31C6 | 0.07 | 1.7 |
| TIG1 | 0.06 | 1.6 |

Example 20: Functional Characterization of Antagonistic Anti-TIGIT Clones

A. TIGIT Functional Assay with Jurkat-hTIGIT Cells

To characterize the functional consequence of blocking human TIGIT receptor, we co-cultured Jurkat cells, that express hTIGIT and a luciferase reporter activated upon TCR engagement (Thaw-and-Use TIGIT Effector cells from Promega), with CHO-K1 cell line engineered to express human PVR/CD155 and TCR activator (Thaw-and-Use CD155 aAPC/CHO-K1 from Promega). The activation of TIGIT-overexpressing Jurkat cells can be induced by contact with CD155-expressing CHO-K1 cells upon TCR engagement on Jurkat cells and can be increased in presence of antagonist anti-TIGIT antibody. To compare the potency of the different a-TIGIT clones to increase Jurkat cell activation, the experiment was conducted in presence of increasing antibody concentrations and the EC$_{50}$ values were calculated.

CD155 aAPC/CHO-K1 (Promega, CS198811) cells were seeded according to manufacturer's recommendations and incubated at 37° C., 5% CO2 incubator O/N. The next day, TIGIT Effector cells (Promega, CS198811) were added according to manufacturer's recommendations to the CD155 aAPC/CHO-K1 cell plates containing fresh full medium with anti-TIGIT antibody at increasing concentrations (0.03; 0.11; 0.33; 1.06; 3.34; 10.56; 33.38; 105.49; and 333 nM) and incubated at 37° C., 5% CO2 during 6 hours. After the 6 hours of incubation, activation of TIGIT Effector cell was assessed by measuring the luciferase activity by using Bio-Glo™ Luciferase Assay System (Promega, G7941).

As shown in FIG. 24A and summarized in Table 20, anti-TIGIT antibody 31282 has the best efficacy in term of $EC_{50}$ value and maximum induction of luciferase signal in the assay. Activity observed for clone produced in HEK (31282_up) or CHO-K1 (31282 wu) cells is comparable with a maximum luciferase signal that is 8 folds higher than control isotype (Bioexcell, BE0297) and with an $EC_{50}$ concentration measured at 3.3 nM and 3.5 nM respectively. By way of comparison, clones 4.1D3, 22G2 and 31C6 have a maximum activity between 5.3 and 6.7 fold over isotype control, associated with an $EC_{50}$ between 5 and 10 nM. $EC_{50}$ values for clone 313M32 and TIG1 could not be determined due to a low activity and poor fitting of the curves at the concentrations tested (FIG. 24A).

TABLE 20

$EC_{50}$ data and comparison of different a-TIGIT clones for functional activity on Jurkat-hTIGIT cells

| Clone name | Induction over Isotype control (fold change) | $EC_{50}$ (nM) | Fold change of $EC_{50}$ over $EC_{50}$ of best clone (31282_up) |
|---|---|---|---|
| 31282_wu | 8.4 | 3.5 | 1.1 |
| 31282_up | 8.0 | 3.3 | 1 |
| 313M32 | / | P.F. | / |
| 4.1D3 | 5.8 | 10.3 | 3.1 |
| 22G2 | 5.3 | 5.2 | 1.6 |
| 31C6 | 6.7 | 5.3 | 1.6 |
| TIG1 | / | P.F. | / |

P.F.: poor fit

B. TIGIT Functional Assay on Human Primary CD8+ T Cells from Healthy Volunteers

To characterize the functional consequence of blocking human TIGIT receptor, we co-cultured human primary CD8+ T cells from PBMC of healthy human donors with CHO-K1 cell line engineered to express human PVR/CD155 and to activate human T cells. We observed that the release of IFNg by CD8+ T cells in presence of engineered CD155-expressing CHO-K1 cells could be increased by blocking hTIGIT with anti-TIGIT antagonistic antibodies. To compare the potency of these antibodies to increase IFNg release, the experiment was conducted in the presence of increasing antibody concentrations and the $EC_{50}$ values were calculated.

CD155 aAPC/CHO-K1 (Promega, CS198811) cells were seeded in U-bottom 96-well plates according to manufacturer's recommendations and incubated at 37° C., 5% CO2 incubator O/N. The next day, CD8+ T cells were purified according to manufacturer's recommendations by using negative selection kit (Stemcell Technologies, 17953) from frozen human peripheral blood mononuclear cells isolated from total blood of healthy donors (Immunehealth). Purified CD8 T cells and increasing concentrations (0,011 nM, 0,033 nM, 0.11 nM, 0.33 nM, 1.06 nM, 3.3 nM, 10.6 nM, 33.3 nM and 105.5 nM) of antibodies were then added to CD155 aAPC/CHO-K1 (100,000 CD8 T cells/100 ul of full medium containing antibody) and incubated at 37° C., 5% CO2 during 5 days. Finally, IFNg concentrations were assessed in cell supernatant using an ELISA assay (Affymetrix eBioscience, 88-7316-86) that was run according to manufacturer's recommendations.

As shown in FIG. 24B and summarized in Table 21, a-TIGIT clone 31282 and 4.1D3 display the best induction of IFNg secretion with a respective 2.7 and 2.9 fold increase over isotype control antibody. Clone 31282 has the best efficacy for induction of IFNg production in terms of $EC_{50}$ concentration, which was measured at 0.13 nM. Clone 31C6 shows an $EC_{50}$ value 2.3 fold different while clone 22G2 and 4.1D3 are 3.1 and 10.8 fold less potent than clone 31282. No value could be determined for clone 313M32 due to a low activity and poor fitting of the curves at the concentrations tested (FIG. 24B).

TABLE 21

$EC_{50}$ data and comparison of different a-TIGIT clones for functional activity on human primary CD8+ T cells

| Clone | Induction over over isotype control (fold change) | $EC_{50}$ (nM) | Fold change of $EC_{50}$ over $EC_{50}$ of best clone (31282_wu) |
|---|---|---|---|
| 31282_wu | 2.7 | 0.13 | 1 |
| 313M32 | / | P.F. | / |
| 4.1D3 | 2.9 | 1.43 | 10.8 |
| 22G2 | 1.5 | 0.41 | 3.1 |
| 31C6 | 1.6 | 0.30 | 2.3 |

C. TIGIT Functional Assay on Human Primary CD3+ T Cells from Cancer Patients

To characterize the functional consequence of blocking human TIGIT receptor on T cells from cancer patients, human primary CD3+ T cells from PBMC of a cancerous patient were co-cultured with a CHO-K1 cell line engineered to express human PVR/CD155 and to activate human T cells (CHO-TCR-CD155). We observed that the release of IFNg by CD3+ T cells in the presence of engineered CD155-expressing CHO-K1 cells could be increased by blocking hTIGIT with anti-TIGIT antagonist antibody 31282.

CD155 aAPC/CHO-K1 (Promega, CS198811) cells were seeded in U-bottom 96-well plates according to manufacturer's recommendations and incubated at 37° C., 5% CO2 incubator O/N. The day after, CD3+ T cells were purified according to manufacturer's recommendations by using negative selection kit (Stemcell Technologies, 17951) from fresh human peripheral blood mononuclear cells isolated from total blood from a cancerous patient (HNSCC) collected 24 h earlier (Biopartners). Purified CD3+ T cells and 66.7 nM of antibodies were then added to CD155 aAPC/CHO-K1 (100,000 CD3 T cells/100 ul of full medium containing antibody) and incubated at 37° C., 5% CO2 for 5 days. Finally, IFNg concentrations were assessed in cell supernatant using an ELISA assay (Affymetrix eBioscience, 88-7316-86) that was run according to manufacturer's recommendations.

As shown in FIG. 24C, antibody 31282 induced a strong functional activity to increase IFNg secretion, demonstrating the potential of this a-TIGIT antibody to reactivate PBMC T cells from cancer patients.

D. A-TIGIT Clone 31282 Increases Intracellular Cytokine Production in T Cells from Cancer Patient PBMC and Dissociated Tumour Cells (DTC)

In this example, intracellular flow cytometry staining was performed to assess the T cell cytokine production from freshly isolated matched PBMC and tumour infiltrated lymphocytes within dissociated tumour cells (DTC) from kidney carcinoma cancer patients. For DTC, tumours were minced mechanically then incubated with Tumor Dissociation Kit (Miltenyi Biotech #130-095-929) under rotation in a gentleMACS dissociator, following manufacturer instructions for specific tumor types. Cells were stimulated for 16 h with a T cell stimulation bead cocktail (Dynabeads, Thermo Fisher) before performing intracellular staining. During the last 3 hours of stimulation, protein Transport Inhibitor Cocktail (eBioscience) and Cell stimulation cocktail (eBioscience) were added to the cells. Conjugated antibodies were purchased from Ebioscience/Thermo Fisher Scientific, BioLegend or BD Biosciences. Surface staining was performed per manufacturer's instruction using filtered FACS buffer (PBS+2 mM EDTA+0.1% BSA) and Brilliant Stain buffer (BD #563794). Cells were blocked with appropriate Human FcBlock (BD #564220) prior to surface staining. For intracellular staining, cells were fixed and permeabilized using BD Cytofix/cytoperm solution (BD Biosciences). Cells were stained with the following antibody panel: anti-CD45-BB515 (Clone HI30, BD Horizon 564585), anti-CD73-BV421 (Clone AD2, BD Horizon 562430), anti-CD8a-BV510 (Clone SK1, BD Horizon 563919), anti-CD3-BV650 (Clone SK7, BD Horizon 563999), anti-IFNγ-BV711 (Clone 4S.B3, BD Horizon 564793), anti-IL-2-APC (MQ1-17H12, eBioscience 17-7029-82), anti-CD4-APC-R700 (Clone RPA-T4, BD Horizon 564975), LVD efluor 780 (eBioscience 65-0865-14), anti-TIGIT-PE (Clone MBSA43, eBioscience E13456-108), anti-CD39-PE-Dazzle594 (Clone A1, Biolegend 328224) and TNFα-PE-cy7 (Clone Mab11, eBioscience 25-7349-82). Acquisition was performed on a FACS Fortessa (BD Biosciences) and analyzed with FlowJo software (FlowJo, LLC). Viable cells were gated on Forward and Side scatter. T cells subsets were gated as followed: $CD45^+$ $CD3^+$ for PBMC and $CD45^+$ $CD3^+CD4^+$ and $CD45^+$ $CD3^+$ $CD8^+$ for DTC. Cytokine-secreting T cells were gated using unstained and unstimulated controls.

FIG. 24D shows that intracellular content of IL2, IFNg and TNFa were all increased upon activation in presence of a-TIGIT clone 31282. This increase was observed in $CD3^+$ T cells from PBMC in accordance with data illustrated in FIG. 24C but also in both $CD4^+$ and $CD8^+$ TIL from dissociated tumour cells. This demonstrates the potential of a-TIGIT clone 31282 to increase the activation of PBMC and TIL populations from cancer patient T cells.

Example 21: A-TIGIT Clone 31282 Induces Preferential Cytotoxicity of Treg in PBMC from Cancer Patients In this example, isolated PBMCs from a lung cancer patient were resuspended in complete RPMI medium (supplemented with 10% FBS heat inactivated+50 U Penicillin+50 U Streptomycin). $2.5 \times 10^5$ human PBMCs were distributed per well in 96 U well plate. Anti-human TIGIT antibody clone 31282, human IgG1 isotype control (BioXcell BE0297) or Rituximab (InvivoGen hcd20-mab1) were added at a final concentration of 6.6 nM to each corresponding well. Cells were incubated for 20 h at 37° C. with 5% CO2. Then cells were collected and stained with the following antibody panel: LVD efluor 520 (eBioscience 65-0867-14), ant-TCRab-PercP-Cy5.5 (Clone IP26, Biolegend 306723), anti-CD4-BV510 (Clone SK3, BD Horizon 562970), anti-CD8-APC-Cy7 (Clone SK1, Biolegend 344714), anti-CD25-BV605 (Clone 2A3, Biolegend 562660), anti-CD127-APC (A019D5, Biolegend 351316), anti-CCR7-BV421 (Clone G043H7, Biolegend 353207) and anti-CD45RO-PE-Cy7 (Clone UCHL1, Biolegend 304229). Results are presented on gated live cells. Absolute quantification is done using AccuCheck Counting beads (Life technologies) following manufacturer's specifications. After calculation of absolute cell numbers per µl, % of specific lysis is calculated using the following formula=(1−(absolute number of cells per µl on 31282 TIGIT antibody treated sample/average of triplicate of control isotype treated samples))×100. Results are presented as mean % of specific lysis on triplicates +/−SD. The cytotoxic activity of ADCC/ADCP effector cells was assessed by measuring % of specific cell lysis on gated $CD19^+$ cells upon incubation with Rituximab.

As shown in FIG. 25, anti-TIGIT clone 31282 triggers higher specific lysis on Tregs cells (30.1+/−3%) than on $CD45RO^+CCR7^{+/-}CD8^+$ T cells (total memory $CD8^+$ T cells) (−1.48+/−6%) or $CD45RO^+CCR7^{+/-}CD4^+$ T (total memory $CD4^+$ T cells) (0.64+/−3%). Rituximab positive control triggers 77.9% (+/−6.8%) of specific lysis on gated $CD19^+$ cells. Overall data demonstrate a preferential depletion of Treg cells from cancer patient PBMC as compared to total memory $CD4^+$ and $CD8^+$ T cell populations. Similar preferential depletion of Treg cells was observed using cells from a patient with colon adenocarcinoma.

Example 22: Characterization of TIGIT Expression on Immune Populations from Cancer Patient PBMC and Dissociated Tumour Cells Flow cytometry analyses were performed to assess the expression of TIGIT on immune cell subsets from freshly isolated matched PBMC and tumour infiltrated lymphocytes within dissociated tumour cells (DTC) from cancer patients. Samples from different indications were acquired: Ovarian cancer, Kidney cancer, HNSSC, Cutaneous carcinoma, Melanoma and Lung cancer. For DTC, tumours were minced mechanically then incubated with Tumor Dissociation Kit (Miltenyi Biotech #130-095-929) under rotation in a gentleMACS dissociator, following manufacturer instructions for specific tumour types. PBMC were isolated from whole blood on a density gradient medium (Lymphoprep Axis-Shield #1115758). Phenotyping data were compared with frozen PBMC isolated from healthy individuals (n=10).

Cells were stained per manufacturer's instruction using filtered FACS buffer (PBS+2 mM EDTA+0.1% BSA) and Brilliant Stain buffer (BD #563794). Cells were blocked with appropriate Human FcBlock (BD #564220) prior to staining and were fixed using IC fixation buffer (eBioscience #00-8222-49) prior acquisition. DTC were stained with the following antibody panel: anti-CD45-BB515 (Clone H130, BD Horizon 564585), anti-CD73-BV421 (Clone AD2, BD Horizon 562430), anti-CD8a-BV510 (Clone SK1, BD Horizon 563919), anti-CD3-BV650 (Clone SK7, BD Horizon 563999), anti-CD56-BV711 (Clone 5.1H1, Biolegend 362542), anti-CD279-BV785 (Clone EH12.2H7, Biolegend 329930), anti-CD127-APC (Clone A019D5, Biolegend 351316), anti-CD4-APC-R700 (Clone RPA-T4, BD Horizon 564975), LVD efluor 780 (eBioscience 65-0865-14), anti-TIGIT-PE (Clone MBSA43, eBioscience E13456-108), anti-CD39-PE-Dazzle594 (Clone A1, Biolegend 328224) and CD25-PE-cy7 (Clone BC96, Biolegend 302612). PBMC were stained with the following antibody panel: anti-CD45RO-BB515 (Clone UCHL1, BD Horizon 564529), anti-CD73-BV421 (Clone AD2, BD Horizon 562430), anti-CD8a-BV510 (Clone SK1, BD Horizon 563919), anti-CD3-BV650 (Clone SK7, BD Horizon 563999), anti-CD56-BV711 (Clone 5.1H11, Biolegend 362542), anti-CD197-BV786 (Clone 3D12, BD Horizon 563710), anti-CD127-APC (Clone A019D5, Biolegend 351316), anti-CD4-APC-R700 (Clone RPA-T4, BD Horizon 564975), LVD efluor 780 (eBioscience 65-0865-14), anti-TIGIT-PE (Clone MBSA43, eBioscience E13456-108), anti-CD39-PE-Dazzle594 (Clone A1, Biolegend 328224)

and CD25-PE-cy7 (Cl bone BC96, Biolegend 302612). Acquisition was performed on a FACS Fortessa (BD Biosciences) and analyzed with FlowJo software (FlowJo, LLC). Viable cells were gated on Forward and Side scatter. Various Immune cells subsets were gated as followed: $CD3^+$ $CD4^+$ $CD127^+$ $CD25^-$ ($CD3^+$ $CD4^+$ non-Treg cells), $CD3^+$ $CD4^+$ $CD127^{low}$ $CD25^+$ (regulatory T cells), $CD3^+$ $CD8^+$ ($CD3^+$ $CD8^+$ T cells), $CD3^-$ $CD56^+$ (NK cells), $CD3^+$ $CD56^+$ (NKT cells), $CD3^-$ $CD56^-$ (non- T/NK cells). Quantibrite PE beads (BD #340495) were run at the same instrument settings and used to convert fluorescence data into number of antibodies bound per cell.

Frequency of TIGIT expression on different immune populations is represented in FIG. 26A and TIGIT density for each subset is represented in FIG. 26B using Box and whiskers representation using the Tukey method to compute percentiles.

Data show that TIGIT frequency on T cell subset is higher on PBMC from cancer patients as compared to PBMC from healthy donors. This frequency is further increased on DTC TILS (FIG. 26A). While the same observation is made looking at the density of TIGIT on the surface of $CD3^+$ $CD4^+$ non-Treg cells and $CD4^+$ Treg cells, for $CD3^+$ $CD8^+$ T cells the number of TIGIT molecules per cell is decreased on DTC TILS (FIG. 26B).

Example 23: Structural and Functional Epitope Mapping of TIGIT and Clone 31282

To further characterize and understand the interaction between anti-TIGIT mAb clone 31282 and TIGIT recombinant protein, the crystal structure of 31282 in complex with TIGIT was determined by X-ray diffraction.

A. TIGIT and Fab Expression, Purification and Crystallization

Human TIGIT residues 23-128 was produced by Proteros Biostructures GmbH. TIGIT (23-128) with N-terminal HIS-tag (thrombin cleavable) was cloned into pET15b and expressed in LB medium in B121(DE3) at 37° C. in inclusion bodies. Inclusion bodies (IBs) were washed with buffer containing Tris/HCl pH 7.4 and Tris/HCl pH 7.4, 0.05% Brij-35. IBs were denaturated with 6 M Gdm/HCl, 50 mM Tris pH 8.5 and 10 mM DTT. Refolding was performed in 50 mM Tris/HCl pH8, 1 mM GSH, 0.5 mM GSSG, 150 mM NaCl. Refolded protein was purified on HIS-trap. The N-terminal HIS-tag was removed via Thrombin cleavage and further purification on Superdex-75 equilibrated in 50 mM Tris/HCl pH 7.5, 200 mM NaCl.

For Fab fragment expression, HEK293F cell were grown in Freestyle F17 with 1% penicillin/streptomycin, 2 mM L-glutamine and 0.1% Pluronic. Expanded cultures for transfection were cultivated in 3 L Erlenmeyer flasks (Corning, 2 L cell culture working volume, 37° C., 8% v/v $CO_2$, 80-120 rpm, 50 mm amplitude). The culture was diluted one day before transfection and the cell number adjusted to $1 \times 10^6$ cells/ml. The volume of the expression culture was 6 L. A transient transfection was performed with plasmids for light and heavy chain of Fab. A MasterMix of DNA/FectoPro (FectoPro, PolyPlus) was prepared in pure F17 Medium and incubated for 10 minutes (according to PolyPlus protocol). This transfection mix was added to the cell suspension dropwise and the Booster was added immediately. 18 hrs after transfection the culture was fed with 3 g/L glucose.

For purification of the Fab fragment, 6 L supernatant of HEK293 cell culture was harvested by centrifugation 6 days after transfection and applied to a 30 ml KappaSelect column. KappaSelect was washed with PBS pH 7.4, eluted with sodium citrate pH 3 and Fab containing fractions were neutralized with Tris buffer. Fab was further purified on Superdex S-200 column equilibrated in 20 mM Tris pH 8, 100 mM NaCl and stored at −80° C. until further use.

For the Fab-TIGIT complex formation, purified TIGIT was mixed with purified Fab in a ratio of 1.5:1 and the complex was purified on Superdex-200 equilibrated in 20 mM Tris pH 8, 100 mM NaCl. The Fab-TIGIT complex was concentrated to 35 mg/ml for crystallization. The Fab-TIGIT complex was crystallized at 277K using the vapour diffusion method by mixing 0.1 µl protein solution (35.3 mg/ml in 20 mM TRIS pH 8.0; 100 mM NaCl) in a 1:1 ratio with reservoir solution (0.10 M Sodium cacodylate pH 6.00; 15% (w/v) PEG4000). Crystals were cryo-protected by immersing them in reservoir solution with 25% glycerol added.

B. Data Collection and Processing

A cryo-protocol was established using Proteros Biostructures GmbH Standard Protocols. Crystals have been flash-frozen and measured at a temperature of 100 K. X-ray diffraction data was collected from Fab:TIGIT complex crystals at the SWISS LIGHT SOURCE (SLS, Villigen, Switzerland) using cryogenic conditions. The crystals belong to space group P1. Data were processed using the programmes XDS and XSCALE. Data collection and processing statistics can be found in Table 22.

TABLE 22

| Data collection and processing statistics | |
|---|---|
| X-Ray source | PXII/X10SA (SLS[1]) |
| Wavelenght [Å] | 1.0000 |
| Detector | PILATUS 6M |
| Temperature [K] | 100 |
| Space group | P1 |
| Cell: a; b; c; [Å] | 41.73; 71.46; 110.26 |
| α; β; γ; [°] | 96.7; 95.8; 106.5 |
| Resolution [Å] | 2.31 (2.56-2.31) |
| Unique reflections | 50537 (13271) |
| Multiplicity | 2.0 (1.9) |
| Completeness [%] | 96.1 (95.3) |
| $R_{sym}$ [%] | 8.1 (43.5) |
| $R_{meas}$ [%] | 11.0 (59.1) |
| Mean(I)/sd[3] | 8.11 (1.94) |

[1]SWISS LIGHT SOURCE (SLS, Villigen, Switzerland)
[2]values in parenthesis refer to the highest resolution bin
[3]calculated from independent reflections C. Structure Modelling and Refinement The phase information necessary to determine and analyse the structure was obtained by molecular replacement. A previously solved structure of Fab was used as a search model. Subsequent model building and refinement was performed according to standard protocols with the software packages CCP4 and COOT. For the calculation of the free R-factor, a measure to cross-validate the correctness of the final model, about 2.5% of measured reflections were excluded from the refinement procedure (see Table 23).

TLS refinement (using REFMAC5, CCP4) has been carried out, which resulted in lower R-factors and higher quality of the electron density map. Automatically generated local NCS restraints have been applied (keyword "ncsr local" of newer REFMAC5 versions). The ligand parameterisation and generation of the corresponding library files were carried out with CHEMSKETCH and LIBCHECK (CCP4), respectively.

The water model was built with the "Find waters" algorithm of COOT by putting water molecules in peaks of the Fo-Fc map contoured at 3.0 followed by refinement with REFMAC5 and checking all waters with the validation tool of COOT. The criteria for the list of suspected waters were: B-factor greater 80 Å2, 2Fo-Fc map less than 1.2σ, distance to closest contact less than 2.3 Å or more than 3.5 Å. The suspected water molecules and those in the ligand binding site (distance to ligand less than 10 Å) were checked manually. The final complex structure was refined with PHENIX. We chose the refinement parameter including XYZ coordinates, Real space, Individual B-factors and Group B-factors. Optimize X-ray/stereochemistry weight and NCS restraints were also chosen for refinement. The Ramachandran Plot of the final model shows 95.39% of all residues in the preferred region, 3.95% in the allowed region. Statistics of the final structure and the refinement process are listed in Table 23.

TABLE 23

Refinement statistics[1]

| | |
|---|---|
| Resolution [Å] | 108.40-2.31 |
| Number of reflections (working/test) | 49289/1247 |
| $R_{work}$ | 0.2025 |
| $R_{free}$ [%] | 0.2466 |
| Total number of atoms: | |
| Protein | 8282 |
| Water | 676 |
| Deviation from ideal geometry: [3] | |
| Bond lengths [Å] | 0.003 |
| Bond angles [deg] | 0.771 |
| Ramachandran plot: [2] | |
| Preferred regions [%] | 95.39 |
| Allowed regions [%] | 3.95 |
| Disallowed regions [%] | 0.66 |

[1] values as defined in PHENIX
[2] Calculated with COOT

D. Overall Structure

The heavy and light chains of the human Fab antibody fragment show the typical folding of human antibodies (FIG. 27A). There are two hetero-trimers in the asymmetric unit with basically the same overall conformation. The model comprises residues 23 to 128 of TIGIT, residues 1 to 224 of the heavy chain of clone 31282 and residues 1 to 214 of the light chain of clone 31282. One short loop region of the heavy chain is not fully defined by electron density and has thus not been included in the model.

Diffraction images were analysed using FoldX program to estimate energy contribution of residues and define interaction hotspots. The amino acid residues forming the binding interface are well defined in the electron density map. The interpreted X-ray diffraction data show clearly the interactions between the Fab and TIGIT (FIGS. 27B and 27C). Clone 31282 light chain CDR are interacting with 2 regions of TIGIT with CDR L1 Arg30 and Tyr33 contacting TIGIT residues Asn58 and Glu60; with CDR L1 Arg30 and CDR L3 Phe93 contacting TIGIT residue Ile109. CDR L2 has no contact with TIGIT (Table 24). Clone 31282 heavy chain interacts with different regions of TIGIT with CDR H1 Tyr33 contacting TIGIT on residue Leu73; with CDR H2 Val50, Ser54 and Ser57 contacting TIGIT on residue Leu73; with CDR H3 Asp102, Tyr103 and Trp104 contacting TIGIT on residue Gln56, Ile68, Leu73 and His76.

Based on this crystal structure of the a-TIGIT clone 31282/TIGIT complex, the residues of TIGIT that are contacted by clone 31282 (epitope residues for TIGIT bound by clone 31282) and the residues of clone 31282 that are contacted by TIGIT (paratope residues for clone 31282 bound by TIGIT) were determined. Tables 24 and 25 and FIG. 27C show the residues of TIGIT in contact with the light (Table 24) or heavy (Table 25) chain residues of clone 31282. Contact residues were defined as each amino acid meeting each of the following criteria: (i) it has a calculated binding free energy contribution greater than 0.3 kcal/mol, (ii) it has an experimental averaged B-factor lower than the mean B-factor of all residues in the X-ray structure, (iii) it makes at least 3 pairs of heavy-atom interatomic contacts with antibody atoms at a distance less than or equal to 4.0 Angstroms, (iv) it does not make only solvent-exposed hydrogen bond or ionic interactions, (v) if it is a non-aromatic polar residue (Asn, Gln, Ser, Thr, Asp, Glu, Lys, or Arg), it makes at least one hydrogen bond or ionic interaction with the antibody.

TABLE 24

Summary of epitope residues of TIGIT and corresponding paratope residues on the light chain of clone 31282

| TIGIT Amino Acid | Clone 31282 Amino Acid Light Chain |
|---|---|
| Asn 58 | Tyr 33 |
| Glu 60 | Arg 30 |
| | Tyr 33 |
| Ile 109 | Arg30 |
| | Phe 93 |

TABLE 25

Summary of epitope residues of TIGIT and corresponding paratope residues on the heavy chain of clone 31282

| TIGIT Amino Acid | Clone 31282 Amino Acid Heavy Chain |
|---|---|
| Gln 56 | Trp 104 |
| Ile 68 | Tyr 103 |
| | Trp104 |
| Leu 73 | Tyr33 |
| | Val50 |
| | Ser 54 |
| | Val 50 |
| His 76 | Asp 102 |
| | Tyr 103 |
| | Trp104 |

Example 24: Competition Assay Between a-TIGIT Clones 31282 and 32959

Anti-TIGIT antibody clone 32959 of human IgG1 isotype was produced in HEK cells and purified as described in Example 17 above.

Jurkat cells overexpressing human TIGIT (Jurkat-hTIGIT) were collected and distributed at $5.10^4$ cells/well and incubated with antagonist a-TIGIT clone 31282 at the following concentrations: 0 nM (No Ab), 0.08 nM, 0.16 nM, 0.8 nM and 8 nM that represent a range of concentration from 0 to 100 times the Kd of this clone. Excess of antibody was washed, and cells were incubated with decreasing concentration (8; 4; 2; 1; 0.5; 0.25; 0.125; 0.062; 0.031; 0.016; 0.008 and 0.004 nM) of directly coupled (AF647) anti-TIGIT clone 32959 for 30 min at 4° C. Geometric mean fluorescence intensity was analysed using LSR BD Fortessa. Cell binding was recorded as the median florescence intensity of AF647. For calculation of $EC_{50}$ binding of clone 32959, the half-maximal concentration of binding ($EC_{50}$) to hTIGIT-Jurkat was calculated using a four-variable curve-fit equation in Prism, and the obtained values are shown in Table 26 and illustrated in FIG. 28. The results show a strong binding of a-TIGIT clone 32959, independently of the concentration of clone 31282, demonstrating the absence of competition with an antagonist a-TIGIT antibody.

TABLE 26

$EC_{50}$ concentration for binding of a-TIGIT clone 32959 to Jurkat-hTIGIT in presence of increasing concentration of antagonist a-TIGIT clone 31282

|  | a-TIGIT 31282 at 0 nM | a-TIGIT 31282 at 0.08 nM | a-TIGIT 31282 at 0.16 nM | a-TIGIT 31282 at 0.8 nM | a-TIGIT 31282 at 8 nM |
|---|---|---|---|---|---|
| $EC_{50}$ (nM) binding for a-TIGIT clone 32959 | 0.22 | 0.33 | 0.37 | 0.49 | 0.39 |
| Cell binding Jurkat Human TIGIT FON (Fold Over Negative) for a-TIGIT clone 32959 | 588 | | | | |

Example 25: Determination of Pharmacokinetic Profile of Clone 31282 after Single i.v. Injection in Cynomolgus Monkey Cynomolgus monkeys received a-TIGIT clone 31282 IgG1 or IgG4 via i.v. bolus injection. Antibody was administered at 3 different concentrations (0.1 mg/kg; 1 mg/kg; 10 mg/kg) to 2 animals (1 male and 1 female). Blood was collected through 504 hours post-dose on Day 1. Blood samples were processed for plasma and analyzed for concentration of a-TIGIT clone 31282 IgG1 or IgG4 using an ELISA method. Plasma concentration-time data from individual animals were used to calculate toxicokinetic parameter values for a-TIGIT clone 31282 IgG1 and IgG4 after IV dosing using the intravascular model in Phoenix WinNonlin (version 6.3, Pharsight, a Certara Company, Princeton, NJ).

Following IV bolus dosing of a-TIGIT clone 31282 IgG1 and IgG4 at 0.1, 1, and 10 mg/kg, IgG1 concentrations were quantifiable in plasma of male and female monkeys through 240 h, 336 h, and 504 h post-dose, respectively, and IgG4 was quantifiable through 168 h, 240 h, and 504 h, respectively (FIG. 29 and Table 27). There were no apparent sex-related differences in systemic exposure (Cmax and AUClast) to IgG1 and IgG4 after i.v. bolus dosing of a-TIGIT clone 31282 IgG1 or IgG4, with ratios (males/females) ranging from 0.855 to 1.16.

Following i.v. bolus dosing of a-TIGIT clone 31282 IgG1 to male and female monkeys, plasma IgG1 concentrations declined biphasically at all dose levels, with mean terminal half-life (t½) ranging from 84.7-174 h (FIG. 29). Systemic clearance (CL) was consistent across the doses studied, ranging from 0.280 to 0.392 mL/h/kg. Apparent volume of distribution at steady state (Vss) was consistent among the dose levels tested, with values ranging from 53.7-66.5 mL/kg. The 10-fold increases in a-TIGIT clone 31282 IgG1 dose in the range of 0.1 to 1 mg/kg and from 1 to 10 mg/kg resulted in approximately proportional increases in exposure (9.57- to 14.5-fold increases).

Following i.v. administration of a-TIGIT clone 31282 IgG4 to male and female monkeys, plasma IgG4 concentrations declined biphasically at all dose levels tested, with t½ of 148-334 h (FIG. 29 and Table 28). CL was consistent among the dose levels tested, ranging from 0.160 to 0.219 mL/h/kg. Mean Vss ranged from 41.2-70.7 mL/kg. The 10-fold increases in a-TIGIT clone 31282 IgG4 dose in the range of 0.1 to 1 mg/kg and from 1 to 10 mg/kg resulted in approximately proportional increases in exposure to IgG4 (9.32- to 12.5-fold increases).

TABLE 27

Summary of mean Toxicokinetics parameters for a-TIGIT clone 31282 human IgG1 after i.v. bolus in Cynomolgus monkey
a-TIGIT clone 31282 human IgG1

| Dose (mg/kg) | 0.1 | 1 | 10 |
|---|---|---|---|
| $C_{max}$ (ug/ml) | 2.34 | 22.4 | 268 |
| $t_{max}$ (h) | 1 | 1 | 1 |
| $AUC_{last}$ (h*ug/ml) | 224 | 2330 | 33700 |
| $t_{1/2}$ (h) | 174 | 84.7 | 111 |
| Cl (mL/h/kg) | 0.292 | 0.392 | 0.280 |
| $V_{ss}$ (mL/kg) | 66.5 | 57.2 | 53.7 |

TABLE 28

Summary of mean Toxicokinetics parameters for a-TIGIT clone 31282 human IgG4 after i.v. bolus in Cynomolgus monkey
a-TIGIT clone 31282 human IgG4

| Dose (mg/kg) | 0.1 | 1 | 10 |
|---|---|---|---|
| $C_{max}$ (ug/ml) | 2.81 | 26.2 | 283 |
| $t_{max}$ (h) | 1 | 1 | 1 |
| $AUC_{last}$ (h*ug/ml) | 238 | 2690 | 39100 |
| $t_{1/2}$ (h) | 251 | 334 | 182 |
| Cl (mL/h/kg) | 0.190 | 0.160 | 0.216 |
| $V_{ss}$ (mL/kg) | 65.7 | 70.7 | 57.5 |

Example 26: Characterization of TIGIT Expression on Human Tumour Cell Populations Flow cytometry analyses were performed to assess the expression of TIGIT on normal and tumour T or B cells in blood samples from cancer patients with different indication of blood cancer.

Sézary Syndrome patient samples were tested to compare TIGIT expression on malignant and normal $CD4^+$ T cell populations. To separate these populations, a pre-determination of the malignant clone TCR-Vb rearrangement was performed using Beckman Coulter TCR-Vb repertoire kit (#1M3497). Once the malignant clone was identified, TIGIT expression was profiled on immune cells of Sezary Syndrome patients using the following commercial reagents: anti-CD3 Krome Orange (#B00068), anti-CD4-PE (#A07751), anti, CD8-PC7 (#737661), anti-CD56-PC5 (#A07789), anti-CD45-Pacific Blue (#A74763), anti-CD19-AF750 (#A94681) and anti-Vb8-FITC (#1M1233) (all from Beckman-Coulter) and anti-TIGIT-APC (clone MBSA43, ebiosciences #17-9500-42). Flow-cytometry analyses of Sezary Syndrome patient samples were performed on a CytoFlex apparatus (Beckman-Coulter). Data were analyzed with FloJo software (FlowJo, LLC).

A representative example is shown on FIG. 30A. Gating strategy for this donor that has a malignant TCR-Vb8 clone is shown in FIG. 30A with malignant cells being $CD45^+$ $CD3^+CD4^+Vb8^+$ and normal CD4+ T cells being $CD45^+$ $CD3^+CD4^+Vb8^-$. A strong expression of TIGIT is observed on the malignant $CD4^+$ T cells compared to the normal $CD4^+$ T cells (respective MFI of 4987 and 999) (FIG. 30B). Similarly, flow cytometry analyses were performed to assess the expression of TIGIT on normal and malignant B cells in bone marrow samples from patients with CLL. The samples were stained with the following antibody panel: LVD efluor 780 (eBioscience 65-0865-14), anti-CD45-BB515 (Clone H130, BD Horizon 564585), anti-CD5-BV510 (Clone UCHT2, Biolegend 363381), anti-CD19-BV711 (Clone SJ25C1, BD Horizon 563036) and anti-TIGIT-PE (Clone MBSA43, eBioscience E13456-108). Acquisition was performed on FACS Fortessa (BD Biosciences) and analyzed with FlowJo software (FlowJo, LLC). Viable cells were gated on Forward and Side scatter. Various cell-subsets were gated as followed: CD45$^+$ CD19$^+$ CD5$^-$ (Normal B cells) and CD45$^+$ CD19$^+$ CD5$^+$ (Malignant B-CLL).

A representative example is shown on FIG. 31 with gating strategy illustrated in FIG. 31A. A high proportion of malignant B-CLL cells are positive for TIGIT (75%), in contrast to normal B cells (1%) (MFIs of 1440 and 810, respectively) (FIG. 31B).

Overall, the data obtained demonstrate that tumour cells express TIGIT in specific blood cancer indications.

Example 27: Anti-Tumour Activity of Anti-TIGIT Antagonistic Antibody in Monotherapy in Mouse T Cell Lymphoma Model For this experiment, EL4 T cell lymphoma cells (ATCC® TIB-39™) were engineered to stably express mouse TIGIT (EL4-mTIGIT). EL4 cells transduced with a similar vector coding for GFP were used as control (EL4-GFP). Pools of cells were subcloned to obtain clones of EL4-mTIGIT and EL4-GFP. The anti-TIGIT antibody used was a modified version of antibody 29527 (which cross-reacts with mouse TIGIT), modified such that residue 27 of VH FR3 is mutated from L to V and where residue 6 of VH FR4 is mutated from M to T and produced on a human IgG1 isotype. The sequence of the modified 29527 antibody (29527m) VH domain is shown below. The VL sequence of antibody 29527m corresponds to the VL of 29527 (SEQ ID NO: 240).

```
29527m      QVQLVESGGGVVQPGRSLRLSCAASGFTFSSSYMHWVR
VH (SEQ     QAPGKGLEWVAVIGADGSNKYYADSVEGRFTISRDNSK
ID NO:      NTLYLQMNSLRAEDTAVYYCAKPVPRRRGLDVWGQGTT
371         VTVSS
```

Female Balb/c mice of 8 weeks were inoculated with 1×10$^6$ EL4-mTIGIT cells or 2×10$^5$ EL4-GFP cells subcutaneously. On day 7 after innoculation, when tumor volumes were on average around 110 mm$^3$, mice were randomized in treatment groups with equal tumor volume (n=15 per group for EL4-mTIGIT and n=10 per group for EL4-GFP). Mice were treated with 200 µg of anti-TIGIT or isotype control antibody (hIgG1, BioXcell) by intraperitoneal injections on day 7, day 10, day 13 and day 16 after tumour innoculation. Tumor growth was monitored and tumor volumes were measured with electronic calipers three times a week from day 7 until day 26. Mice were sacrificed when tumor volume exceeded 2000 mm$^3$. Tumor growth curves were statistically analyzed by a linear mixed model. Differences between treatment groups were evaluated by testing the interaction of time*treatment group.

FIG. 32 illustrates tumor growth curves in mice inoculated with EL4-mTIGIT (A-C) or EL4-GFP (D-F). Median tumor growth curves (A and D) as well as individual tumor growth curves for mice treated with hIgG1 isotype control (B and E) or antagonist a-TIGIT Ab (C and F) are represented. In mice inoculated with EL4-mTIGIT cells, there was a significant suppression of tumor growth when treated with anti-TIGIT Ab compared to isotype control treated group (p<0.001). Whereas in the group treated with isotype control antibody, 3 out of 15 mice demonstrated a control of tumor growth with a volume below 700 mm$^3$ at the end of the model, this number was increased to 8 out of 15 mice in the group treated with antagonist anti-TIGIT antibody. No anti-tumor efficacy or complete response could be observed in EL4-GFP tumor bearing mice when comparing antagonist a-TIGIT treatment to isotype control antibody. Together, these data demonstrate that antagonist a-TIGIT antibody (hIgG1) has significant antitumor efficacy in a model with tumor cells expressing TIGIT.

Example 28: Anti-Tumour Activity of Anti-TIGIT Antagonistic Antibody in Combination with Immune Checkpoint Antibodies in CT26 Colon Carcinoma Mouse Models In addition to the combination of anti-TIGIT Ab with an anti-PD1 antibody (Examples 12, 13 and 14), the antitumor efficacy of an anti-TIGIT antibody was also evaluated in combination with agonist antibodies specific for co-stimulatory molecules 4-1BB, OX40 and GITR, as well as with an antagonist antibody specific for checkpoint inhibitory molecule ICOS.

CT26 tumour cell line was purchased from ATCC® (CRL-2638™). Female balb/c mice of 8 weeks were subcutaneously inoculated in the right flank with 500.000 cells. On day 9 after inoculation, when tumor volumes were on average around 75 mm$^3$, mice were randomized in treatment groups with equal tumor volume (n=10 mice per group). All the antibodies were given intraperitoneally every 3 days starting on the day of randomization for a total of 3 injections. The anti-TIGIT antibody used was a modified version of antibody 29527m (which cross-reacts with mouse TIGIT), modified such that residue 27 of VH FR3 is mutated from L to V and where residue 6 of VH FR4 is mutated from M to T) and produced on a mouse IgG2a isotype, that was given at 20 µg/mouse. Anti-4-1 BB (clone 3H3, BioXCell, BE0239) was given at 5 ug/mouse, a-OX-40 (clone OX-86, BioXCell, BE0031) was given at 20 ug/mouse, a-GITR (clones DTA-1, BioXCell, BE0063) was given at 10 ug/mouse; and a-ICOS (clone 7E.17G9, BioXCell, BE0059) was given at 200 ug/mouse. Tumor growth was monitored and tumor volumes were measured with electronic calipers three times a week from day 7 until day 35. Mice were sacrificed when tumor volume exceeded 2000 mm$^3$. Tumor growth curves were statistically analyzed by a linear mixed model on logarithmically transformed tumor volumes. Differences between treatment groups were evaluated by testing the interaction of time*treatment group. This resulted in a good model fit for the vast majority of the data, except for very small tumor volumes (below 10 mm$^3$). Therefore, these small tumor volumes were treated as missing values. To test for a synergistic effect arising from combining the anti-TIGIT antibody with the corresponding immune checkpoint antibody (IC—i.e. anti-41 BB, anti-OX40, anti-GITR, and anti-ICOS), treatment groups were re-coded by a combination of two variables; anti-TIGIT (yes/no) and IC (yes/no). A synergistic effect, on top of the additive effect of each treatment (anti-TIGIT*time and IC*time) was evaluated by testing the interaction term anti-TIGIT*IC*time.

FIG. 33A shows median tumor growth curves per group as well as individual growth curves for mice treated by anti-TIGIT in monotherapy or in combination with anti-4-1BB. There was significant suppression of tumor growth in mice treated with anti-TIGIT+anti-4-1BB compared to anti- TIGIT or anti-4-1BB monotherapy (p=0.0005 and p<0.0001 respectively). The combination of anti-TIGIT and anti-4-1BB antibodies resulted in 6/10 mice showing a complete response (where tumor is <30 mm$^3$ and considered as non-measurable), as compared with 1/10 or 0/10 complete response in groups treated respectively with a-TIGIT or a-4-1BB as a single agent. These data demonstrate the significant anti-tumor efficacy of anti-TIGIT therapy in combination with anti-4-188 for treatment of pre-established tumors.

FIG. 33B shows median tumor growth curves per group as well as individual growth curves for mice treated by anti-TIGIT in monotherapy or in combination with anti-OX-40. There was significant suppression of tumor growth in mice treated with anti-TIGIT+anti-OX-40 compared to anti-TIGIT or anti-OX-40 monotherapy (p=0.0002 and p<0.0001, respectively). The combination of anti-TIGIT+anti-OX-40 achieved synergistic anti-tumor efficacy that was more than the additive effect of both monotherapy treatments (p=0.02). The combination of anti-TIGIT and anti-OX-40 antibodies resulted in 7/10 mice showing a complete response as compared with 1/10 or 0/10 complete response in groups treated respectively with a-TIGIT or a-OX-40 as a single agent. These data demonstrate the significant and synergistic anti-tumor efficacy of anti-TIGIT therapy in combination with anti-OX-40 for treatment of pre-established tumors.

FIG. 33C shows median tumor growth curves per group as well as individual growth curves for mice treated by anti-TIGIT in monotherapy or in combination with anti-GITR. There was significant suppression of tumor growth in mice treated with anti-TIGIT+anti-GITR compared to anti-TIGIT or anti-GITR monotherapy (p<0.0001). The combination of anti-TIGIT+anti-GITR achieved synergistic anti-tumor efficacy that was more than the additive effect of both monotherapy treatments (p=0.01). The combination of anti-TIGIT and anti-GITR antibodies resulted in 6/10 mice showing a complete response as compared with 1/10 or 0/10 in groups treated respectively with anti-TIGIT or anti-GITR as a single agent. These data demonstrate the significant and synergistic anti-tumor efficacy of anti-TIGIT therapy in combination with anti-GITR for treatment of pre-established tumors.

FIG. 33D shows median tumor growth curves per group as well as individual growth curves for mice treated by anti-TIGIT in monotherapy or in combination with anti-ICOS. There was significant suppression of tumor growth in mice treated with anti-TIGIT+anti-ICOS compared to anti-TIGIT or anti-ICOS monotherapy (p=0.003 and p=0.0001 respectively). The combination of anti-TIGIT and anti-ICOS antibodies resulted in 1/10 mice showing a complete response (where tumor is <30 mm$^3$ and considered as non-measurable), as compared with 1/10 or 0/10 in groups treated respectively with anti-TIGIT or anti-ICOS antibodies asa single agent. These data demonstrate the significant and synergistic anti-tumor efficacy of anti-TIGIT therapy in combination with anti-ICOS for treatment of pre-established tumors.

Example 29: Activity of Anti-TIGIT Antagonistic Antibody on γδ T Cells

γδ (gamma-delta, or g/d)T cells are a population of unconventional T cells with described antitumor activity (Zhao et al. 2018. J Transl Med. 16:122) and antiviral activity (e.g. CMV infection) and also have been implicated in autoimmune diseases (Malik S et al. 2016. Front Immunol. 7:14).

Flow cytometry analyses were performed to assess the expression of TIGIT on γδ T cells on PBMC freshly isolated from healthy individuals with a seronegative or seropositive status for Cytomegalovirus (CMV) (CMV status was assessed by the EFS Nouvelle Aquitaine, Bordeaux, France). Cells were stained per manufacturer's instruction using filtered FACS buffer (PBS+2 mM EDTA+0.1% BSA). Acquisition was performed on a FACS Fortessa (BD Biosciences) and analyzed with BD FACS DIVA software (BD Biosciences). Cells were gated on Forward and Side scatter and viability. γδ T cells were gated as follows: CD3$^+$ TCRγδ$^+$ Vδ2$^-$ (VΩ$^-$γδ T cells) using the following antibodies: anti-TCR γδ APC, clone REA591 #130-109-280 from Miltenyi; anti-TCR Vδ2-PE-Vio 770, clone REA771, #130-111-012 from Miltenyi; BV421 mouse anti-human CD3, clone UCHT1, #560365 from BD Biosciences; Zombie Aqua Fixable viable kit, #423101 from Biolegend.

Similar to conventional αβ T cells, non-conventional Vδ2$^-$γδ T cells express TIGIT in both CMV negative and positive human populations (anti-TIGIT, clone MBSA43, #12-98500-42 from eBioscience) (FIG. 34A). To characterize the functional consequence of blocking TIGIT receptor on this cell population, magnetically isolated Vδ1$^+$ γδ T cells (anti-TCR Vd1-FITC, clone REA173 #130-100-532 and anti-FITC Microbeads #130-048-701 both from Miltenyi) or total PBMC from CMV positive donors were activated with anti-Vδ1 (10 ug/ml) (clone R9.1, #IM1761 from Beckman Coulter) and IL-15 (20 ng/ml), #200-15-50 UG from Peprotech), IL-2 (100 U/ml, #200-02-1 MG Peprotech) was additionally added to isolated Vδ1$^+$γδ T cells, in presence or absence of TIGIT-ligand CD155 (#9174-CD-050 from R&D Systems). FIG. 34B shows a dose-dependent decrease in IFNγ secretion (ELISA kit, #3420-1 h-20 from Mabtech) mediated by the addition of TIGIT-ligand CD155 (0, 0.1, 1 and 10 ug/ml) with a maximal inhibition reached at 1 ug/ml of CD155. The addition of anti-TIGIT Ab clone 31282 (10 ug/ml) fully restores IFNγ production to level equal or higher to the condition without CD155 ligand while human IgG1 isotype control has very limited effect. FIG. 34C demonstrates similar inhibitory effect mediated by CD155 (10 μg/ml) after anti-Vδ1 activation of total PBMC and a total restoration of IFNγ secretion when a-TIGIT clone 31282 is added to the mix. These data demonstrate that, similar to αβ T cells, activity of γδ T cells can be impaired by ligation of CD155 to TIGIT and that anti-TIGIT antibodies fully prevent this inhibition.

Example 30: Anti-Tumour Activity of Anti-TIGIT Antagonistic Antibody as Single Agent in Hepatocellular Carcinoma Mouse Model For this experiment, 5 million of Hepa1-6 hepatocellular carcinoma cells (Crown Bioscience Inc.) were subcutaneously inoculated in the right flank of female C57Bl/6 mice. The anti-TIGIT antibody used was 29527m, a modified version of antibody 29527 (which cross-reacts with mouse TIGIT) modified such that residue 27 of VH FR3 is mutated from L to V and where residue 6 of VH FR4 is mutated from M to T) and produced on a mouse IgG2a isotype. On day 3 after inoculation, when tumor volumes were on average around 65 mm$^3$, mice were randomized in treatment groups with equal tumor volume (n=10 per group). Mice were treated with 200 μg of anti-TIGIT or isotype control antibody (mIgG2a, BioXcell BE0085) by intraperitoneal injections on day 3, day 6 and day 9 after tumour inoculation. Tumor growth was monitored and tumor volumes were measured with electronic calipers 2 times a week from day 3 until day 20. Mice were sacrificed when tumor volume exceeded 2000 mm$^3$. Tumor growth curves were statistically analyzed by a linear mixed model. Differences between treatment groups were evaluated by testing the interaction of time*treatment group.

FIG. 35 illustrates tumor growth curves in mice inoculated with Hepa1-6 cells. Median tumor growth curves (A) as well as individual tumor growth curves for mice treated with mIgG2a isotype control (B) or antagonist a-TIGIT mAb (C) are represented. There was a significant suppression of tumor growth when treated with anti-TIGIT Ab compared to isotype control treated group ($p<0.0001$). Those data demonstrate that antagonist a-TIGIT antibody has a significant antitumor efficacy when used as single agent in a murine hepatocellular carcinoma model.

Example 31: Anti-Tumour Activity of Anti-TIGIT Antagonistic Antibody as Single Agent or in Combination with Immune Checkpoint Antibodies in Pancreatic Adenocarcinoma Mouse Model In addition to the efficacy of a-TIGIT antagonist mAb observed in models described to be responsive to immunotherapy (examples 12-14, 27, 28 and 30), the efficacy of a-TIGIT mAb, as single agent or in combination, was also tested in a less immunogenic model of pancreatic adenocarcinoma model (PancO2).

PanO2 tumour cell line was purchased from National Cancer Institute (NCI 0507406 p3). Female C57Bl/6 mice of 8 weeks old were subcutaneously inoculated in the right flank with 5.000.000 cells. On day 7 after inoculation, when tumor volumes were on average around 55 mm$^3$, mice were randomized in treatment groups with equal tumor volume (n=10 mice per group). All the antibodies were given intraperitoneally every 3 days starting on the day of randomization, for a total of 3 injections. The anti-TIGIT mAb used was 29527m, a modified version of antibody 29527 (which cross-reacts with mouse TIGIT), modified such that residue 27 of VH FR3 is mutated from L to V and where residue 6 of VH FR4 is mutated from M to T and produced on a mouse IgG2a isotype, that was given at 200 µg/mouse. Anti-4-1BB (clone 3H3, BioXCell, BE0239) was given at 200 ug/mouse, a-OX-40 (clone OX-86, BioXCell, BE0031) was given at 200 ug/mouse, a-GITR (clones DTA-1, BioXCell, BE0063) was given at 10 ug/mouse. Tumor growth was monitored and tumor volumes were measured with electronic calipers three times a week from day 7 until day 42. Mice were sacrificed when tumor volume exceeded 2000 mm$^3$. Tumor growth curves were statistically analyzed by a linear mixed model on logarithmically transformed tumor volumes. Differences between treatment groups were evaluated by testing the interaction of time*treatment group. To test for a synergistic effect arising from combining the anti-TIGIT antibody with the corresponding immune checkpoint antibody (IC—i.e. anti-41 BB, anti-OX40 and anti-GITR), treatment groups were re-coded by a combination of two variables; anti-TIGIT (yes/no) and IC (yes/no). A synergistic effect, on top of the additive effect of each treatment (anti-TIGIT*time and IC*time) was evaluated by testing the interaction term anti-TIGIT*IC*time.

FIG. 36A shows the median tumor growth curves per group and FIG. 36B shows individual growth curves for mice treated by anti-TIGIT mAb as single agent or in combination with anti-4-1BB. There was no significant tumor suppression in mice treated with aTIGIT when compared to isotype treated mice ($p=0.91$). There was a significant suppression of tumor growth in mice treated with anti-TIGIT+anti-4-1BB compared to anti-TIGIT or anti-4-1BB monotherapy ($p<0.0001$ and $p=0.0001$ respectively). The combination of anti-TIGIT and anti-4-1BB antibodies resulted in 2/10 mice showing a complete response while no complete response occurred in groups treated with a-TIGIT or a-4-1BB as a single agent. These data demonstrate the significant anti-tumor efficacy of anti-TIGIT therapy in combination with anti-4-1BB for treatment of pre-established tumors.

FIG. 37A shows median tumor growth curves per group and FIG. 37B shows individual growth curves for mice treated by anti-TIGIT in monotherapy or in combination with anti-OX-40. There was significant suppression of tumor growth in mice treated with anti-TIGIT+anti-OX-40 compared to anti-TIGIT or anti-OX-40 monotherapy ($p<0.0001$ and $p=0.0001$ respectively). These data demonstrate the significant and synergistic anti-tumor efficacy of anti-TIGIT therapy in combination with anti-OX-40 for treatment of pre-established tumors.

FIG. 38A shows median tumor growth curves per group and FIG. 38B shows the growth curves for mice treated by anti-TIGIT in monotherapy or in combination with anti-GITR. There was significant suppression of tumor growth in mice treated with anti-TIGIT+anti-GITR compared to anti-TIGIT or anti-GITR monotherapy ($p<0.0001$ for both comparisons). These data demonstrate the significant and synergistic anti-tumor efficacy of anti-TIGIT therapy in combination with anti-GITR for treatment of pre-established tumors.

The effect of a-TIGIT therapy as single agent or in combination with a-4-1-BB was also tested in an orthotopic model of pancreatic adenocarcinoma (PancO2) to define the antitumor efficacy in a setting that is more clinically representative. Female C57Bl/6 mice of 8 weeks old were orthotopically inoculated in the pancreas with 2×10$^6$ syngeneic PancO2 tumor cells engineered to express Luciferase. On day 6 after inoculation, bioluminescnet signal measured and mice randomized in treatment groups with equal bioluminescent signal (n=10 mice per group). The treatment with mAb was given intraperitoneally every 3 days starting on the day of randomization for a total of 4 injections. The anti-TIGIT mAb used was 29527m, a modified version of antibody 29527 (which cross-reacts with mouse TIGIT), modified such that residue 27 of VH FR3 is mutated from L to V and where residue 6 of VH FR4 is mutated from M to T and produced on a mouse IgG2a isotype, that was given at 200 µg/mouse. Anti-4-1BB mAb (clone 3H3, BioXCell, BE0239) was given at 200 ug/mouse. Tumor progression was monitored based on bioluminescent signal measured at days 6, 14, 18 and 22 after tumor cell implantation. Curves for tumor progression based on bioluminescent signal were statistically analyzed by a linear mixed model on logarithmically transformed signal. Differences between treatment groups were evaluated by testing the interaction of time*treatment group. Mice were monitored every day and sacrificed based on a score sheet for scoring endpoint. Survival curves were drawn and statistically analysed using log-rang (Mantel-Cox) test.

FIG. 39A shows median bioluminescent signal over time and FIG. 39B shows individual curves per treatment groups. FIGS. 39A and 39B show a significant tumor growth suppression in mice treated with aTIGIT mAb as single agent when compared to isotype treated mice ($p=0.008$). There was a significant suppression of tumor growth in mice treated with anti-TIGIT+anti-4-1BB combination compared to anti-TIGIT or anti-4-1BB monotherapy (p=0.0001 and p=0.004 respectively), while anti-4-1BB alone had no effect. FIG. 39C represents the survival curves per treatment group. Results shows that aTIGIT mAb had a significant effect on mice survival when used as single agent (p=0.04) or in combination with a4-1BB (p=0.007). These data demonstrate the significant anti-tumor efficacy of anti-TIGIT mAb therapy as single agent and in combination with anti-4-1BB for treatment of orthotopic pancreatic adenocarcinoma.

Example 32: Anti-Tumour Activity of Anti-TIGIT Antagonistic Antibody as Single Agent in a Humanized Lung Carcinoma A549 Model The antitumor efficacy of a-TIGIT mAb 31282 that is not cross-reactive to mouse TIGIT (Table 3) was evaluated in a humanized system with of NSG mice inoculated with human tumor and adoptively transferred with human PBMCs cells.

To this aim, several human tumor cell lines were characterized for the expression of different TIGIT ligands CD155, CD112 and CD113). Human A549 lung carcinoma cell line was positive for the different ligands as illustrated on by Flow cytometry data on FIG. 40A.

A549 lung carcinoma cells were subcutaneously implanted at day −20 in the right flank of NOD SCID Gamma mice at a concentration of $2 \times 10^6$ cells/mouse. At day 0, mice were randomized in treatment groups with equal mean tumour volume per group and received intravenous injection of $3 \times 10^6$ human PBMCs. Anti-TIGIT mAb 31282 or human IgG1 isotype control were given intraperitoneally at 200 ug/mouse every 3 days starting 1 day after PBMC transfer for a total of 3 injections. Tumor growth was monitored and tumor volumes were measured with electronic calipers two times a week starting from day 1 post PBMCs transfer. Mice were sacrificed when tumor volume exceeded 2000 mm$^3$. Tumor growth curves were statistically analyzed by a linear mixed model on logarithmically transformed tumor volumes. Differences between treatment groups were evaluated by testing the interaction of time*treatment group. Additionally, tumor growth inhibition (TGI) per mouse was calculated using the following formula: % TGI on day X=$1-(T_x-T_c/C_x-C_0)*100$, where T is the tumor volume of one treated mouse (on day 0 and day X after PBMC implant) and C is the median tumor volume of the mice in the reference group. Then, a mean TGI was calculated for a-TIGIT mAb treated group.

FIG. 40B shows median tumor growth curves per group and FIG. 6C shows individual growth curves for mice treated by isotype control (left) or anti-TIGIT mAb (right). Linear mixed model analysis shows that there was a significant suppression of tumor growth in mice treated with anti-TIGIT compared to isotype (p<0.0001). Significant tumor growth inhibition was observed at day 7 (75% TGI, p=0.01), day 11 (54% TGI, p=0.01), day 13 (59% TGI p<0.01), and day 15 (41% TGI, p<0.01) after PBMCs implantation. These data demonstrate the significant anti-tumor efficacy of anti-TIGIT mAB 31282 in a humanized A549 lung tumor model.

Example 33: Activity of Anti-TIGIT Antagonistic Antibody on γδ T Cells

γ7 (gamma/delta) T cells are a population of unconventional T cells with described antitumor activity (Zhao et al. 2018. J Transl Med. 16:122) and antiviral activity (e.g. CMV infection) and also have been implicated in autoimmune diseases (Malik S et al. 2016. Front Immunol. 7:14).

Similar to conventional αβ T cells, non-conventional Vδ2-γδ T cells express TIGIT in both CMV negative and positive human populations (Example 8 and 29). To characterize the functional consequence of blocking TIGIT receptor on this cell population, total PBMC from CMV positive donors were plated at 100000 cells well in 96 well plate and activated with anti-Vδ1 (10 ug/ml) (clone R9.1, #1M1761 from Beckman Coulter) and IL-15 (20 ng/ml). Recombinant CD155 (PVR-621H Creative Biomart) was added to the wells at 10 µg/ml. a-TIGIT mAb 31282 was added in a 6 points, 3.16 fold dilution curve starting at 1 µg/ml. hIgG1 isotype was used as control at the highest concentration. Supernatant was collected after 48 hours of culture and IFNγ secretion was measured by ELISA.

Figure 41:
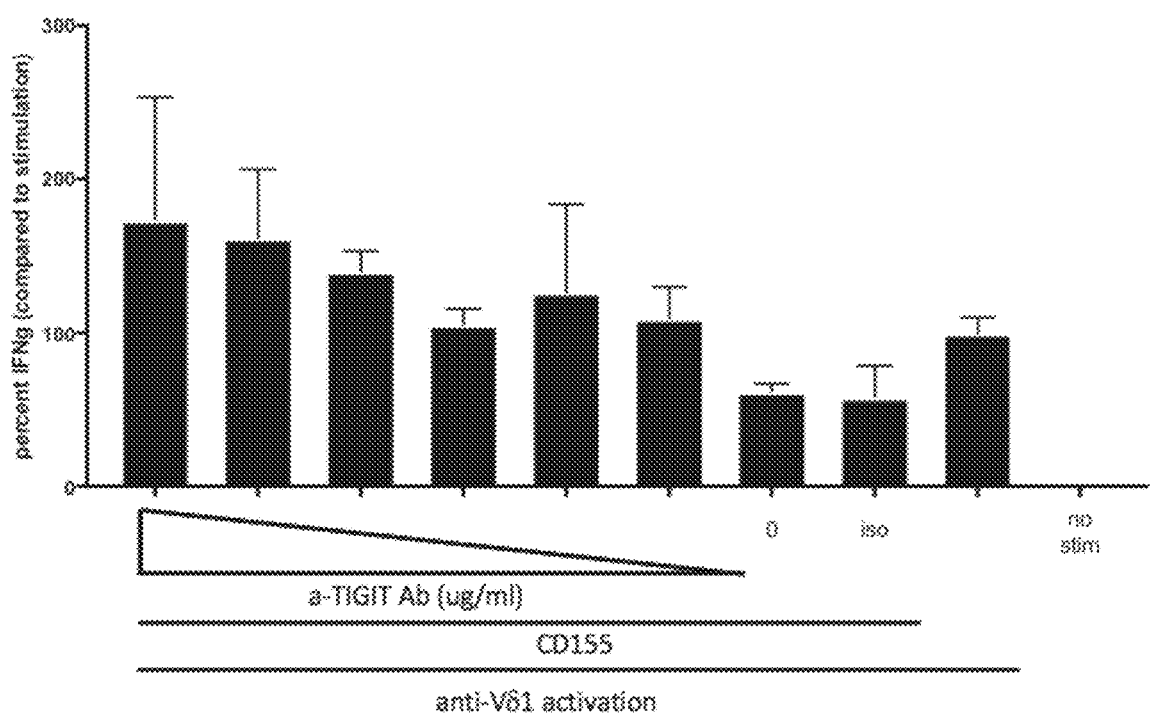

FIG. 41 demonstrates inhibitory effect mediated by CD155 (10 µg/ml) after anti-Vδ1 activation of total PBMC and a dose-dependent restoration of IFNγ secretion when a-TIGIT clone 31282 is added to the mix, while the isotype control has no effect. Interestingly, results show that treatment with a-TIGIT mAb 31282 increases the secretion of IFNγ at level superior to the control condition without CD155 showing both CD155-mediated and independent effect of a-TIGIT to stimulate γδ T cells These data demonstrate that, similar to αβ T cells, activity of γδ T cells can be positively modulated by a-TIGIT mAb 31282 that increases activity of this population, as shown by the increase of IFNγ secretion.

Example 34: Antibody Dependent Cellular Toxicity (ADCC) Activity Induced by Anti-TIGIT Antagonistic Antibody 31282 on Malignant Cells from Patients with Sézary Syndrome TIGIT is a target known to be expressed on immune cells. In addition, TIGIT expression has also been observed on CD4$^+$ tumor cells in specific blood cancer indications (Jariwala et al. (2017) J. Invest Dermatol 137:1; Example 26) Flow cytometry analyses were performed to assess that a-TIGIT mAb 31282 can induce Antibody Dependent Cellular Toxicity (ADCC) and deplete TIGIT expressing malignant cell.

Patient samples were tested first to monitor TIGIT expression on malignant and normal CD4$^+$ T cell populations. To separate these populations, a pre-determination of the malignant clone TCR-Vb rearrangement was performed using Beckman Coulter TCR-Vb repertoire kit (#1M3497). Once the malignant clone was identified, TIGIT expression was profiled on immune cells of Sezary Syndrome patients using the following commercial reagents: anti-CD3 Krome Orange (#B00068), anti-CD4-PE(#A07751), anti-CD8-PC7 (#737661), anti-CD56-PC5 (#A07789), anti-CD45-Pacific Blue (#A74763), anti-CD19-AF750 (#A94681) and anti-Vb20-FITC (#IM1562) (all from Beckman-Coulter) and anti-TIGIT-APC (clone MBSA43, ebiosciences #17-9500-42). Flow-cytometry analyses of Sezary Syndrome patient samples were performed on a CytoFlex apparatus (Beckman-Coulter). Data were analyzed with FloJo software (FlowJo, LLC).

A representative example is shown on FIG. 42. Gating strategy for this donor that has a malignant TCR-Vb20 clone is shown in FIG. 42A with malignant cells being CD45$^+$CD3$^+$CD4$^+$Vb20$^+$ and normal CD4+ T cells being CD45$^+$CD3$^+$CD4$^+$Vb20$^-$. All malignant CD4$^+$T cells are positive for TIGIT (99.6%), in contrast to normal CD4$^+$ T cells (28.9%).

For the ADCC assay, PBMC were prepared by gradient density from heparinized venous blood of Sezary patients (SS). NK and CD4+ T cells were purified by MACS (negative selection) according to the manufacturer recommendations (Miltenyi biotec). Sorted CD4+ T cells were pre-incubated for 30 min at RT with an isotype control, a-TIGIT mAb (31282) or a-CD52 mAb, (sharing similar sequence as alemtuzumab) as positive control, all at 10 µg/ml and then mixed with autologous NK lymphocytes at E/T ratios of 0/1, 1/5, 1/1 and 5/1. Incubation was conducted for 4 h30 at 37° C. Non-malignant and malignant CD4+ T cell and NK death was monitored by flow cytometry through the incorporation of 7-AAD.

A representative example is show on FIG. 42B with negligible level of NK-cell mediated cytotoxicity in the presence of isotype but a NK-cell dependent cytotoxic activity of tumor cells obtained with a-TIGIT mAb that increased with the E/T ratio. Cytotoxicity towards non-malignant CD4+ T cells was limited and NK cells were preserved.

All references, issued patents, and patent applications cited within the body of the instant specification are hereby incorporated by reference in their entirety, for all purposes. Additionally, PCT/US2018/43968 is hereby incorporated by reference in its entirely and for all purposes.

Example 35: Anti-Tumour Activity of Anti-TIGIT Antagonistic Antibody in Combination with Chemotherapy and $A_{2A}R$ Antagonist in CT26 Colon Carcinoma Mouse Model In addition to the combination of anti-TIGIT Ab with immune checkpoint antibodies (Examples 12, 13, 14 and 28), the antitumor efficacy of an anti-TIGIT antibody was evaluated in combination with chemotherapeutic agent doxorubicin or $A_{2A}R$ antagonist and in a triple combination of anti-TIGIT Ab with $A_{2A}R$ antagonist and doxorubicin. The $A_{2A}R$ antagonist used corresponds to compound 8b in PCT/EP2019/074208, which is incorporated herein by reference).

CT26 tumour cell line, purchased from ATCC® (CRL-2638™), were subcutaneously inoculated with 500.000 cells in the right flank of female balb/c mice of 8 weeks. On day 9 after inoculation, when tumor volumes were on average around 90 mm³, mice were randomized in treatment groups with equal tumor volume (n=8 mice per group). Anti-TIGIT Ab (29527m) or mIgG2a isotype control were given intraperitoneally at the dose of 20 µg/mouse every 3 days starting on the day of randomization for a total of 3 injections. Beginning the same day, mice were treated p.o. at a dose of 0.6 mg/kg of $A_{2A}R$ antagonist or vehicle, QD for 32 days. Starting one day after randomization, 6 mg/kg of doxorubicin or control PBS was administered i.v., mice received 2 administrations, 4 days apart.

Tumor growth was monitored and tumor volumes were measured with electronic calipers three times a week from day 9 until day 50. Mice were sacrificed when tumor volume exceeded 2000 mm³. Tumor growth curves were statistically analyzed by a linear mixed model on logarithmically transformed tumor volumes. Differences between treatment groups were evaluated by testing the interaction of time*treatment group.

FIG. 43 shows median tumor growth curves per group (A) as well as individual growth curves (B) for mice treated with single agent therapies or the specified combinations. Intraperitoneal injection of 1 mg/kg of anti-TIGIT mAb 29527m at days 9, 12 and 15 after tumor cell implant, significantly suppressed tumor growth compared to mice treated with control isotype (p=0.0009) as previously reported in example 12.

Administration of 2 doses of doxorubicin at the dose of 6 mg/kg had no effect on tumor growth (p=0.14) while combination with anti-TIGIT improved anti-tumor efficacy (p=0.008 and p=0.0002 when compared to anti-TIGIT or doxorubicin respective monotherapies).

Administration of 0.6 mg/kg of $A_{2A}R$ inhibitor with anti-TIGIT 29527m did not improve anti-tumor effect when compared to anti-TIGIT single agent therapy.

$A_{2A}R$ inhibitor administered at 0.6 mg/kg with doxorubicin given at 6 mg/kg achieved significant anti-tumor effect when compared to stand alone administration of doxorubicin (p=0.0003).

Suppression of tumor growth in mice treated with a combination of anti-TIGIT, $A_{2A}R$ inhibitor and doxorubicin was significantly higher than tumor growth suppression achieved with respective double combination therapies (p<0.0001 when compared to anti-TIGIT+$A_{2A}R$ inhibitor or when compared to doxorubicin+$A_{2A}R$ inhibitor, p=0.003 when compared to anti-TIGIT+doxorubicin), with 5 complete responders in this group of 8 mice.

Example 36: Quantification of TIGIT Expression in Presence of Antagonist a-TIGIT Ab To allow measure of TIGIT expression in presence of antagonist a-TIGIT antibodies that compete with each other and with TIGIT natural ligands (CD155, CD112, CD113) for binding to TIGIT receptor, we screened for a-TIGIT Ab that is not competitive with antagonist Abs. Clone 32959 was selected to be an Ab able to bind TIGIT in presence of antagonist a-TIGIT clone 31282. To demonstrate this potential, venous blood from healthy human donors collected into EDTA was distributed in 50 µL aliquots and incubated with decreasing concentrations of unlabeled clone 31282 and incubated for 1 hour at 37° C. Following incubation, samples were washed and supernatant discarded. Afterwards, test samples were stained with anti-CD45-PercP (clone H130) from BioLegend and CD4− BV421(clone L200), CD8a-BV510 (clone SK1), CD45RO− BB515 (clone UCHL1), CD25− BV605 (clone 2A3), CD127− BV786 (clone HIL-7R-M21), CD56− BV650 (clone NCAM16.2) from BD bioscience and TIGIT using either 31282 PE labelled or 32959 conjugated to AF647. Each blood sample was incubated at 4° C. for 30 min. Red blood cells were lysed with BD lysing buffer, white cells were pelleted and washed, and finally resuspended in IC Fixation buffer diluted in PBS. Acquisition was made on an LSR Fortessa (BD Biosciences) and flow cytometry data were analyzed using FlowJo V10.5.3.

The normalized frequency of free TIGIT was calculated according to the following formula: Y=(A/B)*100. Where A=31282-PE $\%_{31282\ at\ concentration\ x}$ and B=31282-PE $\%_{31282\ untreated}$ for the detection with this clone, while for detection with clone 32959-AF647, A=32959-AF647*$\%_{31282\ at\ concentration\ x}$ and B=32959-AF647$\%_{31282\ untreated}$.

The normalized frequency of free TIGIT+ among CD3+ CD8+ cell population is shown in FIG. 44 after incubation with different concentrations of 31282 uncoupled and subsequent detection by FACS staining with either 31282-PE (A) or with anti-TIGIT 32959-AF647 (B) simultaneously on the condition. The detection of TIGIT+ cells with 32959 after incubation with 31282 corroborates the absence of competition possibly due to the recognition of non-overlapping epitopes by each anti-TIGIT antibody clone.

Example 37: Use of a-Idiotypic Antibody 32869 Against Clone 31282 in Assays to Measure Concentration of Clone 31282 in Human Serum Samples (PK Assay)

Anti-idiotypic Ab clone 32869, a human IgG1, was selected from the HuCAL® library after demonstration of specific binding to antagonist a-TIGIT clone 31282.

The anti-idiotypic Ab clone 32869, produced in HEK293 cells on a human IgG1 isotype, was used to develop an ELISA assay for the quantification of clone 31282 in human serum samples in order to follow the pharmacokinetic (PK) of the clone during clinical studies.

The ELISA assay is based on the Meso Scale Discovery (MSD) Platform using electrochemiluminescence detection technology. Anti-idiotypic antibody clone 32869 (0.5 µg/mL) is coated to a high binding MSD plate. Serum samples dilutions are then incubated for 1 hr, plates are washed and binding of the clone 31282 to the coated anti-idiotypic antibody is detected with a Sulfo-TAG hIgG1 32869 (0.5 µg/mL) in the presence of reading buffer. A voltage is applied to the plate electrodes, causing the bound Sulfo-TAG to emit light via electrochemical stimulation. The intensity of the emitted light is proportional to the clone 31282 concentration in the serum samples (FIG. 45).

```
32869 HEAVY CHAIN (SEQ ID NO: 372):
MGWSCIILFLVATATGVHSEVQLVQSGAEVKKPGESLKISCKGSGYSFTG

YWIAWVRQMPGKGLEWMGIIYPGNSDTRYSPSFQGQVTISADKSISTAYL

QWSSLKASDTAMYYCARVSGVGSIWMAFDIWGQGTLVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSD

IAVEWESNGQPENNYKTTPPVLDSDGSFFLYSKLTVDKSRWQQGNVFSCS

VMHEALHNHYTQKSLSLSPGK*

32869 LIGHT CHAIN (SE ID NO: 373):
MGWSCIILFLVATATGVHSDIVLTQPPSVSGAPGQRVTISCSGSSSNIGS

NSVSWYQQLPGTAPKLLIYSNNQRPSGVPDRFSGSKSGTSASLAITGLQA

EDEADYYCGSYDSSINLYVFGGGTKLTVLGQPKAAPSVTLFPPSSEELQA

NKATLVCLISDFYPGAVTVAWKADSSPVKAGVETTTPSKQSNNKYAASSY

LSLTPEQWKSHRSYSCQVTHEGSTVEKTVAPTECS*
```

The invention claimed is:

1. A method of promoting T cell activity comprising contacting a population of human γδ T cells with an antibody or antigen binding fragment thereof which binds to human TIGIT, wherein the antibody or antigen binding fragment thereof comprises a heavy chain variable domain comprising a heavy chain CDR1 (HCDR1), a heavy chain CDR2 (HCDR2), and a heavy chain CDR3 (HCDR3), wherein HCDR1 comprises SEQ ID NO: 16, HCDR2 comprises SEQ ID NO: 17, and HCDR3 comprises SEQ ID NO: 18; and a light chain variable domain comprising a light chain CDR1 (LCDR1), a light chain CDR2 (LCDR2), and a light chain CDR3 (LCDR3), wherein LCDR1 comprises SEQ ID NO: 61, LCDR2 comprises SEQ ID NO: 62, and LCDR3 comprises SEQ ID NO: 63.

2. A method of promoting T cell activity according to claim 1, wherein the method is performed in vitro.

3. A method of promoting T cell activity according to claim 1, wherein the method is performed in vivo in a human subject.

4. A method of promoting T cell activity according to claim 3, wherein the human subject has cancer.

5. A method of promoting T cell activity according to claim 3, wherein the human subject has a viral infection.

6. A method of treating cancer in a human subject, comprising administering to the human subject an antibody or antigen binding fragment thereof which binds to human TIGIT, wherein the cancer is selected from the group consisting of: hepatocellular carcinoma, pancreatic carcinoma, lung carcinoma, colon carcinoma, kidney carcinoma, cutaneous carcinoma, and Sezary Syndrome, and wherein the antibody or antigen binding fragment thereof comprises a heavy chain variable domain comprising a heavy chain CDR1 (HCDR1), a heavy chain CDR2 (HCDR2), and a heavy chain CDR3 (HCDR3), wherein HCDR1 comprises SEQ ID NO: 16, HCDR2 comprises SEQ ID NO: 17, and HCDR3 comprises SEQ ID NO: 18; and a light chain variable domain comprising a light chain CDR1 (LCDR1), a light chain CDR2 (LCDR2), and a light chain CDR3 (LCDR3), wherein LCDR1 comprises SEQ ID NO: 61, LCDR2 comprises SEQ ID NO: 62, and LCDR3 comprises SEQ ID NO: 63.

7. A method of treating cancer according to claim 6, wherein the method further comprises administering to the human subject one or more of an anti-PD1 antibody, an anti-PD-L1 antibody, an anti-41BB antibody, an anti-OX40 antibody, an anti-GITR antibody, and an anti-ICOS antibody.

8. A method of treating cancer according to claim 6, wherein the antibody or antigen binding fragment comprises a heavy chain variable domain having the amino acid sequence of SEQ ID NO: 221, or an amino acid sequence exhibiting at least 90%, 95%, 97%, 98% or 99% sequence identity to SEQ ID NO: 221; and a light chain variable domain having the amino acid sequence of SEQ ID NO: 222, or an amino acid sequence exhibiting at least 90%, 95%, 97%, 98% or 99% sequence identity to SEQ ID NO: 222.

9. A method of treating cancer according to claim 6, wherein the antibody or antigen binding fragment comprises a heavy chain variable domain comprising the amino acid sequence of SEQ ID NO: 219, or an amino acid sequence exhibiting at least 90%, 95%, 97%, 98% or 99% sequence identity to SEQ ID NO: 219; and a light chain variable domain comprising the amino acid sequence of SEQ ID NO: 220, or an amino acid sequence exhibiting at least 90%, 95%, 97%, 98% or 99% sequence identity to SEQ ID NO: 220.

10. A method of promoting T cell activity according to claim 1, wherein the antibody is a human IgG antibody.

11. A method of promoting T cell activity according to claim 3, wherein the antibody displays one or more effector functions selected from antibody-dependent cell mediated cytotoxicity (ADCC), complement dependent cytotoxicity (CDC) and antibody dependent cell-mediated phagocytosis (ADCP) against cells expressing human TIGIT on the cell surface.

12. A method of treating cancer according to claim 6, wherein the method comprises administering the antibody or antigen binding fragment thereof in combination with a chemotherapeutic agent.

13. The method of treating cancer according to claim 12, wherein the chemotherapeutic agent is doxorubicin.

14. A method of promoting T cell activity according to claim 1, wherein the antibody or antigen binding fragment comprises a heavy chain variable domain having the amino acid sequence of SEQ ID NO: 221, or an amino acid sequence exhibiting at least 90%, 95%, 97%, 98% or 99% sequence identity to SEQ ID NO: 221; and comprises a light chain variable domain having the amino acid sequence of SEQ ID NO: 222, or an amino acid sequence exhibiting at least 90%, 95%, 97%, 98% or 99% sequence identity to SEQ ID NO: 222.

15. A method of promoting T cell activity according to claim 1, wherein the antibody or antigen binding fragment comprises a heavy chain variable domain having the amino acid sequence of SEQ ID NO: 219, or an amino acid sequence exhibiting at least 90%, 95%, 97%, 98% or 99% sequence identity to SEQ ID NO: 219; and comprises a light chain variable domain having the amino acid sequence of SEQ ID NO: 220, or an amino acid sequence exhibiting at least 90%, 95%, 97%, 98% or 99% sequence identity to SEQ ID NO: 220.

16. A method of promoting T cell activity according to claim 1, wherein the method further comprises contacting the population of γδ T cells with one or more of an anti-PD1 antibody, an anti-PD-L1 antibody, an anti-41BB antibody, an anti-OX40 antibody, an anti-GITR antibody, and an anti-ICOS antibody.

17. A method of promoting T cell activity according to claim 3, wherein the human subject has a viral infection that is a CMV infection.

18. A method of promoting T cell activity according to claim 1, wherein the antibody is a human IgG1 antibody.

19. A method of treating cancer according to claim 8, wherein the method further comprises administering to the human subject one or more of an anti-PD1 antibody, an anti-PD-L1 antibody, an anti-41BB antibody, an anti-OX40 antibody, an anti-GITR antibody, and an anti-ICOS antibody.

20. A method of treating cancer according to claim 9, wherein the method further comprises administering to the human subject one or more of an anti-PD1 antibody, an anti-PD-L1 antibody, an anti-41BB antibody, an anti-OX40 antibody, an anti-GITR antibody, and an anti-ICOS antibody.

* * * * *

SEQUENCE LISTING

```
<160> NUMBER OF SEQ ID NOS: 373

<210> SEQ ID NO 1
<211> LENGTH: 9
<212> TYPE: PRT
<213> ORGANISM: Homo sapiens

<400> SEQUENCE: 1

Phe Thr Phe Ser Ser Tyr Gly Met Ser
1               5

<210> SEQ ID NO 2
<211> LENGTH: 17
<212> TYPE: PRT
<213> ORGANISM: Homo sapiens

<400> SEQUENCE: 2

Asn Ile Lys Gln Asp Gly Ser Glu Lys Tyr Tyr Val Asp Ser Val Lys
1               5                   10                  15

Gly

<210> SEQ ID NO 3
<211> LENGTH: 20
<212> TYPE: PRT
<213> ORGANISM: Homo sapiens

<400> SEQUENCE: 3

Ala Arg Val Ser Tyr Tyr Tyr Asp Ser Ser Lys Leu Arg Trp Ala Glu
1               5                   10                  15

Tyr Phe Gln His
            20

<210> SEQ ID NO 4
<211> LENGTH: 9
```

```
<212> TYPE: PRT
<213> ORGANISM: Homo sapiens

<400> SEQUENCE: 4

Phe Thr Phe Glu Ser Tyr Gly Met Val
1               5

<210> SEQ ID NO 5
<211> LENGTH: 17
<212> TYPE: PRT
<213> ORGANISM: Homo sapiens

<400> SEQUENCE: 5

Ser Ile Leu Tyr Asp Gly Ser Asn Arg Tyr Tyr Ala Asp Ser Val Lys
1               5                   10                  15

Gly

<210> SEQ ID NO 6
<211> LENGTH: 20
<212> TYPE: PRT
<213> ORGANISM: Homo sapiens

<400> SEQUENCE: 6

Ala Arg Val Ser Tyr Tyr Asp Ser Val Glu Leu Arg Trp Ala Glu
1               5                   10                  15

Tyr Phe Gln His
            20

<210> SEQ ID NO 7
<211> LENGTH: 9
<212> TYPE: PRT
<213> ORGANISM: Homo sapiens

<400> SEQUENCE: 7

Tyr Thr Phe Thr Ser Tyr Tyr Met His
1               5

<210> SEQ ID NO 8
<211> LENGTH: 17
<212> TYPE: PRT
<213> ORGANISM: Homo sapiens

<400> SEQUENCE: 8

Val Ile Asn Pro Ser Gly Gly Ser Thr Ser Tyr Ala Gln Lys Phe Gln
1               5                   10                  15

Gly

<210> SEQ ID NO 9
<211> LENGTH: 14
<212> TYPE: PRT
<213> ORGANISM: Homo sapiens

<400> SEQUENCE: 9

Ala Arg Asp His Ser Asp Tyr Trp Ser Gly Ile Leu Asp Val
1               5                   10

<210> SEQ ID NO 10
<211> LENGTH: 9
<212> TYPE: PRT
<213> ORGANISM: Homo sapiens

<400> SEQUENCE: 10

Tyr Thr Phe Glu Lys Tyr Tyr Met His
```

```
<210> SEQ ID NO 11
<211> LENGTH: 17
<212> TYPE: PRT
<213> ORGANISM: Homo sapiens

<400> SEQUENCE: 11

Val Ile Gly Pro Ser Gly Ala Ser Thr Ser Tyr Ala Gln Lys Phe Gln
1               5                   10                  15

Gly

<210> SEQ ID NO 12
<211> LENGTH: 14
<212> TYPE: PRT
<213> ORGANISM: Homo sapiens

<400> SEQUENCE: 12

Ala Arg Asp His Ser Asp Tyr Trp Ser Gly Ile Leu His Ser
1               5                   10

<210> SEQ ID NO 13
<211> LENGTH: 9
<212> TYPE: PRT
<213> ORGANISM: Homo sapiens

<400> SEQUENCE: 13

Tyr Thr Phe Thr Ser Tyr Tyr Met His
1               5

<210> SEQ ID NO 14
<211> LENGTH: 17
<212> TYPE: PRT
<213> ORGANISM: Homo sapiens

<400> SEQUENCE: 14

Val Ile Gly Pro Ser Gly Ala Ser Thr Ser Tyr Ala Gln Lys Phe Gln
1               5                   10                  15

Gly

<210> SEQ ID NO 15
<211> LENGTH: 14
<212> TYPE: PRT
<213> ORGANISM: Homo sapiens

<400> SEQUENCE: 15

Ala Arg Asp His Ser Asp Tyr Trp Ser Gly Ile Met Glu Val
1               5                   10

<210> SEQ ID NO 16
<211> LENGTH: 9
<212> TYPE: PRT
<213> ORGANISM: Homo sapiens

<400> SEQUENCE: 16

Tyr Thr Phe Thr Ser Tyr Tyr Met His
1               5

<210> SEQ ID NO 17
<211> LENGTH: 17
<212> TYPE: PRT
<213> ORGANISM: Homo sapiens

<400> SEQUENCE: 17
```

Val Ile Gly Pro Ser Gly Ala Ser Thr Ser Tyr Ala Gln Lys Phe Gln
1               5                   10                  15

Gly

<210> SEQ ID NO 18
<211> LENGTH: 14
<212> TYPE: PRT
<213> ORGANISM: Homo sapiens

<400> SEQUENCE: 18

Ala Arg Asp His Ser Asp Tyr Trp Ser Gly Ile Met Glu Val
1               5                   10

<210> SEQ ID NO 19
<211> LENGTH: 10
<212> TYPE: PRT
<213> ORGANISM: Homo sapiens

<400> SEQUENCE: 19

Tyr Ser Ile Ser Ser Gly Tyr Tyr Trp Ala
1               5                   10

<210> SEQ ID NO 20
<211> LENGTH: 16
<212> TYPE: PRT
<213> ORGANISM: Homo sapiens

<400> SEQUENCE: 20

Ser Ile Tyr His Ser Gly Ser Thr Tyr Tyr Asn Pro Ser Leu Lys Ser
1               5                   10                  15

<210> SEQ ID NO 21
<211> LENGTH: 17
<212> TYPE: PRT
<213> ORGANISM: Homo sapiens

<400> SEQUENCE: 21

Ala Ile Glu Gly Ala Asn Tyr Tyr Asp Phe Gly Tyr Val Ala Phe Asp
1               5                   10                  15

Ile

<210> SEQ ID NO 22
<211> LENGTH: 11
<212> TYPE: PRT
<213> ORGANISM: Homo sapiens

<400> SEQUENCE: 22

Gly Ser Ile Ser Ser Gly Ser Tyr Tyr Leu Ala
1               5                   10

<210> SEQ ID NO 23
<211> LENGTH: 16
<212> TYPE: PRT
<213> ORGANISM: Homo sapiens

<400> SEQUENCE: 23

Ser Ile Phe Arg Ser Gly Ser Thr Tyr Tyr Asn Pro Ser Leu Glu Ser
1               5                   10                  15

<210> SEQ ID NO 24
<211> LENGTH: 17
<212> TYPE: PRT
<213> ORGANISM: Homo sapiens

```
<400> SEQUENCE: 24

Ala Ile Glu Gly Ala Asn Phe Lys Asp Phe Gly Tyr Val Ala Phe Asp
1               5                   10                  15

Ile

<210> SEQ ID NO 25
<211> LENGTH: 11
<212> TYPE: PRT
<213> ORGANISM: Homo sapiens

<400> SEQUENCE: 25

Gly Ser Ile Ser Ser Arg Tyr Tyr Trp Ala
1               5                   10

<210> SEQ ID NO 26
<211> LENGTH: 16
<212> TYPE: PRT
<213> ORGANISM: Homo sapiens

<400> SEQUENCE: 26

Ser Ile Gly Thr Ser Gly Ser Thr Tyr Tyr Asn Pro Ser Leu Lys Ser
1               5                   10                  15

<210> SEQ ID NO 27
<211> LENGTH: 17
<212> TYPE: PRT
<213> ORGANISM: Homo sapiens

<400> SEQUENCE: 27

Ala Ile Glu Gly Ala Asn Phe Arg Asp Phe Gly Tyr Val Ala Phe Asp
1               5                   10                  15

Ile

<210> SEQ ID NO 28
<211> LENGTH: 9
<212> TYPE: PRT
<213> ORGANISM: Homo sapiens

<400> SEQUENCE: 28

Gly Thr Phe Ser Ser Tyr Ala Ile Ser
1               5

<210> SEQ ID NO 29
<211> LENGTH: 17
<212> TYPE: PRT
<213> ORGANISM: Homo sapiens

<400> SEQUENCE: 29

Gly Ile Ile Pro Ile Phe Gly Thr Ala Asn Tyr Ala Gln Lys Phe Gln
1               5                   10                  15

Gly

<210> SEQ ID NO 30
<211> LENGTH: 15
<212> TYPE: PRT
<213> ORGANISM: Homo sapiens

<400> SEQUENCE: 30

Ala Arg Leu His Leu Gly Ser Ser Ala Tyr Tyr Gly Met Asp Val
1               5                   10                  15
```

```
<210> SEQ ID NO 31
<211> LENGTH: 9
<212> TYPE: PRT
<213> ORGANISM: Homo sapiens

<400> SEQUENCE: 31

Gly Thr Phe Gln Asn Tyr Ala Ile Ser
1               5

<210> SEQ ID NO 32
<211> LENGTH: 17
<212> TYPE: PRT
<213> ORGANISM: Homo sapiens

<400> SEQUENCE: 32

Val Ile Val Pro Ile Phe Gly Thr Ala Asn Tyr Ala Gln Lys Phe Gln
1               5                   10                  15

Gly

<210> SEQ ID NO 33
<211> LENGTH: 15
<212> TYPE: PRT
<213> ORGANISM: Homo sapiens

<400> SEQUENCE: 33

Ala Arg Leu His Leu Gly Gln Lys Ala Tyr Tyr Gly Met Asp Val
1               5                   10                  15

<210> SEQ ID NO 34
<211> LENGTH: 9
<212> TYPE: PRT
<213> ORGANISM: Homo sapiens

<400> SEQUENCE: 34

Phe Thr Phe Gly Asp Tyr Ala Met His
1               5

<210> SEQ ID NO 35
<211> LENGTH: 17
<212> TYPE: PRT
<213> ORGANISM: Homo sapiens

<400> SEQUENCE: 35

Gly Ile Thr Trp Asn Ser Gly Ser Ile Gly Tyr Ala Asp Ser Val Lys
1               5                   10                  15

Gly

<210> SEQ ID NO 36
<211> LENGTH: 12
<212> TYPE: PRT
<213> ORGANISM: Homo sapiens

<400> SEQUENCE: 36

Ala Lys Pro Val Pro Lys Ser Arg Gly Leu Asp Val
1               5                   10

<210> SEQ ID NO 37
<211> LENGTH: 9
<212> TYPE: PRT
<213> ORGANISM: Homo sapiens

<400> SEQUENCE: 37

Phe Thr Phe Arg Asp Tyr Ala Met His
1               5
```

<210> SEQ ID NO 38
<211> LENGTH: 17
<212> TYPE: PRT
<213> ORGANISM: Homo sapiens

<400> SEQUENCE: 38

Gly Ile Thr Trp Asn Ser Gly Leu Ile Gly Tyr Ala Asp Ser Val Lys
1               5                   10                  15

Gly

<210> SEQ ID NO 39
<211> LENGTH: 12
<212> TYPE: PRT
<213> ORGANISM: Homo sapiens

<400> SEQUENCE: 39

Ala Lys Pro Val Pro Arg Leu Arg Gly Leu Asp Val
1               5                   10

<210> SEQ ID NO 40
<211> LENGTH: 9
<212> TYPE: PRT
<213> ORGANISM: Homo sapiens

<400> SEQUENCE: 40

Phe Thr Phe Gly Ser Tyr Tyr Met His
1               5

<210> SEQ ID NO 41
<211> LENGTH: 17
<212> TYPE: PRT
<213> ORGANISM: Homo sapiens

<400> SEQUENCE: 41

Val Ile Trp Pro Asp Gly Ser Asn Lys Leu Tyr Ala Asp Ser Val Lys
1               5                   10                  15

Gly

<210> SEQ ID NO 42
<211> LENGTH: 12
<212> TYPE: PRT
<213> ORGANISM: Homo sapiens

<400> SEQUENCE: 42

Ala Lys Pro Val Pro Lys Ser Arg Ala Leu Asp Val
1               5                   10

<210> SEQ ID NO 43
<211> LENGTH: 9
<212> TYPE: PRT
<213> ORGANISM: Homo sapiens

<400> SEQUENCE: 43

Phe Thr Phe Ser Ser Ser Tyr Met His
1               5

<210> SEQ ID NO 44
<211> LENGTH: 17
<212> TYPE: PRT
<213> ORGANISM: Homo sapiens

<400> SEQUENCE: 44

```
Val Ile Gly Ala Asp Gly Ser Asn Lys Tyr Tyr Ala Asp Ser Val Glu
1               5                   10                  15

Gly

<210> SEQ ID NO 45
<211> LENGTH: 12
<212> TYPE: PRT
<213> ORGANISM: Homo sapiens

<400> SEQUENCE: 45

Ala Lys Pro Val Pro Arg Arg Arg Gly Leu Asp Val
1               5                   10

<210> SEQ ID NO 46
<211> LENGTH: 11
<212> TYPE: PRT
<213> ORGANISM: Homo sapiens

<400> SEQUENCE: 46

Arg Ala Ser Gln Ser Val Ser Ser Tyr Leu Ala
1               5                   10

<210> SEQ ID NO 47
<211> LENGTH: 7
<212> TYPE: PRT
<213> ORGANISM: Homo sapiens

<400> SEQUENCE: 47

Asp Ala Ser Lys Arg Ala Thr
1               5

<210> SEQ ID NO 48
<211> LENGTH: 9
<212> TYPE: PRT
<213> ORGANISM: Homo sapiens

<400> SEQUENCE: 48

Gln Gln Val His Asn Phe Pro Leu Thr
1               5

<210> SEQ ID NO 49
<211> LENGTH: 11
<212> TYPE: PRT
<213> ORGANISM: Homo sapiens

<400> SEQUENCE: 49

Arg Ala Ser Gln Ser Val Ser Ser Tyr Leu Ala
1               5                   10

<210> SEQ ID NO 50
<211> LENGTH: 7
<212> TYPE: PRT
<213> ORGANISM: Homo sapiens

<400> SEQUENCE: 50

Asp Ala Ser Lys Arg Ala Thr
1               5

<210> SEQ ID NO 51
<211> LENGTH: 9
<212> TYPE: PRT
<213> ORGANISM: Homo sapiens

<400> SEQUENCE: 51
```

Gln Gln Val His Asn Phe Pro Leu Thr
1               5

<210> SEQ ID NO 52
<211> LENGTH: 12
<212> TYPE: PRT
<213> ORGANISM: Homo sapiens

<400> SEQUENCE: 52

Arg Ala Ser Gln Ser Val Arg Ser Ser Tyr Leu Ala
1               5                   10

<210> SEQ ID NO 53
<211> LENGTH: 7
<212> TYPE: PRT
<213> ORGANISM: Homo sapiens

<400> SEQUENCE: 53

Gly Ala Ser Ser Arg Ala Thr
1               5

<210> SEQ ID NO 54
<211> LENGTH: 9
<212> TYPE: PRT
<213> ORGANISM: Homo sapiens

<400> SEQUENCE: 54

Gln Gln Tyr Phe Ser Pro Pro Trp Thr
1               5

<210> SEQ ID NO 55
<211> LENGTH: 12
<212> TYPE: PRT
<213> ORGANISM: Homo sapiens

<400> SEQUENCE: 55

Arg Ala Ser Gln Ser Val Arg Ser Ser Tyr Leu Ala
1               5                   10

<210> SEQ ID NO 56
<211> LENGTH: 7
<212> TYPE: PRT
<213> ORGANISM: Homo sapiens

<400> SEQUENCE: 56

Gly Ala Ser Ser Arg Ala Thr
1               5

<210> SEQ ID NO 57
<211> LENGTH: 9
<212> TYPE: PRT
<213> ORGANISM: Homo sapiens

<400> SEQUENCE: 57

Gln Gln Tyr Phe Ser Pro Pro Trp Thr
1               5

<210> SEQ ID NO 58
<211> LENGTH: 12
<212> TYPE: PRT
<213> ORGANISM: Homo sapiens

<400> SEQUENCE: 58

Arg Ala Ser Gln Ser Val Arg Ser Ser Tyr Leu Ala
1               5                   10

```
<210> SEQ ID NO 59
<211> LENGTH: 7
<212> TYPE: PRT
<213> ORGANISM: Homo sapiens

<400> SEQUENCE: 59

Gly Ala Ser Ser Arg Ala Thr
1               5

<210> SEQ ID NO 60
<211> LENGTH: 9
<212> TYPE: PRT
<213> ORGANISM: Homo sapiens

<400> SEQUENCE: 60

Gln Gln Tyr Phe Ser Pro Pro Trp Thr
1               5

<210> SEQ ID NO 61
<211> LENGTH: 12
<212> TYPE: PRT
<213> ORGANISM: Homo sapiens

<400> SEQUENCE: 61

Arg Ala Ser Gln Ser Val Arg Ser Ser Tyr Leu Ala
1               5                   10

<210> SEQ ID NO 62
<211> LENGTH: 7
<212> TYPE: PRT
<213> ORGANISM: Homo sapiens

<400> SEQUENCE: 62

Gly Ala Ser Ser Arg Ala Thr
1               5

<210> SEQ ID NO 63
<211> LENGTH: 9
<212> TYPE: PRT
<213> ORGANISM: Homo sapiens

<400> SEQUENCE: 63

Gln Gln Tyr Phe Ser Pro Pro Trp Thr
1               5

<210> SEQ ID NO 64
<211> LENGTH: 11
<212> TYPE: PRT
<213> ORGANISM: Homo sapiens

<400> SEQUENCE: 64

Arg Ala Ser Gln Ser Val Ser Ser Asn Leu Ala
1               5                   10

<210> SEQ ID NO 65
<211> LENGTH: 7
<212> TYPE: PRT
<213> ORGANISM: Homo sapiens

<400> SEQUENCE: 65

Gly Ala Ser Thr Arg Ala Thr
1               5
```

```
<210> SEQ ID NO 66
<211> LENGTH: 9
<212> TYPE: PRT
<213> ORGANISM: Homo sapiens

<400> SEQUENCE: 66

Gln Gln Ser Pro Pro Trp Pro Arg Thr
1               5

<210> SEQ ID NO 67
<211> LENGTH: 11
<212> TYPE: PRT
<213> ORGANISM: Homo sapiens

<400> SEQUENCE: 67

Arg Ala Ser Gln Ser Val Ser Ser Asn Leu Ala
1               5                   10

<210> SEQ ID NO 68
<211> LENGTH: 7
<212> TYPE: PRT
<213> ORGANISM: Homo sapiens

<400> SEQUENCE: 68

Gly Ala Ser Thr Arg Ala Thr
1               5

<210> SEQ ID NO 69
<211> LENGTH: 9
<212> TYPE: PRT
<213> ORGANISM: Homo sapiens

<400> SEQUENCE: 69

Gln Gln Ser Pro Pro Trp Pro Arg Thr
1               5

<210> SEQ ID NO 70
<211> LENGTH: 11
<212> TYPE: PRT
<213> ORGANISM: Homo sapiens

<400> SEQUENCE: 70

Arg Ala Ser Gln Ser Val Ser Ser Asn Leu Ala
1               5                   10

<210> SEQ ID NO 71
<211> LENGTH: 7
<212> TYPE: PRT
<213> ORGANISM: Homo sapiens

<400> SEQUENCE: 71

Gly Ala Ser Thr Arg Ala Thr
1               5

<210> SEQ ID NO 72
<211> LENGTH: 9
<212> TYPE: PRT
<213> ORGANISM: Homo sapiens

<400> SEQUENCE: 72

Gln Gln Ser Pro Pro Trp Pro Arg Thr
1               5

<210> SEQ ID NO 73
<211> LENGTH: 11
```

```
<212> TYPE: PRT
<213> ORGANISM: Homo sapiens

<400> SEQUENCE: 73

Arg Ala Ser Gln Ser Ile Ser Ser Tyr Leu Asn
1               5                   10

<210> SEQ ID NO 74
<211> LENGTH: 7
<212> TYPE: PRT
<213> ORGANISM: Homo sapiens

<400> SEQUENCE: 74

Ala Ala Ser Ser Leu Gln Ser
1               5

<210> SEQ ID NO 75
<211> LENGTH: 9
<212> TYPE: PRT
<213> ORGANISM: Homo sapiens

<400> SEQUENCE: 75

Gln Gln Arg Tyr Val Phe Pro Pro Thr
1               5

<210> SEQ ID NO 76
<211> LENGTH: 11
<212> TYPE: PRT
<213> ORGANISM: Homo sapiens

<400> SEQUENCE: 76

Arg Ala Ser Gln Ser Ile Ser Ser Tyr Leu Asn
1               5                   10

<210> SEQ ID NO 77
<211> LENGTH: 7
<212> TYPE: PRT
<213> ORGANISM: Homo sapiens

<400> SEQUENCE: 77

Ala Ala Ser Ser Leu Gln Ser
1               5

<210> SEQ ID NO 78
<211> LENGTH: 9
<212> TYPE: PRT
<213> ORGANISM: Homo sapiens

<400> SEQUENCE: 78

Gln Gln Arg Tyr Val Phe Pro Pro Thr
1               5

<210> SEQ ID NO 79
<211> LENGTH: 11
<212> TYPE: PRT
<213> ORGANISM: Homo sapiens

<400> SEQUENCE: 79

Arg Ala Ser Gln Gly Ile Ser Ser Trp Leu Ala
1               5                   10

<210> SEQ ID NO 80
<211> LENGTH: 7
<212> TYPE: PRT
<213> ORGANISM: Homo sapiens
```

```
<400> SEQUENCE: 80

Gly Ala Ser Ser Leu Gln Ser
1               5

<210> SEQ ID NO 81
<211> LENGTH: 9
<212> TYPE: PRT
<213> ORGANISM: Homo sapiens

<400> SEQUENCE: 81

Gln Gln Ala Phe Tyr Leu Pro Trp Thr
1               5

<210> SEQ ID NO 82
<211> LENGTH: 11
<212> TYPE: PRT
<213> ORGANISM: Homo sapiens

<400> SEQUENCE: 82

Arg Ala Ser Gln Gly Ile Ser Ser Trp Leu Ala
1               5                   10

<210> SEQ ID NO 83
<211> LENGTH: 7
<212> TYPE: PRT
<213> ORGANISM: Homo sapiens

<400> SEQUENCE: 83

Gly Ala Ser Ser Leu Gln Ser
1               5

<210> SEQ ID NO 84
<211> LENGTH: 9
<212> TYPE: PRT
<213> ORGANISM: Homo sapiens

<400> SEQUENCE: 84

Gln Gln Ala Phe Tyr Leu Pro Trp Thr
1               5

<210> SEQ ID NO 85
<211> LENGTH: 11
<212> TYPE: PRT
<213> ORGANISM: Homo sapiens

<400> SEQUENCE: 85

Arg Ala Ser Gln Gly Ile Ser Ser Trp Leu Ala
1               5                   10

<210> SEQ ID NO 86
<211> LENGTH: 7
<212> TYPE: PRT
<213> ORGANISM: Homo sapiens

<400> SEQUENCE: 86

Gly Ala Ser Ser Leu Gln Ser
1               5

<210> SEQ ID NO 87
<211> LENGTH: 9
<212> TYPE: PRT
<213> ORGANISM: Homo sapiens

<400> SEQUENCE: 87
```

```
Gln Gln Ala Phe Tyr Leu Pro Trp Thr
1               5

<210> SEQ ID NO 88
<211> LENGTH: 11
<212> TYPE: PRT
<213> ORGANISM: Homo sapiens

<400> SEQUENCE: 88

Arg Ala Ser Gln Gly Ile Ser Ser Trp Leu Ala
1               5                   10

<210> SEQ ID NO 89
<211> LENGTH: 7
<212> TYPE: PRT
<213> ORGANISM: Homo sapiens

<400> SEQUENCE: 89

Gly Ala Ser Ser Leu Gln Ser
1               5

<210> SEQ ID NO 90
<211> LENGTH: 9
<212> TYPE: PRT
<213> ORGANISM: Homo sapiens

<400> SEQUENCE: 90

Gln Gln Ala Phe Tyr Leu Pro Trp Thr
1               5

<210> SEQ ID NO 91
<211> LENGTH: 26
<212> TYPE: PRT
<213> ORGANISM: Homo sapiens

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly
            20                  25

<210> SEQ ID NO 92
<211> LENGTH: 14
<212> TYPE: PRT
<213> ORGANISM: Homo sapiens

<400> SEQUENCE: 92

Trp Val Arg Gln Ala Pro Gly Lys Gly Leu Glu Trp Val Ala
1               5                   10

<210> SEQ ID NO 93
<211> LENGTH: 30
<212> TYPE: PRT
<213> ORGANISM: Homo sapiens

<400> SEQUENCE: 93

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys
            20                  25                  30

<210> SEQ ID NO 94
<211> LENGTH: 11
```

```
<212> TYPE: PRT
<213> ORGANISM: Homo sapiens

<400> SEQUENCE: 94

Trp Gly Gln Gly Thr Leu Val Thr Val Ser Ser
1               5                   10

<210> SEQ ID NO 95
<211> LENGTH: 26
<212> TYPE: PRT
<213> ORGANISM: Homo sapiens

<400> SEQUENCE: 95

Glu Val Gln Leu Val Glu Ser Gly Gly Gly Val Val Gln Pro Gly Arg
1               5                   10                  15

Ser Leu Arg Leu Ser Cys Ala Ala Ser Gly
            20                  25

<210> SEQ ID NO 96
<211> LENGTH: 14
<212> TYPE: PRT
<213> ORGANISM: Homo sapiens

<400> SEQUENCE: 96

Trp Val Arg Gln Ala Pro Gly Lys Gly Leu Glu Trp Val Ala
1               5                   10

<210> SEQ ID NO 97
<211> LENGTH: 30
<212> TYPE: PRT
<213> ORGANISM: Homo sapiens

<400> SEQUENCE: 97

Arg Phe Thr Val Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 98
<211> LENGTH: 11
<212> TYPE: PRT
<213> ORGANISM: Homo sapiens

<400> SEQUENCE: 98

Trp Gly Gln Gly Thr Leu Val Thr Val Ser Ser
1               5                   10

<210> SEQ ID NO 99
<211> LENGTH: 26
<212> TYPE: PRT
<213> ORGANISM: Homo sapiens

<400> SEQUENCE: 99

Gln Val Gln Leu Val Gln Ser Gly Ala Glu Val Lys Lys Pro Gly Ala
1               5                   10                  15

Ser Val Lys Val Ser Cys Lys Ala Ser Gly
            20                  25

<210> SEQ ID NO 100
<211> LENGTH: 14
<212> TYPE: PRT
<213> ORGANISM: Homo sapiens

<400> SEQUENCE: 100
```

Trp Val Arg Gln Ala Pro Gly Gln Gly Leu Glu Trp Met Gly
1               5                   10

<210> SEQ ID NO 101
<211> LENGTH: 30
<212> TYPE: PRT
<213> ORGANISM: Homo sapiens

<400> SEQUENCE: 101

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys
            20                  25                  30

<210> SEQ ID NO 102
<211> LENGTH: 11
<212> TYPE: PRT
<213> ORGANISM: Homo sapiens

<400> SEQUENCE: 102

Trp Gly Gln Gly Thr Met Val Thr Val Ser Ser
1               5                   10

<210> SEQ ID NO 103
<211> LENGTH: 26
<212> TYPE: PRT
<213> ORGANISM: Homo sapiens

<400> SEQUENCE: 103

Gln Val Gln Leu Val Gln Ser Gly Ala Glu Val Lys Lys Pro Gly Ala
1               5                   10                  15

Ser Val Lys Val Ser Cys Lys Ala Ser Gly
            20                  25

<210> SEQ ID NO 104
<211> LENGTH: 14
<212> TYPE: PRT
<213> ORGANISM: Homo sapiens

<400> SEQUENCE: 104

Trp Val Arg Gln Ala Pro Gly Gln Gly Leu Glu Trp Met Gly
1               5                   10

<210> SEQ ID NO 105
<211> LENGTH: 30
<212> TYPE: PRT
<213> ORGANISM: Homo sapiens

<400> SEQUENCE: 105

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys
            20                  25                  30

<210> SEQ ID NO 106
<211> LENGTH: 11
<212> TYPE: PRT
<213> ORGANISM: Homo sapiens

<400> SEQUENCE: 106

Trp Gly Gln Gly Thr Met Val Thr Val Ser Ser
1               5                   10

<210> SEQ ID NO 107
<211> LENGTH: 26
<212> TYPE: PRT
<213> ORGANISM: Homo sapiens

<400> SEQUENCE: 107

Gln Val Gln Leu Val Gln Ser Gly Ala Glu Val Lys Lys Pro Gly Ala
1               5                   10                  15

Ser Val Lys Val Ser Cys Lys Ala Ser Gly
            20                  25

<210> SEQ ID NO 108
<211> LENGTH: 14
<212> TYPE: PRT
<213> ORGANISM: Homo sapiens

<400> SEQUENCE: 108

Trp Val Arg Gln Ala Pro Gly Gln Gly Leu Glu Trp Met Gly
1               5                   10

<210> SEQ ID NO 109
<211> LENGTH: 30
<212> TYPE: PRT
<213> ORGANISM: Homo sapiens

<400> SEQUENCE: 109

Arg Val Thr Leu Thr Arg Asp Thr Ser Thr Ser Thr Val Tyr Met Glu
1               5                   10                  15

Leu Ser Ser Leu Arg Ser Glu Asp Thr Ala Val Tyr Tyr Cys
            20                  25                  30

<210> SEQ ID NO 110
<211> LENGTH: 11
<212> TYPE: PRT
<213> ORGANISM: Homo sapiens

<400> SEQUENCE: 110

Trp Gly Gln Gly Thr Met Val Thr Val Ser Ser
1               5                   10

<210> SEQ ID NO 111
<211> LENGTH: 26
<212> TYPE: PRT
<213> ORGANISM: Homo sapiens

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly
            20                  25

<210> SEQ ID NO 112
<211> LENGTH: 14
<212> TYPE: PRT
<213> ORGANISM: Homo sapiens

<400> SEQUENCE: 112

Trp Val Arg Gln Ala Pro Gly Gln Gly Leu Glu Trp Met Gly
1               5                   10

<210> SEQ ID NO 113
<211> LENGTH: 30
<212> TYPE: PRT

```
<213> ORGANISM: Homo sapiens

<400> SEQUENCE: 113

Arg Val Thr Leu Thr Arg Asp Thr Ser Thr Ser Val Tyr Met Glu
1               5                   10                  15

Leu Ser Ser Leu Arg Ser Glu Asp Thr Ala Val Tyr Tyr Cys
            20                  25                  30

<210> SEQ ID NO 114
<211> LENGTH: 11
<212> TYPE: PRT
<213> ORGANISM: Homo sapiens

<400> SEQUENCE: 114

Trp Gly Gln Gly Thr Thr Val Thr Val Ser Ser
1               5                   10

<210> SEQ ID NO 115
<211> LENGTH: 26
<212> TYPE: PRT
<213> ORGANISM: Homo sapiens

<400> SEQUENCE: 115

Gln Val Gln Leu Gln Glu Ser Gly Pro Gly Leu Val Lys Pro Ser Glu
1               5                   10                  15

Thr Leu Ser Leu Thr Cys Ala Val Ser Gly
            20                  25

<210> SEQ ID NO 116
<211> LENGTH: 14
<212> TYPE: PRT
<213> ORGANISM: Homo sapiens

<400> SEQUENCE: 116

Trp Ile Arg Gln Pro Pro Gly Lys Gly Leu Glu Trp Ile Gly
1               5                   10

<210> SEQ ID NO 117
<211> LENGTH: 30
<212> TYPE: PRT
<213> ORGANISM: Homo sapiens

<400> SEQUENCE: 117

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 118
<211> LENGTH: 11
<212> TYPE: PRT
<213> ORGANISM: Homo sapiens

<400> SEQUENCE: 118

Trp Gly Gln Gly Thr Met Val Thr Val Ser Ser
1               5                   10

<210> SEQ ID NO 119
<211> LENGTH: 26
<212> TYPE: PRT
<213> ORGANISM: Homo sapiens

<400> SEQUENCE: 119
```

Gln Val Gln Leu Gln Glu Ser Gly Pro Gly Leu Val Lys Pro Ser Glu
1               5                   10                  15

Thr Leu Ser Leu Thr Cys Thr Val Ser Gly
            20                  25

<210> SEQ ID NO 120
<211> LENGTH: 14
<212> TYPE: PRT
<213> ORGANISM: Homo sapiens

<400> SEQUENCE: 120

Trp Ile Arg Gln Pro Pro Gly Lys Gly Leu Glu Trp Ile Gly
1               5                   10

<210> SEQ ID NO 121
<211> LENGTH: 30
<212> TYPE: PRT
<213> ORGANISM: Homo sapiens

<400> SEQUENCE: 121

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 122
<211> LENGTH: 11
<212> TYPE: PRT
<213> ORGANISM: Homo sapiens

<400> SEQUENCE: 122

Trp Gly Gln Gly Thr Met Val Thr Val Ser Ser
1               5                   10

<210> SEQ ID NO 123
<211> LENGTH: 26
<212> TYPE: PRT
<213> ORGANISM: Homo sapiens

<400> SEQUENCE: 123

Gln Leu Gln Leu Gln Glu Ser Gly Pro Gly Leu Val Lys Pro Ser Glu
1               5                   10                  15

Thr Leu Ser Leu Thr Cys Thr Val Ser Gly
            20                  25

<210> SEQ ID NO 124
<211> LENGTH: 14
<212> TYPE: PRT
<213> ORGANISM: Homo sapiens

<400> SEQUENCE: 124

Trp Ile Arg Gln Pro Pro Gly Lys Gly Leu Glu Trp Ile Gly
1               5                   10

<210> SEQ ID NO 125
<211> LENGTH: 30
<212> TYPE: PRT
<213> ORGANISM: Homo sapiens

<400> SEQUENCE: 125

Arg Val Thr Ile Ser Val Asp Thr Ser Lys Asn Gln Phe Ser Leu Lys
1               5                   10                  15

Leu Ser Ser Val Thr Ala Thr Asp Thr Ala Val Tyr Tyr Cys

```
<210> SEQ ID NO 126
<211> LENGTH: 11
<212> TYPE: PRT
<213> ORGANISM: Homo sapiens

<400> SEQUENCE: 126

Trp Gly Gln Gly Thr Met Val Thr Val Ser Ser
1               5                   10

<210> SEQ ID NO 127
<211> LENGTH: 26
<212> TYPE: PRT
<213> ORGANISM: Homo sapiens

<400> SEQUENCE: 127

Gln Val Gln Leu Val Gln Ser Gly Ala Glu Val Lys Lys Pro Gly Ser
1               5                   10                  15

Ser Val Lys Val Ser Cys Lys Ala Ser Gly
            20                  25

<210> SEQ ID NO 128
<211> LENGTH: 14
<212> TYPE: PRT
<213> ORGANISM: Homo sapiens

<400> SEQUENCE: 128

Trp Val Arg Gln Ala Pro Gly Gln Gly Leu Glu Trp Met Gly
1               5                   10

<210> SEQ ID NO 129
<211> LENGTH: 30
<212> TYPE: PRT
<213> ORGANISM: Homo sapiens

<400> SEQUENCE: 129

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 130
<211> LENGTH: 11
<212> TYPE: PRT
<213> ORGANISM: Homo sapiens

<400> SEQUENCE: 130

Trp Gly Gln Gly Thr Thr Val Thr Val Ser Ser
1               5                   10

<210> SEQ ID NO 131
<211> LENGTH: 26
<212> TYPE: PRT
<213> ORGANISM: Homo sapiens

<400> SEQUENCE: 131

Gln Val Gln Leu Val Gln Ser Gly Ala Glu Val Lys Lys Pro Gly Ser
1               5                   10                  15

Ser Val Lys Val Ser Cys Lys Ala Ser Gly
            20                  25

<210> SEQ ID NO 132
```

```
<211> LENGTH: 14
<212> TYPE: PRT
<213> ORGANISM: Homo sapiens

<400> SEQUENCE: 132

Trp Val Arg Gln Ala Pro Gly Gln Gly Leu Glu Trp Met Gly
1               5                   10

<210> SEQ ID NO 133
<211> LENGTH: 30
<212> TYPE: PRT
<213> ORGANISM: Homo sapiens

<400> SEQUENCE: 133

Arg Val Thr Val Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 134
<211> LENGTH: 11
<212> TYPE: PRT
<213> ORGANISM: Homo sapiens

<400> SEQUENCE: 134

Trp Gly Gln Gly Thr Thr Val Thr Val Ser Ser
1               5                   10

<210> SEQ ID NO 135
<211> LENGTH: 26
<212> TYPE: PRT
<213> ORGANISM: Homo sapiens

<400> SEQUENCE: 135

Glu Val Gln Leu Val Glu Ser Gly Gly Gly Leu Val Gln Pro Gly Arg
1               5                   10                  15

Ser Leu Arg Leu Ser Cys Ala Ala Ser Gly
            20                  25

<210> SEQ ID NO 136
<211> LENGTH: 14
<212> TYPE: PRT
<213> ORGANISM: Homo sapiens

<400> SEQUENCE: 136

Trp Val Arg Gln Ala Pro Gly Lys Gly Leu Glu Trp Val Ser
1               5                   10

<210> SEQ ID NO 137
<211> LENGTH: 30
<212> TYPE: PRT
<213> ORGANISM: Homo sapiens

<400> SEQUENCE: 137

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Leu Tyr Tyr Cys
            20                  25                  30

<210> SEQ ID NO 138
<211> LENGTH: 11
<212> TYPE: PRT
<213> ORGANISM: Homo sapiens
```

```
<400> SEQUENCE: 138

Trp Gly Gln Gly Thr Met Val Thr Val Ser Ser
1               5                   10

<210> SEQ ID NO 139
<211> LENGTH: 26
<212> TYPE: PRT
<213> ORGANISM: Homo sapiens

<400> SEQUENCE: 139

Gln Val Gln Leu Val Glu Ser Gly Gly Gly Leu Val Gln Pro Gly Arg
1               5                   10                  15

Ser Leu Arg Leu Ser Cys Ala Ala Ser Gly
            20                  25

<210> SEQ ID NO 140
<211> LENGTH: 14
<212> TYPE: PRT
<213> ORGANISM: Homo sapiens

<400> SEQUENCE: 140

Trp Val Arg Gln Ala Pro Gly Lys Gly Leu Glu Trp Val Ser
1               5                   10

<210> SEQ ID NO 141
<211> LENGTH: 30
<212> TYPE: PRT
<213> ORGANISM: Homo sapiens

<400> SEQUENCE: 141

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Leu Tyr Tyr Cys
            20                  25                  30

<210> SEQ ID NO 142
<211> LENGTH: 11
<212> TYPE: PRT
<213> ORGANISM: Homo sapiens

<400> SEQUENCE: 142

Trp Gly Gln Gly Thr Met Val Thr Val Ser Ser
1               5                   10

<210> SEQ ID NO 143
<211> LENGTH: 26
<212> TYPE: PRT
<213> ORGANISM: Homo sapiens

<400> SEQUENCE: 143

Glu Val Gln Leu Val Glu Ser Gly Gly Gly Val Val Gln Pro Gly Arg
1               5                   10                  15

Ser Leu Arg Leu Ser Cys Ala Ala Ser Gly
            20                  25

<210> SEQ ID NO 144
<211> LENGTH: 14
<212> TYPE: PRT
<213> ORGANISM: Homo sapiens

<400> SEQUENCE: 144

Trp Val Arg Gln Ala Pro Gly Lys Gly Leu Glu Trp Val Ala
1               5                   10
```

<210> SEQ ID NO 145
<211> LENGTH: 30
<212> TYPE: PRT
<213> ORGANISM: Homo sapiens

<400> SEQUENCE: 145

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Leu Tyr Tyr Cys
            20                  25                  30

<210> SEQ ID NO 146
<211> LENGTH: 11
<212> TYPE: PRT
<213> ORGANISM: Homo sapiens

<400> SEQUENCE: 146

Trp Gly Gln Gly Thr Met Val Thr Val Ser Ser
1               5                   10

<210> SEQ ID NO 147
<211> LENGTH: 26
<212> TYPE: PRT
<213> ORGANISM: Homo sapiens

<400> SEQUENCE: 147

Gln Val Gln Leu Val Glu Ser Gly Gly Val Val Gln Pro Gly Arg
1               5                   10                  15
Ser Leu Arg Leu Ser Cys Ala Ala Ser Gly
            20                  25

<210> SEQ ID NO 148
<211> LENGTH: 14
<212> TYPE: PRT
<213> ORGANISM: Homo sapiens

<400> SEQUENCE: 148

Trp Val Arg Gln Ala Pro Gly Lys Gly Leu Glu Trp Val Ala
1               5                   10

<210> SEQ ID NO 149
<211> LENGTH: 30
<212> TYPE: PRT
<213> ORGANISM: Homo sapiens

<400> SEQUENCE: 149

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Leu Tyr Tyr Cys
            20                  25                  30

<210> SEQ ID NO 150
<211> LENGTH: 11
<212> TYPE: PRT
<213> ORGANISM: Homo sapiens

<400> SEQUENCE: 150

Trp Gly Gln Gly Thr Met Val Thr Val Ser Ser
1               5                   10

<210> SEQ ID NO 151
<211> LENGTH: 23

```
<212> TYPE: PRT
<213> ORGANISM: Homo sapiens

<400> SEQUENCE: 151

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 152
<211> LENGTH: 15
<212> TYPE: PRT
<213> ORGANISM: Homo sapiens

<400> SEQUENCE: 152

Trp Tyr Gln Gln Lys Pro Gly Gln Ala Pro Arg Leu Leu Ile Tyr
1               5                   10                  15

<210> SEQ ID NO 153
<211> LENGTH: 32
<212> TYPE: PRT
<213> ORGANISM: Homo sapiens

<400> SEQUENCE: 153

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 154
<211> LENGTH: 10
<212> TYPE: PRT
<213> ORGANISM: Homo sapiens

<400> SEQUENCE: 154

Phe Gly Gly Gly Thr Lys Val Glu Ile Lys
1               5                   10

<210> SEQ ID NO 155
<211> LENGTH: 23
<212> TYPE: PRT
<213> ORGANISM: Homo sapiens

<400> SEQUENCE: 155

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 156
<211> LENGTH: 15
<212> TYPE: PRT
<213> ORGANISM: Homo sapiens

<400> SEQUENCE: 156

Trp Tyr Gln Gln Lys Pro Gly Gln Ala Pro Arg Leu Leu Ile Tyr
1               5                   10                  15

<210> SEQ ID NO 157
<211> LENGTH: 32
<212> TYPE: PRT
<213> ORGANISM: Homo sapiens

<400> SEQUENCE: 157
```

```
Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
                20                  25                  30
```

<210> SEQ ID NO 158
<211> LENGTH: 10
<212> TYPE: PRT
<213> ORGANISM: Homo sapiens

<400> SEQUENCE: 158

```
Phe Gly Gly Gly Thr Lys Val Glu Ile Lys
1               5                   10
```

<210> SEQ ID NO 159
<211> LENGTH: 23
<212> TYPE: PRT
<213> ORGANISM: Homo sapiens

<400> SEQUENCE: 159

```
Glu Ile Val Leu Thr Gln Ser Pro Gly Thr Leu Ser Leu Ser Pro Gly
1               5                   10                  15

Glu Arg Ala Thr Leu Ser Cys
                20
```

<210> SEQ ID NO 160
<211> LENGTH: 15
<212> TYPE: PRT
<213> ORGANISM: Homo sapiens

<400> SEQUENCE: 160

```
Trp Tyr Gln Gln Lys Pro Gly Gln Ala Pro Arg Leu Leu Ile Tyr
1               5                   10                  15
```

<210> SEQ ID NO 161
<211> LENGTH: 32
<212> TYPE: PRT
<213> ORGANISM: Homo sapiens

<400> SEQUENCE: 161

```
Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
                20                  25                  30
```

<210> SEQ ID NO 162
<211> LENGTH: 10
<212> TYPE: PRT
<213> ORGANISM: Homo sapiens

<400> SEQUENCE: 162

```
Phe Gly Gly Gly Thr Lys Val Glu Ile Lys
1               5                   10
```

<210> SEQ ID NO 163
<211> LENGTH: 23
<212> TYPE: PRT
<213> ORGANISM: Homo sapiens

<400> SEQUENCE: 163

```
Glu Ile Val Leu Thr Gln Ser Pro Gly Thr Leu Ser Leu Ser Pro Gly
1               5                   10                  15
```

```
Glu Arg Ala Thr Leu Ser Cys
        20

<210> SEQ ID NO 164
<211> LENGTH: 15
<212> TYPE: PRT
<213> ORGANISM: Homo sapiens

<400> SEQUENCE: 164

Trp Tyr Gln Gln Lys Pro Gly Gln Ala Pro Arg Leu Leu Ile Tyr
1               5                   10                  15

<210> SEQ ID NO 165
<211> LENGTH: 32
<212> TYPE: PRT
<213> ORGANISM: Homo sapiens

<400> SEQUENCE: 165

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 166
<211> LENGTH: 10
<212> TYPE: PRT
<213> ORGANISM: Homo sapiens

<400> SEQUENCE: 166

Phe Gly Gly Gly Thr Lys Val Glu Ile Lys
1               5                   10

<210> SEQ ID NO 167
<211> LENGTH: 23
<212> TYPE: PRT
<213> ORGANISM: Homo sapiens

<400> SEQUENCE: 167

Glu Ile Val Leu Thr Gln Ser Pro Gly Thr Leu Ser Leu Ser Pro Gly
1               5                   10                  15

Glu Arg Ala Thr Leu Ser Cys
        20

<210> SEQ ID NO 168
<211> LENGTH: 15
<212> TYPE: PRT
<213> ORGANISM: Homo sapiens

<400> SEQUENCE: 168

Trp Tyr Gln Gln Lys Pro Gly Gln Ala Pro Arg Leu Leu Ile Tyr
1               5                   10                  15

<210> SEQ ID NO 169
<211> LENGTH: 32
<212> TYPE: PRT
<213> ORGANISM: Homo sapiens

<400> SEQUENCE: 169

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30
```

```
<210> SEQ ID NO 170
<211> LENGTH: 10
<212> TYPE: PRT
<213> ORGANISM: Homo sapiens

<400> SEQUENCE: 170

Phe Gly Gly Gly Thr Lys Val Glu Ile Lys
1               5                   10

<210> SEQ ID NO 171
<211> LENGTH: 23
<212> TYPE: PRT
<213> ORGANISM: Homo sapiens

<400> SEQUENCE: 171

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 172
<211> LENGTH: 15
<212> TYPE: PRT
<213> ORGANISM: Homo sapiens

<400> SEQUENCE: 172

Trp Tyr Gln Gln Lys Pro Gly Gln Ala Pro Arg Leu Leu Ile Tyr
1               5                   10                  15

<210> SEQ ID NO 173
<211> LENGTH: 32
<212> TYPE: PRT
<213> ORGANISM: Homo sapiens

<400> SEQUENCE: 173

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 174
<211> LENGTH: 10
<212> TYPE: PRT
<213> ORGANISM: Homo sapiens

<400> SEQUENCE: 174

Phe Gly Gly Gly Thr Lys Val Glu Ile Lys
1               5                   10

<210> SEQ ID NO 175
<211> LENGTH: 23
<212> TYPE: PRT
<213> ORGANISM: Homo sapiens

<400> SEQUENCE: 175

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 176
<211> LENGTH: 15
<212> TYPE: PRT
<213> ORGANISM: Homo sapiens
```

```
<400> SEQUENCE: 176

Trp Tyr Gln Gln Lys Pro Gly Gln Ala Pro Arg Leu Leu Ile Tyr
1               5                   10                  15

<210> SEQ ID NO 177
<211> LENGTH: 32
<212> TYPE: PRT
<213> ORGANISM: Homo sapiens

<400> SEQUENCE: 177

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 178
<211> LENGTH: 10
<212> TYPE: PRT
<213> ORGANISM: Homo sapiens

<400> SEQUENCE: 178

Phe Gly Gly Gly Thr Lys Val Glu Ile Lys
1               5                   10

<210> SEQ ID NO 179
<211> LENGTH: 23
<212> TYPE: PRT
<213> ORGANISM: Homo sapiens

<400> SEQUENCE: 179

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 180
<211> LENGTH: 15
<212> TYPE: PRT
<213> ORGANISM: Homo sapiens

<400> SEQUENCE: 180

Trp Tyr Gln Gln Lys Pro Gly Gln Ala Pro Arg Leu Leu Ile Tyr
1               5                   10                  15

<210> SEQ ID NO 181
<211> LENGTH: 32
<212> TYPE: PRT
<213> ORGANISM: Homo sapiens

<400> SEQUENCE: 181

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 182
<211> LENGTH: 10
<212> TYPE: PRT
<213> ORGANISM: Homo sapiens

<400> SEQUENCE: 182

Phe Gly Gly Gly Thr Lys Val Glu Ile Lys
```

<210> SEQ ID NO 183
<211> LENGTH: 23
<212> TYPE: PRT
<213> ORGANISM: Homo sapiens

<400> SEQUENCE: 183

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 184
<211> LENGTH: 15
<212> TYPE: PRT
<213> ORGANISM: Homo sapiens

<400> SEQUENCE: 184

Trp Tyr Gln Gln Lys Pro Gly Gln Ala Pro Arg Leu Leu Ile Tyr
1               5                   10                  15

<210> SEQ ID NO 185
<211> LENGTH: 32
<212> TYPE: PRT
<213> ORGANISM: Homo sapiens

<400> SEQUENCE: 185

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 186
<211> LENGTH: 10
<212> TYPE: PRT
<213> ORGANISM: Homo sapiens

<400> SEQUENCE: 186

Phe Gly Gly Gly Thr Lys Val Glu Ile Lys
1               5                   10

<210> SEQ ID NO 187
<211> LENGTH: 23
<212> TYPE: PRT
<213> ORGANISM: Homo sapiens

<400> SEQUENCE: 187

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 188
<211> LENGTH: 15
<212> TYPE: PRT
<213> ORGANISM: Homo sapiens

<400> SEQUENCE: 188

Trp Tyr Gln Gln Lys Pro Gly Lys Ala Pro Lys Leu Leu Ile Tyr
1               5                   10                  15

<210> SEQ ID NO 189

```
<211> LENGTH: 32
<212> TYPE: PRT
<213> ORGANISM: Homo sapiens

<400> SEQUENCE: 189

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 190
<211> LENGTH: 10
<212> TYPE: PRT
<213> ORGANISM: Homo sapiens

<400> SEQUENCE: 190

Phe Gly Gly Gly Thr Lys Val Glu Ile Lys
1               5                   10

<210> SEQ ID NO 191
<211> LENGTH: 23
<212> TYPE: PRT
<213> ORGANISM: Homo sapiens

<400> SEQUENCE: 191

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 192
<211> LENGTH: 15
<212> TYPE: PRT
<213> ORGANISM: Homo sapiens

<400> SEQUENCE: 192

Trp Tyr Gln Gln Lys Pro Gly Lys Ala Pro Lys Leu Leu Ile Tyr
1               5                   10                  15

<210> SEQ ID NO 193
<211> LENGTH: 32
<212> TYPE: PRT
<213> ORGANISM: Homo sapiens

<400> SEQUENCE: 193

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 194
<211> LENGTH: 10
<212> TYPE: PRT
<213> ORGANISM: Homo sapiens

<400> SEQUENCE: 194

Phe Gly Gly Gly Thr Lys Val Glu Ile Lys
1               5                   10

<210> SEQ ID NO 195
<211> LENGTH: 23
<212> TYPE: PRT
<213> ORGANISM: Homo sapiens
```

-continued

```
<400> SEQUENCE: 195

Asp Ile Gln Leu Thr Gln Ser Pro Ser Val Ser Ala Ser Val Gly
1               5                   10                  15

Asp Arg Val Thr Ile Thr Cys
            20

<210> SEQ ID NO 196
<211> LENGTH: 15
<212> TYPE: PRT
<213> ORGANISM: Homo sapiens

<400> SEQUENCE: 196

Trp Tyr Gln Gln Lys Pro Gly Lys Ala Pro Lys Leu Leu Ile Tyr
1               5                   10                  15

<210> SEQ ID NO 197
<211> LENGTH: 32
<212> TYPE: PRT
<213> ORGANISM: Homo sapiens

<400> SEQUENCE: 197

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 198
<211> LENGTH: 10
<212> TYPE: PRT
<213> ORGANISM: Homo sapiens

<400> SEQUENCE: 198

Phe Gly Gly Gly Thr Lys Val Glu Ile Lys
1               5                   10

<210> SEQ ID NO 199
<211> LENGTH: 23
<212> TYPE: PRT
<213> ORGANISM: Homo sapiens

<400> SEQUENCE: 199

Asp Ile Gln Leu Thr Gln Ser Pro Ser Val Ser Ala Ser Val Gly
1               5                   10                  15

Asp Arg Val Thr Ile Thr Cys
            20

<210> SEQ ID NO 200
<211> LENGTH: 15
<212> TYPE: PRT
<213> ORGANISM: Homo sapiens

<400> SEQUENCE: 200

Trp Tyr Gln Gln Lys Pro Gly Lys Ala Pro Lys Leu Leu Ile Tyr
1               5                   10                  15

<210> SEQ ID NO 201
<211> LENGTH: 32
<212> TYPE: PRT
<213> ORGANISM: Homo sapiens

<400> SEQUENCE: 201

Gly Val Pro Ser Arg Phe Ser Gly Ser Gly Ser Gly Thr Asp Phe Thr
1               5                   10                  15
```

-continued

Leu Thr Ile Ser Ser Leu Gln Pro Glu Asp Phe Ala Thr Tyr Tyr Cys
            20                  25                  30

<210> SEQ ID NO 202
<211> LENGTH: 10
<212> TYPE: PRT
<213> ORGANISM: Homo sapiens

<400> SEQUENCE: 202

Phe Gly Gly Gly Thr Lys Val Glu Ile Lys
1               5                   10

<210> SEQ ID NO 203
<211> LENGTH: 23
<212> TYPE: PRT
<213> ORGANISM: Homo sapiens

<400> SEQUENCE: 203

Asp Ile Gln Leu Thr Gln Ser Pro Ser Ser Val Ser Ala Ser Val Gly
1               5                   10                  15

Asp Arg Val Thr Ile Thr Cys
            20

<210> SEQ ID NO 204
<211> LENGTH: 15
<212> TYPE: PRT
<213> ORGANISM: Homo sapiens

<400> SEQUENCE: 204

Trp Tyr Gln Gln Lys Pro Gly Lys Ala Pro Lys Leu Leu Ile Tyr
1               5                   10                  15

<210> SEQ ID NO 205
<211> LENGTH: 32
<212> TYPE: PRT
<213> ORGANISM: Homo sapiens

<400> SEQUENCE: 205

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 206
<211> LENGTH: 10
<212> TYPE: PRT
<213> ORGANISM: Homo sapiens

<400> SEQUENCE: 206

Phe Gly Gly Gly Thr Lys Val Glu Ile Lys
1               5                   10

<210> SEQ ID NO 207
<211> LENGTH: 23
<212> TYPE: PRT
<213> ORGANISM: Homo sapiens

<400> SEQUENCE: 207

Asp Ile Gln Leu Thr Gln Ser Pro Ser Ser Val Ser Ala Ser Val Gly
1               5                   10                  15

Asp Arg Val Thr Ile Thr Cys
            20

<210> SEQ ID NO 208
<211> LENGTH: 15
<212> TYPE: PRT
<213> ORGANISM: Homo sapiens

<400> SEQUENCE: 208

Trp Tyr Gln Gln Lys Pro Gly Lys Ala Pro Lys Leu Leu Ile Tyr
1               5                   10                  15

<210> SEQ ID NO 209
<211> LENGTH: 32
<212> TYPE: PRT
<213> ORGANISM: Homo sapiens

<400> SEQUENCE: 209

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 210
<211> LENGTH: 10
<212> TYPE: PRT
<213> ORGANISM: Homo sapiens

<400> SEQUENCE: 210

Phe Gly Gly Gly Thr Lys Val Glu Ile Lys
1               5                   10

<210> SEQ ID NO 211
<211> LENGTH: 127
<212> TYPE: PRT
<213> ORGANISM: Homo sapiens

<400> SEQUENCE: 211

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Ser Tyr Tyr Asp Ser Ser Lys Leu Arg Trp Ala Glu
            100                 105                 110

Tyr Phe Gln His Trp Gly Gln Gly Thr Leu Val Thr Val Ser Ser
        115                 120                 125

<210> SEQ ID NO 212
<211> LENGTH: 107
<212> TYPE: PRT
<213> ORGANISM: Homo sapiens

<400> SEQUENCE: 212

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Lys Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Val His Asn Phe Pro Leu
                85                  90                  95

Thr Phe Gly Gly Gly Thr Lys Val Glu Ile Lys
            100                 105

<210> SEQ ID NO 213
<211> LENGTH: 127
<212> TYPE: PRT
<213> ORGANISM: Homo sapiens

<400> SEQUENCE: 213

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Glu Ser Tyr
                20                  25                  30

Gly Met Val Trp Val Arg Gln Ala Pro Gly Lys Gly Leu Glu Trp Val
            35                  40                  45

Ala Ser Ile Leu Tyr Asp Gly Ser Asn Arg Tyr Tyr Ala Asp Ser Val
        50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Tyr Tyr Tyr Asp Ser Val Glu Leu Arg Trp Ala Glu
                100                 105                 110

Tyr Phe Gln His Trp Gly Gln Gly Thr Leu Val Thr Val Ser Ser
            115                 120                 125

<210> SEQ ID NO 214
<211> LENGTH: 107
<212> TYPE: PRT
<213> ORGANISM: Homo sapiens

<400> SEQUENCE: 214

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Lys Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Val His Asn Phe Pro Leu
                85                  90                  95

Thr Phe Gly Gly Gly Thr Lys Val Glu Ile Lys
            100                 105

<210> SEQ ID NO 215
<211> LENGTH: 121
<212> TYPE: PRT
<213> ORGANISM: Homo sapiens

<400> SEQUENCE: 215

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Val Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp His Ser Asp Tyr Trp Ser Gly Ile Leu Asp Val Trp Gly
                100                 105                 110

Gln Gly Thr Met Val Thr Val Ser Ser
            115                 120

<210> SEQ ID NO 216
<211> LENGTH: 108
<212> TYPE: PRT
<213> ORGANISM: Homo sapiens

<400> SEQUENCE: 216

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Phe Ser Pro Pro
                85                  90                  95

Trp Thr Phe Gly Gly Gly Thr Lys Val Glu Ile Lys
                100                 105

<210> SEQ ID NO 217
<211> LENGTH: 121
<212> TYPE: PRT
<213> ORGANISM: Homo sapiens

<400> SEQUENCE: 217

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Glu Lys Tyr
                20                  25                  30

Tyr Met His Trp Val Arg Gln Ala Pro Gly Gln Gly Leu Glu Trp Met
            35                  40                  45

Gly Val Ile Gly Pro Ser Gly Ala Ser Thr Ser Tyr Ala Gln Lys Phe

```
                    50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp His Ser Asp Tyr Trp Ser Gly Ile Leu His Ser Trp Gly
            100                 105                 110

Gln Gly Thr Met Val Thr Val Ser Ser
        115                 120
```

<210> SEQ ID NO 218
<211> LENGTH: 108
<212> TYPE: PRT
<213> ORGANISM: Homo sapiens

<400> SEQUENCE: 218

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Arg Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Phe Ser Pro Pro
                 85                  90                  95

Trp Thr Phe Gly Gly Gly Thr Lys Val Glu Ile Lys
            100                 105
```

<210> SEQ ID NO 219
<211> LENGTH: 121
<212> TYPE: PRT
<213> ORGANISM: Homo sapiens

<400> SEQUENCE: 219

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Tyr Met His Trp Val Arg Gln Ala Pro Gly Gln Gly Leu Glu Trp Met
         35                  40                  45

Gly Val Ile Gly Pro Ser Gly Ala Ser Thr Ser Tyr Ala Gln Lys Phe
 50                  55                  60

Gln Gly Arg Val Thr Leu Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp His Ser Asp Tyr Trp Ser Gly Ile Met Glu Val Trp Gly
            100                 105                 110

Gln Gly Thr Met Val Thr Val Ser Ser
        115                 120
```

<210> SEQ ID NO 220
<211> LENGTH: 108
<212> TYPE: PRT

<213> ORGANISM: Homo sapiens

<400> SEQUENCE: 220

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Phe Ser Pro Pro
                85                  90                  95

Trp Thr Phe Gly Gly Gly Thr Lys Val Glu Ile Lys
            100                 105

<210> SEQ ID NO 221
<211> LENGTH: 121
<212> TYPE: PRT
<213> ORGANISM: Homo sapiens

<400> SEQUENCE: 221

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Val Ile Gly Pro Ser Gly Ala Ser Thr Ser Tyr Ala Gln Lys Phe
    50                  55                  60

Gln Gly Arg Val Thr Leu Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp His Ser Asp Tyr Trp Ser Gly Ile Met Glu Val Trp Gly
            100                 105                 110

Gln Gly Thr Thr Val Thr Val Ser Ser
        115                 120

<210> SEQ ID NO 222
<211> LENGTH: 108
<212> TYPE: PRT
<213> ORGANISM: Homo sapiens

<400> SEQUENCE: 222

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

```
Pro Glu Asp Phe Ala Val Tyr Tyr Cys Gln Gln Tyr Phe Ser Pro Pro
                85                  90                  95

Trp Thr Phe Gly Gly Gly Thr Lys Val Glu Ile Lys
            100                 105

<210> SEQ ID NO 223
<211> LENGTH: 124
<212> TYPE: PRT
<213> ORGANISM: Homo sapiens

<400> SEQUENCE: 223

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Ala Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Ile Glu Gly Ala Asn Tyr Tyr Asp Phe Gly Tyr Val Ala Phe Asp
            100                 105                 110

Ile Trp Gly Gln Gly Thr Met Val Thr Val Ser Ser
        115                 120

<210> SEQ ID NO 224
<211> LENGTH: 107
<212> TYPE: PRT
<213> ORGANISM: Homo sapiens

<400> SEQUENCE: 224

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Pro Pro Trp Pro Arg
                85                  90                  95

Thr Phe Gly Gly Gly Thr Lys Val Glu Ile Lys
            100                 105

<210> SEQ ID NO 225
<211> LENGTH: 125
<212> TYPE: PRT
<213> ORGANISM: Homo sapiens

<400> SEQUENCE: 225

Gln Val Gln Leu Gln Glu Ser Gly Pro Gly Leu Val Lys Pro Ser Glu
1               5                   10                  15
```

Thr Leu Ser Leu Thr Cys Thr Val Ser Gly Gly Ser Ile Ser Ser Gly
                20                  25                  30

Ser Tyr Tyr Leu Ala Trp Ile Arg Gln Pro Pro Gly Lys Gly Leu Glu
            35                  40                  45

Trp Ile Gly Ser Ile Phe Arg Ser Gly Ser Thr Tyr Tyr Asn Pro Ser
    50                  55                  60

Leu Glu Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Ile Glu Gly Ala Asn Phe Lys Asp Phe Gly Tyr Val Ala Phe
                100                 105                 110

Asp Ile Trp Gly Gln Gly Thr Met Val Thr Val Ser Ser
            115                 120                 125

<210> SEQ ID NO 226
<211> LENGTH: 107
<212> TYPE: PRT
<213> ORGANISM: Homo sapiens

<400> SEQUENCE: 226

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Pro Pro Trp Pro Arg
                85                  90                  95

Thr Phe Gly Gly Gly Thr Lys Val Glu Ile Lys
                100                 105

<210> SEQ ID NO 227
<211> LENGTH: 125
<212> TYPE: PRT
<213> ORGANISM: Homo sapiens

<400> SEQUENCE: 227

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Arg Tyr Tyr Trp Ala Trp Ile Arg Gln Pro Pro Gly Lys Gly Leu Glu
            35                  40                  45

Trp Ile Gly Ser Ile Gly Thr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Thr Asp Thr Ala Val Tyr Tyr
                85                  90                  95

Cys Ala Ile Glu Gly Ala Asn Phe Arg Asp Phe Gly Tyr Val Ala Phe
                100                 105                 110

Asp Ile Trp Gly Gln Gly Thr Met Val Thr Val Ser Ser
            115                 120                 125

<210> SEQ ID NO 228
<211> LENGTH: 107
<212> TYPE: PRT
<213> ORGANISM: Homo sapiens

<400> SEQUENCE: 228

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Pro Pro Trp Pro Arg
                85                  90                  95

Thr Phe Gly Gly Gly Thr Lys Val Glu Ile Lys
            100                 105

<210> SEQ ID NO 229
<211> LENGTH: 122
<212> TYPE: PRT
<213> ORGANISM: Homo sapiens

<400> SEQUENCE: 229

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu His Leu Gly Ser Ser Ala Tyr Tyr Gly Met Asp Val Trp
            100                 105                 110

Gly Gln Gly Thr Thr Val Thr Val Ser Ser
            115                 120

<210> SEQ ID NO 230
<211> LENGTH: 107
<212> TYPE: PRT
<213> ORGANISM: Homo sapiens

<400> SEQUENCE: 230

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile

```
              35                  40                  45
Tyr Ala Ala Ser Ser Leu Gln Ser Gly Val Pro Ser Arg Phe Ser Gly
             50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Arg Tyr Val Phe Pro Pro
                 85                  90                  95
Thr Phe Gly Gly Gly Thr Lys Val Glu Ile Lys
            100                 105
```

<210> SEQ ID NO 231
<211> LENGTH: 122
<212> TYPE: PRT
<213> ORGANISM: Homo sapiens

<400> SEQUENCE: 231

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Gln Asn Tyr
             20                  25                  30
Ala Ile Ser Trp Val Arg Gln Ala Pro Gly Gln Gly Leu Glu Trp Met
         35                  40                  45
Gly Val Ile Val Pro Ile Phe Gly Thr Ala Asn Tyr Ala Gln Lys Phe
     50                  55                  60
Gln Gly Arg Val Thr Val Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                 85                  90                  95
Ala Arg Leu His Leu Gly Gln Lys Ala Tyr Tyr Gly Met Asp Val Trp
            100                 105                 110
Gly Gln Gly Thr Thr Val Thr Val Ser Ser
            115                 120
```

<210> SEQ ID NO 232
<211> LENGTH: 107
<212> TYPE: PRT
<213> ORGANISM: Homo sapiens

<400> SEQUENCE: 232

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
             20                  25                  30
Leu Asn Trp Tyr Gln Gln Lys Pro Gly Lys Ala Pro Lys Leu Leu Ile
         35                  40                  45
Tyr Ala Ala Ser Ser Leu Gln Ser Gly Val Pro Ser Arg Phe Ser Gly
     50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Arg Tyr Val Phe Pro Pro
                 85                  90                  95
Thr Phe Gly Gly Gly Thr Lys Val Glu Ile Lys
            100                 105
```

<210> SEQ ID NO 233
<211> LENGTH: 119
<212> TYPE: PRT

<213> ORGANISM: Homo sapiens

<400> SEQUENCE: 233

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Gly Asp Tyr
            20                  25                  30

Ala Met His Trp Val Arg Gln Ala Pro Gly Lys Gly Leu Glu Trp Val
        35                  40                  45

Ser Gly Ile Thr Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Pro Val Pro Lys Ser Arg Gly Leu Asp Val Trp Gly Gln Gly
            100                 105                 110

Thr Met Val Thr Val Ser Ser
        115

<210> SEQ ID NO 234
<211> LENGTH: 107
<212> TYPE: PRT
<213> ORGANISM: Homo sapiens

<400> SEQUENCE: 234

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Phe Tyr Leu Pro Trp
                85                  90                  95

Thr Phe Gly Gly Gly Thr Lys Val Glu Ile Lys
            100                 105

<210> SEQ ID NO 235
<211> LENGTH: 119
<212> TYPE: PRT
<213> ORGANISM: Homo sapiens

<400> SEQUENCE: 235

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Arg Asp Tyr
            20                  25                  30

Ala Met His Trp Val Arg Gln Ala Pro Gly Lys Gly Leu Glu Trp Val
        35                  40                  45

Ser Gly Ile Thr Trp Asn Ser Gly Leu Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Pro Val Pro Arg Leu Arg Gly Leu Asp Val Trp Gly Gln Gly
            100                 105                 110

Thr Met Val Thr Val Ser Ser
        115

<210> SEQ ID NO 236
<211> LENGTH: 107
<212> TYPE: PRT
<213> ORGANISM: Homo sapiens

<400> SEQUENCE: 236

Asp Ile Gln Leu Thr Gln Ser Pro Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Phe Tyr Leu Pro Trp
                85                  90                  95

Thr Phe Gly Gly Gly Thr Lys Val Glu Ile Lys
            100                 105

<210> SEQ ID NO 237
<211> LENGTH: 119
<212> TYPE: PRT
<213> ORGANISM: Homo sapiens

<400> SEQUENCE: 237

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Gly Ser Tyr
            20                  25                  30

Tyr Met His Trp Val Arg Gln Ala Pro Gly Lys Gly Leu Glu Trp Val
        35                  40                  45

Ala Val Ile Trp Pro Asp Gly Ser Asn Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Pro Val Pro Lys Ser Arg Ala Leu Asp Val Trp Gly Gln Gly
            100                 105                 110

Thr Met Val Thr Val Ser Ser
        115

<210> SEQ ID NO 238
<211> LENGTH: 107
<212> TYPE: PRT
<213> ORGANISM: Homo sapiens

<400> SEQUENCE: 238

```
Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Phe Tyr Leu Pro Trp
                85                  90                  95

Thr Phe Gly Gly Gly Thr Lys Val Glu Ile Lys
            100                 105

<210> SEQ ID NO 239
<211> LENGTH: 119
<212> TYPE: PRT
<213> ORGANISM: Homo sapiens

<400> SEQUENCE: 239

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Ser
            20                  25                  30

Tyr Met His Trp Val Arg Gln Ala Pro Gly Lys Gly Leu Glu Trp Val
        35                  40                  45

Ala Val Ile Gly Ala Asp Gly Ser Asn Lys Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Pro Val Pro Arg Arg Gly Leu Asp Val Trp Gly Gln Gly
            100                 105                 110

Thr Met Val Thr Val Ser Ser
        115

<210> SEQ ID NO 240
<211> LENGTH: 107
<212> TYPE: PRT
<213> ORGANISM: Homo sapiens

<400> SEQUENCE: 240

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Phe Tyr Leu Pro Trp
                85                  90                  95
```

Thr Phe Gly Gly Gly Thr Lys Val Glu Ile Lys
            100                 105

<210> SEQ ID NO 241
<211> LENGTH: 381
<212> TYPE: DNA
<213> ORGANISM: Homo sapiens

<400> SEQUENCE: 241
gaggtgcagc tggtggagtc tgggggaggc ttggtccagc ctgggggtc cctgagactc      60 tcctgtgcag cctctggatt cacctttagt agctatggga tgagctgggt ccgccaggct     120
ccagggaagg gctggagtg gtggccaac ataaagcaag atggaagtga aaatactat        180 gtggactctg tgaagggccg attcaccatc tccagagaca cgccaagaa ctcactgtat      240 ctgcaaatga acagcctgag agccgaggac acggcggtgt actactgcgc tagagtatct    300
tactactacg acagcagcaa actacgatgg gcagaatact tccaacactg gggacagggt    360
acattggtca ccgtctcctc a                                              381

<210> SEQ ID NO 242
<211> LENGTH: 321
<212> TYPE: DNA
<213> ORGANISM: Homo sapiens

<400> SEQUENCE: 242
gaaattgtgt tgacacagtc tccagccacc ctgtctttgt ctccagggga aagagccacc    60
ctctcctgca gggccagtca gagtgttagc agctacttag cctggtacca acagaaacct    120
ggccaggctc ccaggctcct catctatgat gcatccaaaa gggccactgg catcccagcc    180
aggttcagtg gcagtgggtc tgggacagac ttcactctca ccatcagcag cctagagcct    240
gaagattttg cagtttatta ctgtcagcag gtccacaatt tccctctcac ttttggcgga   300
gggaccaagg ttgagatcaa a                                              321

<210> SEQ ID NO 243
<211> LENGTH: 381
<212> TYPE: DNA
<213> ORGANISM: Homo sapiens

<400> SEQUENCE: 243
gaagtccagc tggtggaatc tgggggaggc gtggtccagc ctggaggtc cctgagactc      60 tcctgtgcag cgtctggatt caccttcgag agctatggca tggtttgggt ccgccaggcc    120
ccaggcaagg gctggagtg gtggcatcg atattgtatg atggaagtaa tagatactat      180
gcagactccg tgaagggccg attcaccgtc tccagagaca attccaagaa cacgctgtat    240
ctgcaaatga acagcctgag agccgaggac acggcggtgt actactgcgc tagagtatct    300
tactactacg acagcgttga gctacgatgg gcagaatact tccaacactg gggacagggt    360
acattggtca ccgtctcctc a                                              381

<210> SEQ ID NO 244
<211> LENGTH: 321
<212> TYPE: DNA
<213> ORGANISM: Homo sapiens

<400> SEQUENCE: 244
gaaattgtgt tgacacagtc tccagccacc ctgtctttgt ctccagggga aagagccacc    60
ctctcctgca gggccagtca gagtgttagc agctacttag cctggtacca acagaaacct   120

```
ggccaggctc ccaggctcct catctatgat gcatccaaaa gggccactgg catcccagcc        180
aggttcagtg gcagtgggtc tgggacagac ttcactctca ccatcagcag cctagagcct        240
gaagattttg cagtttatta ctgtcagcag gtccacaatt tccctctcac ttttggcgga        300
gggaccaagg ttgagatcaa a                                                  321
```

<210> SEQ ID NO 245
<211> LENGTH: 363
<212> TYPE: DNA
<213> ORGANISM: Homo sapiens

<400> SEQUENCE: 245

```
caggtgcagc tggtgcagtc tggggctgag gtgaagaagc ctggggcctc agtgaaggtt        60
tcctgcaagg catctggata caccttcacc agctactata tgcactgggt gcgacaggcc       120
cctggacaag gcttgagtg gatgggagtc atcaaccta gtggtggtag cacaagctac         180
gcacagaagt tccagggcag agtcaccatg accaggaca cgtccacgag cacagtctac        240
atggagctga gcagcctgag atctgaggac acggcggtgt actactgcgc cagagaccac       300
tccgactact ggagcggaat actagacgta tggggtcagg gtacaatggt caccgtctcc       360
tca                                                                      363
```

<210> SEQ ID NO 246
<211> LENGTH: 324
<212> TYPE: DNA
<213> ORGANISM: Homo sapiens

<400> SEQUENCE: 246

```
gaaattgtgt tgacgcagtc tccaggcacc ctgtctttgt ctccagggga aagagccacc        60
ctctcctgca gggccagtca gagtgttagg agcagctact tagcctggta ccagcagaaa       120
cctggccagg ctcccaggct cctcatctat ggtgcatcca gcagggccac tggcatccca       180
gacaggttca gtggcagtgg gtctgggaca gacttcactc tcaccatcag cagactggag       240
cctgaagatt ttgcagtgta ttactgtcag cagtacttca gtcctccttg acttttggc        300 ggagggacca aggttgagat caaa                                              324
```

<210> SEQ ID NO 247
<211> LENGTH: 363
<212> TYPE: DNA
<213> ORGANISM: Homo sapiens

<400> SEQUENCE: 247

```
caggtgcagc tggtgcagtc tggggctgag gtgaagaagc ctggggcctc agtgaaggtt        60
tcctgcaagg catctggata caccttcgag aagtactata tgcactgggt gcgacaggcc       120
cctggacaag gcttgagtg gatgggagtg atcggtccta gtggtgctag cacaagctac        180
gcacagaagt tccagggcag agtcaccatg accaggaca cgtccacgag cacagtctac        240
atggagctga gcagcctgag atctgaggac acggcggtgt actactgcgc cagagaccac       300
tccgactact ggagcggaat actacattcg tggggtcagg gtacaatggt caccgtctcc       360
tca                                                                      363
```

<210> SEQ ID NO 248
<211> LENGTH: 324
<212> TYPE: DNA
<213> ORGANISM: Homo sapiens

<400> SEQUENCE: 248

```
gaaattgtgt tgacgcagtc tccaggcacc ctgtctttgt ctccagggga aagagccacc      60
ctctcctgca gggccagtca gagtgttagg agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtacttca gtcctccttg acttttggc      300 ggagggacca aggttgagat caaa                                            324

<210> SEQ ID NO 249
<211> LENGTH: 363
<212> TYPE: DNA
<213> ORGANISM: Homo sapiens

<400> SEQUENCE: 249
caggtgcagc tggtgcagtc tggggctgag gtgaagaagc ctggggcctc agtgaaggtt      60
tcctgcaagg catctggata caccttcact agctactata tgcactgggt gcgacaggcc     120
cctggacaag gcttgagtg atgggagtg atcggtccta gtggtgctag cacaagctac       180
gcacagaagt tccagggcag agtcaccttg accaggggaca cgtccacgag cacagtctac    240
atggagctga gcagcctgag atctgaggac acggcggtgt actactgcgc cagagaccac    300
tccgactact ggagcggaat aatggaggta tggggtcagg gtacaatggt caccgtctcc    360
tca                                                                  363

<210> SEQ ID NO 250
<211> LENGTH: 324
<212> TYPE: DNA
<213> ORGANISM: Homo sapiens

<400> SEQUENCE: 250
gaaattgtgt tgacgcagtc tccaggcacc ctgtctttgt ctccagggga aagagccacc      60
ctctcctgca gggccagtca gagtgttagg agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtacttca gtcctccttg acttttggc      300 ggagggacca aggttgagat caaa                                            324

<210> SEQ ID NO 251
<211> LENGTH: 363
<212> TYPE: DNA
<213> ORGANISM: Homo sapiens

<400> SEQUENCE: 251
caggtgcagc tggtgcagtc tggggctgag gtgaagaagc ctggggcctc agtgaaggtt      60
tcctgcaagg catctggata caccttcact agctactata tgcactgggt gcgacaggcc     120
cctggacaag gcttgagtg atgggagtg atcggtccta gtggtgctag cacaagctac       180
gcacagaagt tccagggcag agtcaccttg accaggggaca cgtccacgag cacagtctac    240
atggagctga gcagcctgag atctgaggac acggcggtgt actactgcgc cagagaccac    300
tccgactact ggagcggaat aatggaggta tggggtcagg gtacaactgt caccgtctcc    360
tca                                                                  363

<210> SEQ ID NO 252
```

```
<211> LENGTH: 324
<212> TYPE: DNA
<213> ORGANISM: Homo sapiens

<400> SEQUENCE: 252
gaaattgtgt tgacgcagtc tccaggcacc ctgtctttgt ctccagggga aagagccacc    60
ctctcctgca gggccagtca gagtgttagg agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtacttca gtcctccttg acttttggc   300 ggagggacca aggttgagat caaa                                          324

<210> SEQ ID NO 253
<211> LENGTH: 372
<212> TYPE: DNA
<213> ORGANISM: Homo sapiens

<400> SEQUENCE: 253
caggtgcagc tgcaggagtc gggcccagga ctggtgaagc cttcggagac cctgtccctc    60
acctgcgctg tctctggtta ctccatcagc agtggttact actgggcttg gatccggcag   120
cccccaggga aggggctgga gtggattggg agtatctatc atagtgggag cacctactac   180
aacccgtccc tcaagagtcg agtcaccata tcagtagaca cgtccaagaa ccagttctcc   240
ctgaagctga gttctgtgac cgccgcagac acggcggtgt actactgcgc catagaagga   300
gctaactact acgacttcgg atatgtagca ttcgacatat ggggtcaggg tacaatggtc   360
accgtctcct ca                                                       372

<210> SEQ ID NO 254
<211> LENGTH: 321
<212> TYPE: DNA
<213> ORGANISM: Homo sapiens

<400> SEQUENCE: 254
gaaatagtga tgacgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tccccccccct ggcctaggac ttttggcgga   300
gggaccaagg ttgagatcaa a                                             321

<210> SEQ ID NO 255
<211> LENGTH: 375
<212> TYPE: DNA
<213> ORGANISM: Homo sapiens

<400> SEQUENCE: 255
caggtgcagc tgcaggagtc gggcccagga ctggtgaagc cttcggagac cctgtccctc    60
acctgcactg tctctggtgg ctccatcagc agtgggagtt actacttggc gtggatccgc   120
cagcccccag ggaagggcct ggagtggatt gggagtatct ttcggagtgg agcacctac   180 tacaacccgt ccctcgagag tcgagtcacc atatcggtag acacgtccaa gaaccagttc   240
tccctgaagc tgagttctgt gaccgccgca gacacggcgg tgtactactg cgccatagaa   300
ggagctaact ttaaggactt cggatatgta gcattcgaca tatggggtca gggtacaatg   360
```

```
gtcaccgtct cctca                                                      375

<210> SEQ ID NO 256
<211> LENGTH: 321
<212> TYPE: DNA
<213> ORGANISM: Homo sapiens

<400> SEQUENCE: 256
gaaatagtga tgacgcagtc tccagccacc ctgtctgtgt ctccagggga aagagccacc       60
ctctcctgca gggccagtca gagtgttagc agcaacttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttatta ctgtcagcag tccccccccct ggcctaggac ttttggcgga     300
gggaccaagg ttgagatcaa a                                               321

<210> SEQ ID NO 257
<211> LENGTH: 375
<212> TYPE: DNA
<213> ORGANISM: Homo sapiens

<400> SEQUENCE: 257
cagctgcagc tgcaggagtc gggcccagga ctggtgaagc cttcggagac cctgtccctc       60
acctgcactg tctctggtgg ctccatcagc agtagtaggt actactgggc gtggatccgc     120
cagcccccag ggaaggggct ggagtggatt gggagtatcg ggacgagtgg gagcacctac     180
tacaacccgt ccctcaagag tcgagtcacc atatccgtag acacgtccaa gaaccagttc     240
tccctgaagc tgagttctgt gaccgccaca gacacggcgg tgtactactg cgccatagaa     300
ggagctaact ttcgggactt cggatatgta gcattcgaca tatggggtca gggtacaatg     360
gtcaccgtct cctca                                                      375

<210> SEQ ID NO 258
<211> LENGTH: 321
<212> TYPE: DNA
<213> ORGANISM: Homo sapiens

<400> SEQUENCE: 258
gaaatagtga tgacgcagtc tccagccacc ctgtctgtgt ctccagggga aagagccacc       60
ctctcctgca gggccagtca gagtgttagc agcaacttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttatta ctgtcagcag tccccccccct ggcctaggac ttttggcgga     300
gggaccaagg ttgagatcaa a                                               321

<210> SEQ ID NO 259
<211> LENGTH: 366
<212> TYPE: DNA
<213> ORGANISM: Homo sapiens

<400> SEQUENCE: 259
caggtgcagc tggtgcagtc tggggctgag gtgaagaagc ctgggtcctc ggtgaaggtc       60
tcctgcaagg cttctggagg caccttcagc agctatgcta tcagctgggt gcgacaggcc     120
cctggacaag ggcttgagtg gatgggaggg atcatcccta tctttggtac agcaaactac     180
```

```
gcacagaagt tccagggcag agtcacgatt accgcggacg aatccacgag cacagcctac    240
atggagctga gcagcctgag atctgaggac acggcggtgt actactgcgc taggttgcac    300
ctgggatcca gcgcctacta cggcatggat gtatggggcc agggaacaac tgtcaccgtc    360
tcctca                                                               366
```

<210> SEQ ID NO 260
<211> LENGTH: 321
<212> TYPE: DNA
<213> ORGANISM: Homo sapiens

<400> SEQUENCE: 260

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcaa agatacgtct cccctcctac ttttggcgga   300
gggaccaagg ttgagatcaa a                                             321
```

<210> SEQ ID NO 261
<211> LENGTH: 366
<212> TYPE: DNA
<213> ORGANISM: Homo sapiens

<400> SEQUENCE: 261

```
caggtgcagc tggtgcagtc tggggctgag gtgaagaagc ctgggtcctc ggtgaaggtc    60
tcctgcaagg cttctggagg caccttccag aactatgcta tcagctgggt gcgacaggcc   120
cctggacaag gccttgagtg gatgggagtt atcgtgccta tctttggtac agcaaactac   180
gcacagaagt tccagggcag agtcacggtt accgcggacg aatccacgag cacagcctac   240
atggagctga gcagcctgag atctgaggac acggcggtgt actactgcgc taggttgcac   300
ctgggacaga aggcctacta cggcatggat gtatggggcc agggaacaac tgtcaccgtc   360
tcctca                                                              366
```

<210> SEQ ID NO 262
<211> LENGTH: 321
<212> TYPE: DNA
<213> ORGANISM: Homo sapiens

<400> SEQUENCE: 262

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcaa agatacgtct cccctcctac ttttggcgga   300
gggaccaagg ttgagatcaa a                                             321
```

<210> SEQ ID NO 263
<211> LENGTH: 357
<212> TYPE: DNA
<213> ORGANISM: Homo sapiens

<400> SEQUENCE: 263

```
gaagtgcagc tggtggagtc tgggggaggc ttggtacagc ctggcaggtc cctgagactc    60
```

```
tcctgtgcag cctctggatt cacctttggt gattatgcca tgcactgggt ccggcaagct    120
ccagggaagg gcctggagtg ggtctcaggt attacttgga atagtggtag cataggctat    180
gcggactctg tgaagggccg attcaccatc tccagagaca acgccaagaa ctccctgtat    240
ctgcaaatga acagtctgag agctgaggac acggcgttgt actactgcgc caagccagtg    300
ccaaaatcta gaggcctaga cgtatggggt cagggtacaa tggtcaccgt ctcctca       357
```

<210> SEQ ID NO 264
<211> LENGTH: 321
<212> TYPE: DNA
<213> ORGANISM: Homo sapiens

<400> SEQUENCE: 264

```
gacatccagt tgacccagtc tccatcttcc gtgtctgcat ctgtaggaga cagagtcacc     60
atcacttgtc gggcgagtca gggtattagc agctggttag cctggtatca gcagaaacca    120
gggaaagccc ctaagctcct gatctatggt gcatccagtt tgcaaagtgg ggtcccatca    180
aggttcagcg gcagtggatc tgggacagat ttcactctca ccatcagcag cctgcagcct    240
gaagattttg caacttatta ctgtcagcag gcattctacc tcccttggac ttttggcgga    300
gggaccaagg ttgagatcaa a                                              321
```

<210> SEQ ID NO 265
<211> LENGTH: 357
<212> TYPE: DNA
<213> ORGANISM: Homo sapiens

<400> SEQUENCE: 265

```
caggtgcagc tggtggagtc tgggggaggc ttggtacagc ctggcaggtc cctgagactc     60
tcctgtgcag cctctggatt cacctttcgg gattatgcca tgcactgggt ccggcaagct    120
ccagggaagg gcctggagtg ggtctcaggt attacttgga atagtggttt gataggctat    180
gcggactctg tgaagggccg attcaccatc tccagagaca acgccaagaa ctccctgtat    240
ctgcaaatga acagtctgag agctgaggac acggcgttgt actactgcgc caagccagtg    300
ccacgtttga gaggcctaga cgtatggggt cagggtacaa tggtcaccgt ctcctca       357
```

<210> SEQ ID NO 266
<211> LENGTH: 321
<212> TYPE: DNA
<213> ORGANISM: Homo sapiens

<400> SEQUENCE: 266

```
gacatccagt tgacccagtc tccatcttcc gtgtctgcat ctgtaggaga cagagtcacc     60
atcacttgtc gggcgagtca gggtattagc agctggttag cctggtatca gcagaaacca    120
gggaaagccc ctaagctcct gatctatggt gcatccagtt tgcaaagtgg ggtcccatca    180
aggttcagcg gcagtggatc tgggacagat ttcactctca ccatcagcag cctgcagcct    240
gaagattttg caacttatta ctgtcagcag gcattctacc tcccttggac ttttggcgga    300
gggaccaagg ttgagatcaa a                                              321
```

<210> SEQ ID NO 267
<211> LENGTH: 357
<212> TYPE: DNA
<213> ORGANISM: Homo sapiens

<400> SEQUENCE: 267

```
gaagtccagc tggtggaatc tgggggaggc gtggtccagc ctgggaggtc cctgagactc        60
tcctgtgcag cgtctggatt caccttcggg agctattata tgcactgggt ccgccaggct       120
ccaggcaagg ggctggagtg ggtggcagtt atatggcctg atggaagtaa taaactgtat       180
gcagactccg tgaagggccg attcaccatc tccagagaca attccaagaa cacgctgtat       240
ctgcaaatga acagcctgag agccgaggac acggcgttgt actactgcgc caagccagtg       300
ccaaaatcta gagcgcttga cgtatggggt cagggtacaa tggtcaccgt ctcctca          357
```

<210> SEQ ID NO 268
<211> LENGTH: 321
<212> TYPE: DNA
<213> ORGANISM: Homo sapiens

<400> SEQUENCE: 268

```
gacatccagt tgacccagtc tccatcttcc gtgtctgcat ctgtaggaga cagagtcacc        60
atcacttgtc gggcgagtca gggtattagc agctggttag cctggtatca gcagaaacca       120
gggaaagccc ctaagctcct gatctatggt gcatccagtt tgcaaagtgg ggtcccatca       180
aggttcagcg gcagtggatc tgggacagat ttcactctca ccatcagcag cctgcagcct       240
gaagattttg caacttatta ctgtcagcag gcattctacc tcccttggac ttttggcgga       300
gggaccaagg ttgagatcaa a                                                  321
```

<210> SEQ ID NO 269
<211> LENGTH: 357
<212> TYPE: DNA
<213> ORGANISM: Homo sapiens

<400> SEQUENCE: 269

```
caggtgcagc tggtggagtc tgggggaggc gtggtccagc ctgggaggtc cctgagactc        60
tcctgtgcag cgtctggatt caccttcagt agctcttata tgcactgggt ccgccaggct       120
ccaggcaagg ggctggagtg ggtggcagtt ataggtgcgg atggaagtaa taaatactat       180
gcagactccg tggagggccg attcaccatc tccagagaca attccaagaa cacgctgtat       240
ctgcaaatga acagcctgag agctgaggac acggcgttgt actactgcgc caagccagtg       300
ccacggcgta gaggcctaga cgtatggggt cagggtacaa tggtcaccgt ctcctca          357
```

<210> SEQ ID NO 270
<211> LENGTH: 321
<212> TYPE: DNA
<213> ORGANISM: Homo sapiens

<400> SEQUENCE: 270

```
gacatccagt tgacccagtc tccatcttcc gtgtctgcat ctgtaggaga cagagtcacc        60
atcacttgtc gggcgagtca gggtattagc agctggttag cctggtatca gcagaaacca       120
gggaaagccc ctaagctcct gatctatggt gcatccagtt tgcaaagtgg ggtcccatca       180
aggttcagcg gcagtggatc tgggacagat ttcactctca ccatcagcag cctgcagcct       240
gaagattttg caacttatta ctgtcagcag gcattctacc tcccttggac ttttggcgga       300
gggaccaagg ttgagatcaa a                                                  321
```

<210> SEQ ID NO 271
<211> LENGTH: 11
<212> TYPE: PRT
<213> ORGANISM: Homo sapiens

<400> SEQUENCE: 271

```
Gly Ser Ile Ser Ser Gly Ser Tyr Tyr Leu Ala
1               5                   10
```

<210> SEQ ID NO 272
<211> LENGTH: 16
<212> TYPE: PRT
<213> ORGANISM: Homo sapiens

<400> SEQUENCE: 272

```
Ser Ile Phe Arg Ser Gly Ser Thr Tyr Tyr Asn Pro Ser Leu Glu Ser
1               5                   10                  15
```

<210> SEQ ID NO 273
<211> LENGTH: 17
<212> TYPE: PRT
<213> ORGANISM: Homo sapiens

<400> SEQUENCE: 273

```
Ala Ile Glu Gly Ala Asn Phe Lys Asp Phe Gly Tyr Val Ala Phe Asp
1               5                   10                  15

Ile
```

<210> SEQ ID NO 274
<211> LENGTH: 11
<212> TYPE: PRT
<213> ORGANISM: Homo sapiens

<400> SEQUENCE: 274

```
Gly Ser Ile Ser Ser Gly Ser Tyr Tyr Leu Ala
1               5                   10
```

<210> SEQ ID NO 275
<211> LENGTH: 16
<212> TYPE: PRT
<213> ORGANISM: Homo sapiens

<400> SEQUENCE: 275

```
Ser Ile Phe Arg Ser Gly Ser Thr Tyr Tyr Asn Pro Ser Leu Glu Ser
1               5                   10                  15
```

<210> SEQ ID NO 276
<211> LENGTH: 17
<212> TYPE: PRT
<213> ORGANISM: Homo sapiens

<400> SEQUENCE: 276

```
Ala Ile Glu Gly Ala Asn Phe Lys Asp Phe Gly Tyr Val Ala Phe Asp
1               5                   10                  15

Ile
```

<210> SEQ ID NO 277
<211> LENGTH: 11
<212> TYPE: PRT
<213> ORGANISM: Homo sapiens

<400> SEQUENCE: 277

```
Gly Ser Ile Ser Ser Gly Ser Tyr Tyr Leu Ala
1               5                   10
```

<210> SEQ ID NO 278
<211> LENGTH: 16
<212> TYPE: PRT
<213> ORGANISM: Homo sapiens

```
<400> SEQUENCE: 278

Ser Ile Phe Arg Ser Gly Ser Thr Tyr Tyr Asn Pro Ser Leu Glu Ser
1               5                   10                  15

<210> SEQ ID NO 279
<211> LENGTH: 17
<212> TYPE: PRT
<213> ORGANISM: Homo sapiens

<400> SEQUENCE: 279

Ala Ile Glu Gly Ala Asn Phe Lys Asp Phe Gly Tyr Val Ala Phe Asp
1               5                   10                  15

Ile

<210> SEQ ID NO 280
<211> LENGTH: 9
<212> TYPE: PRT
<213> ORGANISM: Homo sapiens

<400> SEQUENCE: 280

Gly Thr Phe Ser Ser Tyr Ala Ile Ser
1               5

<210> SEQ ID NO 281
<211> LENGTH: 17
<212> TYPE: PRT
<213> ORGANISM: Homo sapiens

<400> SEQUENCE: 281

Gly Ile Ile Pro Ile Phe Gly Thr Ala Asn Tyr Ala Gln Lys Phe Gln
1               5                   10                  15

Gly

<210> SEQ ID NO 282
<211> LENGTH: 13
<212> TYPE: PRT
<213> ORGANISM: Homo sapiens

<400> SEQUENCE: 282

Ala Arg Glu Ala Gln Ser Tyr Arg Val Pro Phe Asp Ile
1               5                   10

<210> SEQ ID NO 283
<211> LENGTH: 11
<212> TYPE: PRT
<213> ORGANISM: Homo sapiens

<400> SEQUENCE: 283

Arg Ala Ser Gln Ser Val Ser Ser Asn Leu Ala
1               5                   10

<210> SEQ ID NO 284
<211> LENGTH: 7
<212> TYPE: PRT
<213> ORGANISM: Homo sapiens

<400> SEQUENCE: 284

Gly Ala Ser Thr Arg Ala Thr
1               5

<210> SEQ ID NO 285
<211> LENGTH: 9
```

```
<212> TYPE: PRT
<213> ORGANISM: Homo sapiens

<400> SEQUENCE: 285

Gln Gln Ser Pro Pro Trp Pro Arg Thr
1               5

<210> SEQ ID NO 286
<211> LENGTH: 11
<212> TYPE: PRT
<213> ORGANISM: Homo sapiens

<400> SEQUENCE: 286

Arg Ala Ser Gln Ser Val Ser Ser Tyr Leu Ala
1               5                   10

<210> SEQ ID NO 287
<211> LENGTH: 7
<212> TYPE: PRT
<213> ORGANISM: Homo sapiens

<400> SEQUENCE: 287

Asp Ala Ser Asn Arg Ala Thr
1               5

<210> SEQ ID NO 288
<211> LENGTH: 9
<212> TYPE: PRT
<213> ORGANISM: Homo sapiens

<400> SEQUENCE: 288

Gln Gln Glu Asn Pro Arg Pro Arg Thr
1               5

<210> SEQ ID NO 289
<211> LENGTH: 11
<212> TYPE: PRT
<213> ORGANISM: Homo sapiens

<400> SEQUENCE: 289

Arg Ala Ser Lys Ser Val Ser Ser Asn Leu Ala
1               5                   10

<210> SEQ ID NO 290
<211> LENGTH: 7
<212> TYPE: PRT
<213> ORGANISM: Homo sapiens

<400> SEQUENCE: 290

Phe Ala Ser Thr Arg Ala Thr
1               5

<210> SEQ ID NO 291
<211> LENGTH: 9
<212> TYPE: PRT
<213> ORGANISM: Homo sapiens

<400> SEQUENCE: 291

Gln Gln Thr Ser Pro Trp Pro Arg Thr
1               5

<210> SEQ ID NO 292
<211> LENGTH: 11
<212> TYPE: PRT
<213> ORGANISM: Homo sapiens
```

<400> SEQUENCE: 292

Arg Ala Ser Gln Ser Val Ser Ser Asn Leu Ala
1               5                   10

<210> SEQ ID NO 293
<211> LENGTH: 7
<212> TYPE: PRT
<213> ORGANISM: Homo sapiens

<400> SEQUENCE: 293

Gly Ala Ser Thr Arg Ala Thr
1               5

<210> SEQ ID NO 294
<211> LENGTH: 10
<212> TYPE: PRT
<213> ORGANISM: Homo sapiens

<400> SEQUENCE: 294

Gln Gln Tyr Ala Ile Trp Pro Pro Phe Thr
1               5                   10

<210> SEQ ID NO 295
<211> LENGTH: 26
<212> TYPE: PRT
<213> ORGANISM: Homo sapiens

<400> SEQUENCE: 295

Gln Leu Gln Leu Gln Glu Ser Gly Pro Gly Leu Val Lys Pro Ser Glu
1               5                   10                  15

Thr Leu Ser Leu Thr Cys Thr Val Ser Gly
            20                  25

<210> SEQ ID NO 296
<211> LENGTH: 14
<212> TYPE: PRT
<213> ORGANISM: Homo sapiens

<400> SEQUENCE: 296

Trp Ile Arg Gln Pro Pro Gly Lys Gly Leu Glu Trp Ile Gly
1               5                   10

<210> SEQ ID NO 297
<211> LENGTH: 30
<212> TYPE: PRT
<213> ORGANISM: Homo sapiens

<400> SEQUENCE: 297

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 298
<211> LENGTH: 11
<212> TYPE: PRT
<213> ORGANISM: Homo sapiens

<400> SEQUENCE: 298

Trp Gly Gln Gly Thr Thr Val Thr Val Ser Ser
1               5                   10

```
<210> SEQ ID NO 299
<211> LENGTH: 26
<212> TYPE: PRT
<213> ORGANISM: Homo sapiens

<400> SEQUENCE: 299

Gln Leu Gln Leu Gln Glu Ser Gly Pro Gly Leu Val Lys Pro Ser Glu
1               5                   10                  15

Thr Leu Ser Leu Thr Cys Thr Val Ser Gly
            20                  25

<210> SEQ ID NO 300
<211> LENGTH: 14
<212> TYPE: PRT
<213> ORGANISM: Homo sapiens

<400> SEQUENCE: 300

Trp Ile Arg Gln Pro Pro Gly Lys Gly Leu Glu Trp Ile Gly
1               5                   10

<210> SEQ ID NO 301
<211> LENGTH: 30
<212> TYPE: PRT
<213> ORGANISM: Homo sapiens

<400> SEQUENCE: 301

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 302
<211> LENGTH: 11
<212> TYPE: PRT
<213> ORGANISM: Homo sapiens

<400> SEQUENCE: 302

Trp Gly Gln Gly Thr Thr Val Thr Val Ser Ser
1               5                   10

<210> SEQ ID NO 303
<211> LENGTH: 26
<212> TYPE: PRT
<213> ORGANISM: Homo sapiens

<400> SEQUENCE: 303

Gln Leu Gln Leu Gln Glu Ser Gly Pro Gly Leu Val Lys Pro Ser Glu
1               5                   10                  15

Thr Leu Ser Leu Thr Cys Thr Val Ser Gly
            20                  25

<210> SEQ ID NO 304
<211> LENGTH: 14
<212> TYPE: PRT
<213> ORGANISM: Homo sapiens

<400> SEQUENCE: 304

Trp Ile Arg Gln Pro Pro Gly Lys Gly Leu Glu Trp Ile Gly
1               5                   10

<210> SEQ ID NO 305
<211> LENGTH: 30
<212> TYPE: PRT
<213> ORGANISM: Homo sapiens
```

<400> SEQUENCE: 305

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 306
<211> LENGTH: 11
<212> TYPE: PRT
<213> ORGANISM: Homo sapiens

<400> SEQUENCE: 306

Trp Gly Gln Gly Thr Thr Val Thr Val Ser Ser
1               5                   10

<210> SEQ ID NO 307
<211> LENGTH: 26
<212> TYPE: PRT
<213> ORGANISM: Homo sapiens

<400> SEQUENCE: 307

Gln Val Gln Leu Val Gln Ser Gly Ala Glu Val Lys Lys Pro Gly Ser
1               5                   10                  15

Ser Val Lys Val Ser Cys Lys Ala Ser Gly
            20                  25

<210> SEQ ID NO 308
<211> LENGTH: 14
<212> TYPE: PRT
<213> ORGANISM: Homo sapiens

<400> SEQUENCE: 308

Trp Val Arg Gln Ala Pro Gly Gln Gly Leu Glu Trp Met Gly
1               5                   10

<210> SEQ ID NO 309
<211> LENGTH: 30
<212> TYPE: PRT
<213> ORGANISM: Homo sapiens

<400> SEQUENCE: 309

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 310
<211> LENGTH: 11
<212> TYPE: PRT
<213> ORGANISM: Homo sapiens

<400> SEQUENCE: 310

Trp Gly Gln Gly Thr Met Val Thr Val Ser Ser
1               5                   10

<210> SEQ ID NO 311
<211> LENGTH: 23
<212> TYPE: PRT
<213> ORGANISM: Homo sapiens

<400> SEQUENCE: 311

Glu Ile Val Met Thr Gln Ser Pro Ala Thr Leu Ser Val Ser Pro Gly

```
                1               5                    10                   15
Glu Arg Ala Thr Leu Ser Cys
            20

<210> SEQ ID NO 312
<211> LENGTH: 15
<212> TYPE: PRT
<213> ORGANISM: Homo sapiens

<400> SEQUENCE: 312

Trp Tyr Gln Gln Lys Pro Gly Gln Ala Pro Arg Leu Leu Ile Tyr
1               5                   10                  15

<210> SEQ ID NO 313
<211> LENGTH: 32
<212> TYPE: PRT
<213> ORGANISM: Homo sapiens

<400> SEQUENCE: 313

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 314
<211> LENGTH: 10
<212> TYPE: PRT
<213> ORGANISM: Homo sapiens

<400> SEQUENCE: 314

Phe Gly Gly Gly Thr Lys Val Glu Ile Lys
1               5                   10

<210> SEQ ID NO 315
<211> LENGTH: 23
<212> TYPE: PRT
<213> ORGANISM: Homo sapiens

<400> SEQUENCE: 315

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 316
<211> LENGTH: 15
<212> TYPE: PRT
<213> ORGANISM: Homo sapiens

<400> SEQUENCE: 316

Trp Tyr Gln Gln Lys Pro Gly Gln Ala Pro Arg Leu Leu Ile Tyr
1               5                   10                  15

<210> SEQ ID NO 317
<211> LENGTH: 32
<212> TYPE: PRT
<213> ORGANISM: Homo sapiens

<400> SEQUENCE: 317

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30
```

<210> SEQ ID NO 318
<211> LENGTH: 10
<212> TYPE: PRT
<213> ORGANISM: Homo sapiens

<400> SEQUENCE: 318

Phe Gly Gly Gly Thr Lys Val Glu Ile Lys
1               5                   10

<210> SEQ ID NO 319
<211> LENGTH: 23
<212> TYPE: PRT
<213> ORGANISM: Homo sapiens

<400> SEQUENCE: 319

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 320
<211> LENGTH: 15
<212> TYPE: PRT
<213> ORGANISM: Homo sapiens

<400> SEQUENCE: 320

Trp Tyr Gln Gln Lys Pro Gly Gln Ala Pro Arg Leu Leu Ile Tyr
1               5                   10                  15

<210> SEQ ID NO 321
<211> LENGTH: 32
<212> TYPE: PRT
<213> ORGANISM: Homo sapiens

<400> SEQUENCE: 321

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 322
<211> LENGTH: 10
<212> TYPE: PRT
<213> ORGANISM: Homo sapiens

<400> SEQUENCE: 322

Phe Gly Gly Gly Thr Lys Val Glu Ile Lys
1               5                   10

<210> SEQ ID NO 323
<211> LENGTH: 23
<212> TYPE: PRT
<213> ORGANISM: Homo sapiens

<400> SEQUENCE: 323

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 324
<211> LENGTH: 15

<212> TYPE: PRT
<213> ORGANISM: Homo sapiens

<400> SEQUENCE: 324

Trp Tyr Gln Gln Lys Pro Gly Gln Ala Pro Arg Leu Leu Ile Tyr
1               5                   10                  15

<210> SEQ ID NO 325
<211> LENGTH: 32
<212> TYPE: PRT
<213> ORGANISM: Homo sapiens

<400> SEQUENCE: 325

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 326
<211> LENGTH: 10
<212> TYPE: PRT
<213> ORGANISM: Homo sapiens

<400> SEQUENCE: 326

Phe Gly Gly Gly Thr Lys Val Glu Ile Lys
1               5                   10

<210> SEQ ID NO 327
<211> LENGTH: 125
<212> TYPE: PRT
<213> ORGANISM: Homo sapiens

<400> SEQUENCE: 327

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Tyr Leu Ala Trp Ile Arg Gln Pro Pro Gly Lys Gly Leu Glu
        35                  40                  45

Trp Ile Gly Ser Ile Phe Arg Ser Gly Ser Thr Tyr Tyr Asn Pro Ser
    50                  55                  60

Leu Glu Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Ile Glu Gly Ala Asn Phe Lys Asp Phe Gly Tyr Val Ala Phe
            100                 105                 110

Asp Ile Trp Gly Gln Gly Thr Thr Val Thr Val Ser Ser
        115                 120                 125

<210> SEQ ID NO 328
<211> LENGTH: 107
<212> TYPE: PRT
<213> ORGANISM: Homo sapiens

<400> SEQUENCE: 328

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

```
Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Ser Pro Pro Trp Pro Arg
                 85                  90                  95

Thr Phe Gly Gly Gly Thr Lys Val Glu Ile Lys
                100                 105
```

<210> SEQ ID NO 329
<211> LENGTH: 125
<212> TYPE: PRT
<213> ORGANISM: Homo sapiens

<400> SEQUENCE: 329

```
Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Gly
                 20                  25                  30

Ser Tyr Tyr Leu Ala Trp Ile Arg Gln Pro Pro Gly Lys Gly Leu Glu
             35                  40                  45

Trp Ile Gly Ser Ile Phe Arg Ser Gly Ser Thr Tyr Tyr Asn Pro Ser
 50                  55                  60

Leu Glu Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Ile Glu Gly Ala Asn Phe Lys Asp Phe Gly Tyr Val Ala Phe
            100                 105                 110

Asp Ile Trp Gly Gln Gly Thr Thr Val Thr Val Ser Ser
        115                 120                 125
```

<210> SEQ ID NO 330
<211> LENGTH: 107
<212> TYPE: PRT
<213> ORGANISM: Homo sapiens

<400> SEQUENCE: 330

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Glu Asn Pro Arg Pro Arg
                 85                  90                  95

Thr Phe Gly Gly Gly Thr Lys Val Glu Ile Lys
                100                 105
```

<210> SEQ ID NO 331
<211> LENGTH: 125

```
<212> TYPE: PRT
<213> ORGANISM: Homo sapiens

<400> SEQUENCE: 331

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Tyr Leu Ala Trp Ile Arg Gln Pro Pro Gly Lys Gly Leu Glu
        35                  40                  45

Trp Ile Gly Ser Ile Phe Arg Ser Gly Ser Thr Tyr Tyr Asn Pro Ser
    50                  55                  60

Leu Glu Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Ile Glu Gly Ala Asn Phe Lys Asp Phe Gly Tyr Val Ala Phe
            100                 105                 110

Asp Ile Trp Gly Gln Gly Thr Thr Val Thr Val Ser Ser
        115                 120                 125

<210> SEQ ID NO 332
<211> LENGTH: 107
<212> TYPE: PRT
<213> ORGANISM: Homo sapiens

<400> SEQUENCE: 332

Glu Ile Val Met Thr Gln Ser Pro Ala Thr Leu Ser Val Ser Pro Gly
1               5                   10                  15

Glu Arg Ala Thr Leu Ser Cys Arg Ala Ser Lys Ser Val Ser Ser Asn
            20                  25                  30

Leu Ala Trp Tyr Gln Gln Lys Pro Gly Gln Ala Pro Arg Leu Leu Ile
        35                  40                  45

Tyr Phe Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Thr Ser Pro Trp Pro Arg
                85                  90                  95

Thr Phe Gly Gly Gly Thr Lys Val Glu Ile Lys
            100                 105

<210> SEQ ID NO 333
<211> LENGTH: 120
<212> TYPE: PRT
<213> ORGANISM: Homo sapiens

<400> SEQUENCE: 333

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
```

```
                65                  70                  75                  80
Met Glu Leu Ser Ser Leu Arg Ser Glu Asp Thr Ala Val Tyr Tyr Cys
                        85                  90                  95
Ala Arg Glu Ala Gln Ser Tyr Arg Val Pro Phe Asp Ile Trp Gly Gln
                    100                 105                 110
Gly Thr Met Val Thr Val Ser Ser
            115                 120

<210> SEQ ID NO 334
<211> LENGTH: 108
<212> TYPE: PRT
<213> ORGANISM: Homo sapiens

<400> SEQUENCE: 334

Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Val Ser Ser Asn
            20                  25                  30
Leu Ala Trp Tyr Gln Gln Lys Pro Gly Gln Ala Pro Arg Leu Leu Ile
        35                  40                  45
Tyr Gly Ala Ser Thr Arg Ala Thr Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Ala Ile Trp Pro Pro
                85                  90                  95
Phe Thr Phe Gly Gly Gly Thr Lys Val Glu Ile Lys
            100                 105

<210> SEQ ID NO 335
<211> LENGTH: 375
<212> TYPE: DNA
<213> ORGANISM: Homo sapiens

<400> SEQUENCE: 335
cagctgcagc tgcaggagtc gggcccagga ctggtgaagc cttcggagac cctgtccctc     60
acctgcactg tctctggtgg ctccatcagc agtgggagtt actacttggc gtggatccgc    120
cagcccccag ggaaggggct ggagtggatt gggagtatct tcggagtgg gagcacctac     180
tacaacccgt ccctcgagag tcgagtcacc atatcggtag acacgtccaa gaaccagttc    240
tccctgaagc tgagttctgt gaccgccgca gacacggcgg tgtactactg cgccatagaa    300
ggagctaact ttaaggactt cggatatgta gcattcgaca tatggggtca gggtacaact    360
gtcaccgtct cctca                                                    375

<210> SEQ ID NO 336
<211> LENGTH: 321
<212> TYPE: DNA
<213> ORGANISM: Homo sapiens

<400> SEQUENCE: 336
gaaatagtga tgacgcagtc tccagccacc ctgtctgtgt ctccagggga aagagccacc     60
ctctcctgca gggccagtca gagtgttagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag tccccccccct ggcctaggac ttttggcgga   300
```

```
gggaccaagg ttgagatcaa a                                            321
```

<210> SEQ ID NO 337
<211> LENGTH: 375
<212> TYPE: DNA
<213> ORGANISM: Homo sapiens

<400> SEQUENCE: 337

```
cagctgcagc tgcaggagtc gggcccagga ctggtgaagc cttcggagac cctgtccctc     60
acctgcactg tctctggtgg ctccatcagc agtgggagtt actacttggc gtggatccgc    120
cagcccccag ggaaggggct ggagtggatt gggagtatct ttcggagtgg gagcacctac    180
tacaacccgt ccctcgagag tcgagtcacc atatcggtag acacgtccaa gaaccagttc    240
tccctgaagc tgagttctgt gaccgccgca gacacggcgg tgtactactg cgccatagaa    300
ggagctaact ttaaggactt cggatatgta gcattcgaca tatggggtca gggtacaact    360
gtcaccgtct cctca                                                    375
```

<210> SEQ ID NO 338
<211> LENGTH: 321
<212> TYPE: DNA
<213> ORGANISM: Homo sapiens

<400> SEQUENCE: 338

```
gaaattgtgt tgacacagtc tccagccacc ctgtctttgt ctccagggga aagagccacc     60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag gaaaacccca ggcctaggac ttttggcgga    300
gggaccaagg ttgagatcaa a                                             321
```

<210> SEQ ID NO 339
<211> LENGTH: 375
<212> TYPE: DNA
<213> ORGANISM: Homo sapiens

<400> SEQUENCE: 339

```
cagctgcagc tgcaggagtc gggcccagga ctggtgaagc cttcggagac cctgtccctc     60
acctgcactg tctctggtgg ctccatcagc agtgggagtt actacttggc gtggatccgc    120
cagcccccag ggaaggggct ggagtggatt gggagtatct ttcggagtgg gagcacctac    180
tacaacccgt ccctcgagag tcgagtcacc atatcggtag acacgtccaa gaaccagttc    240
tccctgaagc tgagttctgt gaccgccgca gacacggcgg tgtactactg cgccatagaa    300
ggagctaact ttaaggactt cggatatgta gcattcgaca tatggggtca gggtacaact    360
gtcaccgtct cctca                                                    375
```

<210> SEQ ID NO 340
<211> LENGTH: 321
<212> TYPE: DNA
<213> ORGANISM: Homo sapiens

<400> SEQUENCE: 340

```
gaaatagtga tgacgcagtc tccagccacc ctgtctgtgt ctccagggga aagagccacc     60
ctctcctgca gggccagtaa aagtgtttcc agcaacttag cctggtacca gcagaaacct    120
```

```
ggccaggctc ccaggctcct catctatttc gcatccacca gggccaccgg tatcccagcc      180
aggttcagtg gcagtgggtc tgggacagag ttcactctca ccatcagcag cctgcagtct      240
gaagattttg cagtttatta ctgtcagcag acttcgccct ggcctaggac ttttggcgga      300
gggaccaagg ttgagatcaa a                                                321
```

<210> SEQ ID NO 341
<211> LENGTH: 360
<212> TYPE: DNA
<213> ORGANISM: Homo sapiens

<400> SEQUENCE: 341

```
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatccctt tctttggtac agcaaactac      180
gcacagaagt tccagggcag agtcacgatt accgcggacg aatccacgag cacagcctac      240
atggagctga gcagcctgag atctgaggac acggcggtgt actactgcgc cagagaggct      300
caatcctaca gggttccatt cgacatatgg ggtcagggta caatggtcac cgtctcctca      360
```

<210> SEQ ID NO 342
<211> LENGTH: 324
<212> TYPE: DNA
<213> ORGANISM: Homo sapiens

<400> SEQUENCE: 342

```
gaaatagtga tgacgcagtc tccagccacc ctgtctgtgt ctccagggga aagagccacc       60
ctctcctgca gggccagtca gagtgttagc agcaacttag cctggtacca gcagaaacct      120
ggccaggctc ccaggctcct catctatggt gcatccacca gggccactgg tatcccagcc      180
aggttcagtg gcagtgggtc tgggacagag ttcactctca ccatcagcag cctgcagtct      240
gaagattttg cagtttatta ctgtcagcag tacgccatct ggcctccttt cacttttggc      300
ggagggacca aggttgagat caaa                                             324
```

<210> SEQ ID NO 343
<211> LENGTH: 126
<212> TYPE: PRT
<213> ORGANISM: Rattus norvegicus

<400> SEQUENCE: 343

```
Glu Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
             20                  25                  30

Ser Ala Ala Trp Asn Trp Ile Arg Gln Ser Pro Ser Arg Gly Leu Glu
         35                  40                  45

Trp Leu Gly Lys Thr Tyr Tyr Arg Phe Lys Trp Tyr Ser Asp Tyr Ala
     50                  55                  60

Val Ser Val Lys Gly Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Phe Tyr Cys Thr Arg Glu Ser Thr Thr Tyr Asp Leu Leu Ala Gly Pro
            100                 105                 110

Phe Asp Tyr Trp Gly Gln Gly Thr Leu Val Thr Val Ser Ser
        115                 120                 125
```

<210> SEQ ID NO 344
<211> LENGTH: 113
<212> TYPE: PRT
<213> ORGANISM: Rattus norvegicus

<400> SEQUENCE: 344

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Leu Tyr Ser
            20                  25                  30

Ser Asn Asn Lys Lys Tyr Leu Ala Trp Tyr Gln Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Phe Thr Phe Gly Pro Gly Thr Lys Val Glu Ile
            100                 105                 110

Lys

<210> SEQ ID NO 345
<211> LENGTH: 130
<212> TYPE: PRT
<213> ORGANISM: Mus musculus

<400> SEQUENCE: 345

Gln Val His Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ile Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Tyr Val Ser Gly Asn Tyr Tyr Asn Val Asp Tyr
            100                 105                 110

Tyr Phe Phe Gly Val Asp Val Trp Gly Gln Gly Thr Thr Val Thr Val
        115                 120                 125

Ser Ser
    130

<210> SEQ ID NO 346
<211> LENGTH: 109
<212> TYPE: PRT
<213> ORGANISM: Mus musculus

<400> SEQUENCE: 346

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr

```
                    20                  25                  30
Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Leu Phe Thr Phe Gly Pro Gly Thr Lys Val Asp Ile Lys
            100                 105

<210> SEQ ID NO 347
<211> LENGTH: 119
<212> TYPE: PRT
<213> ORGANISM: Mus musculus

<400> SEQUENCE: 347

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Tyr
                20                  25                  30

Val Met His Trp Val Arg Gln Ala Pro Gly Gln Gly Leu Glu Trp Ile
            35                  40                  45

Gly Tyr Ile Asp Pro Tyr Asn Asp Gly Ala Lys Tyr Ala Gln Lys Phe
    50                  55                  60

Gln Gly Arg Val Thr Leu Thr Ser Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Pro Tyr Gly Trp Tyr Phe Asp Val Trp Gly Gln Gly
            100                 105                 110

Thr Thr Val Thr Val Ser Ser
            115

<210> SEQ ID NO 348
<211> LENGTH: 107
<212> TYPE: PRT
<213> ORGANISM: Mus musculus

<400> SEQUENCE: 348

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu His Ile Tyr Ser Tyr
                20                  25                  30

Leu Ser Trp Tyr Gln Gln Lys Pro Gly Lys Ala Pro Lys Leu Leu Ile
            35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Gly Ser Pro Leu
                85                  90                  95

Thr Phe Gly Gln Gly Thr Arg Leu Glu Ile Lys
            100                 105
```

```
<210> SEQ ID NO 349
<211> LENGTH: 118
<212> TYPE: PRT
<213> ORGANISM: Mus musculus

<400> SEQUENCE: 349

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Ser Thr Ser Tyr Asn Pro Ser Leu
    50                  55                  60

Arg Ser Arg Val Thr Ile Ser Arg Asp Thr Ser Lys Asn Gln Phe Phe
65                  70                  75                  80

Leu Lys Leu Ser Ser Val Thr Ala Ala Asp Thr Ala Val Tyr Tyr Cys
                85                  90                  95

Ala Arg Arg Gln Val Gly Leu Gly Phe Ala Tyr Trp Gly Gln Gly Thr
            100                 105                 110

Leu Val Thr Val Ser Ser
        115

<210> SEQ ID NO 350
<211> LENGTH: 99
<212> TYPE: PRT
<213> ORGANISM: Mus musculus

<400> SEQUENCE: 350

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Trp
                85                  90                  95

Thr Phe Gly

<210> SEQ ID NO 351
<211> LENGTH: 119
<212> TYPE: PRT
<213> ORGANISM: Mus musculus

<400> SEQUENCE: 351

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Asn Phe
            20                  25                  30

Gly Met His Trp Val Arg Gln Ala Pro Glu Lys Gly Leu Glu Trp Val
        35                  40                  45

Ala Phe Ile Ser Ser Gly Ser Ser Ile Tyr Tyr Ala Asp Thr Val
    50                  55                  60
```

```
Lys Gly Arg Phe Thr Ile Ser Arg Asp Asn Pro Lys Asn Thr Leu Phe
 65                  70                  75                  80

Leu Gln Met Thr Ser Leu Arg Ser Glu Asp Thr Ala Met Tyr Tyr Cys
                 85                  90                  95

Ala Arg Met Arg Leu Asp Tyr Tyr Ala Met Asp Tyr Trp Gly Gln Gly
            100                 105                 110

Thr Ser Val Thr Val Ser Ser
            115

<210> SEQ ID NO 352
<211> LENGTH: 107
<212> TYPE: PRT
<213> ORGANISM: Mus musculus

<400> SEQUENCE: 352

Asp Val Gln Ile Thr Gln Ser Pro Ser Tyr Leu Ala Ala Ser Pro Gly
  1               5                  10                  15

Glu Thr Ile Thr Ile Asn Cys Arg Ala Ser Lys Ser Ile Ser Lys Tyr
             20                  25                  30

Leu Ala Trp Tyr Gln Glu Lys Pro Gly Lys Thr Asn Lys Leu Leu Ile
         35                  40                  45

Tyr Ser Gly Ser Thr Leu Gln Ser Gly Ile Pro Ser Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Met Tyr Tyr Cys Gln Gln His Asn Glu Tyr Pro Trp
                 85                  90                  95

Thr Phe Gly Gly Gly Thr Lys Leu Glu Ile Lys
            100                 105

<210> SEQ ID NO 353
<211> LENGTH: 9
<212> TYPE: PRT
<213> ORGANISM: Homo sapiens

<400> SEQUENCE: 353

Gly Thr Phe Ser Ser Tyr Leu Ile Ser
  1               5

<210> SEQ ID NO 354
<211> LENGTH: 17
<212> TYPE: PRT
<213> ORGANISM: Homo sapiens

<400> SEQUENCE: 354

Gly Ile Tyr Pro Ile Phe Ala Thr Ala Asn Tyr Ala Gln Lys Phe Gln
  1               5                  10                  15

Gly

<210> SEQ ID NO 355
<211> LENGTH: 13
<212> TYPE: PRT
<213> ORGANISM: Homo sapiens

<400> SEQUENCE: 355

Ala Arg Glu Ala Gln Ser Tyr Arg Val Pro Phe Asp Ile
  1               5                  10

<210> SEQ ID NO 356
<211> LENGTH: 11
```

```
<212> TYPE: PRT
<213> ORGANISM: Homo sapiens

<400> SEQUENCE: 356

Arg Ala Ser Gln Ser Val Ser Ser Asn Leu Ala
1               5                   10

<210> SEQ ID NO 357
<211> LENGTH: 7
<212> TYPE: PRT
<213> ORGANISM: Homo sapiens

<400> SEQUENCE: 357

Gly Ala Ser Thr Arg Ala Thr
1               5

<210> SEQ ID NO 358
<211> LENGTH: 10
<212> TYPE: PRT
<213> ORGANISM: Homo sapiens

<400> SEQUENCE: 358

Gln Gln Tyr Ala Ile Trp Pro Pro Phe Thr
1               5                   10

<210> SEQ ID NO 359
<211> LENGTH: 26
<212> TYPE: PRT
<213> ORGANISM: Homo sapiens

<400> SEQUENCE: 359

Gln Val Gln Leu Val Gln Ser Gly Ala Glu Val Lys Lys Pro Gly Ser
1               5                   10                  15

Ser Val Lys Val Ser Cys Lys Ala Ser Gly
            20                  25

<210> SEQ ID NO 360
<211> LENGTH: 14
<212> TYPE: PRT
<213> ORGANISM: Homo sapiens

<400> SEQUENCE: 360

Trp Val Arg Gln Ala Pro Gly Gln Gly Leu Glu Trp Met Gly
1               5                   10

<210> SEQ ID NO 361
<211> LENGTH: 30
<212> TYPE: PRT
<213> ORGANISM: Homo sapiens

<400> SEQUENCE: 361

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 362
<211> LENGTH: 11
<212> TYPE: PRT
<213> ORGANISM: Homo sapiens

<400> SEQUENCE: 362

Trp Gly Gln Gly Thr Met Val Thr Val Ser Ser
1               5                   10
```

```
<210> SEQ ID NO 363
<211> LENGTH: 23
<212> TYPE: PRT
<213> ORGANISM: Homo sapiens

<400> SEQUENCE: 363

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 364
<211> LENGTH: 15
<212> TYPE: PRT
<213> ORGANISM: Homo sapiens

<400> SEQUENCE: 364

Trp Tyr Gln Gln Lys Pro Gly Gln Ala Pro Arg Leu Leu Ile Tyr
1               5                   10                  15

<210> SEQ ID NO 365
<211> LENGTH: 32
<212> TYPE: PRT
<213> ORGANISM: Homo sapiens

<400> SEQUENCE: 365

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 366
<211> LENGTH: 10
<212> TYPE: PRT
<213> ORGANISM: Homo sapiens

<400> SEQUENCE: 366

Phe Gly Gly Gly Thr Lys Val Glu Ile Lys
1               5                   10

<210> SEQ ID NO 367
<211> LENGTH: 120
<212> TYPE: PRT
<213> ORGANISM: Homo sapiens

<400> SEQUENCE: 367

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Leu Ile Ser Trp Val Arg Gln Ala Pro Gly Gln Gly Leu Glu Trp Met
        35                  40                  45

Gly Gly Ile Tyr Pro Ile Phe Ala Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Gln Ser Tyr Arg Val Pro Phe Asp Ile Trp Gly Gln
            100                 105                 110
```

Gly Thr Met Val Thr Val Ser Ser
        115                 120

<210> SEQ ID NO 368
<211> LENGTH: 108
<212> TYPE: PRT
<213> ORGANISM: Homo sapiens

<400> SEQUENCE: 368

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ala Ile Trp Pro Pro
                85                  90                  95

Phe Thr Phe Gly Gly Gly Thr Lys Val Glu Ile Lys
            100                 105

<210> SEQ ID NO 369
<211> LENGTH: 360
<212> TYPE: DNA
<213> ORGANISM: Homo sapiens

<400> SEQUENCE: 369
caggtgcagc tggtgcagtc tggggctgag gtgaagaagc ctgggtcctc ggtgaaggtc      60
tcctgcaagg cttctggagg cacctttcagc agctacctca tcagctgggt gcgacaggcc     120
cctggacaag ggcttgagtg gatgggaggg atctacccta tcttcgcaac agcaaactac     180
gcacagaagt tccagggcag agtcacgatt accgcggacg aatccacgag cacagcctac     240
atggagctga gcagcctgag atctgaggac acggcggtgt actactgcgc cagagaggct     300
caatcctaca gggttccatt cgacatatgg ggtcaggggta caatggtcac cgtctcctca     360

<210> SEQ ID NO 370
<211> LENGTH: 324
<212> TYPE: DNA
<213> ORGANISM: Homo sapiens

<400> SEQUENCE: 370
gaaatagtga tgacgcagtc tccagccacc ctgtctgtgt ctccagggga aagagccacc      60
ctctcctgca gggccagtca gagtgttagc agcaacttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttatta ctgtcagcag tacgccatct ggcctccttt cacttttggc     300
ggagggacca aggttgagat caaa                                             324

<210> SEQ ID NO 371
<211> LENGTH: 119
<212> TYPE: PRT
<213> ORGANISM: Homo sapiens

<400> SEQUENCE: 371

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Ser
            20                  25                  30

Tyr Met His Trp Val Arg Gln Ala Pro Gly Lys Gly Leu Glu Trp Val
        35                  40                  45

Ala Val Ile Gly Ala Asp Gly Ser Asn Lys Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Val Pro Arg Arg Gly Leu Asp Val Trp Gly Gln Gly
            100                 105                 110

Thr Thr Val Thr Val Ser Ser
        115

<210> SEQ ID NO 372
<211> LENGTH: 471
<212> TYPE: PRT
<213> ORGANISM: Homo sapiens

<400> SEQUENCE: 372

Met Gly Trp Ser Cys Ile Ile Leu Phe Leu Val Ala Thr Ala Thr Gly
1               5                   10                  15

Val His Ser Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Gly Tyr Trp Ile Ala Trp Val Arg Gln Met Pro Gly Lys Gly Leu
    50                  55                  60

Glu Trp Met Gly Ile Ile Tyr Pro Gly Asn Ser Asp Thr Arg Tyr Ser
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg Val Ser Gly Val Gly Ser Ile Trp Met Ala Phe
        115                 120                 125

Asp Ile Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

```
Pro Lys Ser Cys Asp Lys Thr His Thr Cys Pro Cys Pro Ala Pro
                245                 250                 255

Glu Leu Leu Gly Gly Pro Ser Val Phe Leu Phe Pro Pro Lys Pro Lys
        260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
        290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
                355                 360                 365

Glu Pro Gln Val Tyr Thr Leu Pro Pro Ser Arg Asp Glu Leu Thr Lys
        370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
                435                 440                 445

Cys Ser Val Met His Glu Ala Leu His Asn His Tyr Thr Gln Lys Ser
                450                 455                 460

Leu Ser Leu Ser Pro Gly Lys
465                 470

<210> SEQ ID NO 373
<211> LENGTH: 235
<212> TYPE: PRT
<213> ORGANISM: Homo sapiens

<400> SEQUENCE: 373

Met Gly Trp Ser Cys Ile Ile Leu Phe Leu Val Ala Thr Ala Thr Gly
1               5                   10                  15

Val His Ser Asp Ile Val Leu Thr Gln Pro Pro Ser Val Ser Gly Ala
                20                  25                  30

Pro Gly Gln Arg Val Thr Ile Ser Cys Ser Gly Ser Ser Ser Asn Ile
        35                  40                  45

Gly Ser Asn Ser Val Ser Trp Tyr Gln Gln Leu Pro Gly Thr Ala Pro
    50                  55                  60

Lys Leu Leu Ile Tyr Ser Asn Asn Gln Arg Pro Ser Gly Val Pro Asp
65                  70                  75                  80

Arg Phe Ser Gly Ser Lys Ser Gly Thr Ser Ala Ser Leu Ala Ile Thr
                85                  90                  95

Gly Leu Gln Ala Glu Asp Glu Ala Asp Tyr Tyr Cys Gly Ser Tyr Asp
                100                 105                 110

Ser Ser Ile Asn Leu Tyr Val Phe Gly Gly Gly Thr Lys Leu Thr Val
        115                 120                 125

Leu Gly Gln Pro Lys Ala Ala Pro Ser Val Thr Leu Phe Pro Pro Ser
130                 135                 140
```

```
Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235
```